United States Patent
Delahay et al.

(10) Patent No.: US 12,116,400 B2
(45) Date of Patent: *Oct. 15, 2024

(54) ALBUMIN VARIANTS AND CONJUGATES

(71) Applicant: SATORIUS ALBUMEDIX LIMITED, Nottingham (GB)

(72) Inventors: Karen Ann Delahay, Nottingham (GB); Christopher John Arthur Finnis, Nottingham (GB); Karl Michael Nicholls, Nottingham (GB)

(73) Assignee: SARTORIUS ALBUMEDIX LIMITED, Nottingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/656,728

(22) Filed: Mar. 28, 2022

(65) Prior Publication Data

US 2023/0039076 A1 Feb. 9, 2023

Related U.S. Application Data

(63) Continuation of application No. 16/820,421, filed on Mar. 16, 2020, now abandoned, which is a continuation of application No. 15/753,947, filed as application No. PCT/EP2016/069748 on Aug. 19, 2016, now Pat. No. 10,633,428.

(30) Foreign Application Priority Data

Aug. 20, 2015 (EP) .................................... 15181822

(51) Int. Cl.
| | |
|---|---|
| C07K 14/765 | (2006.01) |
| A61K 38/38 | (2006.01) |
| A61K 47/42 | (2017.01) |
| A61K 47/64 | (2017.01) |

(52) U.S. Cl.
CPC .......... *C07K 14/765* (2013.01); *A61K 38/385* (2013.01); *A61K 47/42* (2013.01); *A61K 47/643* (2017.08); *C07K 2319/31* (2013.01)

(58) Field of Classification Search
None
See application file for complete search history.

(56) References Cited

U.S. PATENT DOCUMENTS

| | | |
|---|---|---|
| 2,714,586 A | 8/1955 | Lynch et al. |
| 4,302,386 A | 11/1981 | Stevens |
| 4,741,900 A | 5/1988 | Alvarez et al. |
| 4,757,006 A | 7/1988 | Toole, Jr. et al. |
| 4,784,950 A | 11/1988 | Hagen et al. |
| 4,795,805 A | 1/1989 | Itoh et al. |
| 4,868,112 A | 9/1989 | Toole, Jr. |
| 5,073,627 A | 12/1991 | Curtis et al. |
| 5,208,020 A | 5/1993 | Chari et al. |
| 5,223,409 A | 6/1993 | Ladner et al. |
| 5,264,586 A | 11/1993 | Nicolaou et al. |
| 5,294,699 A | 3/1994 | Ohmura et al. |
| 5,380,712 A | 1/1995 | Ballance et al. |
| 5,625,041 A | 4/1997 | Johnson et al. |
| 5,698,426 A | 12/1997 | Huse |
| 5,712,374 A | 1/1998 | Kuntsmann et al. |
| 5,714,377 A | 2/1998 | Tanner et al. |
| 5,714,586 A | 2/1998 | Kunstmann et al. |
| 5,716,808 A | 2/1998 | Raymond |
| 5,728,553 A | 3/1998 | Goodey et al. |
| 5,736,383 A | 4/1998 | Raymond |
| 5,766,883 A | 6/1998 | Ballance et al. |
| 5,773,001 A | 6/1998 | Hamann et al. |
| 5,824,837 A | 10/1998 | Chen et al. |
| 5,854,039 A | 12/1998 | Raymond et al. |
| 5,876,969 A | 3/1999 | Fleer et al. |
| 5,888,768 A | 3/1999 | Raymond |
| 5,948,609 A | 9/1999 | Carter et al. |
| 6,509,313 B1 | 1/2003 | Smith |
| 6,528,313 B1 | 3/2003 | Le Mouellic et al. |
| 6,528,314 B1 | 3/2003 | Le Mouellic et al. |
| 6,599,873 B1 | 7/2003 | Sommer et al. |
| 6,638,768 B1 | 10/2003 | Le Mouellic et al. |
| 6,686,179 B2 | 2/2004 | Fleer et al. |
| 6,905,688 B2 | 6/2005 | Rosen et al. |
| 6,926,898 B2 | 8/2005 | Rosen et al. |
| 6,949,691 B2 | 9/2005 | Carter |
| 6,972,322 B2 | 12/2005 | Fleer et al. |
| 6,987,006 B2 | 1/2006 | Fleer et al. |
| 6,989,365 B2 | 1/2006 | Fleer et al. |
| 6,994,857 B2 | 2/2006 | Rosen et al. |
| 7,041,478 B2 | 5/2006 | Fleer et al. |
| 7,041,802 B2 | 5/2006 | Young et al. |

(Continued)

FOREIGN PATENT DOCUMENTS

| | | |
|---|---|---|
| CA | 2611540 | 5/2009 |
| CA | 2562249 | 4/2016 |

(Continued)

OTHER PUBLICATIONS

Ellgaard et al., 2003, Quality Control in the Endoplasmic Reticulum, Mol Cell Biol. 4: 181-191.
Hong et al., 1996, A Pathway for Targeting Soluble Misfolded Proteins to the Yeast Vacuole, J Cell Biol. 135(3): 623-633.
Adams et al., 2013. The Adaptable Major Histocompatibility Complex (MHC) Fold: Structure and Function of Nonclassical and MHC Class I-Like Molecules. Annu Rev Immunol. 31:529-561.
Akilesh et al., 2007. Neonatal FcR expression in bone marrow-derived cells functions to protect serum IgG from catabolismj Immunol. (Baltimore, Md. : 1950) 179:4580-4588.
Allan et al "Enhanced albumins and albumin fusion technology" May 4, 2012 XP055109701 Retrieved from the Internet: URL:http:\\www.biopharma.novozymes.com/en/information-centre/posters-and-presentations/Documents/PEGS%20poster%202012_EZAL.pdf.

(Continued)

*Primary Examiner* — Anand U Desai
(74) *Attorney, Agent, or Firm* — KNOBBE, MARTENS OLSON & BEAR LLP

(57) ABSTRACT

The present invention relates to conjugation-competent albumins and albumin-related polypeptides, and their conjugates with at least one moiety, and to polynucleotides encoding them.

17 Claims, 17 Drawing Sheets

Specification includes a Sequence Listing.

(56) References Cited

U.S. PATENT DOCUMENTS

| | | |
|---|---|---|
| 7,041,803 B2 | 5/2006 | Ni et al. |
| 7,045,318 B2 | 5/2006 | Ballance |
| 7,053,190 B2 | 5/2006 | Ruben et al. |
| 7,056,701 B2 | 6/2006 | Fleer et al. |
| 7,081,354 B2 | 7/2006 | Fleer et al. |
| 7,094,577 B2 | 8/2006 | Fleer et al. |
| 7,141,547 B2 | 11/2006 | Rosen et al. |
| 7,196,164 B2 | 3/2007 | Rosen et al. |
| 7,253,259 B2 | 8/2007 | Otagiri et al. |
| 7,271,149 B2 | 9/2007 | Glaesner et al. |
| 7,358,416 B2 | 4/2008 | Roopenian |
| 7,410,779 B2 | 8/2008 | Fleer et al. |
| 7,425,622 B2 | 9/2008 | Rosen |
| 7,435,410 B2 | 10/2008 | Fleer et al. |
| 7,465,707 B2 | 12/2008 | Ni et al. |
| 7,482,013 B2 | 1/2009 | Ballance et al. |
| 7,507,413 B2 | 3/2009 | Rosen et al. |
| 7,507,414 B2 | 3/2009 | Rosen et al. |
| 7,514,079 B2 | 4/2009 | Rosen et al. |
| 7,550,432 B2 | 6/2009 | Ballance |
| 7,569,215 B2 | 8/2009 | Wittrup et al. |
| 7,572,619 B2 | 8/2009 | Hauser et al. |
| 7,592,010 B2 | 9/2009 | Rosen et al. |
| 7,597,886 B2 | 10/2009 | Yu et al. |
| 7,615,537 B2 | 11/2009 | Scaria et al. |
| 7,785,599 B2 | 8/2010 | Ballance et al. |
| 7,833,521 B2 | 11/2010 | Fleer et al. |
| 7,850,963 B2 | 12/2010 | Rosen et al. |
| 7,851,596 B2 | 12/2010 | Gentz et al. |
| 7,862,818 B2 | 1/2011 | Roschke et al. |
| 7,951,360 B2 | 5/2011 | Wittrup et al. |
| 7,998,691 B2 | 8/2011 | Kulaksiz et al. |
| 8,012,464 B2 | 9/2011 | Rosen et al. |
| 8,080,651 B2 | 12/2011 | Goldberg |
| 8,541,378 B2 | 9/2013 | Ahn et al. |
| 8,697,650 B2 | 4/2014 | Gao et al. |
| 8,748,380 B2 | 6/2014 | Plumridge et al. |
| 8,822,417 B2 | 9/2014 | Andersen et al. |
| 9,493,545 B2 | 11/2016 | Finnis et al. |
| 9,944,691 B2 | 4/2018 | Delahay |
| 10,208,102 B2 | 2/2019 | Andersen et al. |
| 10,233,228 B2 | 3/2019 | Plumridge et al. |
| 10,329,340 B2 | 6/2019 | Delahay |
| 10,501,524 B2 | 12/2019 | Cameron et al. |
| 10,633,428 B2 | 4/2020 | Delahay et al. |
| 10,696,732 B2 | 6/2020 | Sleep et al. |
| 10,711,050 B2 | 7/2020 | Schmidt et al. |
| 10,934,341 B2 | 3/2021 | Cameron et al. |
| 11,555,061 B2 | 1/2023 | Finnis et al. |
| 11,630,104 B2 * | 4/2023 | Gohel ............... G01N 33/552 |
| | | 435/7.1 |
| 2002/0123080 A1 | 9/2002 | Sonnenschein et al. |
| 2002/0151011 A1 | 10/2002 | Fleer et al. |
| 2003/0091565 A1 | 5/2003 | Beltzer et al. |
| 2003/0104578 A1 | 6/2003 | Ballance |
| 2004/0063635 A1 | 4/2004 | Yu |
| 2004/0171154 A1 | 9/2004 | Storici et al. |
| 2005/0142106 A1 | 6/2005 | Wittrup et al. |
| 2005/0222026 A1 | 10/2005 | Otagiri |
| 2005/0256303 A1 | 11/2005 | Otagiri et al. |
| 2006/0018859 A1 | 1/2006 | Carter |
| 2006/0051859 A1 | 3/2006 | Fu |
| 2006/0171892 A1 | 8/2006 | Woodrow |
| 2006/0178301 A1 | 8/2006 | Jurs |
| 2007/0041987 A1 | 2/2007 | Carter et al. |
| 2007/0092940 A1 | 4/2007 | Eigenbrot |
| 2008/0108560 A1 | 5/2008 | Beals et al. |
| 2008/0167238 A1 | 7/2008 | Rosen et al. |
| 2009/0029914 A1 | 1/2009 | Rosen et al. |
| 2010/0129846 A1 | 5/2010 | Goldknopf |
| 2011/0091412 A1 | 4/2011 | Wittrup et al. |
| 2011/0151490 A1 | 6/2011 | Hillman |
| 2011/0172398 A1 | 7/2011 | Borges et al. |
| 2013/0053322 A1 | 2/2013 | Gao |
| 2013/0225496 A1 | 8/2013 | Plumridge |
| 2014/0128326 A1 | 5/2014 | Cameron |
| 2014/0148392 A1 | 5/2014 | Gao et al. |
| 2014/0234311 A1 | 8/2014 | Sleep et al. |
| 2014/0248682 A1 | 9/2014 | Gao et al. |
| 2014/0315816 A1 | 10/2014 | Andersen et al. |
| 2014/0315817 A1 | 10/2014 | Schmidt et al. |
| 2015/0210752 A1 | 7/2015 | Cameron |
| 2016/0009787 A1 | 1/2016 | Sleep et al. |
| 2016/0033523 A1 | 2/2016 | Cameron et al. |
| 2016/0052993 A1 | 2/2016 | Schmidt et al. |
| 2016/0075756 A1 | 3/2016 | Sleep et al. |
| 2016/0075757 A1 | 3/2016 | Sleep et al. |
| 2016/0075758 A1 | 3/2016 | Sleep et al. |
| 2016/0075759 A1 | 3/2016 | Sleep et al. |
| 2016/0075760 A1 | 3/2016 | Sleep et al. |
| 2016/0075761 A1 | 3/2016 | Sleep et al. |
| 2016/0075762 A1 | 3/2016 | Sleep et al. |
| 2016/0075763 A1 | 3/2016 | Sleep et al. |
| 2017/0081389 A1 | 3/2017 | Finnis et al. |
| 2018/0072792 A1 | 3/2018 | Sleep et al. |
| 2018/0105576 A1 | 4/2018 | Sleep et al. |
| 2018/0105577 A1 | 4/2018 | Sleep et al. |
| 2018/0105578 A1 | 4/2018 | Sleep et al. |
| 2018/0162925 A1 | 6/2018 | Sleep et al. |
| 2018/0222963 A1 | 8/2018 | Sleep et al. |
| 2018/0265568 A1 | 9/2018 | Delahay et al. |
| 2018/0265570 A1 | 9/2018 | Sleep et al. |
| 2018/0334491 A1 | 11/2018 | Schmidt et al. |
| 2019/0113519 A1 | 4/2019 | Cameron et al. |
| 2019/0315836 A1 | 10/2019 | Delahay et al. |
| 2020/0102367 A1 | 4/2020 | Cameron et al. |
| 2020/0102368 A1 | 4/2020 | Andersen et al. |
| 2020/0385442 A1 | 12/2020 | Sleep et al. |
| 2020/0392206 A1 | 12/2020 | Finnis et al. |
| 2021/0070839 A1 | 3/2021 | Delahay et al. |

FOREIGN PATENT DOCUMENTS

| | | |
|---|---|---|
| CN | 1405182 | 3/2003 |
| CN | 101065151 A | 10/2007 |
| CN | 101875693 B | 7/2012 |
| EP | 0286424 | 10/1988 |
| EP | 0319067 | 6/1989 |
| EP | 0413622 | 2/1991 |
| EP | 0438102 | 7/1991 |
| EP | 0464590 | 1/1992 |
| EP | 0510693 | 4/1992 |
| EP | 0305216 | 8/1995 |
| EP | 1681304 | 7/2006 |
| JP | 2005-206577 | 8/2005 |
| JP | 4983148 | 7/2012 |
| KR | 2005-0075134 | 7/2005 |
| RU | 2369404 | 10/2009 |
| WO | WO 1990/13653 | 11/1990 |
| WO | WO 1991/09125 | 6/1991 |
| WO | WO 1992/04367 | 3/1992 |
| WO | WO 1992/06204 | 4/1992 |
| WO | WO 1993/21232 | 10/1993 |
| WO | WO 1994/04687 | 3/1994 |
| WO | WO 1994/11026 | 5/1994 |
| WO | WO 1995/17413 | 6/1995 |
| WO | WO 1995/22625 | 8/1995 |
| WO | WO 1995/23857 | 9/1995 |
| WO | WO 1995/24427 | 9/1995 |
| WO | WO 1997/24445 | 7/1997 |
| WO | WO 1999/28348 | 6/1999 |
| WO | WO 2000/008207 | 2/2000 |
| WO | WO 2000/044772 | 8/2000 |
| WO | WO 2000/069902 | 11/2000 |
| WO | WO 2000/071079 | 11/2000 |
| WO | WO 2001/079258 | 10/2001 |
| WO | WO 2001/079271 | 10/2001 |
| WO | WO 2001/079442 | 10/2001 |
| WO | WO 2001/079443 | 10/2001 |
| WO | WO 2001/079444 | 10/2001 |
| WO | WO 2001/079480 | 10/2001 |
| WO | WO 2002/022809 | 3/2002 |
| WO | WO 2002/043658 | 6/2002 |
| WO | WO 2002/083897 | 10/2002 |

(56) References Cited

FOREIGN PATENT DOCUMENTS

| | | |
|---|---|---|
| WO | WO 2002/102830 | 12/2002 |
| WO | WO 2003/059934 | 7/2003 |
| WO | WO 2003/060071 | 7/2003 |
| WO | WO 2003/066085 | 8/2003 |
| WO | WO 2003/066824 | 8/2003 |
| WO | WO 2004/101620 | 1/2004 |
| WO | WO 2004/011499 | 2/2004 |
| WO | WO 2004/071536 | 8/2004 |
| WO | WO 2004/082640 | 9/2004 |
| WO | WO 2004/083245 | 9/2004 |
| WO | WO 2005/003296 | 1/2005 |
| WO | WO 2005/061718 | 7/2005 |
| WO | WO 2005/061719 | 7/2005 |
| WO | WO 2005/077042 | 8/2005 |
| WO | WO 2005/082423 | 9/2005 |
| WO | WO 2006/066595 | 6/2006 |
| WO | WO 2006/067511 | 6/2006 |
| WO | WO 2006/073195 | 7/2006 |
| WO | WO 2006/118772 | 11/2006 |
| WO | WO 2006/136831 | 12/2006 |
| WO | WO 2007/021494 | 2/2007 |
| WO | WO 2007/071068 | 6/2007 |
| WO | WO 2007/090584 | 8/2007 |
| WO | WO 2007/112940 | 10/2007 |
| WO | WO 2007/144173 | 12/2007 |
| WO | WO 2007/146038 | 12/2007 |
| WO | WO 2008/007146 | 1/2008 |
| WO | WO 2008/030558 | 3/2008 |
| WO | WO 2009/019314 | 2/2009 |
| WO | WO 2009/081201 | 7/2009 |
| WO | WO 2009/126920 | 10/2009 |
| WO | WO 2009/134808 | 11/2009 |
| WO | WO 2010/059315 | 5/2010 |
| WO | WO 2010/065950 | 6/2010 |
| WO | WO 2010/068278 | 6/2010 |
| WO | WO 2010/092135 | 8/2010 |
| WO | WO 2010/118169 | 10/2010 |
| WO | WO 2010/129023 | 11/2010 |
| WO | WO 2010/138814 | 12/2010 |
| WO | WO 2010/141329 | 12/2010 |
| WO | WO 2011/011315 | 1/2011 |
| WO | WO 2011/011797 | 1/2011 |
| WO | WO 2011/018611 | 2/2011 |
| WO | WO 2011/044563 | 4/2011 |
| WO | WO 2011/051489 | 5/2011 |
| WO | WO 2011/079175 | 6/2011 |
| WO | WO 2011/103076 | 8/2011 |
| WO | WO 2011/124718 | 10/2011 |
| WO | WO 2011/146902 | 11/2011 |
| WO | WO 2011/161127 | 12/2011 |
| WO | WO 2012/020143 | 2/2012 |
| WO | WO 2012/059486 | 5/2012 |
| WO | WO 2012/112188 | 8/2012 |
| WO | WO 2012/150319 | 11/2012 |
| WO | WO 2013/010840 | 1/2013 |
| WO | WO 2013/075066 | 5/2013 |
| WO | WO 2013/135896 | 9/2013 |
| WO | WO 2014/005596 | 1/2014 |
| WO | WO 2014/072481 | 5/2014 |
| WO | WO 2014/179657 | 11/2014 |
| WO | WO 2015/036579 | 3/2015 |

OTHER PUBLICATIONS

Altschul et al., 1997, Gapped BLAST and PSI-Blast: A new generation of protein database search programs. Nucleic Acids Res. 25(17):3389-3402.

Amthor et al., 2004, Albumin targeting of damaged muscle fibres in the mdx mouse can be monitored by MRI. Neuromuscular Disorders 14(12): 791-796.

Andersen et al., 2006, The conserved histidine 166 residue of the human neonatal Fc receptor heavy chain is critical for the pH-dependent binding to albumin, Eur J Immunol, 36:3044-3051.

Andersen et al., 2007, A receptor-mediated mechanism to support clinical observation of altered albumin variants, Clinic Chem, 53(12):2216.

Andersen et al., 2008, Ligand binding and antigenic properties of a human neonatal Fc receptor with mutation of two unpaired cysteine residues, FEBS Journal, 275(16):4097-4110.

Andersen et al., 2009, The versatile MHC class I-related FcRn protects IgG and albumin from degradation: implications for development of new diagnostics and therapeutics, Drug Metab Pharmacokinet, 24(4):318-332.

Andersen et al., 2010, Cross-species binding analyses of mouse and human neonatal Fc receptor show dramatic differences in immunoglobulin G and albumin binding. J Biol Chem. 285(7):4826-4836.

Andersen et al., 2010, FcRn binding properties of an abnormal truncated analbuminemic albumin variant, Clinical Biochem, 43:367-372.

Andersen et al., 2012, Structure-based mutagenesis reveals the albumin-binding site of the neonatal Fc receptor, Nature Comm. 3:610 in 9 pages and Supplemental Information in 13 pages.

Andersen et al., 2013, Single-chain variable fragment albumin fusions bind the neonatal Fc receptor (FcRn) in a species-dependent manner: implications for in vivo half-life evaluation of albumin fusion therapeutics, J Biol Chem., 288(33):24277-24285.

Andersen et al., May 2014, Extending serum half-life of albumin by engineering neonatal Fc receptor (FcRn) binding, J Biol Chem., 289(19):13492-502.

Anderson et al., 2006, Perspective—FcRn transports albumin: relevance to immunology and medicine, Trends Immunol, 27(7):343-348.

Averyhart-Fullard et al., 1990. Cloning and Thyroid Hormone Regulation of Albumin mRNA in Rana catesbeiana Tadpole Liver, Mol Endocrinol. 4(10):1556-1563.

Balan et al., 2006, A phase I/II study evaluating escalating doses of recombinant human albumin-interferon-α fusion protein in chronic hepatitis C patients who have failed previous interferon-α-based therapy, Antiviral Therapy, 11(1):35-45.

Ballesta-Claver et al., 2011, Disposable luminol copolymer-based biosensor for uric acid in urine, Analytica Chimica Acta, 702:254-261.

Barash et al., 1993, Synthesis and secretion of human serum albumin by mammary gland explants of virgin and lactating transgenic mice, Trans Res, 2:266-276.

Bar-Or et al., 2006, The formation and rapid clearance of a truncated albumin species in a critically ill patient, Clin Chim Acta 365(1-2):346-349.

Barr et al., 1996, C-Type Natriuretic Peptide, Peptides 17(7):1243-1251.

Barton et al., 1990, Site-directed, recombination-mediated mutagenesis of a complex gene locus. Nucleic Acids Res. 18(24):7349-4955.

Basle, Mar. 26, 2010, Protein chemical modification on endogenous amino acids, Chemistry & Biology, 17:213-227.

Beeken et al., 1962. Studies of I131-albumin catabolismand distribution in normal young male adults. The Journal of clinical investigation 41, 1312-1333.

Bennhold et al., 1959. Comparative studies on the half-life of I131-labeled albumins and nonradioactive human serum albumin in a case of analbuminemia. J Clin Invest. 38:863-872.

Benotti et al., 1979, Protein and caloric or macronutrient metabolic management of the critically ill patient, Crit Care Med, 7(12):520-525.

Bergmann et al., Jun. 2012, Development of a mathematical model for neonatal Fc receptor recycling to design human serum albumin mutants with extended half-lives, Medimmune FcRn recycling model for mutant albumins, poster, 21st Page meeting, Venice Italy, 1 p.

Berntzen et al., 2005, Prolonged and increased expression of soluble FC receptors, IgG and a TCR-Ig fusion protein by transiently transfected adherent 293E cells, J Immun Method. 298:93-104.

Bhattacharya et al., 2000, Binding of the general anesthetics propofol and halothane to human serum albumin. High resolution crystal structures, J Biol Chem. 275(49):38731-38738.

(56) References Cited

OTHER PUBLICATIONS

Bhattacharya et al., 2000, Crystallographic analysis reveals common modes of binding of medium and long-chain fatty acids to human serum albumin, J. Mol. Biol., 303:721-732.
Blackburn, 2007, Maternal, Fetal and Neonatal Physiology: a Clinical Perspective, 3rd ed., pp. 197-198.
Boder et al., 1997. Yeast surface display for screening combinatorial polypeptide libraries. Nat Biotechnol. 15(6):553-557.
Boder et al., 2000. Directed evolution of antibody fragments with monovalent femtomolar antigen-binding affinity. PNAS U.S.A. 97:10701-10705.
Bos et al., 1989. The molecular mechanism of the neutral-to-base transition of human serum albumin. J Biol Chem. 264:953-959.
Bosse et al., 2005, Phase I comparability of recombinant human albumin and human serum albumin, J Clin Pharmacol, 35:57-67.
Bowe et al., 2001, FGF-23 inhibits renal tubular phosphate transport and is a PHEX substrate, Biochem Biophys Res Commun., 284:977-981.
Bowie et al., 1989, Identifying determinants of folding and activity for a protein of unknown structure. PNAS U.S.A. 86(7):2152-2156.
Brennan et al., 2000, Three truncated forms of serum albumin associated with pancreatic pseudocyst, Biochim Biophys Acta 1481(2):337-343.
Broze et al., Feb. 25, 1980, Purification and properties of human coagulation factor VII, J Biol Chem., 255(4):1242-1247.
Bunting et al., 2012, Enhanced albumins and albumin fusion technology: tuning circulatory half-life with Novozymes Albufuse® Flex to meet medical needs, Poster, Biopharma NZ, 1 p.
Burmeister et al., 1994, Crystal structure at 2.2 Å result ion of the MHC-related neonatal Fc receptor, Nature, 372(6504):336-343.
Burmeister et al., 1994, Crystal structure of the complex of rat neonatal Fc receptor with Fc, Nature, 372(6504):379-383.
Cai et al., Jun. 2010, QPSOBT: One codon usage optimization software for protein heterologous expression, J Bioinformatics Sequence Analysis, 2(2):25-29.
Calissano et al., 1996, In vivo site-directed mutagenesis of Neurospora crassa beta-tubulin gene by spheroplasts transformation with oligonucleotides. Fungal Genetics Reports 43(Article 5) pp. 5.
Cantor et al. [Eds], 1980, Box 21-2. Reoxidation and refolding of reduced proteins, in Biophysical chemistry. Part III: The behavior of biological macromolecules, W.H. Freeman & Co., p. 1104.
CAPlus accession No. 2005:1283404, "Standard Albumin Gene . . . . ", STN entry date Dec. 8, 2005; 1 page.
Carlson et al., 1992, Alloalbuminemia in Sweden: structural study and phenotypic distribution of nine albumin variants, PNAS USA 89:8225-8229.
Carter et al., 1989, Three-dimensional structure of human serum albumin, Science, 244(4909):1195-1198.
Chao et al. 2006. Isolating and engineering human antibodies using yeast surface display. Nature protocols 1(2):755-768.
Chapman A.P., 2002, PEGylated antibodies and antibody fragments for improved therapy: A review. Adv. Drug Deliv. Rev. 54:531-545.
Chari et al., 1992, Immunoconjugates Containing Novel Maytansinoids: Promising Anticancer Drugs; Cancer Research 52:127-131.
Chaudhury et al., 2003, The major histocompatibility complex-related Fc receptor for IgG (FcRn) binds albumin and prolongs its lifespan, J Exp Med, 197(3):315-322.
Chaudhury et al., 2006, Albumin binding to FcRn: distinct from the FcRn-IgG interaction, Biochem. 45:4983-4990 and Supplemental Material in 4 pages.
Chen et al., 2003, ZDOCK: an initial-stage protein-docking algorithm, Protein, 52:80-87.
Chen et al., 2013, Human serum albumin from recombinant DNA technology: challenges and strategies, Biochimica et Biophysica Acta, 1830:5515-5525.
Condreay et al., 2007, Baculovirus Expression Vectors for Insect and Mammalian Cells, Current Drug Targets, 8:1126-1131.
Cornell et al., 1981, The environment of the sulfhydryl group in human plasma albumin as determined by spin labelling, Arch Biochem Biophys, 209(1):1-6.
Crystal Structure of Human Serum Albumin AT 2.5 A Resolution, PDB Accession: 1A06. publically available in 1999, 125 pp.
Curry et al., 1998, Crystal structure of human serum albumin complexed with fatty acid reveals on asymmetric distribution of binding sites, Nat Struct Biol, 5(9):827-835.
Curry, S., 2009. Lessons from the crystallographic analysis of small molecule binding to human serum albumin. Drug Metab Pharmacokinet. 24(4):342-357.
Dagnino et al., 2010, A novel frameshift deletion in the albumin gene causes analbuminemia in a young Turkish woman, Clinic Chimica Acta, 411:1711-1715.
Dall'Acqua et al., 2002. Increasing the affinity of a human IgG1 for the neonatal Fc receptor: Biological consequences. J Immunol. 169:5171-5180.
Daniels et al., 2006, The transferrin receptor part II: Targeted delivery of therapeutic agents into cancer cells. Clin Immunol. 121(2):159-176.
Database EMBL accession No. BAG37325; Jan. 12, 2008, "*Homo sapiens* hypothetical protein", 2 pages.
Database NCBI—Access No. 1A06_A (Jun. 1998); pp. 4.
Database NCBI—Access No. AAC63407 (Oct. 1998).
Database NCBI—Access No. AAD09358 (Jan. 1999).
Database NCBI—Access No. AAHF01000013.1 (Mar. 2007) Aspergillus fumigatus in 110 pages.
Database NCBI—Access No. AAL08579 (Sep. 2001).
Database NCBI—Access No. AAL56646 (Jan. 2002).
Database NCBI—Access No. AAM46104 (Jun. 2002).
Database NCBI—Access No. AAN17825.1 (Sep. 2002).
Database NCBI—Access No. AAQ20088 (May 2004).
Database NCBI—Access No. ACF10391 (Jul. 2008).
Database NCBI—Access No. AXS56687 (Jan. 2010) 2 pages.
Database NCBI—Access No. NP _001004887 (Feb. 2011).
Database NCBI—Access No. NP _001127106 (May 2011).
Database NCBI—Access No. P02768 (Apr. 2011).
Database NCBI—Access No. P02770 (May 2011).
Database NCBI—Access No. P07724 (May 2011).
Database NCBI—Access No. P21847 (Nov. 2010); Serum Albumin, 2 pages.
Database NCBI Access No. 103600-Albumin (2011); XP-002660221, 47 pages.
Database NCBI—Access No. P21848 (May 2011).
Database NCBI—Access No. P35747 (May 2011).
Database NCBI—Access No. P83517 (May 2011).
Database NCBI—Access No. Q03156 (May 2011).
Database NCBI—Access No. Q6WDN9-1 (Nov. 2006).
Database NCBI—Access No. Q91274 (Aug. 2010).
Database NCBI—Access No. QXLE4 (May 2011).
Database NCBI—Access No. S59517 (Mar. 2000).
Database NCBI—Accession No. AAA98797 (May 1996).
Database NCBI—Accession No. AAH49971 (Jun. 2007).
Database NCBI—Accession No. AAH85359 (Jul. 2006).
Database Swissprot—Accession No. Q5XLE4.1 (May 2011).
Database Swissprot—Accession No. A6YF56 (Jun. 2010).
Database NCBI—Accession No. XP-517233.2 (Sep. 2006).
Database NCBI—Accession No. NP_001182578.1 (Mar. 2014).
Database Swissprot—Access No. P49822 (Jun. 2009).
Database Swissprot—Access No. O73860 (Jun. 2009).
Database Swissprot—Access No. P01012 (Jun. 2009).
Database Swissprot—Access No. P02768 (May 2009).
Database Swissprot—Access No. P02769 (Jun. 2009).
Database Swissprot—Access No. P08835 (May 2009).
Database Swissprot—Access No. P14639 (May 2009).
Database Swissprot—Access No. P19121 (Jun. 2009).
Database Swissprot—Access No. P49064 (May 2009).
Database Swissprot—Access No. P49065 (May 2009).
Database Swissprot—Access No. Q28522 (May 2009).
Datta-Mannan et al., 2007. Monoclonal antibody clearance: Impact of modulating the interaction of IgG with the neonatal Fc receptor. J Biol Chem. 282(3):1709-1717.
Datta-Mannan et al. 2012. FcRn affinity-pharmacokinetic relationship of five human IgG4 antibodies engineered for improved in vitro FcRn binding properties in cynomolgus monkeys. Drug Metabol Dispos. 40(8):1545-1555.

(56) References Cited

OTHER PUBLICATIONS

Debinski W., 2002, Local treatment of brain tumors with targeted chimera cytotoxic proteins. Cancer Invest. 20(5):801-809.
DeMarco et al., 2007, Schistosome albumin is of host, not parasite, origin, Int J Parasit., 37(11):2101-1208.
Derbyshire et al., 1986, A simple and efficient procedure for saturation mutagenesis using mixed oligodeoxynucleotides. Gene 46(2-3):145-152.
Dickinson et al., Oct. 1999, Bidirectional FcRn-dependent IgG transport in a polarized human intestinal epithelial cell line, J Clin Invest., 104(7):903-911.
Di Stefano et al., 2004, A novel method for coupling doxorubicin to lactosaminated human albumin by an acid sensitive hydrazone bond; synthesis, characterization and preliminary biological properties of the conjugate, Eur J Pharm Sci, 23:393-397.
Dockal et al., Oct. 1, 1999, The three recombinant domains of human serum albumin, J Biol Chem, 274(41):29303-29310.
Doronina et al., 2003, Development of potent monoclonal antibody auristatin conjugates for cancer therapy, Nat Biotechnol, 21:778-784.
Dugaiczyk et al., Jan. 1982, Nucleotide sequence and the encoded amino acids of human serum albumin mRNA, PNAS, USA, 79:71-75.
Edgar R.C., 2004, MUSCLE: multiple sequence alignment with high accuracy and high throughput. Nucleic Acids Res. 32(5):1792-1797.
Edgar R.C., 2004, MUSCLE: a multiple sequence alignment method with reduced time and space complexity. BMC Bioinformatics. 5(1):113 in 19 pages.
Elble, 1992, A simple and efficient procedure for transformation of yeasts, Biotechniques 13(1):18-20.
Elzoghby et al., 2012. Albumin-based nanoparticles as potential controlled release drug delivery systems, J Control Release. 157(2):168-182.
Emsley et al., 2010. Features and development of Coot. Acta crystallographica Section D, Biol. Crystallo. 66:486-501.
Farran et al., 2002, Targeted expression of human serum albumin to potato tubers, Trans Res, 11:337-346.
Feng et al., 2011, Design, expression and characterization of a soluble single-chain functional human neonatal Fc receptor, Prot Expr Purific., 79:66-71.
Ferrara et al., 1999, Pathophysiologic mechanisms of acute graft-vs.-host disease, Biol Blood Marrow Transpl., 5:347-56.
Flanagan, 2009, Protein engineering reaches new frontiers: more detailed knowledge of structure and function drives field forward quickly, Gen Eng Biotech News, 29(12):1-4.
Fleer et al., Oct. 1991, Stable multicopy vectors for high-level secretion of recombinant human serum albumin by kluyveromyces yeasts, Biotech, 9(10):968-975.
Fontaine et al., Long-term stabilization of maleimide-thiol conjugates. Bioconjug Chem. 26(1):145-152.
Francisco et al., Aug. 2003, cAC10-vcMMAE, an anti-CD30-monomethyl auristatin E conjugate with potent and selective antitumor activity, Blood, 102(4):1458-1465.
Franklin et al., May 1980, Localization of the amino acid substitution site in a new variant of human serum albumin, albumin Mexico-2, PNAS. USA, 77(5):2505-2509.
Fritzer et al., 1996, Cytotoxic effects of a doxorubicin-transferrin conjugate in multidrug-resistant KB cells. Biochem Pharmacol. 51(4):489-493.
Fu et al., 2004, Fibroblast growth factor 19 increases metabolic rate and reverses dietary and leptin-deficient diabetes. Endocrinol., 145(6):2594-2603.
Gabrielsson et al. 2007. Pharmacokinetic and Pharmacodynamic Data Analysis: Concepts and Applications, 4th ed. (Swedish Pharmaceutical Press: Stockholm); Table of Contents in 9 pages.
Galliano et al., 1986, Structural characterization of a chain termination mutant of human serum albumin, J Biol Chem, 261:4283-4287.
Galliano et al., 1993, Protein and DNA sequence analysis of a 'private' genetic variant: albumin ortonovo (Glu-505 --> Lys), Biochim Biophys Acta, 1225(1)27-32.
Gama Sosa et al., 2010, Animal transgenesis: an overview, Brain Struct Funct, 214:91-109.
Gao et al., 2004, UpGene: Application of a Web-Based DNA Codon Optimization Algorithm, Biotechnol Prog, 20:443-448.
Garnier et al., 1994, Scale-Up of the Adenovirus Expression System for the Production of Recombinant Protein in Human 293S Cells, Cytotechnology, 15:145-155.
Ghetie et al., 1997. Increasing the serum persistence of an IgG fragment by random mutagenesis. Nature Biotech. 15:637-640.
Ghuman et al., 2005, Structural basis of the drug-binding specificity of human serum albumin. J Mol Bol. 353:38-52.
Gibbs et al., Apr. 13, 2007, Evolutionary and biomedical insights from the Rhesus Macaque genome, Science, 316(5822):222-234.
Gough et al., 2001, Assignment of Homology to Genome Sequences using a Library of Hidden Markov Models that Represent all Proteins of Known Structure. J Mol Biol. 313:903-919.
Graf et al., 2000, Concerted Action of Multiple cis-Acting Sequences Is Required for Rev Dependence of Late Human Immunodeficiency Virus Type 1 Gene Expression, J Virol 74(22):10822-10826.
Grantham et al., 1980, Codon Frequencies in 119 Individual Genes Confirm Consistent Choices of Degenerate Bases According to Genome Type, Nuc. Acids Res. 8(9):1893-1912.
Grosjean et al., 1982, Preferential Codon Usage in Prokaryotic Genes; The Optimal Codon-Anticodon Interaction Energy and the Selective Codon Usage in Efficiently Expressed Genes, Gene, 18:199-209.
Guo et al., 1995, 3'-end-forming signals of yeast mRNA. Mol Cell Biol. 15(11):5983-5990.
Gurbaxani et al., 2006. Analysis of a family of antibodies with different half-lives in mice fails to find a correlation between affinity for FcRn and serum half-life. Mol Immunol. 43(9):1462-1473.
Gustafsson et al., 2004, Codon bias and heterologous protein expression, Trends in Biotechnol. 22(7):346-353.
Gutniak et al., 1992, Antidiabetogenic Effect of Glucagon-like Peptide-1 (7-36) amide in Normal Subjects and Patients with Diabetes Mellitus, N Engl J Med., 326:1316-1322.
Ha et al., 2006, Fatty acids bound to human serum albumin and its structural variants modulate apolipoprotein B secretion in HepG2 cells, Biochem Biophys Acta 1761:717-724.
Haas et al., 1996, Codon usage limitation in the expression of HIV-1 envelope glycoprotein, Curr. Biol. 6:315-324.
Hagen et al., 1986, Characterization of a cDNA coding for human factor VII, PNAS USA, 83:2412-2416.
Hall et al., 2012, Interspecies scaling in pharmacokinetics: a novel whole-body physiologically based modeling framework to discovery drug biodistribution mechanisms In Vivo, J Pharma Sci, 101:1221-1241.
Hallstrom et al., 2008, S-nitroso human serum albumin reduces ischaemia/reperfusion injury in the pig heart after unprotected warm ischaemia, Cardiovascular Res, 77:506-514.
Haspel et al., 1999, Effects of barbiturates on facilitative glucose transporters are pharmacologically specific and isoform selective, J Membr Biol, 169:45-53.
Hassan et al., Oct. 1997, All About Albumin, Review, Clin Chem 43(10):2014a-2015.
Hawkins et al., 2008, Protein nanoparticles as drug carriers in clinical medicine. Adv Drug Deliv Rev. 60(8):876-885.
Hay et al., Apr. 9, 2009, Thio-Transferrin: a recombinant human transferrin engineered for site specific drug conjugation and delivery, Oral Presentation, 5th Annual PEGS, Boston, MA, Novozymes; 22 pages.
He et al., 1992. Atomic structure and chemistry of human serum albumin. Nature 358(6383):209-215.
Henrotte et al., 2004, Investigation of non-covalent interactions between paramagnetic complexes and human serum albumin by electrospray mass spectrometry, Rapid Comm Mass Spectro, 18:1919-1924.
Herzog et al., 1999, Long-term correction of canine hemophilia B by gene transfer of blood coagulation factor IX mediated by adeno-associated viral vector, Nature Med., 5(1):56-63.

(56) References Cited

OTHER PUBLICATIONS

Hillier et al, Apr. 2007, Generation and annotation of the DNA sequences of human chromosomes 2 and 4, Nature, 434:724-731.
Hinman et al., 1993, Preparation and Characterization of Monoclonal Antibody Conjugates of the Calicheamicins: A Novel and Potent Family of Antitumor Antibiotics, Cancer Research 53:3336-3342.
Hinton et al., 2004. Engineered human IgG antibodies with longer serum half-lives in primates. J Biol Chem. 279(8):6213-6216.
Hinton et al., 2006. An engineered human IgG1 antibody with longer serum half-life. J Immunol. 176:346-356.
Ho et al. (1993). X-ray and primary structure of horse serum albumin (*Equus caballus*) at 0.27-nm resolution. Eur J Biochem. 215(1):205-212.
Holm, 1986, Codon usage and gene expression, Nuc. Acids Res. 14(7):3075-3087.
Holm et al., 1998, Dictionary of recurrent domains in protein structures. Proteins 33(1):88-96.
Holm et al., 2000, DaliLite workbench for protein structure comparison. Bioinformatics 16(6):566-567.
Holt et al., 2003, Definition of a novel growth factor-dependent signal cascade for the suppression of bile acid biosynthesis, Genes Dev, 17:1581-1591.
Houghton et al., 1980, The complete amino acid sequence of human fibroblast interferon as deducedusing synthetic oligodeoxyribonucleotide primers of reverse transcriptase, Nucleic Acids Res., 8(13):2885-2894.
Howard et al., 1989, Intracerebral Drug Delivery in Rats with Lesion-Induced Memory Deficits, J. Neurosurg. 71:105-112.
Huang et al., 2007, Efficient gene delivery targeted to the brain using a transferrin-conjugated polyethyleneglycol-modified polyamidoamine dendrimer. FASEB J. 21(4):1117-1125.
Humphreys et al., 2007, Alternative antibody Fab' fragment PEGylation strategies: combination of strong reducing agents, disruption of the interchain disulphide bond and disulphide engineering. Protein Eng Des Sel. 20(5):227-234.
Humphries et al., 1994, Conjugation of synthetic peptides to carrier proteins for cell adhesion studies. J Tissue Cult Meth. 16(3-4):239-242.
Hussain et al., 2006, Fat-free Albumin as a Novel Drug Delivery System. Int'l J Peptide Res Therapeutics 12(3):311-315.
Ikemura, 1982, Correlation between the abundance of yeast transfer RNAs and the occurrence of the respective codons in protein genes. Differences in synonymous codon choice patterns of yeast and *Escherichia coli* with reference to the abundance of isoaccepting transfer RNAs, J Mol Biol. 158:573-597.
Ishima et al., 2007, S-nitrosylation of human variant albumin Iiprizzi (R410C) confers potent antibacterial and cytoprotective properties, J Pharma Exp Therapeutics, 320(3):969-977.
Israel et al., 1993. Immunoglobulin G binding sites on the human foetal intestine: a possible mechanism for the passive transfer of immunity from mother to infant. Immunol. 79(1):77-81.
Ito et al., 1983, Transformation of intact yeast cells treated with alkali cations, J Bacteriol, 153(1):163-168.
Iwao et al., 2006, Oxidation of Arg-410 promotes the elimination of human serum albumin, Biochim Biophys Acta, 1764(4):743-749.
Iwao et al., 2007, Changes of net charge and a-helical content affect the pharmacokinetic properties of human serum albumin, Biochim Biophys Acta, 1774:1582-1590.
Iwao et al., 2007, Effect of one point mutation on the structural and pharmacokinetic properties of human serum albumin, The Pharmaceutical Society of Japan, Summary of Annual Meeting, 127(3):154 (w/Translation).
Iwao et al., 2009, Altered chain-length and glycosylation modify the pharmacokinetics of human serum albumin, Biochem Biophys Acta, 1794(4):634-641.
Jaye et al., 1983, Isolation of a human anti-haemophilic factor IX cDNA clone using a unique 52-base synthetic oligonucleotide probe deduced from the amino acid sequence of bovine factor IX, Nucleic Acids Res. 11(8):2325-2335.
Jerdeva et al., Comparison of FcRn- and plgR-mediated transport in MDCK cells by fluorescence confocal microscopy. Traffic. Sep. 2010;11 (9):1205-20.
Jones D.T., 1999, GenTHREADER: An efficient and reliable protein fold recognition method for genomic sequences. J Mol Biol. 287(4):797-815.
Kabsch et al., 1983, Dictionary of protein secondary structure: pattern recognition of hydrogen-bonded and geometrical features, Biopolymers, 22(12):2577-2637.
Kabsch W., 2010. XDS. Acta crystallographica Section D, Biol Crystallogr. 66:125-132.
Kacskovics et al., 2011, Recent advances using FcRn overexpression, Landes Bioscience 3(5) 431-439.
Kaneko et al., Jan. 2008, Subdomain IIIA of dog albumin contains a binding site similar to site II of human albumin, Drug Metabol Disp. 36:81-86.
Katoh et al., 2002, MAFFT: A novel method for rapid multiple sequence alignment based on fast Fourier transform. Nucleic Acids Res. 30(14):3059-3066.
Katoh et al., 2005, MAFFT Version 5: Improvement in accuracy of multiple sequence alignment. Nucleic Acids Res. 33(2):511-518.
Katoh et al., 2007, PartTree: an algorithm to build an approximate tree from a large number of unaligned sequences. BioInformatics 23(3): 372-374.
Katoh et al., 2009, Multiple alignment of DNA sequences with MAFFT. Methods Mol Biol. 537:39-64.
Katoh et al., 2010, Parallelization of the MAFFT multiple sequence alignment program. Bioinformatics 26(15): 1899-1900.
Kavimandan et al., 2006, Synthesis and characterization of insulin-transferrin conjugates. Bioconjug Chem. 17(6):1376-1384.
Kawamata et al., Aug. 10, 2010 Generation of genetically modified rats from embryonic stem cells, PNAS, 107(32):14223-14228.
Kenanova et al., 2005, Tailoring the pharmacokinetics and positron emission tomography imaging properties of anti-carcinoembryonic antigen single-chain Fv-Fc antibody fragments, Cancer Res, 65(2):622-631.
Kenanova et al., 2007, Radioiodinated versus radiometal-labeled anti-carcinoembryonic antigen single-chain Fv-Fc antibody fragments; optimal pharmacokinetics for therapy, Cancer Res, 67(2):718-726.
Kenanova et al., 2009, HAS domain III as a protein scaffold with defined serum pharmacokinetics, J Nucl Med, 50(Supp 2): 1582-Abstract in 1 page.
Kenanova et al., 2010, Tuning the serum persistence of human serum albumin domain III:diabody fusion proteins, Prot Eng Design Selec, 23(10):789-798.
Khan et al., 2002, Bilirubin binding properties of pigeon serum albumin and its comparison with human serum albumin, J Biol Macromol., 30(3-4):171-178.
Kharitonenkov et al., 2005, FGF-21 as a novel metabolic regulator, J Clin Invest., 115(6):1627-1635.
Kiessling et al., 2002, Magnetic resonance imaging of nude mice with heterotransplanted high-grade squamous cell carcinomas: use of a low-loaded, covalently bound Gd-Hsa conjugate as contrast agent with high tumor affinity. Invest Radiol.37(4):193-198.
Kim et al., Mar. 2003, Development and characterization of a glucagon-like peptide 1-albumin conjugate: the ability to activate the glucagon-like peptide 1 receptor in vivo, Diabetes, 52:751-759.
Kim et al., 2006. Albumin turnover: FcRn-mediated recycling saves as much albumin from degradation as the liver produces. Am J Physiol Gastrointest Liver Physiol. 290:G352-G360.
Kim et al., 2007. Kinetics of FcRn-mediated recycling of IgG and albumin in human: Pathophysiology and therapeutic implications using a simplified mechanism-based model. Clin Immunol. 122(2):146-155.
Kjeldsen et al., 1998, Secretory expression of human albumin domains in *Saccharomyces cerevisiae* and their binding of myristic acid and an acylated insulin analogue. Protein Expr Purif. 13(2):163-169.
Kobayashi et al., 1998, The development of recombinant human serum albumin, Thera Apheresis, 2:257-262.
Kontermann, 2011, Strategies for extended serum half-life or protein therapeutics, Curr Opin Biotech. 22:1-9.

(56) References Cited

OTHER PUBLICATIONS

Kragh-Hansen et al., 2002, Practical aspects of the ligand-binding and enzymatic properties of human serum albumin, Biol Pharm Bull, 25(6):695-704.

Kragh-Hansen et al., 2004, Structural analysis and fatty acid-binding properties of two Croatian variants of human serum albumin, Clinical Chimica Acta, 349(1-2):105-112.

Kragh-Hansen et al., 2005, Effect of genetic variation on the thermal stability of human serum albumin, Biochim Biophys Acta, 1747(1):81-88.

Kratz, 2008, Albumin as a drub carrier: design of prodrugs, drug conjugates and nanoparticles, J Controlled Release, 132(3):171-183.

Kren et al., 1998, In vivo site-directed mutagenesis of the factor IX gene by chimeric RNA/DNA oligonucleotides. Nat Med. 4(3):285-290.

Krieger et al., Jul. 4, 2014, YASARA View—molecular graphics for all devices—from smartphones to workstations. Bioinformatics 30(20) 2981-2982.

Krissinel et al., 2007. Inference of macromolecular assemblies from crystalline state. Journal of molecular biology 372, 774-797 (2007).

Kuo et al., 2010, Neonatal Fc receptor: from immunity to therapeutics, J Clin Immunol, 30(6):777-789.

Kuo et al., 2011. Neonatal Fc receptor and IgG-based therapeutics. mAbs 3(5):422-430.

Kurtzhals et al., 1995, Albumin binding of insulins acylated with fatty acids; characterization of the ligand-protein interaction and correlation between binding affinity and timing of the insulin effect in vivo, Biochem J, 312:725-731.

Kurtzhals et al., 1997, Effect of fatty acids and selected drugs on the albumin binding of a long-acting, acylated insulin analogue, J Pharma Sci, 86:1365-1368.

Labro et al., 1986. A proton nuclear magnetic resonance study of human serum albumin in the neutral pH region. Biochim Biophys Acta 873(2):267-278.

Laftah et al., May 15, 2004, Effect of hepcidin on intestinal iron absorption in mice, Blood, 103(10):3940-3944.

Larsen et al., 2004, Use of the Gottingen minipig as a model of diabetes, with special focus on type 1 diabetes research,, ILAR Journal, 45(3):303-313.

Lawn et al., 1981, The sequence of human serum albumin cDNA and its expression in *E. coli*, Nucl Acids Res. 9(22):6103-6114.

Lee et al., 2005, Evaluation of transferrin-polyethylenimine conjugate for targeted gene delivery. Arch Pharm Res. 28(6):722-729.

Leger et al., 2004, Identification of CJC-1131-albumin bioconjugate as a stable and bioactive GLP-1(7-36) analog, Bioorg Med Chem Lttrs, 14(17):4395-4398.

Leger et al., 2003, Synthesis and in vitro analysis of atrial natriuretic peptide-albumin conjugates, Bioorganic Medical Chem Lttrs, 13:3571-3575.

Li et al., 2001, Bipartite regulation of different components of the MHC class 1 antigen-processing machinery during dendritic cell maturation, Intl Immunol, 13(12):1515-1523.

Li et al., 2008, Germline competent embryonic stem cells derived from rat blastocysts, Cell, 135:1299-1310.

Lim et al., 2004, Transferrin-oligomers as potential carriers in anticancer drug delivery. Pharm Res. 21(11):1985-1992.

Lindahl et al., 2000, Identification of related proteins on family, superfamily and fold level. J Mol Biol. 295(3):613-615.

Liu et al., 2009, A high-yield and scaleable adenovirus vector production process based on high density perfusion culture of HEK 293 cells as suspended aggregates, J Bioscience Bioeng., 107(5):524-529.

Lode et al., Jul. 15, 1998, Targeted Therapy with a Novel Enediyene Antibiotic Calicheamicin ΘI1 Effectively Suppresses Growth and Dissemination of Liver Metastases in a Syngeneic Model of Murine Neuroblastoma, Cancer Research, 58:2925-2928.

Lowman et al., 1991, Selecting high-affinity binding proteins by monovalent phage display. Biochemistry 30(45):10832-10838.

Lubgan et al., 2002, A Transferrin conjugate of adriamycin-synthesis and potential chemotherapeutic efficacy. Cell Mol Biol Lett. 7(Suppl):98.

Luckow et al., 1993, Efficient Generation of Infectious Recombinant Baculoviruses by Site-Specific Transposon-Mediated Insertion of Foreign Genes into a Baculovirus Genome Propagated in *Escherichia coli*, J. Virol. 67(8):4566-4579.

Madison et al., 1994, Genetic variants of human serum albumin in Italy, Proc Nat Acad Sci. USA, 91:6476-6480.

Mahmood, 2004, Chapter 7: Principles, issues and applications of interspecies scaling, in New Drug Development, Sahajwalla ed., Marcel Dekker, Inc., New York, pp. 137-163.

Martin et al., 1982, Irreversible coupling of immunoglobulin fragments to preformed vesicles. An improved method for liposome targeting. J Biol Chem. 257(1):286-288.

Martin et al., 2001. Crystal structure at 2.8 Å of an FcRn/heterodimeric Fc complex: Mechanism of pH-dependent binding. Mol Cell 7(4):867-877.

McClenaghan et al., Aug. 1996, Characterization of a novel glucose-responsive insulin-secreting cell line, BRIN-BD11, produced by electrofusion, Diabetes, 45:1132-1140.

McCoy et al., 2007. Phaser crystallographic software. J Applied Crystallogr. 40:658-674.

McGraw et al., 1987, Functional expression of the human transferrin receptor cDNA in Chinese hamster ovary cells deficient in endogenous transferrin receptor. J Cell Biol. 105(1):207-214.

McGregor, 2008, Discovering and improving novel peptide therapeutics, Curr Opin Pharmacol, 8(5):616-619.

McGuffin et al., 2003, Improvement of the GenTHREADER method for genomic fold recognition. Bioinformatics 19(7):874-881.

Mezo et al., 2010, X-ray crystal structures of monomeric and dimeric peptide inhibitors in complex with the human neonatal Fc receptor, FcRn, J Biol Chem, 285(36):27694-27701.

Miguel et al., 2003, Cooperative enhancement of insulinotropic action of GLP-1 by acetylcholine uncovers paradoxical inhibitory effect of beta cell muscarinic receptor activation on adenylate cyclase activity Biochem Pharm., 65:283-292.

Minchiotti et al., 1987, Structure characterization of two genetic variants of human serum albumin, Biochim Biophys Acta, 916(3):411-418.

Minchiotti et al., 1990, The molecular defect of albumin Castel di Sangro: 536 Lys -→ Glu, Biochem Bioph Acta, 1039:204-208.

Minchiotti et al., 2001, A nucleotide insertion and frameshift cause albumin Kenitra, an extended and O-glycosylated mutant of human serum albumin with two additional disulfide bridges, Eur J Biochem., 268:344-352.

Minchiotti et al., 2008, Mutations and polymorphisms of the gene of the major human blood protein, Serum albumin, Human Mutation 29(8):1007-1016.

Minghetti et al., 1986, Molecular structure of the human albumin gene is revealed by nucleotide sequence within q11-22 of chromosome 4*, J. Bio Chem. 261(15):6747-6757.

Mishra et al., 2006, Targeted brain delivery of AZT via transferrin anchored pegylated albumin nanoparticles. J Drug Targeting 14(1):45-53.

Montoyo et al., 2009, Conditional deletion of the MHC class I-related receptor FcRn reveals the sites of IgG homeostasis in mice, Proc Natl Acad Sci USA, 106(8):2788-2793.

Morrissey et al., Feb. 1, 1993, Quantitation of activated factor VII levels in plasma using a tissue factor mutant selectively deficient in promoting factor VII activation, Blood, 81(3):734-744.

Müller et al., 2007, Improved pharmacokinetics of recombinant bispecific antibody molecules by fusion to human serum albumin, J Bio Chem., 282(17):12650-12660.

Munoz et al., 2009, Constraints to progress in embryonic stem cells from domestic species, Stem Cell Rev and Rep, 5:6-9.

Murshudov et al., 1997. Refinement of macromolecular structures by the maximum-likelihood method. Acta Crystallogr D Biol Crystallogr. 53(Pt 3):240-255.

Nauck et al., 1993, Normalization of fasting hyperglycemia by exogenous glucagon-like peptide 1 (7-36 amide) in type 2 (non-insulin-dependent) diabetic patients, Diabetologia 36:741-744.

(56) References Cited

OTHER PUBLICATIONS

Nauck et al., 1993, Preserved incretin activity of glucagon-like peptide 1 [7-36 amide] but not of synthetic human gastric inhibitory polypeptide in patients with type-2 diabetes mellitus. Clin Invest., 91:301-307.
Needleman et al., 1970, A general method applicable to the search for similarities in the amino acid sequence of two proteins. J Mol Biol., 48(3):443-453.
Ner et al., 1988, A simple and efficient procedure for generating random point mutations and for codon replacements using mixed oligodeoxynucleotides. DNA 7(2):127-134.
Ness et al., 1999, DNA shuffling of subgenomic sequences of subtilisin. Nature Biotechnol. 17(9):893-896.
Neumann et al., 2010, Native albumin for targeted drug delivery, Expert Opin. Drug Deliv., 7(8):1-11.
New Century Pharmaceuticals Inc., 2005 Catalog, Recombinant Serum Albumin: Other Proteins & Antibodies, pp. 1-36.
Nobs et al., 2004, Current methods for attaching targeting ligands to liposomes and nanoparticles. J Pharma Sci. 93(8):1980-1992.
Ober et al., 2001, Differences in promiscuity for antibody—FcRn interactions across species: implications for therapeutic antibodies, Int Immunol 13(12):1551-1559.
Ober et al., 2004, Exocytosis of IgG as mediated by the receptor, FcRn: an analysis at the single-molecule level, PNAS USA, 101(30):11076-11081.
Ober et al., 2004, Visualizing the site and dynamics of IgG salvage by the MHC class I-related receptor, FcRn, J Immunol, 172(4):2021-2029.
Oganesyan et al., 2014, Structural insights into neonatal Fc receptor-based recycling mechanisms, J Biol Chem 289(11):7812-24.
O'Hara et al., 1987, Nucleotide sequence of the gene coding for human factor VII, a vitamin K-dependent protein participating in blood coagulation, PNAS USA, 84:5158-5162.
O'Keefe et al., 1985, Characterization of a transferrin-diphtheria toxin conjugate. J Biol Chem. 260(2):932-937.
Olafsen et al., 2006, Tunable pharmacokinetics; modifying the in vivo half-life of antibodies by directed mutagenesis of the Fc fragment, Nature Protocol, 1(4):2048-2060.
O'Neill et al., 2008, Scale-up of Agrobacterium-mediated transient protein expression in bioreactor-grown Nicotiana glutinosa plant cell suspension culture, Biotechnol Prog., 24:372-376.
Öner et al., 1993, Preparation of small gelatin and albumin microparticles by a carbon dioxide atomization. Pharm Res., 10(9):1385-1388.
Osborn et al., 2002, Pharmacokinetic and pharmacodynamic studies of a human serum albumin-interferon-α fusion protein in cynomolgus monkeys, J Pharmacol Exp Ther, 303(2):540-548.
Otagiri et al., Apr. 2009, Pharmaceutically Important Pre- and Postranslational Modifications on Human Serum Albumin, Biol Pharm Bull., 32(4):527-534.
Pandjaitan et al., 2000, *Escherichia coli* expression and purification of recombinant dog albumin, a cross-reactive animal allergen. J Allergy Clin Immunol. 105(2 Pt):279-285.
Payne et al., 2008, Modulation of chaperone gene expression in mutagenized *Saccharomyces cerevisiae* strains developed for recombinant human albumin production results in increased production of multiple heterologous proteins. Appl Environ Microbiol. 74(24):7759-7766.
Peach et al., 1991, Structural characterization of glycoprotein variant of human serum albumin: albumin Casebrook (494 Asp -→ Asn), Biochim Biophys Acta, 1097:49-54.
Peters, 1985, Serum Albumin, Advances in Protein Chemistry, 37:161-245.
Peters [Ed], 1996, All about Albumin: Biochemistry, Genetics and Medical Applications, Academic Press, Cooperstown, NY, Chapter 2: pp. 9-23.
Peters [Ed], 1996, All about Albumin: Biochemistry, Genetics and Medical Applications, Academic Press, Cooperstown, NY, pp. 10, 170-181, 245-250 in 37 pages.

Petitpas et al., 2001, Crystal Structure Analysis of Warfarin Binding to Human Serum Albumin—Anatomy of Drug Site I. J Biol Chem 276(25):22804-22809.
Petitpas et al., 2001, Crystal structures of human serum albumin complexed with monounsaturated and polyunsaturated fatty acids. J Mol Biol. 314(5):955-960.
Petitpas et al., 2003. Structural basis of albumin-thyroxine interactions and familial dysalbuminemic hyperthyroxinemia. PNAS U.S.A. 100(11):6440-6445 (2003).
Petkova et al., 2006. Enhanced half-life of genetically engineered human IgG1 antibodies in a humanized FcRn mouse model: potential application in humorally mediated autoimmune disease. Int immunol. 18(12):1759-1769.
Piedrahita et al., 2011, Perspectives on transgenic livestock in agriculture and biomedicine: an update, Repro Fertility Develop., 23:56-63.
Pierce, Crosslinking Reagents Technical Handbook, Thermo Fisher Scientific, Rockford, IL, USA; downloaded Feb. 9, 2009 <https://tools.lifetechnologies.com/content/sfs/brochures/1602163-Crosslinking-Reagents>, 48 pp.
Pittman et al., 1993, Biochemical, immunological, and in vivo functional characterization of B-domain-deleted factor VIII, Blood, 81:2925-2935.
Prabhat et al., 2007, Elucidation of intracellular recycling pathways leading to exocytosis of the Fc receptor, FcRn, by using multifocal plane microscopy, Proc Natl Acad Sci USA, 104(14):5889-5894.
Presley et al., 1993, The End2 mutation in CHO cells slows the exit of Transferrin receptors from the recycling compartment but bulk membrane recycling is unaffected. J Cell Biol. 122(6):1231-1241.
Rakestraw et al., 2006. A flow cytometric assay for screening improved heterologous protein secretion in yeast. Biotechnol Prog. 22(4):1200-1208.
Rakestraw et al., 2009, Directed evolution of a secretory leader for the improved expression of heterologous proteins and full-length antibodies in S. cerevisiae, Biotech Bioengin. 103(6):1192-1201.
Rao et al, 2003, Interleukin-2 mutants with enhanced alpha-receptor subunit binding affinity, Protein Engin., 16(12):1081-1087.
Rao et al., 2005, High-affinity CD25-binding IL-2 mutants potently stimulate persistent T cell growth, Biochemistry 44:10696-10701.
Reidhaar-Olson et al., 1988, Combinatorial cassette mutagenesis as a probe of the informational content of protein sequences. Science 241(4861):53-57.
Rice et al., 2000, EMBOSS: The European Molecular Biology Open Software Suite, Trends in Genetics, 16(6):276-277.
Riminucci et al., Sep. 2003, FGF-23 in fibrous dysplasia of bone and its relationship to renal phosphate wasting, J Clin Invest, 112(5):683-92.
Rinderknecht et al., Jun. 10, 1984, Natural Human Interferon-gamma. Complete amino acid sequence and determination of sites of glycosylation, J Biol Chem., 259(11):6790-6797.
Rodewald et al.,1984, Receptor-mediated transport of IgG. J Cell Biol. 99:159s-164s.
Romanos et al., 1992, Foreign gene expression in yeast: a review. Yeast 8: 423-488.
Roopenian et al., 2003, The MHC class I-like IgG receptor controls perinatal IgG transport, IgG homeostasis, and fate of IgG-Fc-coupled drugs, J Immunol, 170(7):3528-3533.
Roopenian et al., 2007, FcRn: the neonatal Fc receptor comes of age, Nat Rev Immunol 7:715-725.
Roopenian et al., 2010, Human FcRn transgenic mice for pharmacokinetic evaluation of therapeutic antibodies, Methods Mol Biol, 602:93-104.
Sabater-Lleal et al., 2006, Human F7 sequence is split into three deep clades that are related to FVII plasma levels, Hum Genet 118:741-751.
Sand et al, Dec. 12, 2014, Interaction with both domain I and III of albumin is required for optimal pH-dependent binding to the neonatal Fc receptor (FcRn)*, J Biol Chem 289(50):34583-35894.
Sandhu et al., 2008. GASCO: Genetic Algorithm Simulation for Codon Optimization. In Silico Biol. 8(2):187-192.
Sayle et al. Sep. 1995, RASMOL: biomolecular graphics for all, TIBS 20, 374-377.

(56) References Cited

OTHER PUBLICATIONS

Scherer et al., 1979, Replacement of chromosome segments with altered DNA sequences constructed in vitro. PNAS U.S.A. 76(10):4951-4955.
Schmidt et al., 2013, Crystal Structure of an HAS/FcRn Complex Reveals Recycling by CompetitiveMimicry of HSA Ligands at a pH-Dependent Hydrophobic Interface, Structure 21:1966-1978 and supplemental material.
Schulte, 2008, Use of albumin fusion technology to prolong the half-life of recombinant factor Vlla, Thromb Res. 122 Suppl. 4:S14-19.
Several (definition), dictionary.com, accessed on Oct. 30, 2015, 4 pp.
Sheffield et al., 2000, Modulation of clearance of recombinant serum albumin by either glycosylation or truncation, Thromb Res., 99(6):613-621.
Shimada et al., 2004, FGF-23 Is a Potent Regulator of Vitamin D Metabolism and Phosphate Homeostasis, J. Clin. Invest, 19(3):429-435.
Shindyalov et al., 1998, Protein structure alignment by incremental combinatorial extension (CE) of the optimal path. Protein Eng. 11(9):739-747.
Sijmons et al., 1990, Production of correctly processed human serum albumin in transgenic plants, Biotechnology (NY), 8(3):217-221.
Silveira et al., 1994, Activation of Coagulation Factor VII During Alimentary Lipemia, Arterioscler Thromb Vsc Biol., 14:60-69.
Simard et al., 2005, Locating high-affinity fatty acid-binding sites on albumin by x-ray crystallography and NMR spectroscopy, PNAS USA, 102(50):17958-17963.
Simard et al., 2006, Location of High and Low Affinity Fatty Acid Binding Sites on Human Serum Albumin Revealed by NMR Drug-competition Analysis, J Mol Biol., 361(2):336-351.
Sleep et al., 1990, The secretion of human serum albumin from the yeast *Saccharomyces cerevisiae* using five different leader sequences, Biotech.8:42-46.
Sleep et al., 1991, *Saccharomyces cerevisiae* strains that overexpress heterologous proteins, Biotechnology (NY) 9(2):183-187.
Sleep et al., 2001, Yeast 2 μ m plasmid copy number is elevated by a mutation in the nuclear gene UBC4, Yeast, 18(5):403-421.
Sleep, 2012, Produce Proteins with Tailored Circulatory Half Life to Meet Patient's Specific Medical Needs, Keynote Address, Drug Delivery Partnerships. Las Vegas, NV. Jan. 25-27, 2012 in 29 pages.
Sleep et al., 2013, Albumin as a versatile platform for drug half-life extension, Biochimica et Biophysica Acta (BBA)—General subjects 1830(12): 5526-5534.
Smith et al., Jun. 2015 (online), A platform for efficient, thiol-stable conjugation to albumin's native single accessible cysteine. Org Biomol Chem. 13(29):7946-7949.
Sogami et al., 1968. Isomerization reactions of charcoal-defatted bovine plasma albumin. The N-F transition and acid expansion. Biochemistry 7(6): 2172-2182.
Sogami et al., 1969. The microheterogeneity of plasma albumins. V. Permutations in disulfide pairings as a probable source of microheterogeneity in bovine albumin. Biochemistry 8(1):49-58.
Sørensen et al., 2004, Whole blood clot formation phenotypes in hemophilia A and rare coagulation disorders. Patterns of response to recombinant factor Vlla, J Thromb Haemo. 2:102-110.
Spiegelberg et al., 1968, Catabolismof human γG-immunoglobulins of different heavy chain subclasses. I. Catabolismof γG-myeloma proteins in man. J Clin Invest. 47(10):2323-2330.
Spiekermann et al., 2002. Receptor-mediated Immunoglobulin G Transport Across Mucosal Barriers in Adult Life. J Exp Med. 196(3):303-10, and correction.
Stapleton et al., 2011. Competition for FcRn-mediated transport gives rise to short half-life of human IgG3 and offers therapeutic potential. Nature Comm. 2:599; 9 pages.
Stehle et al., 1997, Plasma protein (albumin) catabolismby the tumor itself—implications for tumor metabolism and the genesis of cachexia, Crit Rev Oncol Hematol, 26(2):77-100.

Stewart et al., 2003, Interdomain zinc site on human albumin, PNAS USA, 100(7):3701-3706.
Storici et al., 2001, In vivo site-directed mutagenesis using oligonucleotides. Nat Biotechnol. 19(8):773-776.
Sugio et al., Jun. 1999, Crystal structure of human serum albumin at 2.5 Å resolution, Protein Eng. 12(6):439-446.
Sundaram et al, Aug. 21, 1998, Chimeric constructs between human and rat equilibrative nucleoside transporters (hENT1 and rENT1) reveal hENT1 structural domains interacting with coronary vasoactive drugs, J. Bio Chemistry, 273(34):21519-21525.
Suzuki et al., 2010, Importance of Neonatal FcR in Regulating the Serum Half-Life of TherapeuticProteins Containing the Fc Domain of Human IgG1: A Comparative Study of the Affinity of Monoclonal Antibodies and Fc-Fusion Proteins to Human Neonatal FcR, J Immunol. 184:1968-1976.
Syed et al., 1997, Potent antithrombin activity and delayed clearance from the circulation characterize recombinant hirudin genetically fused to albumin, Blood 89(9):3243-3252.
Sykes et al., 1994, Interleukin-2 inhibits graft-versus-host disease-promoting activity of CD4+ cells while preserving CD4- and CD8-mediated graft-versus-Leukemia effects, Blood, 83(9):2560-2569.
Takahashi et al., 1987, Amino acid substitutions in genetic variants of human serum albumin and in sequences inferred from molecular cloning, PNAS USA 84:4413-4417.
Tesar et al., 2006. Ligand valency affects transcytosis, recycling and intracellular trafficking mediated by the neonatal Fc receptor. Traffic. 7(9):1127-1142.
Thibaudeau et al., 2005, Synthesis and evaluation of insulin—human serum albumin conjugates, Bioconjug Chem., 16(4):1000-1008.
Thim et al., 1988, Amino acid sequence and posttranslational modifications of human factor Vlla from plasma and transfected baby hamster kidney cells, Biochemistry, 27:7785-7793.
Thompson et al., 1994, Clustal W: Improving the sensitivity of progressive multiple sequence alignment through sequence weighting, position-specific gap penalties and weight matrix choice. Nucleic Acids Res. 22(22):4673-4680.
Tian et al., 2004, Accurate multiplex gene synthesis from programmable DNA microchips. Nature 432(7020):1050-1054.
Toole et al., 1984, Molecular cloning of a cDNA encoding human antihaemophilic factor. Nature, 312:342-347.
Tsakiridis et al., 1995, Multiple roles of phosphatidylinositol 3-kinase in regulation of glucose transport, amino acid transport, and glucose transporters in L6 skeletal muscle cells, Endocrinol. 136(10):4315-4322.
Ueda et al., 2009, Chemoenzymatic Synthesis of Glycosylated Glucagon-like Peptide 1: Effect of Glycosylation on Proteolytic Resistance and in Vivo Blood Glucose-Lowering Activity, JACS Articles, 131:6237-6245.
UniProt Database Accession No. F7HCHO, Jul. 27, 2011, 2 pp.
UniProt Database Accession No. A6NBZ8 (A6NBZ8_HUMAN), Version 24, modified Mar. 8, 2011, accessed at http://www.uniprot.org/uniprot/A6NBZ8 on Mar. 23, 2011.
Urso et al., 1999, Differences in signaling properties of the cytoplasmic domains of the insulin receptor and insulin-like growth factor receptor in 3T3-L1 adipocytes, J Biol Chem, 274(43):30864-30873.
Valkonen et al., 2003, Effects of inactivation and constitutive expression of the unfolded-protein response pathway on protein production in the yeast *Saccharomyces cerevisiae*. Applied Environ Microbiol., 69(4):2065-2072.
Van Deijk et al., 1983, Evaluation of a Coagulation Assay Determining the Activity State of Factor VII in Plasma, Haemostasis 13:192-197.
Van der Spoel et al., 2005, GROMACS: Fast, flexible, and free, J Comp Chem, 22:1701-1718.
Van Dongen et al., 2007, Immuno-PET: A Navigator in Monoclonal Antibody Development and Applications, The Oncologist Cancer Imaging 12:1379-1389.
Vestberg et al., 1992, High-affinity binding of warfarin, salicylate and diazepam to natural mutants of human serum albumin modified in the c-terminal end, Biochem Pharmacol, 44(8):1515-1521.

(56) References Cited

OTHER PUBLICATIONS

Viuff et al., 2016, Generation of a double transgenic humanized neonatal Fc receptor (FcRn)/albumin mouse to study the pharmacokinetics of albumin-linked drugs, J Controlled Release, 223:22-30.
Wain-Hobson et al. 1981, Preferential codon usage in genes, Gene 13:355-364.
Wang et al., 1997, Regulation of glucose transporters and hexose uptake in 3T3-L1 adipocytes: glucagon-like peptide-1 and insulin interactions, J Mol Endocrinol, 19:241-248.
Wang et al., 2008, Overexpression of fibroblast growth factor 23 suppresses osteoblast differentiation and matrix mineralization in vitro. J Bone Miner Res. 23(6):939-948.
Wang et al. 2011. Monoclonal antibodies with identical Fc sequences can bind to FcRn differentially with pharmacokinetic consequences. Drug Metabol Disposition. 39:1469-1477.
Wani et al., 2006, Familial hypercatabolic hypoproteinemia caused by deficiency of the neonatal Fc receptor, FcRn, due to a mutant β2-microglobulin gene, Proc Natl Acad Sci USA 103(13):5084-5089 and Correction/Retraction in 2 pages.
Ward et al., 2009, Multitasking by exploitation of intracellular transport functions: the many faces of FcRn, Adv Immunol 103:77-115.
Watkins et al., 1993, A donor splice mutation and a single-base deletion produce two carboxy-terminal variants of human serum albumin, PNAS USA, 88:5959-5963.
Watkins et al., 1993, cDNA and protein sequence of polymorphic macaque albumins that differ in bilirubin binding, PNAS USA, 90:2409-2413.
Weaver et al., 2003, Transferrin receptor ligand-targeted toxin conjugate (Tf-CRM107) for therapy of malignant gliomas. J Neurooncol. 65(1):3-13.
Wenning et al., 1998, Quantitative analysis of protein synthesis inhibition and recovery in CRM107 immunotoxin-treated HeLa cells. Biotechnol Bioeng. 57(4):484-496.
Werle et al., 2006, Strategies to improve plasma half life time of peptide and protein drugs, Amino Acids, 30(4):351-367.
West et al., 2000, Crystal structure and immunoglobulin G binding properties of the human major histocompatibility complex-related Fc receptor, Biochemistry 39(32):9698-9708.
Widera et al., 2003, Transcytosis of GCSF-transferrin across rat alveolar epithelial cell monolayers. Pharm Res. 20(8):1231-1238.
Wildgoose et al., 1992, Measurement of basal levels of factor Vlla in hemophilia A and B patients, Blood, 80:25-28.
Wood et al., 1984, Expression of active human factor VIII from recombinant DNA clones, Nature 312:330-337.
Wu et al., 1987, Receptor-mediated in vitro gene transformation by a soluble DNA carrier system, J Biol Chem., 262(10):4429-4432.
Wu et al., Dec. 1989, Urate Oxidase: Primary Structure and Evolutionary Implications, PNAS USA, 86:9412-9416.
Wunder et al., 2003, Albumin-based drug delivery as novel therapeutic approach for rheumatoid arthritis, J Immunol. 170:4793-4801.
Xia et al., 2000, Hypoglycemic effect of insulin-transferrin conjugate in streptozotocin-induced diabetic rats. J Pharmacol Exp Ther. 295(2):594-600.
Yang et al., 2012, Genetic modification of domestic animals for agriculture and biomedical applications, in Ghista [Ed], Biomedical Science, Engineering and Technology, Chapter 29, pp. 697-726.
Yazdi et al., 1994, Quantitative Analysis of Protein Synthesis Inhibition by Transferrin-Toxin Conjugates. Cancer Res. 54(24):6387-6394.
Yeung et al., 2009. Engineering human IgG1 affinity to human neonatal Fc receptor: Impact of affinity improvement on pharmacokinetics in primates. J immunol. 182:7663-7671.
Yin et al., 2007, Select what you need: a comparative evaluation of the advantages and limitations of frequently used expression systems for foreign genes, J Biotech., 127:335-347.
Yoshida et al., 2004, Human neonatal Fc receptor mediates transport of IgG into luminal secretions for delivery of antigens to mucosal dendritic cells Immunity. 20(6):769-83.
Zalevsky et al., Feb. 2010, Enhanced antibody half-life improves in vivo activity, Nature Biotechnology, 28(2):157-159.
Zheng et al., 2012, Minipig as a potential translatable model for monoclonal antibody pharmacokinetics after intravenous and subcutaneous administration, mAbs, 4(2):243-255.
Zhu et al., 2005, Calnexin and ERp57 facilitate the assembly of the neonatal Fc receptor for IgG with beta 2-microglobulin in the endoplasmic reticulum. J Immunol., 175(2):967-76.
Zhu et al., 2001, MHC class I-related neonatal Fc receptor for IgG is functionally expressed in monocytes, intestinal macrophages, and dendritic cells, J Immunol., 166(5):3266-76.
International Search Report and Written Opinion of International Application No. PCT/US2012/065733, date of mailing May 21, 2013.
International Search Report of PCT/US2014/036508 mailed Oct. 9, 2014.
Written Opinion of the International Searching Authority for PCT/US2014/036508 mailed Oct. 9, 2014.
International Search Report, International Patent Application No. PCT/IB2014/003002, mailed Aug. 12, 2015.
International Search Report and Written Opinion dated Oct. 24, 2016 for corresponding PCT Application No. PCT/EP2016/069748, filed Aug. 19, 2016.

* cited by examiner

Figure 1

| | | |
|---|---|---|
| Hu_1_2_3 | 1 | DAHKSEVAHRFKDLGEENFKALVLIAFAQYLQQCPFEDHVKLVNEVTEFAKTCVADESAE |
| Hu_1_3 | 1 | DAHKSEVAHRFKDLGEENFKALVLIAFAQYLQQCPFEDHVKLVNEVTEFAKTCVADESAE |
| Hu_2_3 | 1 | ------------------------------------------------------------ |
| Mac_mul | 1 | DTHKSEVAHRFKDLGEEHFKGLVLVAFSQYLQQCPFEEHVKLVNEVTEFAKTCVADESAE |
| Rat | 1 | EAHKSEIAHRFKDLGEQHFKGLVLIAFSQYLQKCPYEEHIKLVNEVTDFAKTCVADENAE |
| Mouse | 1 | EAHKSEIAHRFNDLGEQHFKGLVLIAFSQYLQKCSYDEHAKLVQEVTDFAKTCVADESAA |

| | | |
|---|---|---|
| Hu_1_2_3 | 61 | NCDKSLHTLFGDKLCTVATLRETYGEMADCCAKQEPERNECFLQHKDDNPNLPRLVRPEV |
| Hu_1_3 | 61 | NCDKSLHTLFGDKLCTVATLRETYGEMADCCAKQEPERNECFLQHKDDNPNLPRLVRPEV |
| Hu_2_3 | 1 | ------------------------------------------------------------ |
| Mac_mul | 61 | NCDKSLHTLFGDKLCTVATLRETYGEMADCCAKQEPERNECFLQHKDDNPNLPPLVRPEV |
| Rat | 61 | NCDKSIHTLFGDKLCAIPKLRENYGELADCCAKQEPERNECFLQHKDDNPNLPPFQRPEA |
| Mouse | 61 | NCDKSLHTLFGDKLCAIPNLRENYGELADCCTKQEPERNECFLQHKDDNPSLPPFERPEA |

| | | |
|---|---|---|
| Hu_1_2_3 | 121 | DVMCTAFHDNEETFLKKYLYEIARRHPYFYAPELLFFAKRYKAAFTECCQAADKAACLLP |
| Hu_1_3 | 121 | DVMCTAFHDNEETFLKKYLYEIARRHPYFYAPELLFFAKRYKAAFTECCQAADKAACLLP |
| Hu_2_3 | 1 | ------------------------------------------------------------ |
| Mac_mul | 121 | DVMCTAFHDNEATFLKKYLYEVARRHPYFYAPELLFFAARYKAAFAECCQAADKAACLLP |
| Rat | 121 | EAMCTSIQNPTIFLGHYLHEVARRHPYFYAPELLYYAEKYNEVLTQCCTESDKAACLTP |
| Mouse | 121 | EAMCTSFKNPTIFVGHYLHEVARRHPYFYAPELLYYAEQYNEILTQCCAEADKESCLTP |

| | | |
|---|---|---|
| Hu_1_2_3 | 181 | KLDELRDEGKASSAKQRLKCASLQKFGERAFKAWAVARLSQRFPKAEFAEVSKLVTDLTK |
| Hu_1_3 | 181 | KLDELRDEGKASSA--------------------------------------------- |
| Hu_2_3 | 1 | --DELRDEGKASSAKQRLKCASLQKFGERAFKAWAVARLSQRFPKAEFAEVSKLVTDLTK |
| Mac_mul | 181 | KLDELRDEGKASSAKQRLKCASLQKFGERAFKAWAVARLSQRFPKAEFAEVSKLVTDLTK |
| Rat | 181 | KLDAVKEKALVAAVRQRMKCSSMQRFGERAFKAWAVARMSQRFPNAEFAEISKLATDLTK |
| Mouse | 181 | KLDGLKEKALVSSVRQRMKCSSMQKFGERAFKAWAVARLSQTFPNAEFAEISKLATDLTK |

| | | |
|---|---|---|
| Hu_1_2_3 | 241 | VHTECCHGDLLECADDRADLAKYICENQDSISSKLKECCEKPLLEKSHCIAEVENDEMPA |
| Hu_1_3 | 195 | ------------------------------------------------------------ |
| Hu_2_3 | 59 | VHTECCHGDLLECADDRADLAKYICENQDSISSKLKECCEKPLLEKSHCIAEVENDEMPA |
| Mac_mul | 241 | VHTECCHGDLLECADDRADLAKYMCENQDSISSKLKECCDKPLLEKSHCLAEVENDEMPA |
| Rat | 241 | VNKECCHGDLLECADDRAELAKYMCENQATISSKLQACCDKPVLQKSQCLAEIEHDNIPA |
| Mouse | 241 | VNKECCHGDLLECADDRAELAKYMCENQATISSKLQTCCDKPLLKKAHCLSEVEHDTMPA |

| | | |
|---|---|---|
| Hu_1_2_3 | 301 | DLPSLAADFVESKDVCKNYAEAKDVFLGMFLYEYARRHPDYSVVLLLRLAKTYETTLEKC |
| Hu_1_3 | 195 | ------------------------------------------------------------ |
| Hu_2_3 | 119 | DLPSLAADFVESKDVCKNYAEAKDVFLGMFLYEYARRHPDYSVVLLLRLAKAYETTLEKC |
| Mac_mul | 301 | DLPSLAADYVEDKEVCKNYAEAKDVFLGMFLYEYARRHPDYSVVLLLRLAKAYEATLEKC |
| Rat | 301 | DLPSLAADFVEDKEVCKNYAEAKDVFLGTFLYEYSRRHPDYSVSLLLRLAKKYEATLEKC |
| Mouse | 301 | DLPALAADFVEDQEVCKNYAEAKDVFLGTFLYEYSRRHPDYSVSLLLRLAKKYEATLEKC |

| | | |
|---|---|---|
| Hu_1_2_3 | 361 | CAAADPHECYAKVFDEFKPLVEEPQNLIKQNCELFEQLGEYKFQNALLVRYTKKVPQVST |
| Hu_1_3 | 195 | -------------------VEEPQNLIKQNCELFEQLGEYKFQNALLVRYTKKVPQVST |
| Hu_2_3 | 179 | CAAADPHECYAKVFDEFKPLVEEPQNLIKQNCELFEQLGEYKFQNALLVRYTKKVPQVST |
| Mac_mul | 361 | CAAADPHECYAKVFDEFQPLVEEPQNLVKQNCELFEQLGEYKFQNALLVRYTKKVPQVST |
| Rat | 361 | CAEDDPPACYGTVLAEFQPLVEEPKNLVKTNCELYEKLGEYGFQNAILVRYTQKAPQVST |
| Mouse | 361 | CAEANPPACYGTVLAEFQPLVEEPKNLVKTNCDLYEKLGEYGFQNAILVRYTQKAPQVST |

Figure 1 (continued)

```
Hu_1_2_3  421  PTLVEVSRNLGKVGSKCCKHPEAKRMPCAEDYLSVVLNQLCVLHEKTPVSDRVTKCCTES
Hu_1_3    235  PTLVEVSRNLGKVGSKCCKHPEAKRMPCAEDYLSVVLNQLCVLHEKTPVSDRVTKCCTES
Hu_2_3    239  PTLVEVSRNLGKVGSKCCKHPEAKRMPCAEDYLSVVLNQLCVLHEKTPVSDRVTKCCTES
Mac_mul   421  PTLVEVSRNLGKVGAKCCKLPEAKRMPCAEDYLSVVLNRLCVLHEKTPVSDRVTKCCTES
Rat       421  PTLVEAARNLGDVGQKCCTLPEAQRLPCVEDYLSAILNRLCVLHEKTPVSDRVTKCCSGS
Mouse     421  PTLVEAARNLGIVGTKCCTLPEDQRLPCVEDYLSAILNRVCLLHEKTPVSHHVTKCCSGS Hu_1_2_3  481  LVNRRPCFSALEVDETYVPKEFNAETFTFHADICTLSEKERQIKKQTALVELVKHKPKAT
Hu_1_3    295  LVNRRPCFSALEVDETYVPKEFNAETFTFHADICTLSEKERQIKKQTALVELVKHKPKAT
Hu_2_3    299  LVNRRPCFSALEVDETYVPKEFNAETFTFHADICTLSEKERQIKKQTALVELVKHKPKAT
Mac_mul   481  LVNRRPCFSALEIDEAYVPKAFNAETFTFHADVCTLSEKEQKKKQTALVELVKHKPKAT
Rat       481  LVERRPCFSALTVDETYVPKEEKAETFTFHSDICTLPDKEKQIKKQTALAELVKHKPKAT
Mouse     481  LVERRPCFSALTVDETYVPKEEKAETFTFHSDICTLPEKEKQIKKQTALAELVKHKPKAT
                                           ↑
                                          500

Hu_1_2_3  541  KEQLKAVMDDFAAFVEKCCKADDKETCFAEEGKKLVAASQAALGL
Hu_1_3    355  KEQLKAVMDDFAAFVEKCCKADDKETCFAEEGKKLVAASQAALGL
Hu_2_3    359  KEQLKAVMDDFAAFVEKCCKADDKETCFAEEGKKLVAASQAALGL
Mac_mul   541  KEQLKTVMDNFAAFVEKCCKADDKEACFAEEGPKFVAASQAALG-
Rat       541  EQQLKTVMGDFAQFVEKCCKAADKDNCFATEGPNLVARSKEAIG-
Mouse     541  AEQLKTVMDDFAQFLETCCKAADKDTCFSTEGPNLVTRCKDAIG-
                  ↑                        ↑
                 550                      573
```

Figure 2

```
Human       1  ------------------------------------DA-HKSEMAHRFKDLGEENFK
Mouse       1  ------------------------------------DA-HKSEIAHRFNDLGEQHFKG
Sheep       1  ------------------------------------DT-HKSEIAHRFNDLGEENFQG
Rabbit      1  ------------------------------------DA-HKSEIAHRFNDMGEEHFIG
Goat        1  ------------------------------------DT-HKSEIAHRFNDLGEENFQG
Chimp       1  MNESSCCSTSLPAFGVEVLDSGHSSSSAYSRGV--FRRDA-HKSEMAHRFKDLGEENFK
Macaque     1  -----------MKWVTFISLLFLFSSAYSRGV--FRRDT-HKSEMAHRFKDLGEEHFKG
Hamster     1  -----------MKWVTFLLLFMSDSAISRGL--FRRDA-HKSEIAHRFKDLGEQHFKG
Guinea_Pig  1  -----------MKWVTFISLLFLFSSVYSRGV--FRRLA-HKSEIAHRFNDLGEGHFKG
Rat         1  -----------MKWVTFLLLFISGSAISRGV--FRRLA-HKSEIAHRFKDLGEQHFKG
Cow         1  -----------MKWVTFISLLLLFSSAYSRGV--FRRDT-HKSEIAHRFKDLGEEHFKG
Horse       1  -----------MKWVTFVSLLFLFSSAYSRGV--LRRDT-HKSEIAHRFNDLGEKHFKG
Donkey      1  -----------MKWVTFISLLFLFSSAYFRGV--LRRDT-HKSEIAHRFNDLGEKHFKG
Dog         1  -----------MKWVTFISLFFLFSSAYSRGI--VRRLA-YKSEIAHRINDLGEEHFIG
Chicken     1  -----------MKWVTLISFIFLFSSATSRNLQRFARDAEHKSEIAHRINDLKEETFK
Pig         1  -----------MKWVTFISLLFLFSSAYSRGV--FRRDT-YKSEIAHRFKDLGEQYFKG
                                                       ↑
                                                  (D1-Start)

Human       22  LVLIAFAQYLQQCPFEHVKLVNEVTEFAKTCVADESAENCDKSLHTLFGDKLCTVATLR
Mouse       22  LVLIAFSQYLQKCSYEHAKLVEEVTEFAKTCVADESAANCDKSLHTLFGDKLCAIPNLR
Sheep       22  LVLIAFSQYLQQCPFEHVKLVKEITEFAKTCVADESHAGCDKSLHTLFGDELCKVATLR
Rabbit      22  LVLITFSQYLQKCPEEHAKLVKEVTELAKACVADESAANCDKSLHDIFGDKICAIPSLR
Goat        22  LVLIAFSQYLQQCPFEHVKLVKEITEFAKTCVADESHAGCDKSLHTLFGDELCKVATLR
Chimp       58  LVLIAFAQYLQQCPFEEHVKLVNEVTEFAKTCVADESAENCDKSLHTLFGDKLCTVATLR
Macaque     46  LVLIAFSQYLQQCPFEEHVKLVNEVTEFAKTCVADESAENCDKSLHTLFGDKLCTVATLR
Hamster     46  LVLIAFSQLQKCPEEHVKLVNEVTEFAKTCVADESAENCDKSLHTLFGDKLCAIPTLR
Guinea_Pig  46  LVLITLSQHLQKSPFEEHVKLVNEVTIFAKACVADESAQNCGKAIATLFGDKVCAIPSLR
Rat         46  LVLIAFSQYLQKCPEEHKLVEVTFAKTCVADENAENCDKSIHTLFGDKLCAIPKLR
Cow         46  LVLIAFSQYLQQCPFEHVKLVNEITEFAKTCVADESHAGCEKSLHTLFGDELCKVAILR
Horse       46  LVLIAFSQYLQQCPFEHVKLVNEVTEFAKKCAADESAENCDKSLHTLFGDKLCTVATLR
Donkey      46  LVLMAFSQYLQQCPFEHVKLVNEVTEFAKKCAADESAENCDKSLHTLFGDKLCTVATLR
Dog         46  LVLIAFSQYLQQCPFEHVKLAKEVTEFAKACAAESANCDKSLHTLFGDKLCTVAILR
Chicken     49  VALITFAQYLQRCSEGLSKLVKDVVEIAQKCVANEDAPECSKPLPIILDELCQVEKLR
Pig         46  LVLIAFSQHLQQCPEEHVKLVREVTEFAKTCVADESAENCDKSIHTLFGDKLCAIPSLR Human       82   ETYGEMADCCAKQEPERNECFLHKDDNPNL-PRLVRPEVDVMCTAFHNEETFLKKYLY
Mouse       82   ENYGELADCCTKQEPERNECFLHHKDDNPSL-PPFERPEALAMCTSFKENPTTEVGHYLH
Sheep       82   ETYGEMADCCEKQEPERNECFLHKDDSPDL-PKLKPEPDTICAEFKADEKKEWGKYLY
Rabbit      82   LTYGLVADCCEKKEPERNECFLHHKDDKPDL-PPFARPEADVLCKAFHDEKAFFGHYLY
Goat        82   ETYGEMADCCEKQEPERNECFLKHKDDSPDL-PKLKPEPDTICAEFKADEKKDWGKYLY
Chimp       118  EKYGEMADCCAKQEPERNECFLHKDDNPNL-PRLVRPEVDVMCTAFHNEGTFIKKYLY
Macaque     106  ETYGEMADCCAKQEPERNECFLHKDDNPNL-PPLVRPEVDVMCTAFHNEATFLKKYLY
Hamster     106  DSYGEIADCCAKKEPERNECFLKHKDDHPNL-PPFVRPEALAMCTSFQLNAVTEGHYLH
Guinea_Pig  106  ETYGELADCCAKEDPERVECFLQHKDDNPNL-PPFERPEPIAICTAFLNNDRELGHYLY
Rat         106  ENYGELADCCAKQEPERNECFLHKDDNPNL-PPFQRPEAIAICTSFQLNPTSELGHYLH
Cow         106  ETYGEMADCCEKQEPERNECFLSHKDDSPDL-PKLKPPNTICDEFKADEKKEWGKYLY
Horse       106  ATYGELADCCEKQEPERNECFLTHKDDHPNL-PKLKPEPDAQCAAFQEDPKFLGKYLY
Donkey      106  ATYGELADCCEKQEPERNECFLTHKDDHPNL-PKLKPEPDAQCAAFQEDPKFLGKYLY
Dog         106  DKYGEMADCCEKQEPRNECFLAHKDDNPGF-PPLVAPEPDAICAAFQNEQLELGKYLY
Chicken     109  DSYGAMADCCSKALPERNECFLSFKVSIPDFVQEYQRPASDVLCQEFQENRVSELGHYLY
Pig         106  EHYGEIADCCEKEEPERNECFLQHKNDNPDI-PKLKPPVAICADFQEDEQKFWGKYLY
```

Figure 2 (continued)

```
Human       141 EVARRHPYFYAPELLYYAKEYKEAFTECCQAADKAACLEPKLDELREEGKASSAKQRLKC
Mouse       141 EVARRHPYFYAPELLYYAEQYNEFLTQCCAEADKESCLTPKLDSYAEKELVSSVEQRMKC
Sheep       140 EVARRHPYFYAPELLYYANKYNGVFQECCQAEDKGACLIPKIDALREKVLASSAFQRLEC
Rabbit      141 EVARRHPYFYAPELLYYAQKYKAITECCEAADKVACLTPKLDALEGKSLISAAQERLEC
Goat        140 EVARRHPYFYAPELLYYANKYNGVFQECCQAEDKGACLIPKIETMREKVLASSAFQRLEC
Chimp       177 EVARRHPYFYAPELLEEAERYKAAFTECCQAADKAACLEPKLDELREEGKASSAKQRLKC
Macaque     165 EVARRHPYFYAPELLEEAALYKAAFAECCQAADKAACLEPKLDELREEGKASSAKQRLKC
Hamster     165 EVARRHPYFYAPELLYYAEKYSAEMTECCGEADKAACITPKLDALKEKELASSVNQRLKC
Guinea_Pig  165 EVSRRHPYFYAPELLYYAEKYKNALTECCEAADKAACLTPKLDAEKEKALVSSAQQRLKC
Rat         165 EVARRHPYFYAPELLYYAEKYNEVLTQCCTESDKAACLTPKLDAVKEKELVAAVPQRMKC
Cow         164 EEARRHPYFYAPELLYYANKYNGVFQECCQAEDKGACLIPKIETMREKVLASSAFQRLEC
Horse       164 EVARRHPYFYEPELLEHAEEYKADFTECCPADDKLACLEPKLDALKEPILLSSAKERLKC
Donkey      164 EVARRHPYFYEPELLEHAEEYKADFTECCPADDKACLEPKLDALKEPILLSSAKERLKC
Dog         165 EEARRHPYFYAPELLYYAQQYKGVFAECCQAADKAACLGPKTEALREKVLLSSAKERFKC
Chicken     169 SVARRHPELYAPAELSEAVDEEHALQSCCKESDVGACLDTKEIVEREKAKGVSVKQQYFC
Pig         164 EEARRHPYFYAPELLYYAIIYKDVEEECCQAADKAACLEPKIEHLREKVLTSAAKQRLKC
                                                              ↑          ↑
                                                           (D2-Start) (D1-End)

Human       201 ASEQKFGERAFKAWAVARLSQEFPKAEFAEVSKEVTDLTKVHTECCHGDLLECADDRADL
Mouse       201 SSVQKFGERAFKAWAVARLSQTFPNADFAEEKEATDLTKVNKECCHGDLLECADDRAEL
Sheep       200 ASEQKFGERALKAWSVARLSQKFPKADFTEVEKEVTDLTKVHKECCHGDLLECADDRADL
Rabbit      201 ASEQKFGERAKAWAEVRLSQEFPKADFTDESKEVTDLTKVHKECCHGDLLECADDRADL
Goat        200 ASEQKFGERALKAWSVARLSQKFPKADFTEVEKEVTDLTKVHKECCHGDLLECADDRADL
Chimp       237 ASEQKFGERAFKAWAVARLSQEFPKAEFAEVSKEVTDLTKVHTECCHGDLLECADDRADL
Macaque     225 ASEQKFGERAFKAWAVARLSQKFPKAEFAEVSKEVTDLTKVHTECCHGDLLECADDRADL
Hamster     225 SSEQEFGQRAFKAWAVAREISQKFPKADFAEEEKEATDLTKEITEECCHGDLLECADDRAEL
Guinea_Pig  225 ASEQKFGERAFKAWSVARLSQKFPKAEFAEESTEVTSLTKVTKECCHGDLLECADDRQEL
Rat         225 SSEQEFGERAFKAWAVAREISQEFPNAEFAEEEKEATDETKEINKECCHGDLLECADDRAEL
Cow         224 ASEQKFGERALKAWSVARLSQKFPKAEFVEVEKEVTDLTKVHKECCHGDLLECADDRADL
Horse       224 SSFQNFGERAVKAWSVARLSQKFPKADFAEVSKEVTDLTKVHKECCHGDLLECADDRADL
Donkey      224 SSFQKFGERAFKAWSVARLSQKFPKADFAEVSKEVTDLTKVHKECCHGDLLECADDRADL
Dog         225 ASEQKFGERAFKAWSVARLSQEFPKADFAEESKEVTDLTKVHKECCHGDLLECADDRADL
Chicken     229 GIEKQFGERVFQARQEIYLSQKEPKAPFSEVSKFVHDSIGVHKECCEGDEECMDDMARE
Pig         224 ASEQKFGERAFKAWSEARLSQEFPKADFTEESKEVTDLAKVHKECCHGDLLECADDRADL Human       261 AKYICENQDSISSKLKECCEKPLLEKSHCIAEVENDEEPADLPSLAADFVESKEVCKNYA
Mouse       261 AKYMCENQAEISSKLQTCCDKPLLKKAHCESEVEEDTMPADLPAEAADFVEDQEVCKNYA
Sheep       260 AKYICEHQDAESSKLKECCDKPELEKSHCIAEVDKDAEPENLPPLTADFAEDKEVCKNYQ
Rabbit      261 AKYECEHQEEISSHLKECCDKPELEKAHCIYGLHNDETPAGLPAMAEEFVEDKEVCKNYE
Goat        260 AKYICEHQDEESSKLKECCDKPELEKSHCIAEEDKDAEPENLPPLTADFAEDKEVCKNYQ
Chimp       297 AKYICENQDSISSKLKECCEKPLLEKSHCEAEVENDEEPADLPSLAADFVESKEVCKNYA
Macaque     285 AKYMCENQDEISSKLKECCEKPLLEKSHCEAEVENDEEPADLPSLAADEVESKEVCKNYA
Hamster     285 AKYMCENQASISSKLQACCDKPMLKKSHCESEVNDEEPADLPSLAADFVEDKEVCKNYA
Guinea_Pig  285 AKYECEHQDSISSKLKECCVKPTLQKAHCILEEQRDEEPTELPDLAVDFVEDKEVCKNEA
Rat         285 AKYMCENQAEISSKLQACCDKPELQKSQCEAEEEDNEPADLPSEAADFVEDKEVCKNYA
Cow         284 AKYICENQDEISSKLKECCDKPELQKSHCEAEEEDAEPENLPPLTADFAEDKEVCKNYQ
Horse       284 AKYICEHQDSISGKLKACCDKPLLQKSHCIAEVKEDEEPSDLPALAADFAEDKEECKHYK
Donkey      284 TKYICEHQDSISGKLKACCDKPLLQKSHCIAEVKEDEEPSDLPALAADFAEDKEECKHYK
Dog         285 AKYECENQDSISEKLKECCDKPELEKSQCEAEVEEEPEDLPSLAADFVEDKEVCKNYQ
Chicken     289 MSNECSEQDVESGKEKECCEKPEVEESQCIMEAEFDEKPADLPSLVEKEEDKEVCKSEE
Pig         284 AKYICENQDEISEKLKECCDKPLLEKSHCIAEAKEDEEPADENPLEHDFVEDKEVCKNYK
```

Figure 2 (continued)

```
Human      321 EAKDVFLGMFLYEYARRHPDYSVVLLLRLAKTYETTLEKCCAAADPHECYAKVFDEFKPL
Mouse      321 EAKDVFLGTFLYEYSRRHPDYSVSLLLRLAKKYEATLEKCCAEANPPACYGTVLAEFQPL
Sheep      320 EAKDVFLGSFLYEYSRRHPLYAVSLLLRLAKEYEATLEDCCAKEDPHACYATVFDKLKHL
Rabbit     321 EAKDIFLGKFLYEYSRRHPDYSVLLLRLGKAYEATLKKCCATDDPHACYAKVLDEFRPL
Goat       320 EAKDVFLGSFLYEYSRRHPLYAVSLLLRLAKEYEATLEDCCAKEDPHACYATVFDKLKHL
Chimp      357 EAKDVFLGMFLYEYARRHPDYSVLLLRLAKTYETTLEKCCAAADPHECYAKVFDEFIPL
Macaque    345 EAKDVFLGMFLYEYARRHPDYSVMLLLRLAKAYEATLEKCCAAADPHECYAKVFDEFIPL
Hamster    345 EAKDVFLGTFLYEYARRHPDYSVALLLRLAKKYEATLEKCCAEADPSACYGKVLDEFCPL
Guinea_Pig 345 EAKDVFLGTFLYEYSRRHPLYSIGNLLRLAKGYEAKLEKCCAEADPHACYAKVFDELOPL
Rat        345 EAKDVFLGTFLYEYSVSLLLRLAKKYEATLEKCCAEGDPPACYGTVLAEFIPL
Cow        344 EAKDAFLGSFLYEYSRRHPLYAVSLLLRLAKEYEATLEECCAKDDPHACYSTVFDKLKHL
Horse      344 DAKDVFLGTFLYEYSRRHPDYSVSLLLRLAKTYEATLEKCCAEADPPACYRTVFDQFTPL
Donkey     344 DAKDVFLGTFLYEYSRRHPDYSVSLLLRMAKTYEATLEKCCAEADPPACYATVFDQFTPL
Dog        345 EAKDVFLGTFLYEYARRHPDYSVSLLLRLAKEYEATLEKCCATDDPPTCYAKVLDEFKPL
Chicken    349 AGHDAETAEIIYEYSRRHPETSTOLIDRIAKGYESLLEKCCKTDNPAECYANAQEQLIOH
Pig        344 EAKHVFLGTFLYEYSRRHPDYSVSLLLRIAKIYEATLEDCCAKEDPPACYATVFDKEFPL Human      381 VEEPQNLIKQNCELFEQLGEYKFQNALLVRYTKKVPQVSTPTLVEISRNLGKVGSKCCKH
Mouse      381 VEEPKNLVKTNCDLLEKLGEYGFQNAILVRYTQKAPQVSTPTLVEAARNLGRVGTKCCTL
Sheep      380 VIEPQNLIKKNCELFEKHGEYGFQNALIVRYTSKAPQVSTPTLVEISRSLGKVGTKCCAK
Rabbit     381 VEEPKNLVKQNCELLEQLGEYNFQNALLVRYTKKVPQVSTPTLVEISRSLGKVGSKCCKH
Goat       380 VIEPQNLIKKNCELFEKHGEYGFQNALIVRYTSKAPQVSTPTLVEISRSLGKVGTKCCAK
Chimp      417 VEEPQNLIKQNCELFEQLGEYKFQNALLVRYTKKVPQVSTPTLVEISRNLGKVGSKCCKH
Macaque    405 VEEPQNLVKQNCELFEQLGEYKFQNALLVRYTKKVPQVSTPTLVEISRNLGKVGAKCCKL
Hamster    405 VEEPKNLVKANCELFEKLGEYGFQNAIIVRYTQKAPQVSTPTLVEAARNLGKVGSKCCVL
Guinea_Pig 405 IEEPKKLVQQNCELFIKLGEYGFQNALAVRYTQKAPQVSTPTLVEYARKLGSVGTKCCSL
Rat        405 VEEPKNLVKTNCELIEKLGEYGFQNALVRYTQKAPQVSTPTLVEAARNLGIVGTKCCTL
Cow        404 VIEPQNLIKQNCIQFEKLGEYGFQNALIVRYTEKVPQVSTPTLVESRSLGKVGTECCTK
Horse      404 VEEPKSLVKKNCILFEEIGEYDFQNALIVRYTKKAPQVSTPTLVEIGRTLGKVGSRCCKL
Donkey     404 VEEPKSLVKKNCILFEEIGEYDFQNALIVRYTKKAPQVSTPTLVEIGRTLGKVGSRCCKL
Dog        405 VIEPQNLVKTNCELFEKLGEYGFQNALLVRYTKKAPQVSTPTLVEISRKLGKVGTKCCKK
Chicken    409 IKETQDIVKTNCILLHDHGEADILKSILIRYTKKMPQVPTDLLIETGKKITTIGTKCCQL
Pig        404 VIEPKNLIKQNCELFEKLGEYGFQNALIVRYTKKVPQVSTPTLVEIARKLGLVGSICCKR
                   ↑        ↑
               (D3-Start) (D2-End)

Human      441 PEAKRMPCAEDYLSVVLNQLCVLHEKTPVSDRVTKCCTESLVNRRPCFSALEVDETYVPK
Mouse      441 PEDQRLPCVEDYLSAILNRVCILHEKTPVSEHVTKCCSGSLVERRPCFSALTVDETYVPK
Sheep      440 PESERIPCTEDYLSIILNRLCVLHEKTPVSEKVTKCCTESLVNRRPCFSDLTIDETYVPK
Rabbit     441 PEAERIPCVEDYLSVILNRLCVLHEKTPVSEKVTKCCSESLVDRRPCFSALGPDETYVPK
Goat       440 PESERIPCTEDYLSIILNRLCVLHEKTPVSEKVTKCCTESLVNRRPCFSDLTIDETYVPK
Chimp      477 PEAKRIPCAEDYLSVVLNQLCVLHEKTPVSDRVTKCCTESLVNRRPCFSALEVDETYVPK
Macaque    465 PEAKRIPCAEDYLSVVLNRLCVLHEKTPVSEKVTKCCTESLVNRRPCFSALEIDEAYVPK
Hamster    465 PEAQRLPCVEDYLSAILNRVCVLHEKTPVSEQVTKCCTGSIVERRPCFSALPVDETYVPK
Guinea_Pig 465 PETERISCTENYLAILNRLCILHEKTPVSEIVTKCCTESLVNRRPCFSALHVDETYVPK
Rat        465 PEAQRLPCVEDYLSAILNRLCVLHEKTPVSEKVTKCCSGSLVERRPCFSALTVDETYVPK
Cow        464 PESERIPCTEDYLSIILNRLCVLHEKTPVSEKVTKCCTESLVNRRPCFSALTPDETYVPK
Horse      464 PESERIPCSENHLAIALNRLCVLHEKTPVSEKITKCCTISLAERRPCFSALEIDEGYVPK
Donkey     464 PESERIPCSENHLAIALNRLCVLHEKTPVSEKITKCCTISLAERRPCFSALEIDEGYIPK
Dog        465 PESERLSCAEDILSVLNRLCVLHEKTPVSEIVTKCCIESLVNRRPCFSILEVDETYVPK
Chicken    469 GEDRRMACSEGYLSIIHDTCRKQETTPINDNVSQCCIQLYANRRPCFIAIGVDTKYVPP
Pig        464 PEEERISCAEDYLSIILNRLCVLHEKTPVSEKVTKCCTESLVNRRPCFSALTPDETYKPK
```

Figure 2 (continued)

```
Human       501 EENAETFTFHADICTLSEKERQIKKQTALVELVKHKPKATKEQLKAVMDDFAAFVEKCCK
Mouse       501 EEKAETFTFHSDICTLPEKEKQIKKQTALAELVKHKPKATAEQLKTVMDDFAQFLDTCCK
Sheep       500 PEDEKFFTFHADICTLPETEKQIKKQTALVELLKHKPKATEEQLKTVMENFVAFVDKCCA
Rabbit      501 EENAETFTFHADICTLPETEKIKKQTALVELVKHKPHATNDQLKTVMGEFTALEDKCCS
Goat        500 PEDGEFFTFHADICTLPETEKQIKKQTALVELLKHKPKATEEQLKTVMENFVAFVDKCCA
Chimp       537 EENAETFTFHADICTLSEKERQIKKQTALVELVKHKPKATKEQLKAVMDDFAAFVEKCCK
Macaque     525 AENAETFTFHADICTLSEKEKQKKQTALVELVKHKPKATKEQLKGVMDNFAAFVEKCCK
Hamster     525 EEKAETFTFHADICSLPEKEKQMKKQAALVELVKHKPKATGPQLETVEGEFTAFEDKCCK
Guinea_Pig  525 PEHAEEFTFHADICTLPEKEKQVKKQMALVELVKHKPKASEEQMKTVMGDFAAFLKKCCD
Rat         525 EEKAETFTFHSDICTLPEKEKQIKKQTALAELVKHKPKATEQLKTVMGDFAQFVDKCCK
Cow         524 ADEKLFTFHADICTLPDTEKQIKKQTALVELLKHKPKATEQLKTVMENFVAFVDKCCA
Horse       524 EEKAETFTFHADICTLPEDEKQIKKQSALAELVKHKPKATKEQLKTVLGNESAFVAKCCG
Donkey      524 EEKAETFTFHADICTLPEDEKQIKKQSALAELVKHKPKATKEQLKTVLGNESAFVAKCCG
Dog         525 EENAETFTFHADICTLPEAEKQKKQTALVELLKHKPKATEEQLKTVMGDFAAFVEKCCA
Chicken     529 PENPEMESEDEKECEAPAEEREVGQMKLLENLEKRKPQMTEQEKTEADGETAMVDKCCK
Pig         524 EEVEGTFTFHADICTLPEDEKQIKKQTALVELLKHKPHATEEQLETVLGNESAFVQKCCA
```

```
Human       561 ADDKETCFAEEGKKLVAASQAALGL--
Mouse       561 AADKETCFSTEGPNLVTRCKDALA---
Sheep       560 ADKECCFVLEGPKLVASTQAALA---
Rabbit      561 ADKEACFAVEGPKLVESSKATLG---
Goat        560 ADKEACFLLEGPKLVASTQAALA---
Chimp       597 ADDKETCFAEEGKKLVAASQAALGL--
Macaque     585 ADKEACFAEEGPKFVAASQAALA---
Hamster     585 ADKEACFSEEGPKLVASSQAALA---
Guinea_Pig  585 ANKEACFTEEGPKLVAKCQATLA---
Rat         585 AADKENCFATEGPNLVARSKEALA---
Cow         584 ADKEACFAVEGPKLVVSEQTALA---
Horse       584 RDKEACFAEEGPKLVASSQLALA---
Donkey      584 ADKEACFAEEGPKLVASSQLALA---
Dog         585 ANKEECFSEEGPKLVAAAQAALV---
Chicken     589 QSDINTCFEEEGANLEVQSRATLEIGA
Pig         584 APDHEACFAVEGPKFVIEIRGILA---
                                         ↑
                                      (D3-End)
```

Figure 4
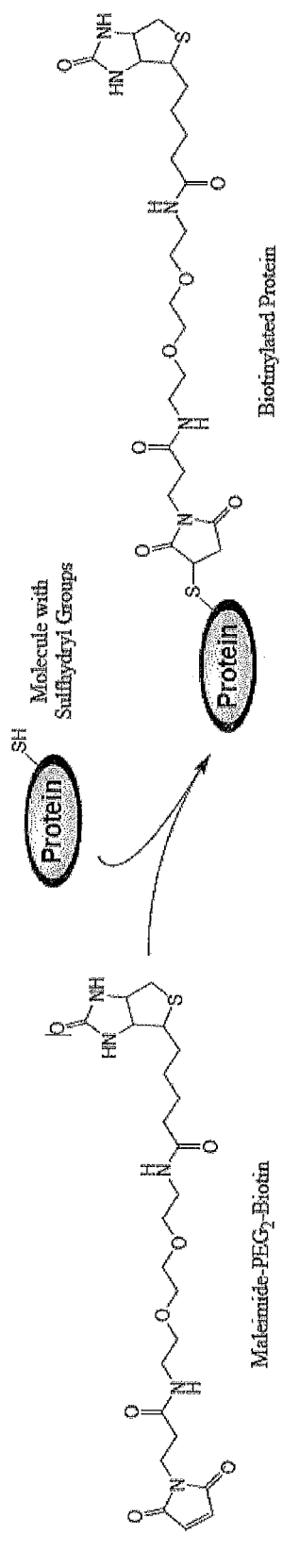
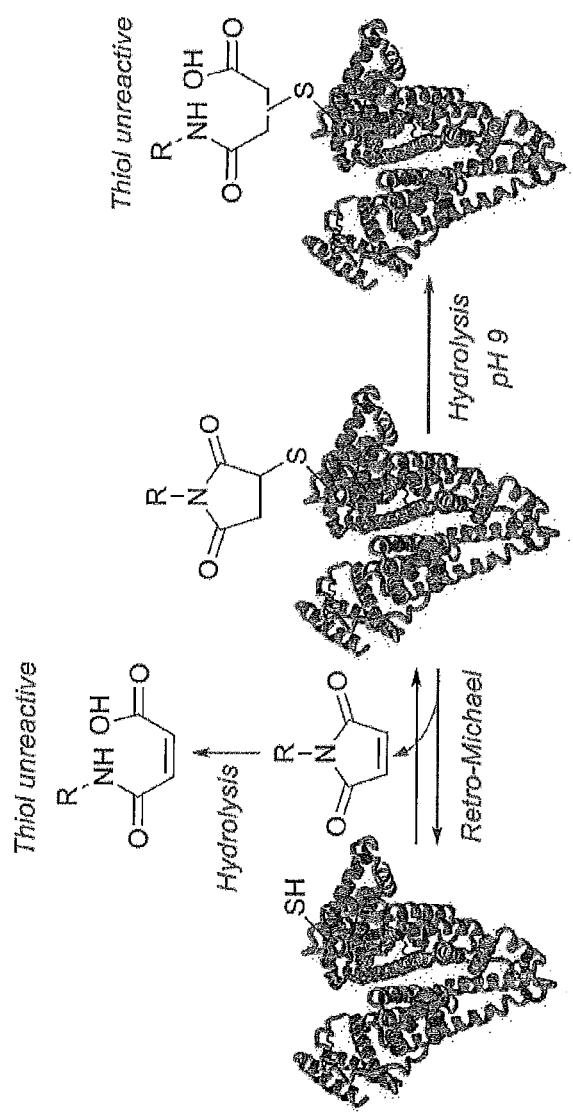

Figure 5
A
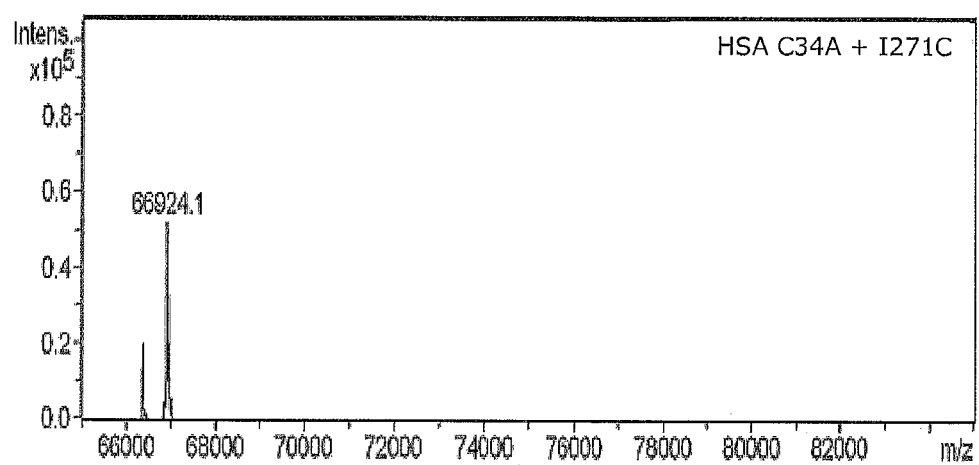
B
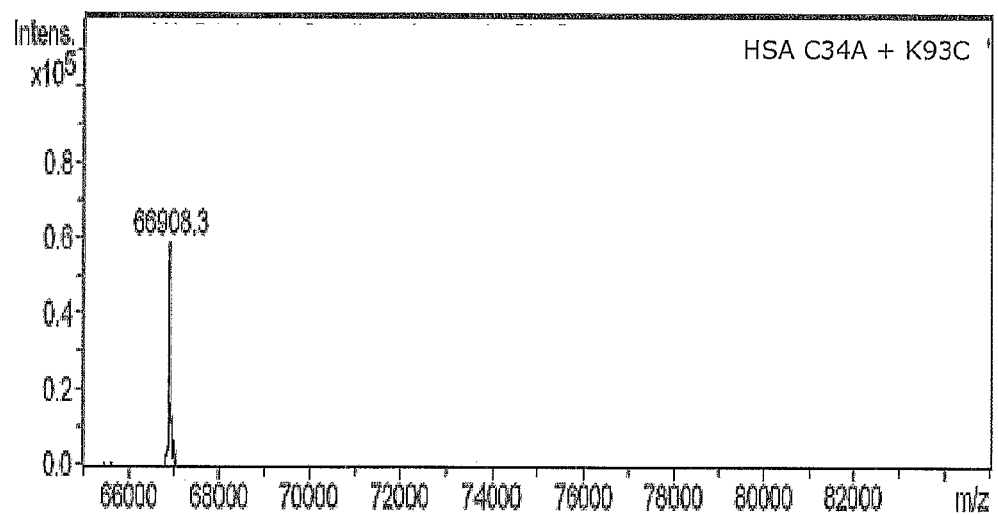

Figure 6
A
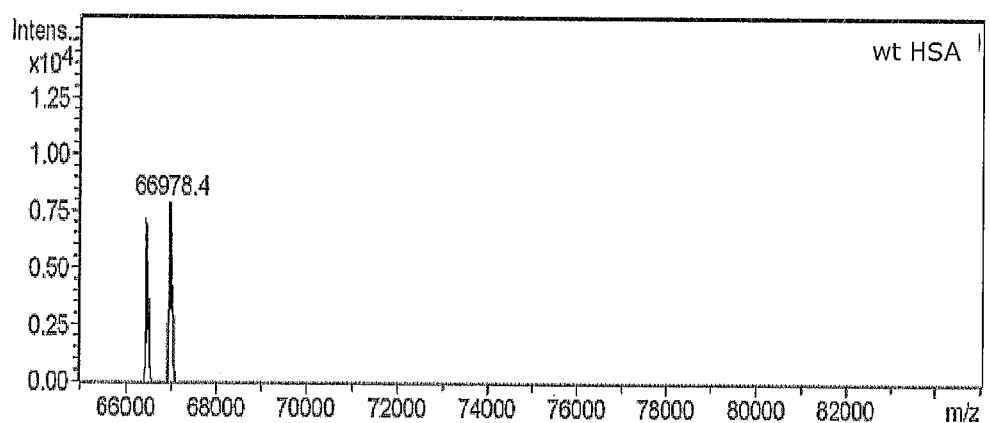
B
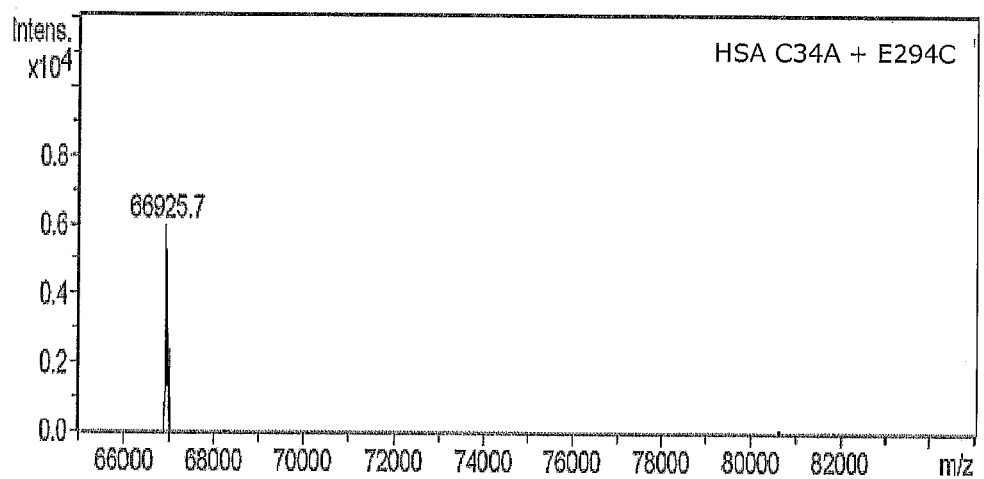

Figure 7
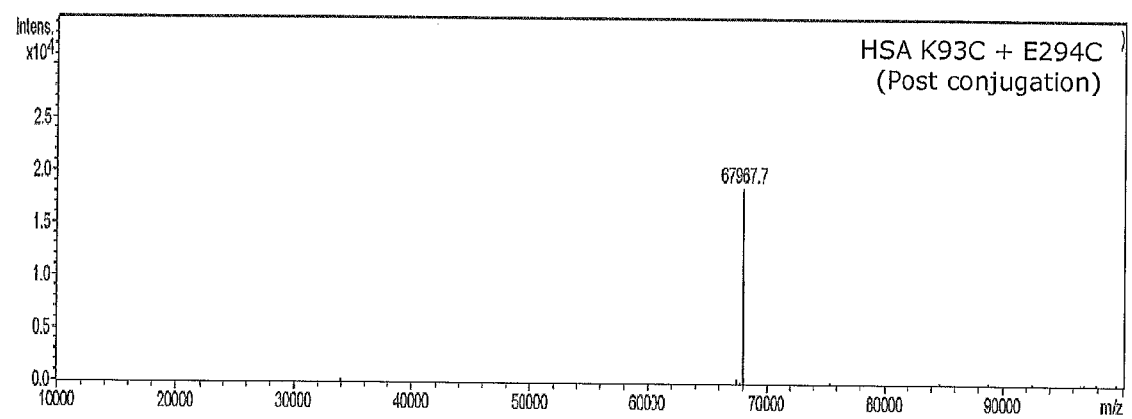
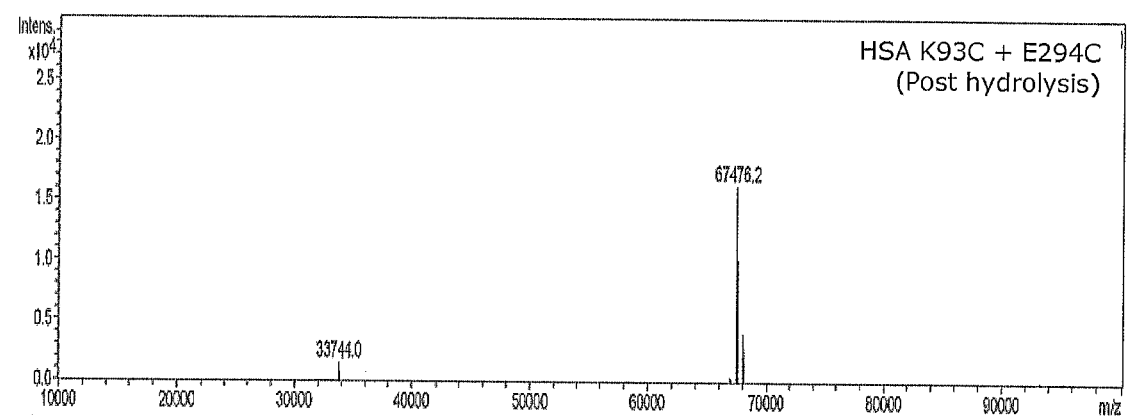
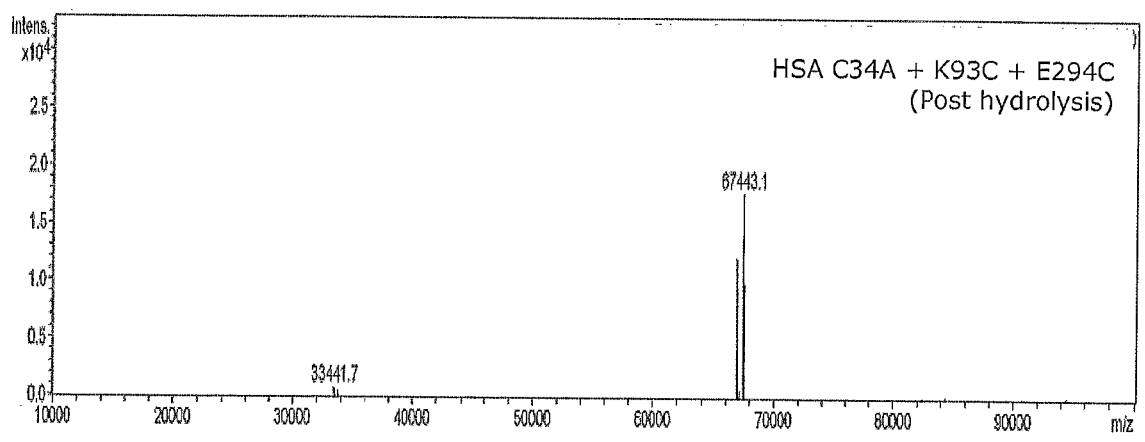

Figure 8
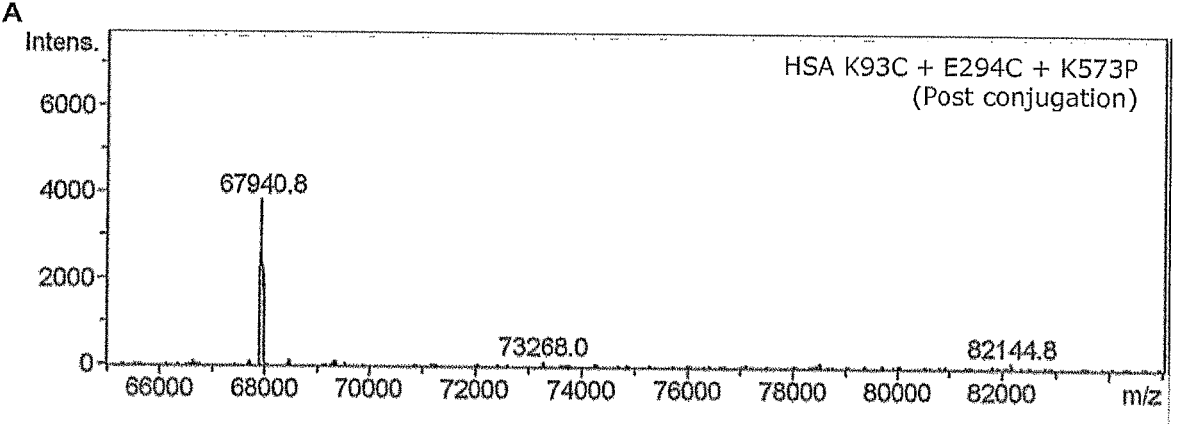
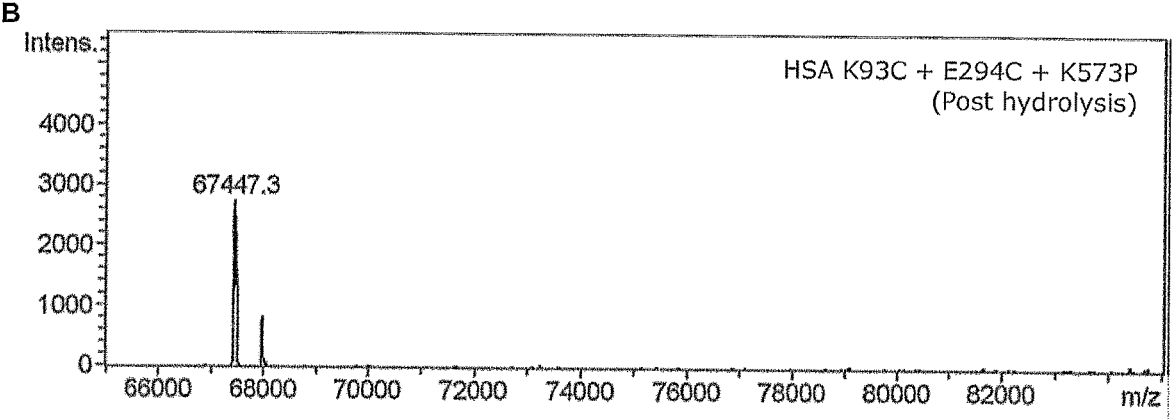

Figure 9
A
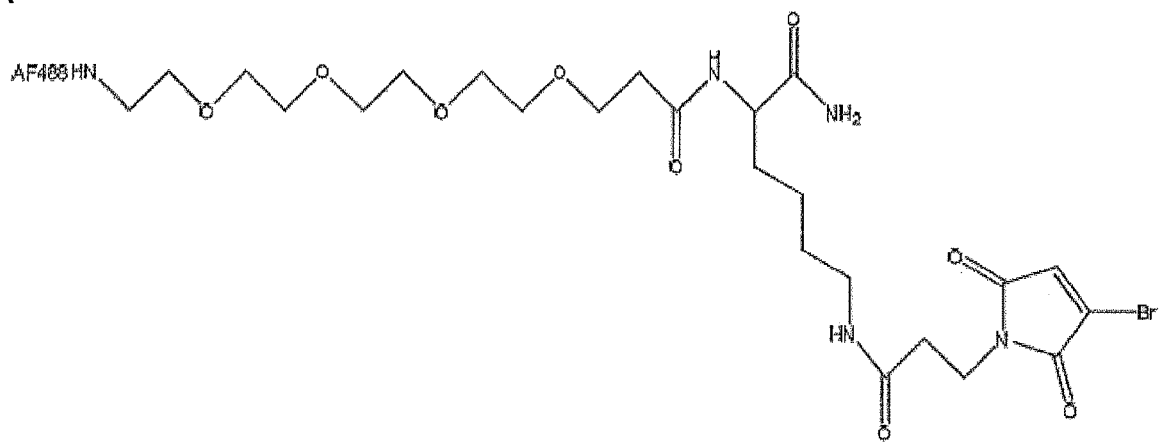
B
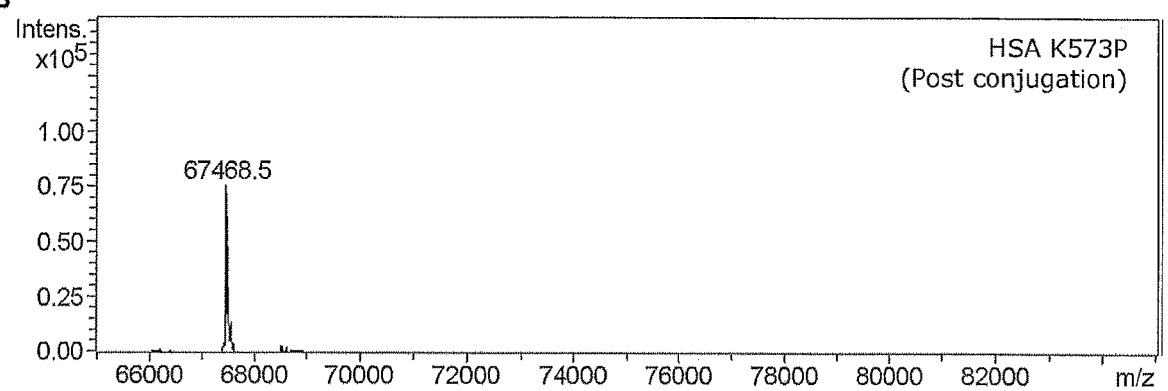
C
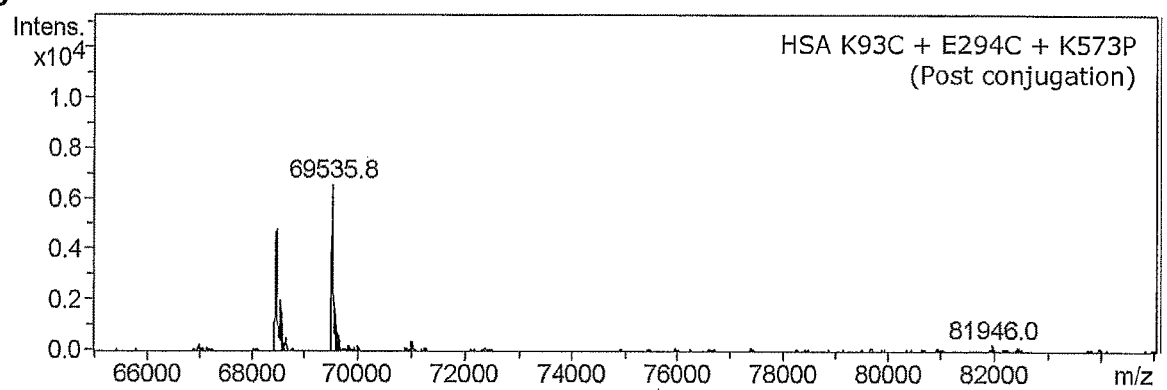

Figure 10
A
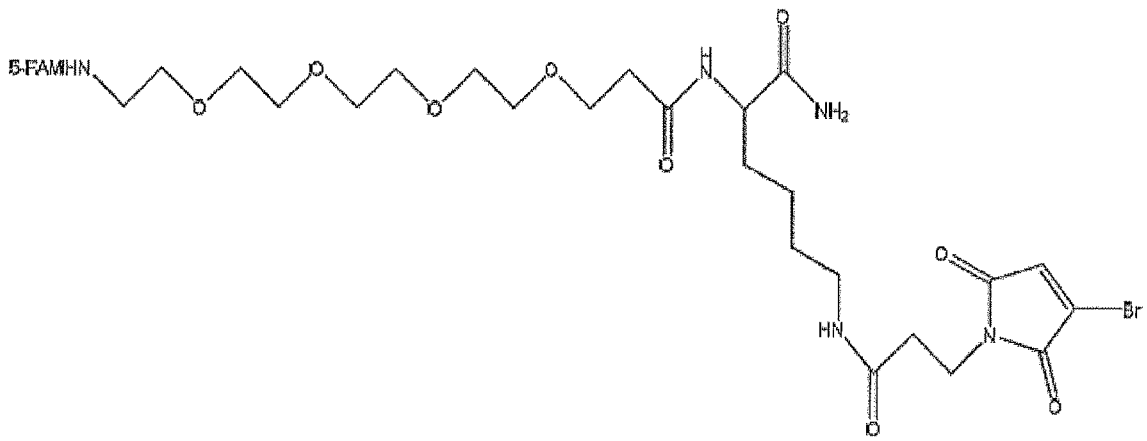
B
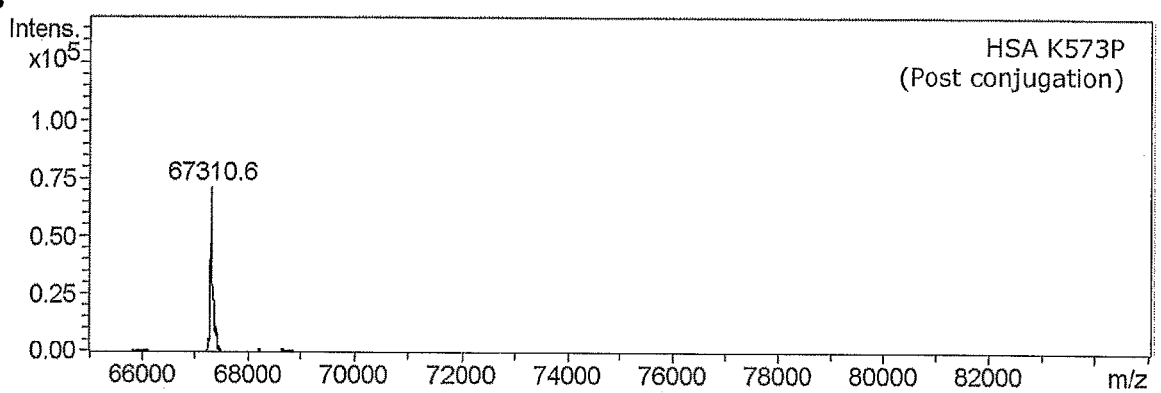
C
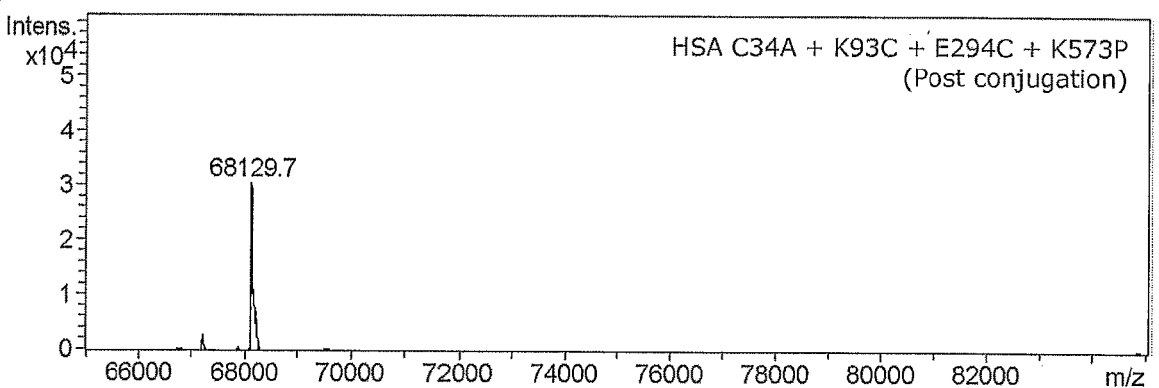

Figure 11
A
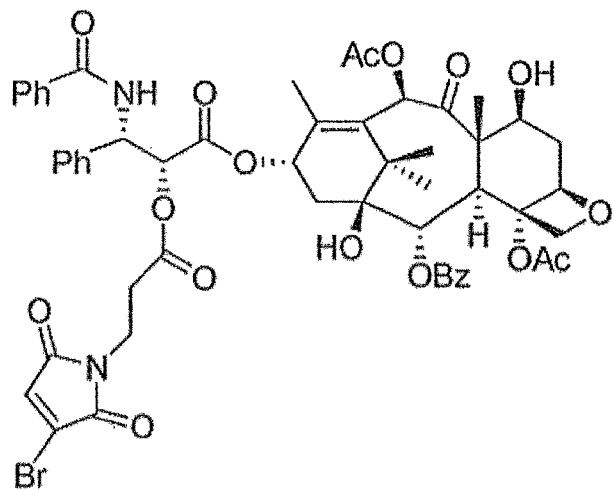
B
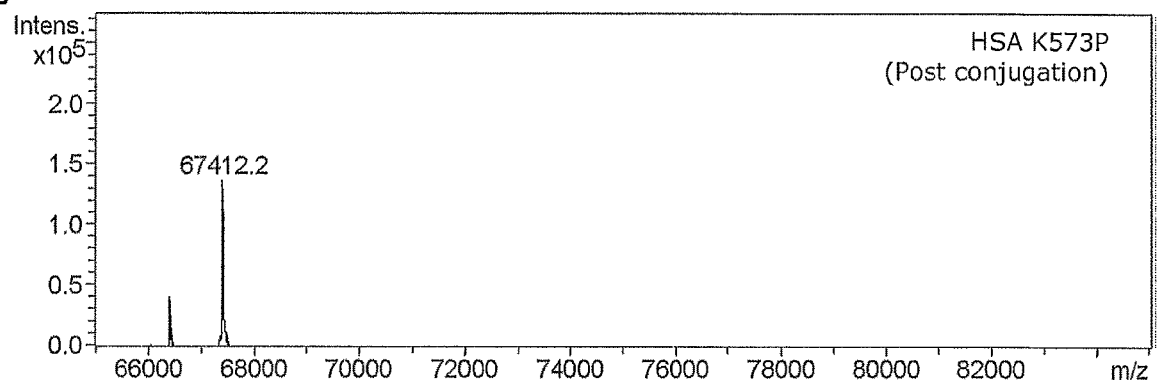
C
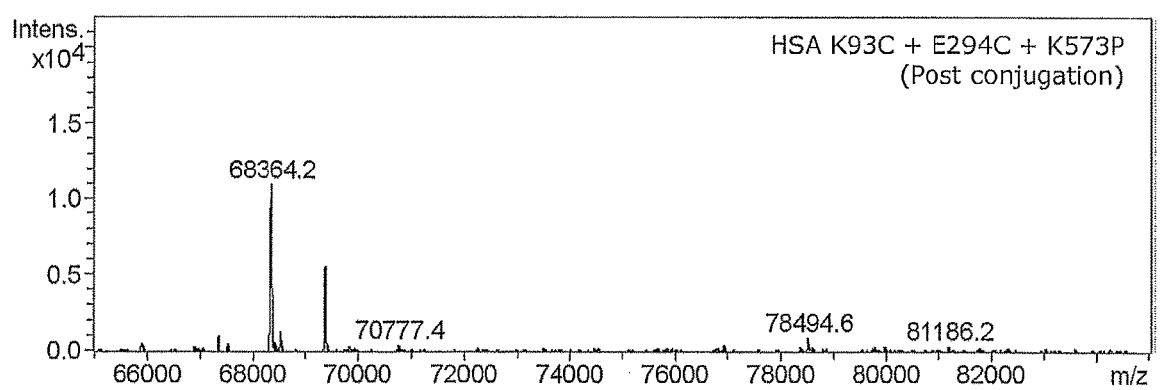

Figure 12
A
NH₂-HGEGT FTSDL SKQME EEAVR LFIEW LKNGG
PSSGA PPPSK(Bromomaleimide-PEG2)-NH₂
Where bromomaleimide-PEG2 =
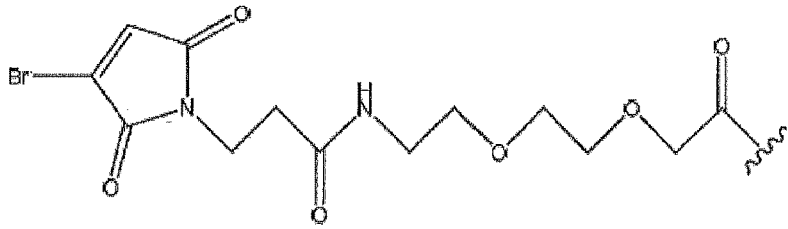
B
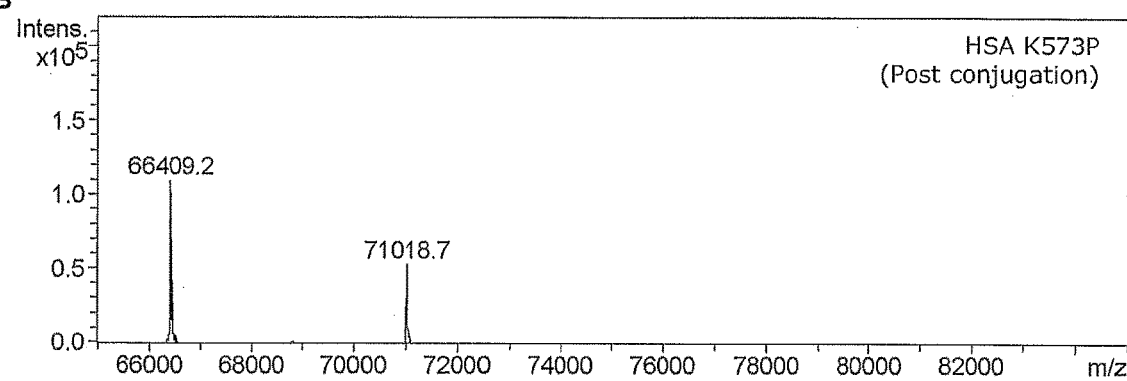
C
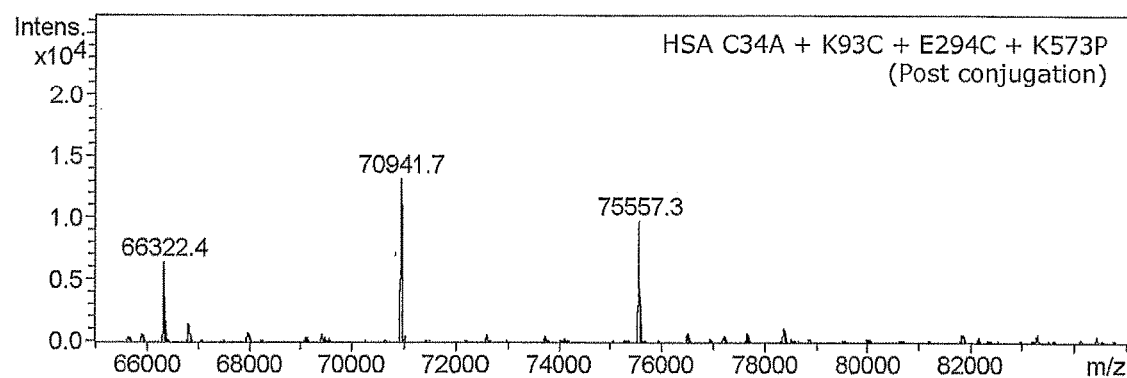

Figure 13
A
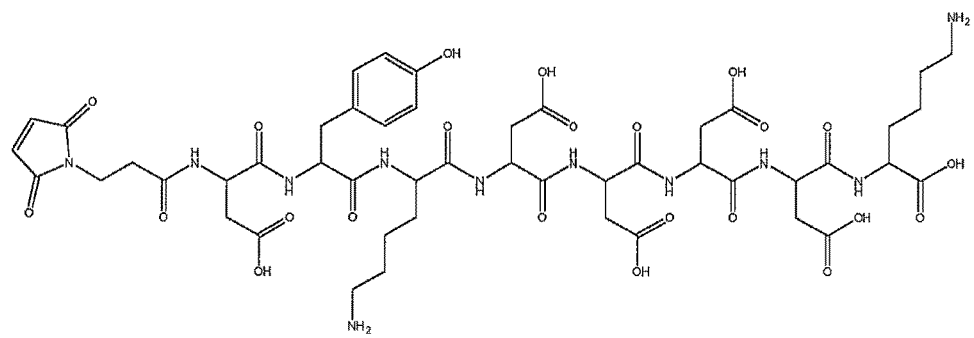
B
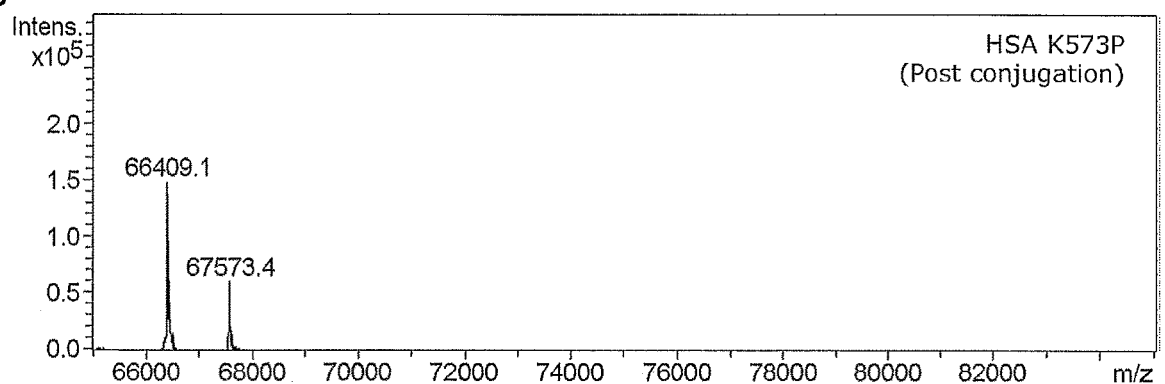
C
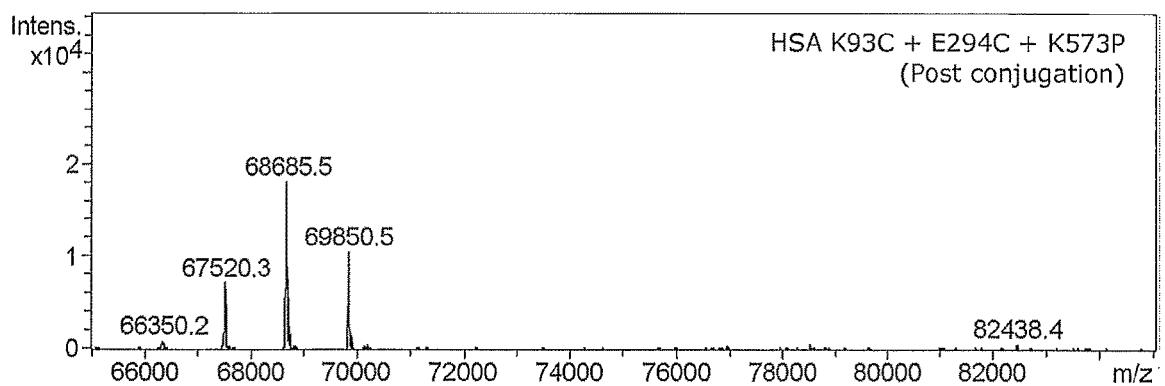

SEQUENCE LISTING

```
<160> NUMBER OF SEQ ID NOS: 152

<210> SEQ ID NO 1
<211> LENGTH: 1761
<212> TYPE: DNA
<213> ORGANISM: Homo sapiens

<400> SEQUENCE: 1
gacgctcaca agtccgaagt cgctcacaga ttcaaggact tgggtgaaga aaacttcaag      60
gctttggtct tgatcgcttt cgctcaatac ttgcaacaat gtccattcga agatcacgtc     120
aagttggtca acgaagttac cgaattcgct aagacttgtg ttgctgacga atccgcggaa     180
aactgtgaca agtccttgca caccttgttc ggtgataagt tgtgtactgt tgctaccttg     240
agagaaacct acggtgaaat ggctgactgt tgtgctaagc aagaaccaga aagaaacgaa     300
tgtttcttgc aacacaagga cgacaaccca aacttgccaa gattggttag accagaagtt     360
gacgtcatgt gtactgcttt ccacgacaac gaagaaacct tcttgaagaa gtacttgtac     420
gaaattgcta gaagacaccc atacttctac gctccagaat tgttgttctt cgctaagaga     480
tacaaggctg ctttcaccga atgttgtcaa gctgctgata aggctgcttg tttgttgcca     540
aagttggatg aattgagaga cgaaggtaag gctagctccg caaagcaaag attgaagtgt     600
gcttccttgc aaaagttcgg tgaaagagct ttcaaggctt gggctgtcgc tagattgtct     660
caaagattcc caaaggctga attcgctgaa gtttctaagt tggttactga cttgactaag     720
gttcacactg aatgttgtca cggtgacttg ttggaatgtg ctgatgacag agctgacttg     780
gctaagtaca tctgtgaaaa ccaagactct atctcttcca agttgaagga atgttgtgaa     840
aagccattgt tggaaaagtc tcactgtatt gctgaagttg aaaacgatga aatgccagct     900
gacttgccat ctttggctgc tgacttcgtt gaatctaagg acgtttgtaa gaactacgct     960
gaagctaagg acgtcttctt gggtatgttc ttgtacgaat acgctagaag acacccagac    1020
tactccgttg tcttgttgtt gagattggct aagacctacg aaactaccct cgagaagtgt    1080
```

-continued

```
tgtgctgctg ctgacccaca cgaatgttac gctaaggttt tcgatgaatt caagccattg    1140
gtcgaagaac cacaaaactt gatcaagcaa aactgtgaat tgttcgaaca attgggtgaa    1200
tacaagttcc aaaacgcttt gttggttaga tacactaaga aggtcccaca agtctccacc    1260
ccaactttgg ttgaagtctc tagaaacttg ggtaaggtcg ttctaagtg ttgtaagcac     1320 ccagaagcta agagaatgcc atgtgctgaa gattacttgt ccgtcgtttt gaaccaattg    1380
tgtgttttgc acgaaaagac cccagtctct gatagagtca ccaagtgttg tactgaatct    1440
ttggttaaca gaagaccatg tttctctgct ttggaagtcg acgaaactta cgttccaaag    1500
gaattcaacg ctgaaacttt caccttccac gctgatatct gtaccttgtc cgaaaaggaa    1560
agacaaatta gaagcaaac tgctttggtt gaattggtca gcacaagcc aaaggctact     1620 aaggaacaat tgaaggctgt catggatgat ttcgctgctt tcgttgaaaa gtgttgtaag    1680
gctgatgata aggaaacttg tttcgctgaa gaaggtaaga agttggtcgc tgcttcccaa    1740
gctgccttag gtttgtaata a                                              1761
```

<210> SEQ ID NO 2
<211> LENGTH: 585
<212> TYPE: PRT
<213> ORGANISM: Homo sapiens

<400> SEQUENCE: 2

```
Asp Ala His Lys Ser Glu Val Ala His Arg Phe Lys Asp Leu Gly Glu
1               5                  10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255
```

```
Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 3
<211> LENGTH: 609
<212> TYPE: PRT
<213> ORGANISM: Homo sapiens
<220> FEATURE:
<221> NAME/KEY: SIGNAL
<222> LOCATION: (1)..(19)
<220> FEATURE:
<221> NAME/KEY: PROPEP
<222> LOCATION: (20)..(24)
<220> FEATURE:
<221> NAME/KEY: mat_peptide
<222> LOCATION: (25)..(609)
```

```
<400> SEQUENCE: 3

Met Lys Trp Val Thr Phe Ile Ser Leu Leu Phe Leu Phe Ser Ser Ala
                    -20                 -15                 -10

Tyr Ser Arg Gly Val Phe Arg Arg Asp Ala His Lys Ser Glu Val Ala
            -5                  -1  1                   5

His Arg Phe Lys Asp Leu Gly Glu Glu Asn Phe Lys Ala Leu Val Leu
        10                  15                  20

Ile Ala Phe Ala Gln Tyr Leu Gln Gln Cys Pro Phe Glu Asp His Val
25                  30                  35                  40

Lys Leu Val Asn Glu Val Thr Glu Phe Ala Lys Thr Cys Val Ala Asp
                45                  50                  55

Glu Ser Ala Glu Asn Cys Asp Lys Ser Leu His Thr Leu Phe Gly Asp
                60                  65                  70

Lys Leu Cys Thr Val Ala Thr Leu Arg Glu Thr Tyr Gly Glu Met Ala
            75                  80                  85

Asp Cys Cys Ala Lys Gln Glu Pro Glu Arg Asn Glu Cys Phe Leu Gln
90                  95                  100

His Lys Asp Asp Asn Pro Asn Leu Pro Arg Leu Val Arg Pro Glu Val
105                 110                 115                 120

Asp Val Met Cys Thr Ala Phe His Asp Asn Glu Thr Phe Leu Lys
                125                 130                 135

Lys Tyr Leu Tyr Glu Ile Ala Arg Arg His Pro Tyr Phe Tyr Ala Pro
        140                 145                 150

Glu Leu Leu Phe Phe Ala Lys Arg Tyr Lys Ala Ala Phe Thr Glu Cys
            155                 160                 165

Cys Gln Ala Ala Asp Lys Ala Ala Cys Leu Leu Pro Lys Leu Asp Glu
        170                 175                 180

Leu Arg Asp Glu Gly Lys Ala Ser Ser Ala Lys Gln Arg Leu Lys Cys
185                 190                 195                 200

Ala Ser Leu Gln Lys Phe Gly Glu Arg Ala Phe Lys Ala Trp Ala Val
                205                 210                 215

Ala Arg Leu Ser Gln Arg Phe Pro Lys Ala Glu Phe Ala Glu Val Ser
                220                 225                 230

Lys Leu Val Thr Asp Leu Thr Lys Val His Thr Glu Cys Cys His Gly
            235                 240                 245

Asp Leu Leu Glu Cys Ala Asp Asp Arg Ala Asp Leu Ala Lys Tyr Ile
250                 255                 260

Cys Glu Asn Gln Asp Ser Ile Ser Ser Lys Leu Lys Glu Cys Cys Glu
265                 270                 275                 280

Lys Pro Leu Leu Glu Lys Ser His Cys Ile Ala Glu Val Glu Asn Asp
                285                 290                 295

Glu Met Pro Ala Asp Leu Pro Ser Leu Ala Ala Asp Phe Val Glu Ser
                300                 305                 310

Lys Asp Val Cys Lys Asn Tyr Ala Glu Ala Lys Asp Val Phe Leu Gly
                315                 320                 325

Met Phe Leu Tyr Glu Tyr Ala Arg Arg His Pro Asp Tyr Ser Val Val
            330                 335                 340

Leu Leu Leu Arg Leu Ala Lys Thr Tyr Glu Thr Thr Leu Glu Lys Cys
345                 350                 355                 360

Cys Ala Ala Ala Asp Pro His Glu Cys Tyr Ala Lys Val Phe Asp Glu
                365                 370                 375

Phe Lys Pro Leu Val Glu Glu Pro Gln Asn Leu Ile Lys Gln Asn Cys
                380                 385                 390
```

```
Glu Leu Phe Glu Gln Leu Gly Glu Tyr Lys Phe Gln Asn Ala Leu Leu
    395                 400                 405

Val Arg Tyr Thr Lys Lys Val Pro Gln Val Ser Thr Pro Thr Leu Val
410                 415                 420

Glu Val Ser Arg Asn Leu Gly Lys Val Gly Ser Lys Cys Cys Lys His
425                 430                 435                 440

Pro Glu Ala Lys Arg Met Pro Cys Ala Glu Asp Tyr Leu Ser Val Val
                445                 450                 455

Leu Asn Gln Leu Cys Val Leu His Glu Lys Thr Pro Val Ser Asp Arg
            460                 465                 470

Val Thr Lys Cys Cys Thr Glu Ser Leu Val Asn Arg Arg Pro Cys Phe
        475                 480                 485

Ser Ala Leu Glu Val Asp Glu Thr Tyr Val Pro Lys Glu Phe Asn Ala
    490                 495                 500

Glu Thr Phe Thr Phe His Ala Asp Ile Cys Thr Leu Ser Glu Lys Glu
505                 510                 515                 520

Arg Gln Ile Lys Lys Gln Thr Ala Leu Val Glu Leu Val Lys His Lys
                525                 530                 535

Pro Lys Ala Thr Lys Glu Gln Leu Lys Ala Val Met Asp Asp Phe Ala
            540                 545                 550

Ala Phe Val Glu Lys Cys Cys Lys Ala Asp Asp Lys Glu Thr Cys Phe
        555                 560                 565

Ala Glu Glu Gly Lys Lys Leu Val Ala Ala Ser Gln Ala Ala Leu Gly
    570                 575                 580

Leu
585

<210> SEQ ID NO 4
<211> LENGTH: 621
<212> TYPE: PRT
<213> ORGANISM: Pan troglodytes

<400> SEQUENCE: 4

Met Asn Glu Ser Ser Cys Cys Ser Thr Ser Leu Pro Ala Phe Gly Val
1               5                   10                  15

Ser Val Leu Asp Ser Gly His Ser Ser Ser Ala Tyr Ser Arg Gly
            20                  25                  30

Val Phe Arg Arg Asp Ala His Lys Ser Glu Val Ala His Arg Phe Lys
        35                  40                  45

Asp Leu Gly Glu Glu Asn Phe Lys Ala Leu Val Leu Val Ala Phe Ala
    50                  55                  60

Gln Tyr Leu Gln Gln Cys Pro Phe Glu Asp His Val Lys Leu Val Asn
65                  70                  75                  80

Glu Val Thr Glu Phe Ala Lys Thr Cys Val Ala Asp Glu Ser Ala Glu
                85                  90                  95

Asn Cys Asp Lys Ser Leu His Thr Leu Phe Gly Asp Lys Leu Cys Thr
            100                 105                 110

Val Ala Thr Leu Arg Glu Lys Tyr Gly Glu Met Ala Asp Cys Cys Ala
        115                 120                 125

Lys Gln Glu Pro Glu Arg Asn Glu Cys Phe Leu Gln His Lys Asp Asp
    130                 135                 140

Asn Pro Asn Leu Pro Arg Leu Val Arg Pro Glu Val Asp Val Met Cys
145                 150                 155                 160
```

```
Thr Ala Phe His Asp Asn Gly Thr Phe Leu Lys Lys Tyr Leu Tyr
            165                 170                 175

Glu Val Ala Arg Arg His Pro Tyr Phe Tyr Ala Pro Glu Leu Leu Phe
                180                 185                 190

Phe Ala Glu Arg Tyr Lys Ala Ala Phe Thr Glu Cys Cys Gln Ala Ala
            195                 200                 205

Asp Lys Ala Ala Cys Leu Leu Pro Lys Leu Asp Glu Leu Arg Asp Glu
            210                 215                 220

Gly Lys Ala Ser Ser Ala Lys Gln Arg Leu Lys Cys Ala Ser Leu Gln
225                 230                 235                 240

Lys Phe Gly Glu Arg Ala Phe Lys Ala Trp Ala Val Ala Arg Leu Ser
                245                 250                 255

Gln Arg Phe Pro Lys Ala Glu Phe Ala Glu Val Ser Lys Leu Val Thr
            260                 265                 270

Asp Leu Thr Lys Val His Thr Glu Cys Cys His Gly Asp Leu Leu Glu
            275                 280                 285

Cys Ala Asp Asp Arg Ala Asp Leu Ala Lys Tyr Ile Cys Glu Asn Gln
            290                 295                 300

Asp Ser Ile Ser Ser Lys Leu Lys Glu Cys Cys Glu Lys Pro Leu Leu
305                 310                 315                 320

Glu Lys Ser His Cys Leu Ala Glu Val Glu Asn Asp Glu Met Pro Ala
                325                 330                 335

Asp Leu Pro Ser Leu Ala Ala Asp Phe Val Glu Ser Lys Glu Val Cys
            340                 345                 350

Lys Asn Tyr Ala Glu Ala Lys Asp Val Phe Leu Gly Met Phe Leu Tyr
            355                 360                 365

Glu Tyr Ala Arg Arg His Pro Asp Tyr Ser Val Val Leu Leu Leu Arg
            370                 375                 380

Leu Ala Lys Thr Tyr Glu Thr Thr Leu Glu Lys Cys Cys Ala Ala Ala
385                 390                 395                 400

Asp Pro His Glu Cys Tyr Ala Lys Val Phe Asp Glu Phe Lys Pro Leu
            405                 410                 415

Val Glu Glu Pro Gln Asn Leu Ile Lys Gln Asn Cys Glu Leu Phe Glu
            420                 425                 430

Gln Leu Gly Glu Tyr Lys Phe Gln Asn Ala Leu Leu Val Arg Tyr Thr
            435                 440                 445

Lys Lys Val Pro Gln Val Ser Thr Pro Thr Leu Val Glu Val Ser Arg
450                 455                 460

Asn Leu Gly Lys Val Gly Ser Lys Cys Cys Lys His Pro Glu Ala Lys
465                 470                 475                 480

Arg Met Pro Cys Ala Glu Asp Tyr Leu Ser Val Val Leu Asn Gln Leu
            485                 490                 495

Cys Val Leu His Glu Lys Thr Pro Val Ser Asp Arg Val Thr Lys Cys
            500                 505                 510

Cys Thr Glu Ser Leu Val Asn Arg Arg Pro Cys Phe Ser Ala Leu Glu
            515                 520                 525

Val Asp Glu Thr Tyr Val Pro Lys Glu Phe Asn Ala Glu Thr Phe Thr
            530                 535                 540

Phe His Ala Asp Ile Cys Thr Leu Ser Glu Lys Glu Arg Gln Ile Lys
545                 550                 555                 560

Lys Gln Thr Ala Leu Val Glu Leu Val Lys His Lys Pro Lys Ala Thr
                565                 570                 575
```

```
Lys Glu Gln Leu Lys Ala Val Met Asp Asp Phe Ala Ala Phe Val Glu
                580                 585                 590

Lys Cys Cys Lys Ala Asp Asp Lys Glu Thr Cys Phe Ala Glu Glu Gly
            595                 600                 605

Lys Lys Leu Val Ala Ala Ser Gln Ala Ala Leu Gly Leu
    610                 615                 620

<210> SEQ ID NO 5
<211> LENGTH: 608
<212> TYPE: PRT
<213> ORGANISM: Macaca mulatta

<400> SEQUENCE: 5

Met Lys Trp Val Thr Phe Ile Ser Leu Leu Phe Leu Phe Ser Ser Ala
1               5                   10                  15

Tyr Ser Arg Gly Val Phe Arg Arg Asp Thr His Lys Ser Glu Val Ala
            20                  25                  30

His Arg Phe Lys Asp Leu Gly Glu Glu His Phe Lys Gly Leu Val Leu
        35                  40                  45

Val Ala Phe Ser Gln Tyr Leu Gln Gln Cys Pro Phe Glu Glu His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Pro Leu Val Arg Pro Glu Val
    130                 135                 140

Asp Val Met Cys Thr Ala Phe His Asp Asn Glu Ala Thr Phe Leu Lys
145                 150                 155                 160

Lys Tyr Leu Tyr Glu Val Ala Arg Arg His Pro Tyr Phe Tyr Ala Pro
                165                 170                 175

Glu Leu Leu Phe Phe Ala Ala Arg Tyr Lys Ala Ala Phe Ala Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Asp Arg Ala Phe Lys Ala Trp Ala Val
225                 230                 235                 240

Ala Arg Leu Ser Gln Lys Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Met
        275                 280                 285

Cys Glu Asn Gln Asp Ser Ile Ser Ser Lys Leu Lys Glu Cys Cys Asp
    290                 295                 300

Lys Pro Leu Leu Glu Lys Ser His Cys Leu Ala Glu Val Glu Asn Asp
305                 310                 315                 320

Glu Met Pro Ala Asp Leu Pro Ser Leu Ala Ala Asp Tyr Val Glu Ser
                325                 330                 335
```

-continued

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Met
            355                 360                 365

Leu Leu Leu Arg Leu Ala Lys Ala Tyr Glu Ala Thr Leu Glu Lys Cys
        370                 375                 380

Cys Ala Ala Ala Asp Pro His Glu Cys Tyr Ala Lys Val Phe Asp Glu
385                 390                 395                 400

Phe Gln Pro Leu Val Glu Pro Gln Asn Leu Val Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ala Lys Cys Cys Lys Leu
    450                 455                 460

Pro Glu Ala Lys Arg Met Pro Cys Ala Glu Asp Tyr Leu Ser Val Val
465                 470                 475                 480

Leu Asn Arg Leu Cys Val Leu His Glu Lys Thr Pro Val Ser Glu Lys
                485                 490                 495

Val Thr Lys Cys Cys Thr Glu Ser Leu Val Asn Arg Arg Pro Cys Phe
            500                 505                 510

Ser Ala Leu Glu Leu Asp Glu Ala Tyr Val Pro Lys Ala Phe Asn Ala
        515                 520                 525

Glu Thr Phe Thr Phe His Ala Asp Met Cys Thr Leu Ser Glu Lys Glu
    530                 535                 540

Lys Gln Val Lys Lys Gln Thr Ala Leu Val Glu Leu Val Lys His Lys
545                 550                 555                 560

Pro Lys Ala Thr Lys Glu Gln Leu Lys Gly Val Met Asp Asn Phe Ala
                565                 570                 575

Ala Phe Val Glu Lys Cys Cys Lys Ala Asp Asp Lys Glu Ala Cys Phe
            580                 585                 590

Ala Glu Glu Gly Pro Lys Phe Val Ala Ala Ser Gln Ala Ala Leu Ala
        595                 600                 605

<210> SEQ ID NO 6
<211> LENGTH: 608
<212> TYPE: PRT
<213> ORGANISM: Mesocricetus auratus

<400> SEQUENCE: 6

Met Lys Trp Val Thr Phe Leu Leu Leu Phe Val Ser Asp Ser Ala
1               5                   10                  15

Phe Ser Arg Gly Leu Phe Arg Arg Asp Ala His Lys Ser Glu Ile Ala
            20                  25                  30

His Arg Phe Lys Asp Leu Gly Glu Gln His Phe Lys Gly Leu Val Leu
        35                  40                  45

Ile Ala Phe Ser Gln Phe Leu Gln Lys Cys Pro Tyr Glu Glu His Val
    50                  55                  60

Lys Leu Val Asn Glu Val Thr Asp Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

-continued

```
Lys Leu Cys Ala Ile Pro Thr Leu Arg Asp Ser Tyr Gly Glu Leu Ala
            100                 105                 110

Asp Cys Cys Ala Lys Lys Glu Pro Glu Arg Asn Glu Cys Phe Leu Lys
            115                 120                 125

His Lys Asp Asp His Pro Asn Leu Pro Pro Phe Val Arg Pro Asp Ala
    130                 135                 140

Glu Ala Met Cys Thr Ser Phe Gln Glu Asn Ala Val Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Lys Tyr Ser Ala Ile Met Thr Glu Cys
                180                 185                 190

Cys Gly Glu Ala Asp Lys Ala Ala Cys Ile Thr Pro Lys Leu Asp Ala
                195                 200                 205

Leu Lys Glu Lys Ala Leu Ala Ser Ser Val Asn Gln Arg Leu Lys Cys
        210                 215                 220

Ser Ser Leu Gln Arg Phe Gly Gln Arg Ala Phe Lys Ala Trp Ala Val
225                 230                 235                 240

Ala Arg Met Ser Gln Lys Phe Pro Lys Ala Asp Phe Ala Glu Ile Thr
                245                 250                 255

Lys Leu Ala Thr Asp Leu Thr Lys Leu Thr Glu Glu Cys Cys His Gly
                260                 265                 270

Asp Leu Leu Glu Cys Ala Asp Asp Arg Ala Glu Leu Ala Lys Tyr Met
            275                 280                 285

Cys Glu Asn Gln Ala Ser Ile Ser Ser Lys Leu Gln Ala Cys Cys Asp
            290                 295                 300

Lys Pro Val Leu Lys Lys Ser His Cys Leu Ser Glu Val Glu Asn Asp
305                 310                 315                 320

Asp Leu Pro Ala Asp Leu Pro Ser Leu Ala Ala Asp Phe Val Glu Asp
                325                 330                 335

Lys Glu Val Cys Lys Asn Tyr Ala Glu Ala Lys Asp Val Phe Leu Gly
                340                 345                 350

Thr Phe Leu Tyr Glu Tyr Ala Arg Arg His Pro Asp Tyr Ser Val Ala
            355                 360                 365

Leu Leu Leu Arg Leu Ala Lys Lys Tyr Glu Ala Thr Leu Glu Lys Cys
    370                 375                 380

Cys Ala Glu Ala Asp Pro Ser Ala Cys Tyr Gly Lys Val Leu Asp Glu
385                 390                 395                 400

Phe Gln Pro Leu Val Glu Glu Pro Lys Asn Leu Val Lys Ala Asn Cys
                405                 410                 415

Glu Leu Phe Glu Lys Leu Gly Glu Tyr Gly Phe Gln Asn Ala Leu Ile
                420                 425                 430

Val Arg Tyr Thr Gln Lys Ala Pro Gln Val Ser Thr Pro Thr Leu Val
            435                 440                 445

Glu Ala Ala Arg Asn Leu Gly Lys Val Gly Ser Lys Cys Cys Val Leu
        450                 455                 460

Pro Glu Ala Gln Arg Leu Pro Cys Val Glu Asp Tyr Ile Ser Ala Ile
465                 470                 475                 480

Leu Asn Arg Val Cys Val Leu His Glu Lys Thr Pro Val Ser Glu Gln
                485                 490                 495

Val Thr Lys Cys Cys Thr Gly Ser Val Val Glu Arg Arg Pro Cys Phe
            500                 505                 510
```

```
Ser Ala Leu Pro Val Asp Glu Thr Tyr Val Pro Lys Glu Phe Lys Ala
            515                 520                 525

Glu Thr Phe Thr Phe His Ala Asp Ile Cys Ser Leu Pro Lys Glu
        530                 535                 540

Lys Gln Met Lys Lys Gln Ala Ala Leu Val Glu Leu Val Lys His Lys
545                 550                 555                 560

Pro Lys Ala Thr Gly Pro Gln Leu Arg Thr Val Leu Gly Glu Phe Thr
                565                 570                 575

Ala Phe Leu Asp Lys Cys Cys Lys Ala Glu Asp Lys Glu Ala Cys Phe
                580                 585                 590

Ser Glu Asp Gly Pro Lys Leu Val Ala Ser Ser Gln Ala Ala Leu Ala
            595                 600                 605

<210> SEQ ID NO 7
<211> LENGTH: 608
<212> TYPE: PRT
<213> ORGANISM: Cavia porcellus

<400> SEQUENCE: 7

Met Lys Trp Val Thr Phe Ile Ser Leu Leu Phe Leu Phe Ser Ser Val
1               5                   10                  15

Tyr Ser Arg Gly Val Phe Arg Arg Glu Ala His Lys Ser Glu Ile Ala
                20                  25                  30

His Arg Phe Asn Asp Leu Gly Glu Gly His Phe Lys Gly Leu Val Leu
            35                  40                  45

Ile Thr Leu Ser Gln His Leu Gln Lys Ser Pro Phe Glu Glu His Val
50                  55                  60

Lys Leu Val Asn Glu Val Thr Asp Phe Ala Lys Ala Cys Val Ala Asp
65                  70                  75                  80

Glu Ser Ala Gln Asn Cys Gly Lys Ala Ile Ala Thr Leu Phe Gly Asp
                85                  90                  95

Lys Val Cys Ala Ile Pro Ser Leu Arg Glu Thr Tyr Gly Glu Leu Ala
            100                 105                 110

Asp Cys Cys Ala Lys Glu Asp Pro Asp Arg Val Glu Cys Phe Leu Gln
        115                 120                 125

His Lys Asp Asp Asn Pro Asn Leu Pro Pro Phe Glu Arg Pro Glu Pro
    130                 135                 140

Glu Ala Leu Cys Thr Ala Phe Lys Glu Asn Asn Asp Arg Phe Ile Gly
145                 150                 155                 160

His Tyr Leu Tyr Glu Val Ser Arg Arg His Pro Tyr Phe Tyr Ala Pro
                165                 170                 175

Glu Leu Leu Tyr Tyr Ala Glu Lys Tyr Lys Asn Ala Leu Thr Glu Cys
            180                 185                 190

Cys Glu Ala Ala Asp Lys Ala Ala Cys Leu Thr Pro Lys Leu Asp Ala
        195                 200                 205

Ile Lys Glu Lys Ala Leu Val Ser Ser Ala Gln Gln Arg Leu Lys Cys
    210                 215                 220

Ala Ser Leu Gln Lys Phe Gly Glu Arg Ala Phe Lys Ala Trp Ser Val
225                 230                 235                 240

Ala Arg Leu Ser Gln Lys Phe Pro Lys Ala Glu Phe Ala Glu Ile Ser
                245                 250                 255

Thr Ile Val Thr Ser Leu Thr Lys Val Thr Lys Glu Cys Cys His Gly
            260                 265                 270

Asp Leu Leu Glu Cys Ala Asp Asp Arg Gln Glu Leu Ala Lys Tyr Met
        275                 280                 285
```

```
Cys Glu His Gln Asp Ser Ile Ser Ser Lys Leu Lys Glu Cys Cys Val
        290                 295                 300

Lys Pro Thr Leu Gln Lys Ala His Cys Ile Leu Glu Ile Gln Arg Asp
305                 310                 315                 320

Glu Leu Pro Thr Glu Leu Pro Asp Leu Ala Val Asp Phe Val Glu Asp
                325                 330                 335

Lys Glu Val Cys Lys Asn Phe Ala Glu Ala Lys Asp Val Phe Leu Gly
            340                 345                 350

Thr Phe Leu Tyr Glu Tyr Ser Arg Arg His Pro Glu Tyr Ser Ile Gly
        355                 360                 365

Met Leu Leu Arg Ile Ala Lys Gly Tyr Glu Ala Lys Leu Glu Lys Cys
370                 375                 380

Cys Ala Glu Ala Asp Pro His Ala Cys Tyr Ala Lys Val Phe Asp Glu
385                 390                 395                 400

Leu Gln Pro Leu Ile Asp Glu Pro Lys Lys Leu Val Gln Gln Asn Cys
                405                 410                 415

Glu Leu Phe Asp Lys Leu Gly Glu Tyr Gly Phe Gln Asn Ala Leu Ala
            420                 425                 430

Val Arg Tyr Thr Gln Lys Ala Pro Gln Val Ser Thr Pro Thr Leu Val
        435                 440                 445

Glu Tyr Ala Arg Lys Leu Gly Ser Val Gly Thr Lys Cys Cys Ser Leu
450                 455                 460

Pro Glu Thr Glu Arg Leu Ser Cys Thr Glu Asn Tyr Leu Ala Leu Ile
465                 470                 475                 480

Leu Asn Arg Leu Cys Ile Leu His Glu Lys Thr Pro Val Ser Glu Arg
                485                 490                 495

Val Thr Lys Cys Cys Thr Glu Ser Leu Val Asn Arg Arg Pro Cys Phe
            500                 505                 510

Ser Ala Leu His Val Asp Glu Thr Tyr Val Pro Lys Pro Phe His Ala
        515                 520                 525

Asp Ser Phe Thr Phe His Ala Asp Ile Cys Thr Leu Pro Glu Lys Glu
530                 535                 540

Lys Gln Val Lys Gln Met Ala Leu Val Glu Leu Val Lys His Lys
545                 550                 555                 560

Pro Lys Ala Ser Glu Glu Gln Met Lys Thr Val Met Gly Asp Phe Ala
                565                 570                 575

Ala Phe Leu Lys Lys Cys Cys Asp Ala Asp Asn Lys Glu Ala Cys Phe
            580                 585                 590

Thr Glu Asp Gly Pro Lys Leu Val Ala Lys Cys Gln Ala Thr Leu Ala
        595                 600                 605

<210> SEQ ID NO 8
<211> LENGTH: 608
<212> TYPE: PRT
<213> ORGANISM: Mus musculus

<400> SEQUENCE: 8

Met Lys Trp Val Thr Phe Leu Leu Leu Leu Phe Val Ser Gly Ser Ala
1               5                   10                  15

Phe Ser Arg Gly Val Phe Arg Arg Glu Ala His Lys Ser Glu Ile Ala
            20                  25                  30

His Arg Tyr Asn Asp Leu Gly Glu Gln His Phe Lys Gly Leu Val Leu
        35                  40                  45
```

```
Ile Ala Phe Ser Gln Tyr Leu Gln Lys Cys Ser Tyr Asp Glu His Ala
 50                  55                  60
Lys Leu Val Gln Glu Val Thr Asp Phe Ala Lys Thr Cys Val Ala Asp
 65                  70                  75                  80
Glu Ser Ala Ala Asn Cys Asp Lys Ser Leu His Thr Leu Phe Gly Asp
                 85                  90                  95
Lys Leu Cys Ala Ile Pro Asn Leu Arg Glu Asn Tyr Gly Glu Leu Ala
             100                 105                 110
Asp Cys Cys Thr Lys Gln Glu Pro Glu Arg Asn Glu Cys Phe Leu Gln
         115                 120                 125
His Lys Asp Asp Asn Pro Ser Leu Pro Pro Phe Glu Arg Pro Glu Ala
 130                 135                 140
Glu Ala Met Cys Thr Ser Phe Lys Glu Asn Pro Thr Thr Phe Met Gly
145                 150                 155                 160
His Tyr Leu His Glu Val Ala Arg Arg His Pro Tyr Phe Tyr Ala Pro
                165                 170                 175
Glu Leu Leu Tyr Tyr Ala Glu Gln Tyr Asn Glu Ile Leu Thr Gln Cys
            180                 185                 190
Cys Ala Glu Ala Asp Lys Glu Ser Cys Leu Thr Pro Lys Leu Asp Gly
        195                 200                 205
Val Lys Glu Lys Ala Leu Val Ser Ser Val Arg Gln Arg Met Lys Cys
 210                215                 220
Ser Ser Met Gln Lys Phe Gly Glu Arg Ala Phe Lys Ala Trp Ala Val
225                 230                 235                 240
Ala Arg Leu Ser Gln Thr Phe Pro Asn Ala Asp Phe Ala Glu Ile Thr
                245                 250                 255
Lys Leu Ala Thr Asp Leu Thr Lys Val Asn Lys Glu Cys Cys His Gly
            260                 265                 270
Asp Leu Leu Glu Cys Ala Asp Asp Arg Ala Glu Leu Ala Lys Tyr Met
        275                 280                 285
Cys Glu Asn Gln Ala Thr Ile Ser Ser Lys Leu Gln Thr Cys Cys Asp
        290                 295                 300
Lys Pro Leu Leu Lys Lys Ala His Cys Leu Ser Glu Val Glu His Asp
305                 310                 315                 320
Thr Met Pro Ala Asp Leu Pro Ala Ile Ala Ala Asp Phe Val Glu Asp
                325                 330                 335
Gln Glu Val Cys Lys Asn Tyr Ala Glu Ala Lys Asp Val Phe Leu Gly
            340                 345                 350
Thr Phe Leu Tyr Glu Tyr Ser Arg Arg His Pro Asp Tyr Ser Val Ser
        355                 360                 365
Leu Leu Leu Arg Leu Ala Lys Lys Tyr Glu Ala Thr Leu Glu Lys Cys
    370                 375                 380
Cys Ala Glu Ala Asn Pro Pro Ala Cys Tyr Gly Thr Val Leu Ala Glu
385                 390                 395                 400
Phe Gln Pro Leu Val Glu Glu Pro Lys Asn Leu Val Lys Thr Asn Cys
                405                 410                 415
Asp Leu Tyr Glu Lys Leu Gly Glu Tyr Gly Phe Gln Asn Ala Ile Leu
            420                 425                 430
Val Arg Tyr Thr Gln Lys Ala Pro Gln Val Ser Thr Pro Thr Leu Val
        435                 440                 445
Glu Ala Ala Arg Asn Leu Gly Arg Val Gly Thr Lys Cys Cys Thr Leu
450                 455                 460
```

```
Pro Glu Asp Gln Arg Leu Pro Cys Val Glu Asp Tyr Leu Ser Ala Ile
465                 470                 475                 480

Leu Asn Arg Val Cys Leu Leu His Glu Lys Thr Pro Val Ser Glu His
            485                 490                 495

Val Thr Lys Cys Cys Ser Gly Ser Leu Val Glu Arg Arg Pro Cys Phe
        500                 505                 510

Ser Ala Leu Thr Val Asp Glu Thr Tyr Val Pro Lys Glu Phe Lys Ala
            515                 520                 525

Glu Thr Phe Thr Phe His Ser Asp Ile Cys Thr Leu Pro Glu Lys Glu
        530                 535                 540

Lys Gln Ile Lys Lys Gln Thr Ala Leu Ala Glu Leu Val Lys His Lys
545                 550                 555                 560

Pro Lys Ala Thr Ala Glu Gln Leu Lys Thr Val Met Asp Asp Phe Ala
            565                 570                 575

Gln Phe Leu Asp Thr Cys Cys Lys Ala Ala Asp Lys Asp Thr Cys Phe
        580                 585                 590

Ser Thr Glu Gly Pro Asn Leu Val Thr Arg Cys Lys Asp Ala Leu Ala
            595                 600                 605

<210> SEQ ID NO 9
<211> LENGTH: 608
<212> TYPE: PRT
<213> ORGANISM: Rattus norvegicus

<400> SEQUENCE: 9

Met Lys Trp Val Thr Phe Leu Leu Leu Leu Phe Ile Ser Gly Ser Ala
1               5                   10                  15

Phe Ser Arg Gly Val Phe Arg Arg Glu Ala His Lys Ser Glu Ile Ala
            20                  25                  30

His Arg Phe Lys Asp Leu Gly Glu Gln His Phe Lys Gly Leu Val Leu
        35                  40                  45

Ile Ala Phe Ser Gln Tyr Leu Gln Lys Cys Pro Tyr Glu Glu His Ile
    50                  55                  60

Lys Leu Val Gln Glu Val Thr Asp Phe Ala Lys Thr Cys Val Ala Asp
65                  70                  75                  80

Glu Asn Ala Glu Asn Cys Asp Lys Ser Ile His Thr Leu Phe Gly Asp
                85                  90                  95

Lys Leu Cys Ala Ile Pro Lys Leu Arg Asp Asn Tyr Gly Glu Leu Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Pro Phe Gln Arg Pro Glu Ala
    130                 135                 140

Glu Ala Met Cys Thr Ser Phe Gln Glu Asn Pro Thr Ser Phe Leu Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Lys Tyr Asn Glu Val Leu Thr Gln Cys
            180                 185                 190

Cys Thr Glu Ser Asp Lys Ala Ala Cys Leu Thr Pro Lys Leu Asp Ala
        195                 200                 205

Val Lys Glu Lys Ala Leu Val Ala Ala Val Arg Gln Arg Met Lys Cys
    210                 215                 220

Ser Ser Met Gln Arg Phe Gly Glu Arg Ala Phe Lys Ala Trp Ala Val
225                 230                 235                 240
```

```
Ala Arg Met Ser Gln Arg Phe Pro Asn Ala Glu Phe Ala Glu Ile Thr
            245                 250                 255

Lys Leu Ala Thr Asp Val Thr Lys Ile Asn Lys Glu Cys Cys His Gly
        260                 265                 270

Asp Leu Leu Glu Cys Ala Asp Asp Arg Ala Glu Leu Ala Lys Tyr Met
    275                 280                 285

Cys Glu Asn Gln Ala Thr Ile Ser Ser Lys Leu Gln Ala Cys Cys Asp
290                 295                 300

Lys Pro Val Leu Gln Lys Ser Gln Cys Leu Ala Glu Ile Glu His Asp
305                 310                 315                 320

Asn Ile Pro Ala Asp Leu Pro Ser Ile Ala Ala Asp Phe Val Glu Asp
                325                 330                 335

Lys Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
        355                 360                 365

Leu Leu Leu Arg Leu Ala Lys Lys Tyr Glu Ala Thr Leu Glu Lys Cys
370                 375                 380

Cys Ala Glu Gly Asp Pro Pro Ala Cys Tyr Gly Thr Val Leu Ala Glu
385                 390                 395                 400

Phe Gln Pro Leu Val Glu Pro Lys Asn Leu Val Lys Thr Asn Cys
                405                 410                 415

Glu Leu Tyr Glu Lys Leu Gly Glu Tyr Gly Phe Gln Asn Ala Val Leu
            420                 425                 430

Val Arg Tyr Thr Gln Lys Ala Pro Gln Val Ser Thr Pro Thr Leu Val
        435                 440                 445

Glu Ala Ala Arg Asn Leu Gly Arg Val Gly Thr Lys Cys Cys Thr Leu
450                 455                 460

Pro Glu Ala Gln Arg Leu Pro Cys Val Glu Asp Tyr Leu Ser Ala Ile
465                 470                 475                 480

Leu Asn Arg Leu Cys Val Leu His Glu Lys Thr Pro Val Ser Glu Lys
                485                 490                 495

Val Thr Lys Cys Cys Ser Gly Ser Leu Val Glu Arg Arg Pro Cys Phe
            500                 505                 510

Ser Ala Leu Thr Val Asp Glu Thr Tyr Val Pro Lys Glu Phe Lys Ala
        515                 520                 525

Glu Thr Phe Thr Phe His Ser Asp Ile Cys Thr Leu Pro Asp Lys Glu
    530                 535                 540

Lys Gln Ile Lys Lys Gln Thr Ala Leu Ala Glu Leu Val Lys His Lys
545                 550                 555                 560

Pro Lys Ala Thr Glu Asp Gln Leu Lys Thr Val Met Gly Asp Phe Ala
                565                 570                 575

Gln Phe Val Asp Lys Cys Cys Lys Ala Ala Asp Lys Asp Asn Cys Phe
            580                 585                 590

Ala Thr Glu Gly Pro Asn Leu Val Ala Arg Ser Lys Glu Ala Leu Ala
        595                 600                 605

<210> SEQ ID NO 10
<211> LENGTH: 607
<212> TYPE: PRT
<213> ORGANISM: Bos taurus
```

<400> SEQUENCE: 10

```
Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
        35                  40                  45

Ile Ala Phe Ser Gln Tyr Leu Gln Gln Cys Pro Phe Asp Glu His Val
    50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
        115                 120                 125

His Lys Asp Asp Ser Pro Asp Leu Pro Lys Leu Lys Pro Asp Pro Asn
    130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
        195                 200                 205

Arg Glu Lys Val Leu Ala Ser Ser Ala Arg Gln Arg Leu Arg Cys Ala
    210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
                245                 250                 255

Leu Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Asp Asn Gln Asp Thr Ile Ser Ser Lys Leu Lys Glu Cys Cys Asp Lys
    290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
                325                 330                 335

Asp Val Cys Lys Asn Tyr Gln Glu Ala Lys Asp Ala Phe Leu Gly Ser
            340                 345                 350

Phe Leu Tyr Glu Tyr Ser Arg Arg His Pro Glu Tyr Ala Val Ser Val
        355                 360                 365

Leu Leu Arg Leu Ala Lys Glu Tyr Glu Ala Thr Leu Glu Glu Cys Cys
    370                 375                 380

Ala Lys Asp Asp Pro His Ala Cys Tyr Ser Thr Val Phe Asp Lys Leu
385                 390                 395                 400
```

```
Lys His Leu Val Asp Glu Pro Gln Asn Leu Ile Lys Gln Asn Cys Asp
                405                 410                 415

Gln Phe Glu Lys Leu Gly Glu Tyr Gly Phe Gln Asn Ala Leu Ile Val
                420                 425                 430

Arg Tyr Thr Arg Lys Val Pro Gln Val Ser Thr Pro Thr Leu Val Glu
                435                 440                 445

Val Ser Arg Ser Leu Gly Lys Val Gly Thr Arg Cys Cys Thr Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
                500                 505                 510

Ala Leu Thr Pro Asp Glu Thr Tyr Val Pro Lys Ala Phe Asp Glu Lys
                515                 520                 525

Leu Phe Thr Phe His Ala Asp Ile Cys Thr Leu Pro Asp Thr Glu Lys
            530                 535                 540

Gln Ile Lys Lys Gln Thr Ala Leu Val Glu Leu Leu Lys His Lys Pro
545                 550                 555                 560

Lys Ala Thr Glu Glu Gln Leu Lys Thr Val Met Glu Asn Phe Val Ala
                565                 570                 575

Phe Val Asp Lys Cys Cys Ala Ala Asp Lys Glu Ala Cys Phe Ala
                580                 585                 590

Val Glu Gly Pro Lys Leu Val Val Ser Thr Gln Thr Ala Leu Ala
                595                 600                 605

<210> SEQ ID NO 11
<211> LENGTH: 607
<212> TYPE: PRT
<213> ORGANISM: Equus caballus

<400> SEQUENCE: 11

Met Lys Trp Val Thr Phe Val Ser Leu Leu Phe Leu Phe Ser Ser Ala
1               5                   10                  15

Tyr Ser Arg Gly Val Leu Arg Arg Asp Thr His Lys Ser Glu Ile Ala
                20                  25                  30

His Arg Phe Asn Asp Leu Gly Glu Lys His Phe Lys Gly Leu Val Leu
            35                  40                  45

Val Ala Phe Ser Gln Tyr Leu Gln Gln Cys Pro Phe Glu Asp His Val
50                  55                  60

Lys Leu Val Asn Glu Val Thr Glu Phe Ala Lys Lys Cys Ala Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Ala Thr Tyr Gly Glu Leu Ala
                100                 105                 110

Asp Cys Cys Glu Lys Gln Glu Pro Glu Arg Asn Glu Cys Phe Leu Thr
            115                 120                 125

His Lys Asp Asp His Pro Asn Leu Pro Lys Leu Lys Pro Glu Pro Asp
130                 135                 140

Ala Gln Cys Ala Ala Phe Gln Glu Asp Pro Asp Lys Phe Leu Gly Lys
145                 150                 155                 160
```

```
Tyr Leu Tyr Glu Val Ala Arg Arg His Pro Tyr Phe Tyr Gly Pro Glu
                165                 170                 175

Leu Leu Phe His Ala Glu Glu Tyr Lys Ala Asp Phe Thr Glu Cys Cys
            180                 185                 190

Pro Ala Asp Asp Lys Leu Ala Cys Leu Ile Pro Lys Leu Asp Ala Leu
        195                 200                 205

Lys Glu Arg Ile Leu Leu Ser Ser Ala Lys Glu Arg Leu Lys Cys Ser
    210                 215                 220

Ser Phe Gln Asn Phe Gly Glu Arg Ala Val Lys Ala Trp Ser Val Ala
225                 230                 235                 240

Arg Leu Ser Gln Lys Phe Pro Lys Ala Asp Phe Ala Glu Val Ser Lys
                245                 250                 255

Ile Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Glu His Gln Asp Ser Ile Ser Gly Lys Leu Lys Ala Cys Cys Asp Lys
    290                 295                 300

Pro Leu Leu Gln Lys Ser His Cys Ile Ala Glu Val Lys Glu Asp Asp
305                 310                 315                 320

Leu Pro Ser Asp Leu Pro Ala Leu Ala Ala Asp Phe Ala Glu Asp Lys
                325                 330                 335

Glu Ile Cys Lys His Tyr Lys Asp Ala Lys Asp Val Phe Leu Gly Thr
            340                 345                 350

Phe Leu Tyr Glu Tyr Ser Arg Arg His Pro Asp Tyr Ser Val Ser Leu
        355                 360                 365

Leu Leu Arg Ile Ala Lys Thr Tyr Glu Ala Thr Leu Glu Lys Cys Cys
    370                 375                 380

Ala Glu Ala Asp Pro Pro Ala Cys Tyr Arg Thr Val Phe Asp Gln Phe
385                 390                 395                 400

Thr Pro Leu Val Glu Glu Pro Lys Ser Leu Val Lys Lys Asn Cys Asp
                405                 410                 415

Leu Phe Glu Glu Val Gly Glu Tyr Asp Phe Gln Asn Ala Leu Ile Val
            420                 425                 430

Arg Tyr Thr Lys Lys Ala Pro Gln Val Ser Thr Pro Thr Leu Val Glu
        435                 440                 445

Ile Gly Arg Thr Leu Gly Lys Val Gly Ser Arg Cys Cys Lys Leu Pro
    450                 455                 460

Glu Ser Glu Arg Leu Pro Cys Ser Glu Asn His Leu Ala Leu Ala Leu
465                 470                 475                 480

Asn Arg Leu Cys Val Leu His Glu Lys Thr Pro Val Ser Glu Lys Ile
                485                 490                 495

Thr Lys Cys Cys Thr Asp Ser Leu Ala Glu Arg Arg Pro Cys Phe Ser
            500                 505                 510

Ala Leu Glu Leu Asp Glu Gly Tyr Val Pro Lys Glu Phe Lys Ala Glu
        515                 520                 525

Thr Phe Thr Phe His Ala Asp Ile Cys Thr Leu Pro Glu Asp Glu Lys
    530                 535                 540

Gln Ile Lys Lys Gln Ser Ala Leu Ala Glu Leu Val Lys His Lys Pro
545                 550                 555                 560

Lys Ala Thr Lys Glu Gln Leu Lys Thr Val Leu Gly Asn Phe Ser Ala
                565                 570                 575
```

-continued

```
Phe Val Ala Lys Cys Cys Gly Arg Glu Asp Lys Glu Ala Cys Phe Ala
                580                 585                 590

Glu Glu Gly Pro Lys Leu Val Ala Ser Ser Gln Leu Ala Leu Ala
            595                 600                 605

<210> SEQ ID NO 12
<211> LENGTH: 607
<212> TYPE: PRT
<213> ORGANISM: Equus asinus

<400> SEQUENCE: 12

Met Lys Trp Val Thr Phe Val Ser Leu Leu Phe Leu Phe Ser Ser Ala
1               5                   10                  15

Tyr Phe Arg Gly Val Leu Arg Arg Asp Thr His Lys Ser Glu Ile Ala
            20                  25                  30

His Arg Phe Asn Asp Leu Gly Glu Lys His Phe Lys Gly Leu Val Leu
        35                  40                  45

Val Ala Phe Ser Gln Tyr Leu Gln Gln Cys Pro Phe Glu Asp His Val
    50                  55                  60

Lys Leu Val Asn Glu Val Thr Glu Phe Ala Lys Lys Cys Ala Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Ala Thr Tyr Gly Glu Leu Ala
            100                 105                 110

Asp Cys Cys Glu Lys Gln Glu Pro Glu Arg Asn Glu Cys Phe Leu Thr
        115                 120                 125

His Lys Asp Asp His Pro Asn Leu Pro Lys Leu Lys Pro Glu Pro Asp
    130                 135                 140

Ala Gln Cys Ala Ala Phe Gln Glu Asp Pro Asp Lys Phe Leu Gly Lys
145                 150                 155                 160

Tyr Leu Tyr Glu Val Ala Arg Arg His Pro Tyr Phe Tyr Gly Pro Glu
                165                 170                 175

Leu Leu Phe His Ala Glu Glu Tyr Lys Ala Asp Phe Thr Glu Cys Cys
            180                 185                 190

Pro Ala Asp Asp Lys Ala Gly Cys Leu Ile Pro Lys Leu Asp Ala Leu
        195                 200                 205

Lys Glu Arg Ile Leu Leu Ser Ser Ala Lys Glu Arg Leu Lys Cys Ser
    210                 215                 220

Ser Phe Gln Lys Phe Gly Glu Arg Ala Phe Lys Ala Trp Ser Val Ala
225                 230                 235                 240

Arg Leu Ser Gln Lys Phe Pro Lys Ala Asp Phe Ala Glu Val Ser Lys
                245                 250                 255

Ile Val Thr Asp Leu Thr Lys Val His Lys Glu Cys Cys His Gly Asp
            260                 265                 270

Leu Leu Glu Cys Ala Asp Asp Arg Ala Asp Leu Thr Lys Tyr Ile Cys
        275                 280                 285

Glu His Gln Asp Ser Ile Ser Gly Lys Leu Lys Ala Cys Cys Asp Lys
    290                 295                 300

Pro Leu Leu Gln Lys Ser His Cys Ile Ala Glu Val Lys Glu Asp Asp
305                 310                 315                 320

Leu Pro Ser Asp Leu Pro Ala Leu Ala Ala Asp Phe Ala Glu Asp Lys
                325                 330                 335

Glu Ile Cys Lys His Tyr Lys Asp Ala Lys Asp Val Phe Leu Gly Thr
            340                 345                 350
```

```
Phe Leu Tyr Glu Tyr Ser Arg Arg His Pro Asp Tyr Ser Val Ser Leu
            355                 360                 365

Leu Leu Arg Ile Ala Lys Thr Tyr Glu Ala Thr Leu Glu Lys Cys Cys
        370                 375                 380

Ala Glu Ala Asp Pro Pro Ala Cys Tyr Ala Thr Val Phe Asp Gln Phe
385                 390                 395                 400

Thr Pro Leu Val Glu Glu Pro Lys Ser Leu Val Lys Lys Asn Cys Asp
                405                 410                 415

Leu Phe Glu Glu Val Gly Glu Tyr Asp Phe Gln Asn Ala Leu Ile Val
            420                 425                 430

Arg Tyr Thr Lys Lys Ala Pro Gln Val Ser Thr Pro Thr Leu Val Glu
        435                 440                 445

Ile Gly Arg Thr Leu Gly Lys Val Gly Ser Arg Cys Cys Lys Leu Pro
    450                 455                 460

Glu Ser Glu Arg Leu Pro Cys Ser Glu Asn His Leu Ala Leu Ala Leu
465                 470                 475                 480

Asn Arg Leu Cys Val Leu His Glu Lys Thr Pro Val Ser Glu Lys Ile
                485                 490                 495

Thr Lys Cys Cys Thr Asp Ser Leu Ala Glu Arg Arg Pro Cys Phe Ser
            500                 505                 510

Ala Leu Glu Leu Asp Glu Gly Tyr Ile Pro Lys Glu Phe Lys Ala Glu
        515                 520                 525

Thr Phe Thr Phe His Ala Asp Ile Cys Thr Leu Pro Glu Asp Glu Lys
    530                 535                 540

Gln Ile Lys Lys Gln Ser Ala Leu Ala Glu Leu Val Lys His Lys Pro
545                 550                 555                 560

Lys Ala Thr Lys Glu Gln Leu Lys Thr Val Leu Gly Asn Phe Ser Ala
                565                 570                 575

Phe Val Ala Lys Cys Cys Gly Ala Glu Asp Lys Glu Ala Cys Phe Ala
            580                 585                 590

Glu Glu Gly Pro Lys Leu Val Ala Ser Ser Gln Leu Ala Leu Ala
        595                 600                 605

<210> SEQ ID NO 13
<211> LENGTH: 608
<212> TYPE: PRT
<213> ORGANISM: Oryctolagus cuniculus

<400> SEQUENCE: 13

Met Lys Trp Val Thr Phe Ile Ser Leu Leu Phe Leu Phe Ser Ser Ala
1               5                   10                  15

Tyr Ser Arg Gly Val Phe Arg Arg Glu Ala His Lys Ser Glu Ile Ala
            20                  25                  30

His Arg Phe Asn Asp Val Gly Glu Glu His Phe Ile Gly Leu Val Leu
        35                  40                  45

Ile Thr Phe Ser Gln Tyr Leu Gln Lys Cys Pro Tyr Glu Glu His Ala
    50                  55                  60

Lys Leu Val Lys Glu Val Thr Asp Leu Ala Lys Ala Cys Val Ala Asp
65                  70                  75                  80

Glu Ser Ala Ala Asn Cys Asp Lys Ser Leu His Asp Ile Phe Gly Asp
                85                  90                  95

Lys Ile Cys Ala Leu Pro Ser Leu Arg Asp Thr Tyr Gly Asp Val Ala
            100                 105                 110
```

```
Asp Cys Cys Glu Lys Lys Pro Glu Arg Asn Glu Cys Phe Leu His
        115                 120                 125

His Lys Asp Asp Lys Pro Asp Leu Pro Pro Phe Ala Arg Pro Glu Ala
130                 135                 140

Asp Val Leu Cys Lys Ala Phe His Asp Glu Lys Ala Phe Phe Gly
145                 150                 155                 160

His Tyr Leu Tyr Glu Val Ala Arg Arg His Pro Tyr Phe Tyr Ala Pro
                165                 170                 175

Glu Leu Leu Tyr Tyr Ala Gln Lys Tyr Lys Ala Ile Leu Thr Glu Cys
                180                 185                 190

Cys Glu Ala Ala Asp Lys Gly Ala Cys Leu Thr Pro Lys Leu Asp Ala
                195                 200                 205

Leu Glu Gly Lys Ser Leu Ile Ser Ala Ala Gln Glu Arg Leu Arg Cys
210                 215                 220

Ala Ser Ile Gln Lys Phe Gly Asp Arg Ala Tyr Lys Ala Trp Ala Leu
225                 230                 235                 240

Val Arg Leu Ser Gln Arg Phe Pro Lys Ala Asp Phe Thr Asp Ile Ser
                245                 250                 255

Lys Ile Val Thr Asp Leu Thr Lys Val His Lys Glu Cys Cys His Gly
                260                 265                 270

Asp Leu Leu Glu Cys Ala Asp Asp Arg Ala Asp Leu Ala Lys Tyr Met
                275                 280                 285

Cys Glu His Gln Glu Thr Ile Ser Ser His Leu Lys Glu Cys Cys Asp
                290                 295                 300

Lys Pro Ile Leu Glu Lys Ala His Cys Ile Tyr Gly Leu His Asn Asp
305                 310                 315                 320

Glu Thr Pro Ala Gly Leu Pro Ala Val Ala Glu Glu Phe Val Glu Asp
                325                 330                 335

Lys Asp Val Cys Lys Asn Tyr Glu Glu Ala Lys Asp Leu Phe Leu Gly
                340                 345                 350

Lys Phe Leu Tyr Glu Tyr Ser Arg Arg His Pro Asp Tyr Ser Val Val
                355                 360                 365

Leu Leu Leu Arg Leu Gly Lys Ala Tyr Glu Ala Thr Leu Lys Lys Cys
                370                 375                 380

Cys Ala Thr Asp Asp Pro His Ala Cys Tyr Ala Lys Val Leu Asp Glu
385                 390                 395                 400

Phe Gln Pro Leu Val Asp Glu Pro Lys Asn Leu Val Lys Gln Asn Cys
                405                 410                 415

Glu Leu Tyr Glu Gln Leu Gly Asp Tyr Asn Phe Gln Asn Ala Leu Leu
                420                 425                 430

Val Arg Tyr Thr Lys Lys Val Pro Gln Val Ser Thr Pro Thr Leu Val
                435                 440                 445

Glu Ile Ser Arg Ser Leu Gly Lys Val Gly Ser Lys Cys Cys Lys His
                450                 455                 460

Pro Glu Ala Glu Arg Leu Pro Cys Val Glu Asp Tyr Leu Ser Val Val
465                 470                 475                 480

Leu Asn Arg Leu Cys Val Leu His Glu Lys Thr Pro Val Ser Glu Lys
                485                 490                 495

Val Thr Lys Cys Cys Ser Glu Ser Leu Val Asp Arg Arg Pro Cys Phe
                500                 505                 510

Ser Ala Leu Gly Pro Asp Glu Thr Tyr Val Pro Lys Glu Phe Asn Ala
                515                 520                 525
```

```
Glu Thr Phe Thr Phe His Ala Asp Ile Cys Thr Leu Pro Glu Thr Glu
        530                 535                 540

Arg Lys Ile Lys Lys Gln Thr Ala Leu Val Glu Leu Val Lys His Lys
545                 550                 555                 560

Pro His Ala Thr Asn Asp Gln Leu Lys Thr Val Val Gly Glu Phe Thr
                565                 570                 575

Ala Leu Leu Asp Lys Cys Cys Ser Ala Glu Asp Lys Glu Ala Cys Phe
                580                 585                 590

Ala Val Glu Gly Pro Lys Leu Val Glu Ser Ser Lys Ala Thr Leu Gly
        595                 600                 605

<210> SEQ ID NO 14
<211> LENGTH: 583
<212> TYPE: PRT
<213> ORGANISM: Capra hircus

<400> SEQUENCE: 14

Asp Thr His Lys Ser Glu Ile Ala His Arg Phe Asn Asp Leu Gly Glu
1               5                   10                  15

Glu Asn Phe Gln Gly Leu Val Leu Ile Ala Phe Ser Gln Tyr Leu Gln
                20                  25                  30

Gln Cys Pro Phe Asp Glu His Val Lys Leu Val Lys Glu Leu Thr Glu
            35                  40                  45

Phe Ala Lys Thr Cys Val Ala Asp Glu Ser His Ala Gly Cys Asp Lys
    50                  55                  60

Ser Leu His Thr Leu Phe Gly Asp Glu Leu Cys Lys Val Ala Thr Leu
65                  70                  75                  80

Arg Glu Thr Tyr Gly Asp Met Ala Asp Cys Cys Glu Lys Gln Glu Pro
                85                  90                  95

Glu Arg Asn Glu Cys Phe Leu Lys His Lys Asp Asp Ser Pro Asp Leu
            100                 105                 110

Pro Lys Leu Lys Pro Glu Pro Asp Thr Leu Cys Ala Glu Phe Lys Ala
        115                 120                 125

Asp Glu Lys Lys Phe Trp Gly Lys Tyr Leu Tyr Glu Val Ala Arg Arg
    130                 135                 140

His Pro Tyr Phe Tyr Ala Pro Glu Leu Leu Tyr Tyr Ala Asn Lys Tyr
145                 150                 155                 160

Asn Gly Val Phe Gln Glu Cys Cys Gln Ala Glu Asp Lys Gly Ala Cys
                165                 170                 175

Leu Leu Pro Lys Ile Glu Thr Met Arg Glu Lys Val Leu Ala Ser Ser
            180                 185                 190

Ala Arg Gln Arg Leu Arg Cys Ala Ser Ile Gln Lys Phe Gly Glu Arg
        195                 200                 205

Ala Leu Lys Ala Trp Ser Val Ala Arg Leu Ser Gln Lys Phe Pro Lys
    210                 215                 220

Ala Asp Phe Thr Asp Val Thr Lys Ile Val Thr Asp Leu Thr Lys Val
225                 230                 235                 240

His Lys Glu Cys Cys His Gly Asp Leu Leu Glu Cys Ala Asp Asp Arg
                245                 250                 255

Ala Asp Leu Ala Lys Tyr Ile Cys Asp His Gln Asp Thr Leu Ser Ser
            260                 265                 270

Lys Leu Lys Glu Cys Cys Asp Lys Pro Val Leu Glu Lys Ser His Cys
        275                 280                 285

Ile Ala Glu Ile Asp Lys Asp Ala Val Pro Glu Asn Leu Pro Pro Leu
    290                 295                 300
```

```
Thr Ala Asp Phe Ala Glu Asp Lys Glu Val Cys Lys Asn Tyr Gln Glu
305                 310                 315                 320

Ala Lys Asp Val Phe Leu Gly Ser Phe Leu Tyr Glu Tyr Ser Arg Arg
                325                 330                 335

His Pro Glu Tyr Ala Val Ser Val Leu Leu Arg Leu Ala Lys Glu Tyr
            340                 345                 350

Glu Ala Thr Leu Glu Asp Cys Cys Ala Lys Glu Asp Pro His Ala Cys
        355                 360                 365

Tyr Ala Thr Val Phe Asp Lys Leu Lys His Leu Val Asp Glu Pro Gln
370                 375                 380

Asn Leu Ile Lys Lys Asn Cys Glu Leu Phe Glu Lys His Gly Glu Tyr
385                 390                 395                 400

Gly Phe Gln Asn Ala Leu Ile Val Arg Tyr Thr Arg Lys Ala Pro Gln
                405                 410                 415

Val Ser Thr Pro Thr Leu Val Glu Ile Ser Arg Ser Leu Gly Lys Val
                420                 425                 430

Gly Thr Lys Cys Cys Ala Lys Pro Glu Ser Glu Arg Met Pro Cys Thr
            435                 440                 445

Glu Asp Tyr Leu Ser Leu Ile Leu Asn Arg Leu Cys Val Leu His Glu
        450                 455                 460

Lys Thr Pro Val Ser Glu Lys Val Thr Lys Cys Cys Thr Glu Ser Leu
465                 470                 475                 480

Val Asn Arg Arg Pro Cys Phe Ser Asp Leu Thr Leu Asp Glu Thr Tyr
                485                 490                 495

Val Pro Lys Pro Phe Asp Gly Glu Ser Phe Thr Phe His Ala Asp Ile
                500                 505                 510

Cys Thr Leu Pro Asp Thr Glu Lys Gln Ile Lys Lys Gln Thr Ala Leu
            515                 520                 525

Val Glu Leu Leu Lys His Lys Pro Lys Ala Thr Asp Glu Gln Leu Lys
        530                 535                 540

Thr Val Met Glu Asn Phe Val Ala Phe Val Asp Lys Cys Cys Ala Ala
545                 550                 555                 560

Asp Asp Lys Glu Gly Cys Phe Leu Leu Glu Gly Pro Lys Leu Val Ala
                565                 570                 575

Ser Thr Gln Ala Ala Leu Ala
            580

<210> SEQ ID NO 15
<211> LENGTH: 607
<212> TYPE: PRT
<213> ORGANISM: Ovis aries

<400> SEQUENCE: 15

Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
                20                  25                  30

His Arg Phe Asn Asp Leu Gly Glu Glu Asn Phe Gln Gly Leu Val Leu
            35                  40                  45

Ile Ala Phe Ser Gln Tyr Leu Gln Gln Cys Pro Phe Asp Glu His Val
        50                  55                  60

Lys Leu Val Lys Glu Leu Thr Glu Phe Ala Lys Thr Cys Val Ala Asp
65                  70                  75                  80
```

```
Glu Ser His Ala Gly Cys Asp Lys Ser Leu His Thr Leu Phe Gly Asp
                85                  90                  95

Glu Leu Cys Lys Val Ala Thr Leu Arg Glu Thr Tyr Gly Asp Met Ala
                100                 105                 110

Asp Cys Cys Glu Lys Gln Glu Pro Glu Arg Asn Glu Cys Phe Leu Asn
                115                 120                 125

His Lys Asp Asp Ser Pro Asp Leu Pro Lys Leu Lys Pro Glu Pro Asp
            130                 135                 140

Thr Leu Cys Ala Glu Phe Lys Ala Asp Glu Lys Lys Phe Trp Gly Lys
145                 150                 155                 160

Tyr Leu Tyr Glu Val Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
                180                 185                 190

Gln Ala Glu Asp Lys Gly Ala Cys Leu Leu Pro Lys Ile Asp Ala Met
                195                 200                 205

Arg Glu Lys Val Leu Ala Ser Ser Ala Arg Gln Arg Leu Arg Cys Ala
                210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Asp Phe Thr Asp Val Thr Lys
                245                 250                 255

Ile Val Thr Asp Leu Thr Lys Val His Lys Glu Cys Cys His Gly Asp
                260                 265                 270

Leu Leu Glu Cys Ala Asp Asp Arg Ala Asp Leu Ala Lys Tyr Ile Cys
                275                 280                 285

Asp His Gln Asp Ala Leu Ser Ser Lys Leu Lys Glu Cys Cys Asp Lys
                290                 295                 300

Pro Val Leu Glu Lys Ser His Cys Ile Ala Glu Val Asp Lys Asp Ala
305                 310                 315                 320

Val Pro Glu Asn Leu Pro Pro Leu Thr Ala Asp Phe Ala Glu Asp Lys
                325                 330                 335

Glu Val Cys Lys Asn Tyr Gln Glu Ala Lys Asp Val Phe Leu Gly Ser
                340                 345                 350

Phe Leu Tyr Glu Tyr Ser Arg Arg His Pro Glu Tyr Ala Val Ser Val
                355                 360                 365

Leu Leu Arg Leu Ala Lys Glu Tyr Glu Ala Thr Leu Glu Asp Cys Cys
                370                 375                 380

Ala Lys Glu Asp Pro His Ala Cys Tyr Ala Thr Val Phe Asp Lys Leu
385                 390                 395                 400

Lys His Leu Val Asp Glu Pro Gln Asn Leu Ile Lys Lys Asn Cys Glu
                405                 410                 415

Leu Phe Glu Lys His Gly Glu Tyr Gly Phe Gln Asn Ala Leu Ile Val
                420                 425                 430

Arg Tyr Thr Arg Lys Ala Pro Gln Val Ser Thr Pro Thr Leu Val Glu
                435                 440                 445

Ile Ser Arg Ser Leu Gly Lys Val Gly Thr Lys Cys Cys Ala Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495
```

```
Thr Lys Cys Cys Thr Glu Ser Leu Val Asn Arg Arg Pro Cys Phe Ser
            500                 505                 510

Asp Leu Thr Leu Asp Glu Thr Tyr Val Pro Lys Pro Phe Asp Glu Lys
            515                 520                 525

Phe Phe Thr Phe His Ala Asp Ile Cys Thr Leu Pro Asp Thr Glu Lys
            530                 535                 540

Gln Ile Lys Lys Gln Thr Ala Leu Val Glu Leu Leu Lys His Lys Pro
545                 550                 555                 560

Lys Ala Thr Asp Glu Gln Leu Lys Thr Val Met Glu Asn Phe Val Ala
            565                 570                 575

Phe Val Asp Lys Cys Cys Ala Ala Asp Asp Lys Glu Gly Cys Phe Val
            580                 585                 590

Leu Glu Gly Pro Lys Leu Val Ala Ser Thr Gln Ala Ala Leu Ala
            595                 600                 605

<210> SEQ ID NO 16
<211> LENGTH: 608
<212> TYPE: PRT
<213> ORGANISM: canis lupus familiaris

<400> SEQUENCE: 16

Met Lys Trp Val Thr Phe Ile Ser Leu Phe Phe Leu Phe Ser Ser Ala
1               5                   10                  15

Tyr Ser Arg Gly Leu Val Arg Arg Glu Ala Tyr Lys Ser Glu Ile Ala
            20                  25                  30

His Arg Tyr Asn Asp Leu Gly Glu Glu His Phe Arg Gly Leu Val Leu
            35                  40                  45

Val Ala Phe Ser Gln Tyr Leu Gln Gln Cys Pro Phe Glu Asp His Val
50                  55                  60

Lys Leu Ala Lys Glu Val Thr Glu Phe Ala Lys Ala Cys Ala Ala Glu
65                  70                  75                  80

Glu Ser Gly Ala Asn Cys Asp Lys Ser Leu His Thr Leu Phe Gly Asp
            85                  90                  95

Lys Leu Cys Thr Val Ala Ser Leu Arg Asp Lys Tyr Gly Asp Met Ala
            100                 105                 110

Asp Cys Cys Glu Lys Gln Glu Pro Asp Arg Asn Glu Cys Phe Leu Ala
            115                 120                 125

His Lys Asp Asp Asn Pro Gly Phe Pro Pro Leu Val Ala Pro Glu Pro
            130                 135                 140

Asp Ala Leu Cys Ala Ala Phe Gln Asp Asn Glu Gln Leu Phe Leu Gly
145                 150                 155                 160

Lys Tyr Leu Tyr Glu Ile Ala Arg Arg His Pro Tyr Phe Tyr Ala Pro
            165                 170                 175

Glu Leu Leu Tyr Tyr Ala Gln Gln Tyr Lys Gly Val Phe Ala Glu Cys
            180                 185                 190

Cys Gln Ala Ala Asp Lys Ala Ala Cys Leu Gly Pro Lys Ile Glu Ala
            195                 200                 205

Leu Arg Glu Lys Val Leu Leu Ser Ser Ala Lys Glu Arg Phe Lys Cys
            210                 215                 220

Ala Ser Leu Gln Lys Phe Gly Asp Arg Ala Phe Lys Ala Trp Ser Val
225                 230                 235                 240

Ala Arg Leu Ser Gln Arg Phe Pro Lys Ala Asp Phe Ala Glu Ile Ser
            245                 250                 255

Lys Val Val Thr Asp Leu Thr Lys Val His Lys Glu Cys Cys His Gly
            260                 265                 270
```

```
Asp Leu Leu Glu Cys Ala Asp Asp Arg Ala Asp Leu Ala Lys Tyr Met
        275                 280                 285

Cys Glu Asn Gln Asp Ser Ile Ser Thr Lys Leu Lys Glu Cys Cys Asp
    290                 295                 300

Lys Pro Val Leu Glu Lys Ser Gln Cys Leu Ala Glu Val Glu Arg Asp
305                 310                 315                 320

Glu Leu Pro Gly Asp Leu Pro Ser Leu Ala Ala Asp Phe Val Glu Asp
                325                 330                 335

Lys Glu Val Cys Lys Asn Tyr Gln Glu Ala Lys Asp Val Phe Leu Gly
            340                 345                 350

Thr Phe Leu Tyr Glu Tyr Ala Arg Arg His Pro Glu Tyr Ser Val Ser
        355                 360                 365

Leu Leu Leu Arg Leu Ala Lys Glu Tyr Glu Ala Thr Leu Glu Lys Cys
    370                 375                 380

Cys Ala Thr Asp Asp Pro Pro Thr Cys Tyr Ala Lys Val Leu Asp Glu
385                 390                 395                 400

Phe Lys Pro Leu Val Asp Glu Pro Gln Asn Leu Val Lys Thr Asn Cys
                405                 410                 415

Glu Leu Phe Glu Lys Leu Gly Glu Tyr Gly Phe Gln Asn Ala Leu Leu
            420                 425                 430

Val Arg Tyr Thr Lys Lys Ala Pro Gln Val Ser Thr Pro Thr Leu Val
        435                 440                 445

Glu Val Ser Arg Lys Leu Gly Lys Val Gly Thr Lys Cys Cys Lys Lys
    450                 455                 460

Pro Glu Ser Glu Arg Met Ser Cys Ala Glu Asp Phe Leu Ser Val Val
465                 470                 475                 480

Leu Asn Arg Leu Cys Val Leu His Glu Lys Thr Pro Val Ser Glu Arg
                485                 490                 495

Val Thr Lys Cys Cys Ser Glu Ser Leu Val Asn Arg Arg Pro Cys Phe
            500                 505                 510

Ser Gly Leu Glu Val Asp Glu Thr Tyr Val Pro Lys Glu Phe Asn Ala
        515                 520                 525

Glu Thr Phe Thr Phe His Ala Asp Leu Cys Thr Leu Pro Glu Ala Glu
    530                 535                 540

Lys Gln Val Lys Lys Gln Thr Ala Leu Val Glu Leu Leu Lys His Lys
545                 550                 555                 560

Pro Lys Ala Thr Asp Glu Gln Leu Lys Thr Val Met Gly Asp Phe Gly
                565                 570                 575

Ala Phe Val Glu Lys Cys Cys Ala Ala Glu Asn Lys Glu Gly Cys Phe
            580                 585                 590

Ser Glu Glu Gly Pro Lys Leu Val Ala Ala Gln Ala Ala Leu Val
        595                 600                 605

<210> SEQ ID NO 17
<211> LENGTH: 615
<212> TYPE: PRT
<213> ORGANISM: Gallus gallus

<400> SEQUENCE: 17

Met Lys Trp Val Thr Leu Ile Ser Phe Ile Phe Leu Phe Ser Ser Ala
1               5                   10                  15

Thr Ser Arg Asn Leu Gln Arg Phe Ala Arg Asp Ala Glu His Lys Ser
            20                  25                  30
```

-continued

```
Glu Ile Ala His Arg Tyr Asn Asp Leu Lys Glu Glu Thr Phe Lys Ala
         35                  40                  45

Val Ala Met Ile Thr Phe Ala Gln Tyr Leu Gln Arg Cys Ser Tyr Glu
         50                  55                  60

Gly Leu Ser Lys Leu Val Lys Asp Val Val Asp Leu Ala Gln Lys Cys
 65                  70                  75                  80

Val Ala Asn Glu Asp Ala Pro Glu Cys Ser Lys Pro Leu Pro Ser Ile
                 85                  90                  95

Ile Leu Asp Glu Ile Cys Gln Val Glu Lys Leu Arg Asp Ser Tyr Gly
                100                 105                 110

Ala Met Ala Asp Cys Cys Ser Lys Ala Asp Pro Glu Arg Asn Glu Cys
                115                 120                 125

Phe Leu Ser Phe Lys Val Ser Gln Pro Asp Phe Val Gln Pro Tyr Gln
                130                 135                 140

Arg Pro Ala Ser Asp Val Ile Cys Gln Glu Tyr Gln Asp Asn Arg Val
145                 150                 155                 160

Ser Phe Leu Gly His Phe Ile Tyr Ser Val Ala Arg Arg His Pro Phe
                165                 170                 175

Leu Tyr Ala Pro Ala Ile Leu Ser Phe Ala Val Asp Phe Glu His Ala
                180                 185                 190

Leu Gln Ser Cys Cys Lys Glu Ser Asp Val Gly Ala Cys Leu Asp Thr
                195                 200                 205

Lys Glu Ile Val Met Arg Glu Lys Ala Lys Gly Val Ser Val Lys Gln
                210                 215                 220

Gln Tyr Phe Cys Gly Ile Leu Lys Gln Phe Gly Asp Arg Val Phe Gln
225                 230                 235                 240

Ala Arg Gln Leu Ile Tyr Leu Ser Gln Lys Tyr Pro Lys Ala Pro Phe
                245                 250                 255

Ser Glu Val Ser Lys Phe Val His Asp Ser Ile Gly Val His Lys Glu
                260                 265                 270

Cys Cys Glu Gly Asp Met Val Glu Cys Met Asp Asp Met Ala Arg Met
                275                 280                 285

Met Ser Asn Leu Cys Ser Gln Gln Asp Val Phe Ser Gly Lys Ile Lys
                290                 295                 300

Asp Cys Cys Glu Lys Pro Ile Val Glu Arg Ser Gln Cys Ile Met Glu
305                 310                 315                 320

Ala Glu Phe Asp Glu Lys Pro Ala Asp Leu Pro Ser Leu Val Glu Lys
                325                 330                 335

Tyr Ile Glu Asp Lys Glu Val Cys Lys Ser Phe Glu Ala Gly His Asp
                340                 345                 350

Ala Phe Met Ala Glu Phe Val Tyr Glu Tyr Ser Arg Arg His Pro Glu
                355                 360                 365

Phe Ser Ile Gln Leu Ile Met Arg Ile Ala Lys Gly Tyr Glu Ser Leu
                370                 375                 380

Leu Glu Lys Cys Cys Lys Thr Asp Asn Pro Ala Glu Cys Tyr Ala Asn
385                 390                 395                 400

Ala Gln Glu Gln Leu Asn Gln His Ile Lys Glu Thr Gln Asp Val Val
                405                 410                 415

Lys Thr Asn Cys Asp Leu Leu His Asp His Gly Glu Ala Asp Phe Leu
                420                 425                 430

Lys Ser Ile Leu Ile Arg Tyr Thr Lys Lys Met Pro Gln Val Pro Thr
                435                 440                 445
```

-continued

```
Asp Leu Leu Glu Thr Gly Lys Lys Met Thr Thr Ile Gly Thr Lys
    450                 455                 460

Cys Cys Gln Leu Gly Glu Asp Arg Arg Met Ala Cys Ser Glu Gly Tyr
465                 470                 475                 480

Leu Ser Ile Val Ile His Asp Thr Cys Arg Lys Gln Glu Thr Thr Pro
                485                 490                 495

Ile Asn Asp Asn Val Ser Gln Cys Cys Ser Gln Leu Tyr Ala Asn Arg
            500                 505                 510

Arg Pro Cys Phe Thr Ala Met Gly Val Asp Thr Lys Tyr Val Pro Pro
        515                 520                 525

Pro Phe Asn Pro Asp Met Phe Ser Phe Asp Glu Lys Leu Cys Ser Ala
530                 535                 540

Pro Ala Glu Glu Arg Glu Val Gly Gln Met Lys Leu Leu Ile Asn Leu
545                 550                 555                 560

Ile Lys Arg Lys Pro Gln Met Thr Glu Glu Gln Ile Lys Thr Ile Ala
                565                 570                 575

Asp Gly Phe Thr Ala Met Val Asp Lys Cys Cys Lys Gln Ser Asp Ile
            580                 585                 590

Asn Thr Cys Phe Gly Glu Glu Gly Ala Asn Leu Ile Val Gln Ser Arg
        595                 600                 605

Ala Thr Leu Gly Ile Gly Ala
    610                 615

<210> SEQ ID NO 18
<211> LENGTH: 607
<212> TYPE: PRT
<213> ORGANISM: Sus scrofa

<400> SEQUENCE: 18

Met Lys Trp Val Thr Phe Ile Ser Leu Leu Phe Leu Phe Ser Ser Ala
1               5                   10                  15

Tyr Ser Arg Gly Val Phe Arg Arg Asp Thr Tyr Lys Ser Glu Ile Ala
            20                  25                  30

His Arg Phe Lys Asp Leu Gly Glu Gln Tyr Phe Lys Gly Leu Val Leu
        35                  40                  45

Ile Ala Phe Ser Gln His Leu Gln Gln Cys Pro Tyr Glu Glu His Val
    50                  55                  60

Lys Leu Val Arg Glu Val Thr Glu Phe Ala Lys Thr Cys Val Ala Asp
65                  70                  75                  80

Glu Ser Ala Glu Asn Cys Asp Lys Ser Ile His Thr Leu Phe Gly Asp
                85                  90                  95

Lys Leu Cys Ala Ile Pro Ser Leu Arg Glu His Tyr Gly Asp Leu Ala
            100                 105                 110

Asp Cys Cys Glu Lys Glu Glu Pro Glu Arg Asn Glu Cys Phe Leu Gln
        115                 120                 125

His Lys Asn Asp Asn Pro Asp Ile Pro Lys Leu Lys Pro Asp Pro Val
    130                 135                 140

Ala Leu Cys Ala Asp Phe Gln Glu Asp Glu Gln Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Ile Ile Tyr Lys Asp Val Phe Ser Glu Cys Cys
            180                 185                 190

Gln Ala Ala Asp Lys Ala Ala Cys Leu Leu Pro Lys Ile Glu His Leu
        195                 200                 205
```

```
Arg Glu Lys Val Leu Thr Ser Ala Ala Lys Gln Arg Leu Lys Cys Ala
            210                 215                 220
Ser Ile Gln Lys Phe Gly Glu Arg Ala Phe Lys Ala Trp Ser Leu Ala
225                 230                 235                 240
Arg Leu Ser Gln Arg Phe Pro Lys Ala Asp Phe Thr Glu Ile Ser Lys
            245                 250                 255
Ile Val Thr Asp Leu Ala Lys Val His Lys Glu Cys Cys His Gly Asp
            260                 265                 270
Leu Leu Glu Cys Ala Asp Asp Arg Ala Asp Leu Ala Lys Tyr Ile Cys
            275                 280                 285
Glu Asn Gln Asp Thr Ile Ser Thr Lys Leu Lys Glu Cys Cys Asp Lys
            290                 295                 300
Pro Leu Leu Glu Lys Ser His Cys Ile Ala Glu Ala Lys Arg Asp Glu
305                 310                 315                 320
Leu Pro Ala Asp Leu Asn Pro Leu Glu His Asp Phe Val Glu Asp Lys
            325                 330                 335
Glu Val Cys Lys Asn Tyr Lys Glu Ala Lys His Val Phe Leu Gly Thr
            340                 345                 350
Phe Leu Tyr Glu Tyr Ser Arg Arg His Pro Asp Tyr Ser Val Ser Leu
            355                 360                 365
Leu Leu Arg Ile Ala Lys Ile Tyr Glu Ala Thr Leu Glu Asp Cys Cys
            370                 375                 380
Ala Lys Glu Asp Pro Pro Ala Cys Tyr Ala Thr Val Phe Asp Lys Phe
385                 390                 395                 400
Gln Pro Leu Val Asp Glu Pro Lys Asn Leu Ile Lys Gln Asn Cys Glu
            405                 410                 415
Leu Phe Glu Lys Leu Gly Glu Tyr Gly Phe Gln Asn Ala Leu Ile Val
            420                 425                 430
Arg Tyr Thr Lys Lys Val Pro Gln Val Ser Thr Pro Thr Leu Val Glu
            435                 440                 445
Val Ala Arg Lys Leu Gly Leu Val Gly Ser Arg Cys Cys Lys Arg Pro
            450                 455                 460
Glu Glu Glu Arg Leu Ser Cys Ala Glu Asp Tyr Leu Ser Leu Val Leu
465                 470                 475                 480
Asn Arg Leu Cys Val Leu His Glu Lys Thr Pro Val Ser Glu Lys Val
            485                 490                 495
Thr Lys Cys Cys Thr Glu Ser Leu Val Asn Arg Arg Pro Cys Phe Ser
            500                 505                 510
Ala Leu Thr Pro Asp Glu Thr Tyr Lys Pro Lys Glu Phe Val Glu Gly
            515                 520                 525
Thr Phe Thr Phe His Ala Asp Leu Cys Thr Leu Pro Glu Asp Glu Lys
            530                 535                 540
Gln Ile Lys Lys Gln Thr Ala Leu Val Glu Leu Leu Lys His Lys Pro
545                 550                 555                 560
His Ala Thr Glu Glu Gln Leu Arg Thr Val Leu Gly Asn Phe Ala Ala
            565                 570                 575
Phe Val Gln Lys Cys Cys Ala Ala Pro Asp His Glu Ala Cys Phe Ala
            580                 585                 590
Val Glu Gly Pro Lys Phe Val Ile Glu Ile Arg Gly Ile Leu Ala
            595                 600                 605

<210> SEQ ID NO 19
<211> LENGTH: 205
```

```
<212> TYPE: PRT
<213> ORGANISM: Artificial sequence
<220> FEATURE:
<223> OTHER INFORMATION: Artificial albumin variant: human serum albumin
      domain 3

<400> SEQUENCE: 19

Val Glu Glu Pro Gln Asn Leu Ile Lys Gln Asn Cys Glu Leu Phe Glu
1               5                   10                  15

Gln Leu Gly Glu Tyr Lys Phe Gln Asn Ala Leu Leu Val Arg Tyr Thr
            20                  25                  30

Lys Lys Val Pro Gln Val Ser Thr Pro Thr Leu Val Glu Val Ser Arg
        35                  40                  45

Asn Leu Gly Lys Val Gly Ser Lys Cys Cys Lys His Pro Glu Ala Lys
    50                  55                  60

Arg Met Pro Cys Ala Glu Asp Tyr Leu Ser Val Val Leu Asn Gln Leu
65                  70                  75                  80

Cys Val Leu His Glu Lys Thr Pro Val Ser Asp Arg Val Thr Lys Cys
                85                  90                  95

Cys Thr Glu Ser Leu Val Asn Arg Arg Pro Cys Phe Ser Ala Leu Glu
            100                 105                 110

Val Asp Glu Thr Tyr Val Pro Lys Glu Phe Asn Ala Glu Thr Phe Thr
        115                 120                 125

Phe His Ala Asp Ile Cys Thr Leu Ser Glu Lys Glu Arg Gln Ile Lys
    130                 135                 140

Lys Gln Thr Ala Leu Val Glu Leu Val Lys His Lys Pro Lys Ala Thr
145                 150                 155                 160

Lys Glu Gln Leu Lys Ala Val Met Asp Asp Phe Ala Ala Phe Val Glu
                165                 170                 175

Lys Cys Cys Lys Ala Asp Asp Lys Glu Thr Cys Phe Ala Glu Glu Gly
            180                 185                 190

Lys Lys Leu Val Ala Ala Ser Gln Ala Ala Leu Gly Leu
        195                 200                 205

<210> SEQ ID NO 20
<211> LENGTH: 403
<212> TYPE: PRT
<213> ORGANISM: Artificial sequence
<220> FEATURE:
<223> OTHER INFORMATION: Artificial albumin variant: human serum albumin
      domain 2 and human serum albumin domain 3

<400> SEQUENCE: 20

Asp Glu Leu Arg Asp Glu Gly Lys Ala Ser Ser Ala Lys Gln Arg Leu
1               5                   10                  15

Lys Cys Ala Ser Leu Gln Lys Phe Gly Glu Arg Ala Phe Lys Ala Trp
            20                  25                  30

Ala Val Ala Arg Leu Ser Gln Arg Phe Pro Lys Ala Glu Phe Ala Glu
        35                  40                  45

Val Ser Lys Leu Val Thr Asp Leu Thr Lys Val His Thr Glu Cys Cys
    50                  55                  60

His Gly Asp Leu Leu Glu Cys Ala Asp Asp Arg Ala Asp Leu Ala Lys
65                  70                  75                  80

Tyr Ile Cys Glu Asn Gln Asp Ser Ile Ser Ser Lys Leu Lys Glu Cys
                85                  90                  95

Cys Glu Lys Pro Leu Leu Glu Lys Ser His Cys Ile Ala Glu Val Glu
            100                 105                 110
```

```
Asn Asp Glu Met Pro Ala Asp Leu Pro Ser Leu Ala Ala Asp Phe Val
            115                 120                 125

Glu Ser Lys Asp Val Cys Lys Asn Tyr Ala Glu Ala Lys Asp Val Phe
130                 135                 140

Leu Gly Met Phe Leu Tyr Glu Tyr Ala Arg Arg His Pro Asp Tyr Ser
145                 150                 155                 160

Val Val Leu Leu Leu Arg Leu Ala Lys Thr Tyr Glu Thr Thr Leu Glu
                165                 170                 175

Lys Cys Cys Ala Ala Ala Asp Pro His Glu Cys Tyr Ala Lys Val Phe
            180                 185                 190

Asp Glu Phe Lys Pro Leu Val Glu Glu Pro Gln Asn Leu Ile Lys Gln
        195                 200                 205

Asn Cys Glu Leu Phe Glu Gln Leu Gly Glu Tyr Lys Phe Gln Asn Ala
    210                 215                 220

Leu Leu Val Arg Tyr Thr Lys Lys Val Pro Gln Val Ser Thr Pro Thr
225                 230                 235                 240

Leu Val Glu Val Ser Arg Asn Leu Gly Lys Val Gly Ser Lys Cys Cys
                245                 250                 255

Lys His Pro Glu Ala Lys Arg Met Pro Cys Ala Glu Asp Tyr Leu Ser
            260                 265                 270

Val Val Leu Asn Gln Leu Cys Val Leu His Glu Lys Thr Pro Val Ser
        275                 280                 285

Asp Arg Val Thr Lys Cys Cys Thr Glu Ser Leu Val Asn Arg Arg Pro
    290                 295                 300

Cys Phe Ser Ala Leu Glu Val Asp Glu Thr Tyr Val Pro Lys Glu Phe
305                 310                 315                 320

Asn Ala Glu Thr Phe Thr Phe His Ala Asp Ile Cys Thr Leu Ser Glu
                325                 330                 335

Lys Glu Arg Gln Ile Lys Lys Gln Thr Ala Leu Val Glu Leu Val Lys
            340                 345                 350

His Lys Pro Lys Ala Thr Lys Glu Gln Leu Lys Ala Val Met Asp Asp
        355                 360                 365

Phe Ala Ala Phe Val Glu Lys Cys Cys Lys Ala Asp Asp Lys Glu Thr
    370                 375                 380

Cys Phe Ala Glu Glu Gly Lys Lys Leu Val Ala Ala Ser Gln Ala Ala
385                 390                 395                 400

Leu Gly Leu

<210> SEQ ID NO 21
<211> LENGTH: 399
<212> TYPE: PRT
<213> ORGANISM: Artificial sequence
<220> FEATURE:
<223> OTHER INFORMATION: Artificial albumin variant: human serum albumin
      domain 1 and human serum albumin domain 3

<400> SEQUENCE: 21

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60
```

```
Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Val Glu Glu Pro Gln Asn Leu Ile Lys Gln Asn Cys Glu Leu
        195                 200                 205

Phe Glu Gln Leu Gly Glu Tyr Lys Phe Gln Asn Ala Leu Leu Val Arg
210                 215                 220

Tyr Thr Lys Lys Val Pro Gln Val Ser Thr Pro Thr Leu Val Glu Val
225                 230                 235                 240

Ser Arg Asn Leu Gly Lys Val Gly Ser Lys Cys Cys Lys His Pro Glu
                245                 250                 255

Ala Lys Arg Met Pro Cys Ala Glu Asp Tyr Leu Ser Val Val Leu Asn
            260                 265                 270

Gln Leu Cys Val Leu His Glu Lys Thr Pro Val Ser Asp Arg Val Thr
        275                 280                 285

Lys Cys Cys Thr Glu Ser Leu Val Asn Arg Arg Pro Cys Phe Ser Ala
290                 295                 300

Leu Glu Val Asp Glu Thr Tyr Val Pro Lys Glu Phe Asn Ala Glu Thr
305                 310                 315                 320

Phe Thr Phe His Ala Asp Ile Cys Thr Leu Ser Glu Lys Glu Arg Gln
                325                 330                 335

Ile Lys Lys Gln Thr Ala Leu Val Glu Leu Val Lys His Lys Pro Lys
            340                 345                 350

Ala Thr Lys Glu Gln Leu Lys Ala Val Met Asp Asp Phe Ala Ala Phe
        355                 360                 365

Val Glu Lys Cys Cys Lys Ala Asp Asp Lys Glu Thr Cys Phe Ala Glu
370                 375                 380

Glu Gly Lys Lys Leu Val Ala Ala Ser Gln Ala Ala Leu Gly Leu
385                 390                 395

<210> SEQ ID NO 22
<211> LENGTH: 410
<212> TYPE: PRT
<213> ORGANISM: Artificial sequence
<220> FEATURE:
<223> OTHER INFORMATION: Artificial albumin variant: two consecutive
      copies of human serum albumin domain 3

<400> SEQUENCE: 22

Val Glu Glu Pro Gln Asn Leu Ile Lys Gln Asn Cys Glu Leu Phe Glu
1               5                   10                  15

Gln Leu Gly Glu Tyr Lys Phe Gln Asn Ala Leu Leu Val Arg Tyr Thr
            20                  25                  30
```

```
Lys Lys Val Pro Gln Val Ser Thr Pro Thr Leu Val Glu Val Ser Arg
        35                  40                  45

Asn Leu Gly Lys Val Gly Ser Lys Cys Cys Lys His Pro Glu Ala Lys
 50                  55                  60

Arg Met Pro Cys Ala Glu Asp Tyr Leu Ser Val Val Leu Asn Gln Leu
 65                  70                  75                  80

Cys Val Leu His Glu Lys Thr Pro Val Ser Asp Arg Val Thr Lys Cys
                 85                  90                  95

Cys Thr Glu Ser Leu Val Asn Arg Arg Pro Cys Phe Ser Ala Leu Glu
                100                 105                 110

Val Asp Glu Thr Tyr Val Pro Lys Glu Phe Asn Ala Glu Thr Phe Thr
                115                 120                 125

Phe His Ala Asp Ile Cys Thr Leu Ser Glu Lys Glu Arg Gln Ile Lys
    130                 135                 140

Lys Gln Thr Ala Leu Val Glu Leu Val Lys His Lys Pro Lys Ala Thr
145                 150                 155                 160

Lys Glu Gln Leu Lys Ala Val Met Asp Asp Phe Ala Ala Phe Val Glu
                165                 170                 175

Lys Cys Cys Lys Ala Asp Asp Lys Glu Thr Cys Phe Ala Glu Glu Gly
                180                 185                 190

Lys Lys Leu Val Ala Ala Ser Gln Ala Ala Leu Gly Leu Val Glu Glu
                195                 200                 205

Pro Gln Asn Leu Ile Lys Gln Asn Cys Glu Leu Phe Glu Gln Leu Gly
                210                 215                 220

Glu Tyr Lys Phe Gln Asn Ala Leu Leu Val Arg Tyr Thr Lys Lys Val
225                 230                 235                 240

Pro Gln Val Ser Thr Pro Thr Leu Val Glu Val Ser Arg Asn Leu Gly
                245                 250                 255

Lys Val Gly Ser Lys Cys Cys Lys His Pro Glu Ala Lys Arg Met Pro
                260                 265                 270

Cys Ala Glu Asp Tyr Leu Ser Val Val Leu Asn Gln Leu Cys Val Leu
                275                 280                 285

His Glu Lys Thr Pro Val Ser Asp Arg Val Thr Lys Cys Cys Thr Glu
    290                 295                 300

Ser Leu Val Asn Arg Arg Pro Cys Phe Ser Ala Leu Glu Val Asp Glu
305                 310                 315                 320

Thr Tyr Val Pro Lys Glu Phe Asn Ala Glu Thr Phe Thr Phe His Ala
                325                 330                 335

Asp Ile Cys Thr Leu Ser Glu Lys Glu Arg Gln Ile Lys Lys Gln Thr
                340                 345                 350

Ala Leu Val Glu Leu Val Lys His Lys Pro Lys Ala Thr Lys Glu Gln
                355                 360                 365

Leu Lys Ala Val Met Asp Asp Phe Ala Ala Phe Val Glu Lys Cys Cys
    370                 375                 380

Lys Ala Asp Asp Lys Glu Thr Cys Phe Ala Glu Glu Gly Lys Lys Leu
385                 390                 395                 400

Val Ala Ala Ser Gln Ala Ala Leu Gly Leu
                405                 410
```

<210> SEQ ID NO 23
<211> LENGTH: 615
<212> TYPE: PRT
<213> ORGANISM: Artificial Sequence
<220> FEATURE:

<223> OTHER INFORMATION: HSA Domain III + HSA Domain III + HSA Domain III

<400> SEQUENCE: 23

```
Val Glu Glu Pro Gln Asn Leu Ile Lys Gln Asn Cys Glu Leu Phe Glu
1               5                   10                  15

Gln Leu Gly Glu Tyr Lys Phe Gln Asn Ala Leu Leu Val Arg Tyr Thr
            20                  25                  30

Lys Lys Val Pro Gln Val Ser Thr Pro Thr Leu Val Glu Val Ser Arg
        35                  40                  45

Asn Leu Gly Lys Val Gly Ser Lys Cys Cys Lys His Pro Glu Ala Lys
    50                  55                  60

Arg Met Pro Cys Ala Glu Asp Tyr Leu Ser Val Val Leu Asn Gln Leu
65                  70                  75                  80

Cys Val Leu His Glu Lys Thr Pro Val Ser Asp Arg Val Thr Lys Cys
                85                  90                  95

Cys Thr Glu Ser Leu Val Asn Arg Arg Pro Cys Phe Ser Ala Leu Glu
            100                 105                 110

Val Asp Glu Thr Tyr Val Pro Lys Glu Phe Asn Ala Glu Thr Phe Thr
        115                 120                 125

Phe His Ala Asp Ile Cys Thr Leu Ser Glu Lys Glu Arg Gln Ile Lys
    130                 135                 140

Lys Gln Thr Ala Leu Val Glu Leu Val Lys His Lys Pro Lys Ala Thr
145                 150                 155                 160

Lys Glu Gln Leu Lys Ala Val Met Asp Asp Phe Ala Ala Phe Val Glu
                165                 170                 175

Lys Cys Cys Lys Ala Asp Asp Lys Glu Thr Cys Phe Ala Glu Glu Gly
            180                 185                 190

Lys Lys Leu Val Ala Ala Ser Gln Ala Ala Leu Gly Leu Val Glu Glu
        195                 200                 205

Pro Gln Asn Leu Ile Lys Gln Asn Cys Glu Leu Phe Glu Gln Leu Gly
    210                 215                 220

Glu Tyr Lys Phe Gln Asn Ala Leu Leu Val Arg Tyr Thr Lys Lys Val
225                 230                 235                 240

Pro Gln Val Ser Thr Pro Thr Leu Val Glu Val Ser Arg Asn Leu Gly
                245                 250                 255

Lys Val Gly Ser Lys Cys Cys Lys His Pro Glu Ala Lys Arg Met Pro
            260                 265                 270

Cys Ala Glu Asp Tyr Leu Ser Val Val Leu Asn Gln Leu Cys Val Leu
        275                 280                 285

His Glu Lys Thr Pro Val Ser Asp Arg Val Thr Lys Cys Cys Thr Glu
    290                 295                 300

Ser Leu Val Asn Arg Arg Pro Cys Phe Ser Ala Leu Glu Val Asp Glu
305                 310                 315                 320

Thr Tyr Val Pro Lys Glu Phe Asn Ala Glu Thr Phe Thr Phe His Ala
                325                 330                 335

Asp Ile Cys Thr Leu Ser Glu Lys Glu Arg Gln Ile Lys Lys Gln Thr
            340                 345                 350

Ala Leu Val Glu Leu Val Lys His Lys Pro Lys Ala Thr Lys Glu Gln
        355                 360                 365

Leu Lys Ala Val Met Asp Asp Phe Ala Ala Phe Val Glu Lys Cys Cys
    370                 375                 380

Lys Ala Asp Asp Lys Glu Thr Cys Phe Ala Glu Glu Gly Lys Lys Leu
385                 390                 395                 400
```

```
Val Ala Ala Ser Gln Ala Ala Leu Gly Leu Val Glu Pro Gln Asn
            405                 410                 415

Leu Ile Lys Gln Asn Cys Glu Leu Phe Glu Gln Leu Gly Glu Tyr Lys
            420                 425                 430

Phe Gln Asn Ala Leu Leu Val Arg Tyr Thr Lys Lys Val Pro Gln Val
            435                 440                 445

Ser Thr Pro Thr Leu Val Glu Val Ser Arg Asn Leu Gly Lys Val Gly
            450                 455                 460

Ser Lys Cys Cys Lys His Pro Glu Ala Lys Arg Met Pro Cys Ala Glu
465                 470                 475                 480

Asp Tyr Leu Ser Val Val Leu Asn Gln Leu Cys Val Leu His Glu Lys
            485                 490                 495

Thr Pro Val Ser Asp Arg Val Thr Lys Cys Cys Thr Glu Ser Leu Val
            500                 505                 510

Asn Arg Arg Pro Cys Phe Ser Ala Leu Glu Val Asp Glu Thr Tyr Val
            515                 520                 525

Pro Lys Glu Phe Asn Ala Glu Thr Phe Thr Phe His Ala Asp Ile Cys
            530                 535                 540

Thr Leu Ser Glu Lys Glu Arg Gln Ile Lys Lys Gln Thr Ala Leu Val
545                 550                 555                 560

Glu Leu Val Lys His Lys Pro Lys Ala Thr Lys Glu Gln Leu Lys Ala
            565                 570                 575

Val Met Asp Asp Phe Ala Ala Phe Val Glu Lys Cys Cys Lys Ala Asp
            580                 585                 590

Asp Lys Glu Thr Cys Phe Ala Glu Glu Gly Lys Lys Leu Val Ala Ala
            595                 600                 605

Ser Gln Ala Ala Leu Gly Leu
            610                 615

<210> SEQ ID NO 24
<211> LENGTH: 604
<212> TYPE: PRT
<213> ORGANISM: Artificial Sequence
<220> FEATURE:
<223> OTHER INFORMATION: HSA Domain I + HSA Domain III + HSA Domain III

<400> SEQUENCE: 24

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140
```

```
Arg His Pro Tyr Phe Tyr Ala Pro Glu Leu Leu Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Val Glu Glu Pro Gln Asn Leu Ile Lys Gln Asn Cys Glu Leu
        195                 200                 205

Phe Glu Gln Leu Gly Glu Tyr Lys Phe Gln Asn Ala Leu Leu Val Arg
    210                 215                 220

Tyr Thr Lys Lys Val Pro Gln Val Ser Thr Pro Thr Leu Val Glu Val
225                 230                 235                 240

Ser Arg Asn Leu Gly Lys Val Gly Ser Lys Cys Cys Lys His Pro Glu
                245                 250                 255

Ala Lys Arg Met Pro Cys Ala Glu Asp Tyr Leu Ser Val Val Leu Asn
            260                 265                 270

Gln Leu Cys Val Leu His Glu Lys Thr Pro Val Ser Asp Arg Val Thr
        275                 280                 285

Lys Cys Cys Thr Glu Ser Leu Val Asn Arg Arg Pro Cys Phe Ser Ala
    290                 295                 300

Leu Glu Val Asp Glu Thr Tyr Val Pro Lys Glu Phe Asn Ala Glu Thr
305                 310                 315                 320

Phe Thr Phe His Ala Asp Ile Cys Thr Leu Ser Glu Lys Glu Arg Gln
                325                 330                 335

Ile Lys Lys Gln Thr Ala Leu Val Glu Leu Val Lys His Lys Pro Lys
            340                 345                 350

Ala Thr Lys Glu Gln Leu Lys Ala Val Met Asp Asp Phe Ala Ala Phe
        355                 360                 365

Val Glu Lys Cys Cys Lys Ala Asp Asp Lys Glu Thr Cys Phe Ala Glu
    370                 375                 380

Glu Gly Lys Lys Leu Val Ala Ala Ser Gln Ala Ala Leu Gly Leu Val
385                 390                 395                 400

Glu Glu Pro Gln Asn Leu Ile Lys Gln Asn Cys Glu Leu Phe Glu Gln
                405                 410                 415

Leu Gly Glu Tyr Lys Phe Gln Asn Ala Leu Leu Val Arg Tyr Thr Lys
            420                 425                 430

Lys Val Pro Gln Val Ser Thr Pro Thr Leu Val Glu Val Ser Arg Asn
        435                 440                 445

Leu Gly Lys Val Gly Ser Lys Cys Cys Lys His Pro Glu Ala Lys Arg
    450                 455                 460

Met Pro Cys Ala Glu Asp Tyr Leu Ser Val Val Leu Asn Gln Leu Cys
465                 470                 475                 480

Val Leu His Glu Lys Thr Pro Val Ser Asp Arg Val Thr Lys Cys Cys
                485                 490                 495

Thr Glu Ser Leu Val Asn Arg Arg Pro Cys Phe Ser Ala Leu Glu Val
            500                 505                 510

Asp Glu Thr Tyr Val Pro Lys Glu Phe Asn Ala Glu Thr Phe Thr Phe
        515                 520                 525

His Ala Asp Ile Cys Thr Leu Ser Glu Lys Glu Arg Gln Ile Lys Lys
    530                 535                 540

Gln Thr Ala Leu Val Glu Leu Val Lys His Lys Pro Lys Ala Thr Lys
545                 550                 555                 560
```

```
Glu Gln Leu Lys Ala Val Met Asp Asp Phe Ala Ala Phe Val Glu Lys
            565                 570                 575
Cys Cys Lys Ala Asp Asp Lys Glu Thr Cys Phe Ala Glu Glu Gly Lys
        580                 585                 590
Lys Leu Val Ala Ala Ser Gln Ala Ala Leu Gly Leu
        595                 600

<210> SEQ ID NO 25
<211> LENGTH: 1758
<212> TYPE: DNA
<213> ORGANISM: Artificial Sequence
<220> FEATURE:
<223> OTHER INFORMATION: HSA coding sequence mutated to introduce
      restriction enzyme sites

<400> SEQUENCE: 25
gatgcacaca agagtgaggt tgctcatcgg tttaaagatt tgggagaaga aaatttcaaa      60
gccttggtgt tgattgcctt tgctcagtat cttcagcagt gtccatttga agatcatgta    120
aaattagtga atgaagtaac tgaatttgca aaaacatgtg ttgctgatga gtccgcggaa    180
aattgtgaca aatcacttca tacccttttt ggagacaaat tatgcacagt tgcaactctt    240
cgtgaaacct atggtgaaat ggctgactgc tgtgcaaaac aagaacctga gaaaatgaa    300 tgcttcttgc aacacaaaga tgacaaccca acctcccccg attggtgag accagaggtt    360 gatgtgatgt gcactgcttt tcatgacaat gaagagacat tttgaaaaaa atacttatat    420
gaaattgcca aagacatcc ttacttttat gcccccggaac tccttttctt tgctaaaagg    480 tataagctg cttttacaga atgttgccaa gctgctgata agctgcctg cctgttgcca    540 aagctcgatg aacttcggga tgaagggaag gctagctctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg ctcgagtgtg ctgatgacag gcggaccctt    780
gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg ctgatcctca tgaatgctat gccaaagtgt tcgatgaatt taaacctctt   1140
gtggaagagc tcagaatttt aatcaaacaa aattgtgagc ttttttgagca gcttggagag   1200 tacaaattcc agaatgcgct attagttcgt tacaccaaga agtaccccca agtgtcaact   1260
ccaactcttg tagaggtctc aagaaaccta ggaaaagtgg atccaaatg ttgtaaacat   1320 cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg cttttcagct ctggaagtcg acgaaacata cgttcccaaa   1500
gagtttaatg ctgaaacatt caccttccat gcagatatat gcacactttc tgagaaggag   1560
agacaaatca gaaacaaac tgcacttgtt gagctcgtga acacaagcc caaggcaaca   1620 aaagagcaac tgaaagctgt tatggatgat ttcgcagctt ttgtagagaa gtgctgcaag   1680
gctgacgata ggagacctg ctttgccgag gagggtaaaa aacttgttgc tgcaagtcaa   1740
gctgccttag gcttataa                                                  1758
```

```
<210> SEQ ID NO 26
<211> LENGTH: 290
<212> TYPE: PRT
<213> ORGANISM: Homo sapiens
<220> FEATURE:
<221> NAME/KEY: misc_feature
<222> LOCATION: (1)..(290)
<223> OTHER INFORMATION: Truncated heavy chain of the major
      histocompatibility complex class I-like Fc receptor (FCGRT)
      (together, SEQ ID No. 30 and SEQ ID No. 31 form FcRN)
<220> FEATURE:
<221> NAME/KEY: misc_feature
<222> LOCATION: (1)..(290)
<223> OTHER INFORMATION: Truncated heavy chain of the major
      histocompatibility complex class I-like Fc receptor (FCGRT)
      (together, SEQ ID No. 26 and SEQ ID No. 27 form FcRN)

<400> SEQUENCE: 26

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160

Ser Gln Arg Trp Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
    210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
        275                 280                 285

Glu Leu
    290
```

-continued

```
<210> SEQ ID NO 27
<211> LENGTH: 119
<212> TYPE: PRT
<213> ORGANISM: Homo sapiens
<220> FEATURE:
<221> NAME/KEY: misc_feature
<222> LOCATION: (1)..(119)
<223> OTHER INFORMATION: Beta-2-microglobulin (together, SEQ ID No. 30
      and SEQ ID No. 31 form FcRN)
<220> FEATURE:
<221> NAME/KEY: misc_feature
<222> LOCATION: (1)..(119)
<223> OTHER INFORMATION: Beta-2-microglobulin (together, SEQ ID No. 26
      and SEQ ID No. 27 form FcRN)

<400> SEQUENCE: 27

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 28
<211> LENGTH: 1758
<212> TYPE: DNA
<213> ORGANISM: Artificial Sequence
<220> FEATURE:
<223> OTHER INFORMATION: Polynucleotide coding sequence (codon optimised
      for expression in yeast) for human serum albumin

<400> SEQUENCE: 28
gacgctcaca agtccgaagt cgctcacaga ttcaaggact gggtgaaga aaacttcaag      60 gctttggtct tgatcgcttt cgctcaatac ttgcaacaat gtccattcga agatcacgtc    120
aagttggtca cgaagttac cgaattcgct aagacttgtg ttgctgacga atctgctgaa     180
aactgtgaca agtccttgca caccttgttc ggtgataagt tgtgtactgt tgctaccttg    240
agagaaacct acggtgaaat ggctgactgt tgtgctaagc aagaaccaga agaaacgaa     300 tgtttcttgc aacacaagga cgacaaccca aacttgccaa gattggttag accagaagtt    360
gacgtcatgt gtactgcttt ccacgacaac gaagaaacct tcttgaagaa gtacttgtac    420
gaaattgcta agacacccc atacttctac gctccagaat tgttgttctt cgctaagaga    480
tacaaggctg ctttcaccga tgttgtcaa gctgctgata ggctgcttg tttgttgcca     540 aagtggatg aattgagaga cgaaggtaag gcttcttccg ctaagcaaag attgaagtgt    600
gcttccttgc aaaagttcgg tgaaagagct ttcaaggctt gggctgtcgc tagattgtct    660
caaagattcc caaggctga attcgctgaa gtttctaagt tggttactga cttgactaag    720
gttcacactg aatgttgtca cggtgacttg ttggaatgtg ctgatgacag agctgacttg    780
gctaagtaca tctgtgaaaa ccaagactct atctcttcca agttgaagga atgttgtgaa    840
```

-continued

```
aagccattgt tggaaaagtc tcactgtatt gctgaagttg aaaacgatga aatgccagct    900
gacttgccat ctttggctgc tgacttcgtt gaatctaagg acgtttgtaa gaactacgct    960
gaagctaagg acgtcttctt gggtatgttc ttgtacgaat acgctagaag acacccagac   1020
tactccgttg tcttgttgtt gagattggct aagacctacg aaactacctt ggaaaagtgt   1080
tgtgctgctg ctgacccaca cgaatgttac gctaaggttt cgatgaatt caagccattg   1140
gtcgaagaac cacaaaactt gatcaagcaa aactgtgaat tgttcgaaca attgggtgaa   1200
tacaagttcc aaaacgcttt gttggttaga tacactaaga aggtcccaca agtctccacc   1260
ccaactttgg ttgaagtctc tagaaacttg ggtaaggtcg ttctaagtg ttgtaagcac    1320
ccagaagcta agagaatgcc atgtgctgaa gattacttgt ccgtcgtttt gaaccaattg   1380
tgtgttttgc acgaaaagac cccagtctct gatagagtca ccaagtgttg tactgaatct   1440
ttggttaaca gaagaccatg tttctctgct ttggaagtcg acgaaactta cgttccaaag   1500
gaattcaacg ctgaaacttt caccttccac gctgatatct gtaccttgtc cgaaaaggaa   1560
agacaaatta gaagcaaac tgctttggtt gaattggtca agcacaagcc aaaggctact    1620
aaggaacaat tgaaggctgt catggatgat ttcgctgctt tcgttgaaaa gtgttgtaag   1680
gctgatgata aggaaacttg tttcgctgaa gaaggtaaga agttggtcgc tgcttcccaa   1740
gctgctttgg gtttgtaa                                                 1758
```

<210> SEQ ID NO 29
<211> LENGTH: 609
<212> TYPE: PRT
<213> ORGANISM: Artificial Sequence
<220> FEATURE:
<223> OTHER INFORMATION: HSA with fusion leader sequence
<220> FEATURE:
<221> NAME/KEY: signal
<222> LOCATION: (1)..(24)
<220> FEATURE:
<221> NAME/KEY: mat_peptide
<222> LOCATION: (25)..(609)

<400> SEQUENCE: 29

```
Met Lys Trp Val Ser Phe Ile Ser Leu Leu Phe Leu Phe Ser Ser Ala
            -20                 -15                 -10

Tyr Ser Arg Ser Leu Asp Lys Arg Asp Ala His Lys Ser Glu Val Ala
        -5                  -1   1               5

His Arg Phe Lys Asp Leu Gly Glu Glu Asn Phe Lys Ala Leu Val Leu
     10                  15                  20

Ile Ala Phe Ala Gln Tyr Leu Gln Gln Cys Pro Phe Glu Asp His Val
 25                  30                  35                  40

Lys Leu Val Asn Glu Val Thr Glu Phe Ala Lys Thr Cys Val Ala Asp
                 45                  50                  55

Glu Ser Ala Glu Asn Cys Asp Lys Ser Leu His Thr Leu Phe Gly Asp
             60                  65                  70

Lys Leu Cys Thr Val Ala Thr Leu Arg Glu Thr Tyr Gly Glu Met Ala
         75                  80                  85

Asp Cys Cys Ala Lys Gln Glu Pro Glu Arg Asn Glu Cys Phe Leu Gln
     90                  95                 100

His Lys Asp Asp Asn Pro Asn Leu Pro Arg Leu Val Arg Pro Glu Val
105                 110                 115                 120

Asp Val Met Cys Thr Ala Phe His Asp Asn Glu Glu Thr Phe Leu Lys
                125                 130                 135
```

```
Lys Tyr Leu Tyr Glu Ile Ala Arg Arg His Pro Tyr Phe Tyr Ala Pro
            140                 145                 150

Glu Leu Leu Phe Phe Ala Lys Arg Tyr Lys Ala Ala Phe Thr Glu Cys
            155                 160                 165

Cys Gln Ala Ala Asp Lys Ala Ala Cys Leu Leu Pro Lys Leu Asp Glu
            170                 175                 180

Leu Arg Asp Glu Gly Lys Ala Ser Ser Ala Lys Gln Arg Leu Lys Cys
185                 190                 195                 200

Ala Ser Leu Gln Lys Phe Gly Glu Arg Ala Phe Lys Ala Trp Ala Val
            205                 210                 215

Ala Arg Leu Ser Gln Arg Phe Pro Lys Ala Glu Phe Ala Glu Val Ser
            220                 225                 230

Lys Leu Val Thr Asp Leu Thr Lys Val His Thr Glu Cys Cys His Gly
            235                 240                 245

Asp Leu Leu Glu Cys Ala Asp Asp Arg Ala Asp Leu Ala Lys Tyr Ile
            250                 255                 260

Cys Glu Asn Gln Asp Ser Ile Ser Ser Lys Leu Lys Glu Cys Cys Glu
265                 270                 275                 280

Lys Pro Leu Leu Glu Lys Ser His Cys Ile Ala Glu Val Glu Asn Asp
            285                 290                 295

Glu Met Pro Ala Asp Leu Pro Ser Leu Ala Ala Asp Phe Val Glu Ser
            300                 305                 310

Lys Asp Val Cys Lys Asn Tyr Ala Glu Ala Lys Asp Val Phe Leu Gly
            315                 320                 325

Met Phe Leu Tyr Glu Tyr Ala Arg Arg His Pro Asp Tyr Ser Val Val
            330                 335                 340

Leu Leu Leu Arg Leu Ala Lys Thr Tyr Glu Thr Thr Leu Glu Lys Cys
345                 350                 355                 360

Cys Ala Ala Ala Asp Pro His Glu Cys Tyr Ala Lys Val Phe Asp Glu
            365                 370                 375

Phe Lys Pro Leu Val Glu Glu Pro Gln Asn Leu Ile Lys Gln Asn Cys
            380                 385                 390

Glu Leu Phe Glu Gln Leu Gly Glu Tyr Lys Phe Gln Asn Ala Leu Leu
            395                 400                 405

Val Arg Tyr Thr Lys Lys Val Pro Gln Val Ser Thr Pro Thr Leu Val
            410                 415                 420

Glu Val Ser Arg Asn Leu Gly Lys Val Gly Ser Lys Cys Cys Lys His
425                 430                 435                 440

Pro Glu Ala Lys Arg Met Pro Cys Ala Glu Asp Tyr Leu Ser Val Val
            445                 450                 455

Leu Asn Gln Leu Cys Val Leu His Glu Lys Thr Pro Val Ser Asp Arg
            460                 465                 470

Val Thr Lys Cys Cys Thr Glu Ser Leu Val Asn Arg Arg Pro Cys Phe
            475                 480                 485

Ser Ala Leu Glu Val Asp Glu Thr Tyr Val Pro Lys Glu Phe Asn Ala
            490                 495                 500

Glu Thr Phe Thr Phe His Ala Asp Ile Cys Thr Leu Ser Glu Lys Glu
505                 510                 515                 520

Arg Gln Ile Lys Lys Gln Thr Ala Leu Val Glu Leu Val Lys His Lys
            525                 530                 535

Pro Lys Ala Thr Lys Glu Gln Leu Lys Ala Val Met Asp Asp Phe Ala
            540                 545                 550
```

```
Ala Phe Val Glu Lys Cys Cys Lys Ala Asp Asp Lys Glu Thr Cys Phe
        555                 560                 565

Ala Glu Glu Gly Lys Lys Leu Val Ala Ala Ser Gln Ala Ala Leu Gly
570                 575                 580

Leu
585

<210> SEQ ID NO 30
<211> LENGTH: 585
<212> TYPE: PRT
<213> ORGANISM: Artificial
<220> FEATURE:
<223> OTHER INFORMATION: HSA C34A

<400> SEQUENCE: 30

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320
```

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Glu Thr Thr Leu Glu Lys Cys Cys Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 31
<211> LENGTH: 36
<212> TYPE: DNA
<213> ORGANISM: Artificial Sequence
<220> FEATURE:
<223> OTHER INFORMATION: C34A reverse primer

<400> SEQUENCE: 31
ttgttgcaag tattgagcga aagcgatcaa gaccaa                                 36

<210> SEQ ID NO 32
<211> LENGTH: 45
<212> TYPE: DNA
<213> ORGANISM: Artificial Sequence
<220> FEATURE:
<223> OTHER INFORMATION: C34A forward primer

<400> SEQUENCE: 32
ttcgctcaat acttgcaaca agctccattc gaagatcacg tcaag                       45

<210> SEQ ID NO 33
<211> LENGTH: 50

```
<212> TYPE: DNA
<213> ORGANISM: Artificial Sequence
<220> FEATURE:
<223> OTHER INFORMATION: L24C forward primer

<400> SEQUENCE: 33
gaagaaaact tcaaggcttt ggtctgtatc gctttcgctc aatacttgca           50

<210> SEQ ID NO 34
<211> LENGTH: 48
<212> TYPE: DNA
<213> ORGANISM: Artificial Sequence
<220> FEATURE:
<223> OTHER INFORMATION: F49C forward primer

<400> SEQUENCE: 34
agttggtcaa cgaagttacc gaatgtgcta agacttgtgt tgctgacg             48

<210> SEQ ID NO 35
<211> LENGTH: 48
<212> TYPE: DNA
<213> ORGANISM: Artificial Sequence
<220> FEATURE:
<223> OTHER INFORMATION: V54C forward primer

<400> SEQUENCE: 35
gttaccgaat tcgctaagac ttgttgtgct gacgaatccg cggaaaac             48

<210> SEQ ID NO 36
<211> LENGTH: 49
<212> TYPE: DNA
<213> ORGANISM: Artificial Sequence
<220> FEATURE:
<223> OTHER INFORMATION: D56C forward primer

<400> SEQUENCE: 36
gaattcgcta agacttgtgt tgcttgtgaa tccgcggaaa actgtgaca            49

<210> SEQ ID NO 37
<211> LENGTH: 48
<212> TYPE: DNA
<213> ORGANISM: Artificial Sequence
<220> FEATURE:
<223> OTHER INFORMATION: L66C forward primer

<400> SEQUENCE: 37
cgcggaaaac tgtgacaagt cctgtcacac cttgttcggt gataagtt             48

<210> SEQ ID NO 38
<211> LENGTH: 49
<212> TYPE: DNA
<213> ORGANISM: Artificial Sequence
<220> FEATURE:
<223> OTHER INFORMATION: A92C forward primer

<400> SEQUENCE: 38
cggtgaaatg gctgactgtt gttgtaagca agaaccagaa agaaacgaa            49

<210> SEQ ID NO 39
<211> LENGTH: 50
<212> TYPE: DNA
<213> ORGANISM: Artificial Sequence
<220> FEATURE:
<223> OTHER INFORMATION: K93C forward primer
```

```
<400> SEQUENCE: 39
gtgaaatggc tgactgttgt gcttgtcaag aaccagaaag aaacgaatgt            50

<210> SEQ ID NO 40
<211> LENGTH: 50
<212> TYPE: DNA
<213> ORGANISM: Artificial Sequence
<220> FEATURE:
<223> OTHER INFORMATION: Q94C forward primer

<400> SEQUENCE: 40
aaatggctga ctgttgtgct aagtgtgaac cagaaagaaa cgaatgtttc            50

<210> SEQ ID NO 41
<211> LENGTH: 50
<212> TYPE: DNA
<213> ORGANISM: Artificial Sequence
<220> FEATURE:
<223> OTHER INFORMATION: E97C forward primer

<400> SEQUENCE: 41
actgttgtgc taagcaagaa ccatgtagaa acgaatgttt cttgcaacac            50

<210> SEQ ID NO 42
<211> LENGTH: 50
<212> TYPE: DNA
<213> ORGANISM: Artificial Sequence
<220> FEATURE:
<223> OTHER INFORMATION: H128C forward primer

<400> SEQUENCE: 42
ttgacgtcat gtgtactgct ttctgtgaca acgaagaaac cttcttgaag            50

<210> SEQ ID NO 43
<211> LENGTH: 49
<212> TYPE: DNA
<213> ORGANISM: Artificial Sequence
<220> FEATURE:
<223> OTHER INFORMATION: F156C forward primer

<400> SEQUENCE: 43
acttctacgc tccagaattg ttgtgtttcg ctaagagata caaggctgc             49

<210> SEQ ID NO 44
<211> LENGTH: 51
<212> TYPE: DNA
<213> ORGANISM: Artificial Sequence
<220> FEATURE:
<223> OTHER INFORMATION: A226C forward primer

<400> SEQUENCE: 44
agattgtctc aaagattccc aaagtgtgaa ttcgctgaag tttctaagtt g          51

<210> SEQ ID NO 45
<211> LENGTH: 50
<212> TYPE: DNA
<213> ORGANISM: Artificial Sequence
<220> FEATURE:
<223> OTHER INFORMATION: A227C forward primer

<400> SEQUENCE: 45
tgtctcaaag attcccaaag gcttgtttcg ctgaagtttc taagttggtt           50

<210> SEQ ID NO 46
```

```
<211> LENGTH: 50
<212> TYPE: DNA
<213> ORGANISM: Artificial Sequence
<220> FEATURE:
<223> OTHER INFORMATION: E230C forward primer

<400> SEQUENCE: 46
gattcccaaa ggctgaattc gcttgtgttt ctaagttggt tactgacttg                    50

<210> SEQ ID NO 47
<211> LENGTH: 51
<212> TYPE: DNA
<213> ORGANISM: Artificial Sequence
<220> FEATURE:
<223> OTHER INFORMATION: D237C forward primer

<400> SEQUENCE: 47
gctgaagttt ctaagttggt tacttgtttg actaaggttc acactgaatg t                  51

<210> SEQ ID NO 48
<211> LENGTH: 50
<212> TYPE: DNA
<213> ORGANISM: Artificial Sequence
<220> FEATURE:
<223> OTHER INFORMATION: K240C forward primer

<400> SEQUENCE: 48
tctaagttgg ttactgactt gacttgtgtt cacactgaat gttgtcacgg                    50

<210> SEQ ID NO 49
<211> LENGTH: 49
<212> TYPE: DNA
<213> ORGANISM: Artificial Sequence
<220> FEATURE:
<223> OTHER INFORMATION: D259C forward primer

<400> SEQUENCE: 49
ggaatgtgct gatgacagag cttgtttggc taagtacatc tgtgaaaac                     49

<210> SEQ ID NO 50
<211> LENGTH: 49
<212> TYPE: DNA
<213> ORGANISM: Artificial Sequence
<220> FEATURE:
<223> OTHER INFORMATION: K262C forward primer

<400> SEQUENCE: 50
tgatgacaga gctgacttgg cttgttacat ctgtgaaaac caagactct                     49

<210> SEQ ID NO 51
<211> LENGTH: 51
<212> TYPE: DNA
<213> ORGANISM: Artificial Sequence
<220> FEATURE:
<223> OTHER INFORMATION: N267C forward primer

<400> SEQUENCE: 51
gacttggcta agtacatctg tgaatgtcaa gactctatct cttccaagtt g                  51

<210> SEQ ID NO 52
<211> LENGTH: 51
<212> TYPE: DNA
<213> ORGANISM: Artificial Sequence
<220> FEATURE:
<223> OTHER INFORMATION: Q268C forward primer
```

```
<400> SEQUENCE: 52
ttggctaagt acatctgtga aaactgtgac tctatctctt ccaagttgaa g            51

<210> SEQ ID NO 53
<211> LENGTH: 51
<212> TYPE: DNA
<213> ORGANISM: Artificial Sequence
<220> FEATURE:
<223> OTHER INFORMATION: I271C forward primer

<400> SEQUENCE: 53
tacatctgtg aaaaccaaga ctcttgttct tccaagttga aggaatgttg t            51

<210> SEQ ID NO 54
<211> LENGTH: 50
<212> TYPE: DNA
<213> ORGANISM: Artificial Sequence
<220> FEATURE:
<223> OTHER INFORMATION: L275C forward primer

<400> SEQUENCE: 54
accaagactc tatctcttcc aagtgtaagg aatgttgtga aaagccattg              50

<210> SEQ ID NO 55
<211> LENGTH: 51
<212> TYPE: DNA
<213> ORGANISM: Artificial Sequence
<220> FEATURE:
<223> OTHER INFORMATION: E277C forward primer

<400> SEQUENCE: 55
gactctatct cttccaagtt gaagtgttgt tgtgaaaagc cattgttgga a            51

<210> SEQ ID NO 56
<211> LENGTH: 51
<212> TYPE: DNA
<213> ORGANISM: Artificial Sequence
<220> FEATURE:
<223> OTHER INFORMATION: L284C forward primer

<400> SEQUENCE: 56
aaggaatgtt gtgaaaagcc attgtgtgaa agtctcact gtattgctga a             51

<210> SEQ ID NO 57
<211> LENGTH: 50
<212> TYPE: DNA
<213> ORGANISM: Artificial Sequence
<220> FEATURE:
<223> OTHER INFORMATION: E294C forward primer

<400> SEQUENCE: 57
aagtctcact gtattgctga gtttgtaac gatgaaatgc cagctgactt               50

<210> SEQ ID NO 58
<211> LENGTH: 50
<212> TYPE: DNA
<213> ORGANISM: Artificial Sequence
<220> FEATURE:
<223> OTHER INFORMATION: E311C forward primer

<400> SEQUENCE: 58
catctttggc tgctgacttc gtttgttcta aggacgtttg taagaactac              50

<210> SEQ ID NO 59
```

```
<211> LENGTH: 49
<212> TYPE: DNA
<213> ORGANISM: Artificial Sequence
<220> FEATURE:
<223> OTHER INFORMATION: K317C forward primer

<400> SEQUENCE: 59
ttcgttgaat ctaaggacgt ttgttgtaac tacgctgaag ctaaggacg                49

<210> SEQ ID NO 60
<211> LENGTH: 50
<212> TYPE: DNA
<213> ORGANISM: Artificial Sequence
<220> FEATURE:
<223> OTHER INFORMATION: A322C forward primer

<400> SEQUENCE: 60
gacgtttgta agaactacgc tgaatgtaag gacgtcttct tgggtatgtt               50

<210> SEQ ID NO 61
<211> LENGTH: 49
<212> TYPE: DNA
<213> ORGANISM: Artificial Sequence
<220> FEATURE:
<223> OTHER INFORMATION: E333C

<400> SEQUENCE: 61
gtcttcttgg gtatgttctt gtactgttac gctagaagac acccagact                49

<210> SEQ ID NO 62
<211> LENGTH: 48
<212> TYPE: DNA
<213> ORGANISM: Artificial Sequence
<220> FEATURE:
<223> OTHER INFORMATION: D340C forward primer

<400> SEQUENCE: 62
cgaatacgct agaagacacc catgttactc cgttgtcttg ttgttgag                 48

<210> SEQ ID NO 63
<211> LENGTH: 48
<212> TYPE: DNA
<213> ORGANISM: Artificial Sequence
<220> FEATURE:
<223> OTHER INFORMATION: E354C forward primer

<400> SEQUENCE: 63
tgttgagatt ggctaagacc tactgtacta ccctcgagaa gtgttgtg                 48

<210> SEQ ID NO 64
<211> LENGTH: 48
<212> TYPE: DNA
<213> ORGANISM: Artificial Sequence
<220> FEATURE:
<223> OTHER INFORMATION: E358C forward primer

<400> SEQUENCE: 64
ctaagaccta cgaaactacc ctctgtaagt gttgtgctgc tgctgacc                 48

<210> SEQ ID NO 65
<211> LENGTH: 46
<212> TYPE: DNA
<213> ORGANISM: Artificial Sequence
<220> FEATURE:
<223> OTHER INFORMATION: K359C forward primer
```

```
<400> SEQUENCE: 65
gacctacgaa actaccctcg agtgttgttg tgctgctgct gaccca                    46

<210> SEQ ID NO 66
<211> LENGTH: 47
<212> TYPE: DNA
<213> ORGANISM: Artificial Sequence
<220> FEATURE:
<223> OTHER INFORMATION: A362C forward primer

<400> SEQUENCE: 66
aaactaccct cgagaagtgt tgttgtgctg ctgacccaca cgaatgt                   47

<210> SEQ ID NO 67
<211> LENGTH: 50
<212> TYPE: DNA
<213> ORGANISM: Artificial Sequence
<220> FEATURE:
<223> OTHER INFORMATION: E382C forward primer

<400> SEQUENCE: 67
tcgatgaatt caagccattg gtctgtgaac cacaaaactt gatcaagcaa                50

<210> SEQ ID NO 68
<211> LENGTH: 51
<212> TYPE: DNA
<213> ORGANISM: Artificial Sequence
<220> FEATURE:
<223> OTHER INFORMATION: L398C forward primer

<400> SEQUENCE: 68
gcaaaactgt gaattgttcg aacaatgtgg tgaatacaag ttccaaaacg c              51

<210> SEQ ID NO 69
<211> LENGTH: 35
<212> TYPE: DNA
<213> ORGANISM: Artificial Sequence
<220> FEATURE:
<223> OTHER INFORMATION: L24C reverse primer

<400> SEQUENCE: 69
gaccaaagcc ttgaagtttt cttcacccaa gtcct                                35

<210> SEQ ID NO 70
<211> LENGTH: 35
<212> TYPE: DNA
<213> ORGANISM: Artificial Sequence
<220> FEATURE:
<223> OTHER INFORMATION: F49C reverse primer

<400> SEQUENCE: 70
ttcggtaact tcgttgacca acttgacgtg atctt                                35

<210> SEQ ID NO 71
<211> LENGTH: 36
<212> TYPE: DNA
<213> ORGANISM: Artificial Sequence
<220> FEATURE:
<223> OTHER INFORMATION: V54C reverse primer

<400> SEQUENCE: 71
acaagtctta gcgaattcgg taacttcgtt gaccaa                               36

<210> SEQ ID NO 72
```

```
<211> LENGTH: 36
<212> TYPE: DNA
<213> ORGANISM: Artificial Sequence
<220> FEATURE:
<223> OTHER INFORMATION: D56C reverse primer

<400> SEQUENCE: 72
agcaacacaa gtcttagcga attcggtaac ttcgtt                               36

<210> SEQ ID NO 73
<211> LENGTH: 33
<212> TYPE: DNA
<213> ORGANISM: Artificial Sequence
<220> FEATURE:
<223> OTHER INFORMATION: L66C reverse primer

<400> SEQUENCE: 73
ggacttgtca cagtttccg cggattcgtc agc                                   33

<210> SEQ ID NO 74
<211> LENGTH: 34
<212> TYPE: DNA
<213> ORGANISM: Artificial Sequence
<220> FEATURE:
<223> OTHER INFORMATION: A92C reverse primer

<400> SEQUENCE: 74
acaacagtca gccatttcac cgtaggtttc tctc                                 34

<210> SEQ ID NO 75
<211> LENGTH: 35
<212> TYPE: DNA
<213> ORGANISM: Artificial Sequence
<220> FEATURE:
<223> OTHER INFORMATION: K93C reverse primer

<400> SEQUENCE: 75
agcacaacag tcagccattt caccgtaggt ttctc                                35

<210> SEQ ID NO 76
<211> LENGTH: 34
<212> TYPE: DNA
<213> ORGANISM: Artificial Sequence
<220> FEATURE:
<223> OTHER INFORMATION: Q94C reverse primer

<400> SEQUENCE: 76
cttagcacaa cagtcagcca tttcaccgta ggtt                                 34

<210> SEQ ID NO 77
<211> LENGTH: 35
<212> TYPE: DNA
<213> ORGANISM: Artificial Sequence
<220> FEATURE:
<223> OTHER INFORMATION: E97C reverse primer

<400> SEQUENCE: 77
tggttcttgc ttagcacaac agtcagccat ttcac                                35

<210> SEQ ID NO 78
<211> LENGTH: 35
<212> TYPE: DNA
<213> ORGANISM: Artificial Sequence
<220> FEATURE:
<223> OTHER INFORMATION: H128C reverse primer
```

-continued

```
<400> SEQUENCE: 78
gaaagcagta cacatgacgt caacttctgg tctaa                              35

<210> SEQ ID NO 79
<211> LENGTH: 35
<212> TYPE: DNA
<213> ORGANISM: Artificial Sequence
<220> FEATURE:
<223> OTHER INFORMATION: F156C reverse primer

<400> SEQUENCE: 79
caacaattct ggagcgtaga agtatgggtg tcttc                              35

<210> SEQ ID NO 80
<211> LENGTH: 34
<212> TYPE: DNA
<213> ORGANISM: Artificial Sequence
<220> FEATURE:
<223> OTHER INFORMATION: A226C reverse primer

<400> SEQUENCE: 80
ctttgggaat ctttgagaca atctagcgac agcc                               34

<210> SEQ ID NO 81
<211> LENGTH: 35
<212> TYPE: DNA
<213> ORGANISM: Artificial Sequence
<220> FEATURE:
<223> OTHER INFORMATION: E227C reverse primer

<400> SEQUENCE: 81
agcctttggg aatctttgag acaatctagc gacag                              35

<210> SEQ ID NO 82
<211> LENGTH: 36
<212> TYPE: DNA
<213> ORGANISM: Artificial Sequence
<220> FEATURE:
<223> OTHER INFORMATION: E230C reverse primer

<400> SEQUENCE: 82
agcgaattca gcctttggga atctttgaga caatct                             36

<210> SEQ ID NO 83
<211> LENGTH: 36
<212> TYPE: DNA
<213> ORGANISM: Artificial Sequence
<220> FEATURE:
<223> OTHER INFORMATION: E237C reverse primer

<400> SEQUENCE: 83
agtaaccaac ttagaaactt cagcgaattc agcctt                             36

<210> SEQ ID NO 84
<211> LENGTH: 36
<212> TYPE: DNA
<213> ORGANISM: Artificial Sequence
<220> FEATURE:
<223> OTHER INFORMATION: K240C reverse primer

<400> SEQUENCE: 84
agtcaagtca gtaaccaact tagaaacttc agcgaa                             36

<210> SEQ ID NO 85
```

```
<211> LENGTH: 34
<212> TYPE: DNA
<213> ORGANISM: Artificial Sequence
<220> FEATURE:
<223> OTHER INFORMATION: D259C reverse primer

<400> SEQUENCE: 85
agctctgtca tcagcacatt ccaacaagtc accg                              34

<210> SEQ ID NO 86
<211> LENGTH: 34
<212> TYPE: DNA
<213> ORGANISM: Artificial Sequence
<220> FEATURE:
<223> OTHER INFORMATION: K262C reverse primer

<400> SEQUENCE: 86
agccaagtca gctctgtcat cagcacattc caac                              34

<210> SEQ ID NO 87
<211> LENGTH: 36
<212> TYPE: DNA
<213> ORGANISM: Artificial Sequence
<220> FEATURE:
<223> OTHER INFORMATION: N267C reverse primer

<400> SEQUENCE: 87
ttcacagatg tacttagcca agtcagctct gtcatc                            36

<210> SEQ ID NO 88
<211> LENGTH: 35
<212> TYPE: DNA
<213> ORGANISM: Artificial Sequence
<220> FEATURE:
<223> OTHER INFORMATION: Q268C reverse primer

<400> SEQUENCE: 88
gttttcacag atgtacttag ccaagtcagc tctgt                             35

<210> SEQ ID NO 89
<211> LENGTH: 36
<212> TYPE: DNA
<213> ORGANISM: Artificial Sequence
<220> FEATURE:
<223> OTHER INFORMATION: I271C reverse primer

<400> SEQUENCE: 89
agagtcttgg ttttcacaga tgtacttagc caagtc                            36

<210> SEQ ID NO 90
<211> LENGTH: 36
<212> TYPE: DNA
<213> ORGANISM: Artificial Sequence
<220> FEATURE:
<223> OTHER INFORMATION: L275C reverse primer

<400> SEQUENCE: 90
cttggaagag atagagtctt ggttttcaca gatgta                            36

<210> SEQ ID NO 91
<211> LENGTH: 37
<212> TYPE: DNA
<213> ORGANISM: Artificial Sequence
<220> FEATURE:
<223> OTHER INFORMATION: E277C reverse primer
```

<400> SEQUENCE: 91
cttcaacttg gaagagatag agtcttggtt ttcacag       37

<210> SEQ ID NO 92
<211> LENGTH: 36
<212> TYPE: DNA
<213> ORGANISM: Artificial Sequence
<220> FEATURE:
<223> OTHER INFORMATION: E284C reverse primer

<400> SEQUENCE: 92
caatggcttt tcacaacatt ccttcaactt ggaaga       36

<210> SEQ ID NO 93
<211> LENGTH: 36
<212> TYPE: DNA
<213> ORGANISM: Artificial Sequence
<220> FEATURE:
<223> OTHER INFORMATION: E294C reverse primer

<400> SEQUENCE: 93
aacttcagca atacagtgag acttttccaa caatgg       36

<210> SEQ ID NO 94
<211> LENGTH: 34
<212> TYPE: DNA
<213> ORGANISM: Artificial Sequence
<220> FEATURE:
<223> OTHER INFORMATION: E311C reverse primer

<400> SEQUENCE: 94
aacgaagtca gcagccaaag atggcaagtc agct       34

<210> SEQ ID NO 95
<211> LENGTH: 34
<212> TYPE: DNA
<213> ORGANISM: Artificial Sequence
<220> FEATURE:
<223> OTHER INFORMATION: K317C reverse primer

<400> SEQUENCE: 95
acaaacgtcc ttagattcaa cgaagtcagc agcc       34

<210> SEQ ID NO 96
<211> LENGTH: 37
<212> TYPE: DNA
<213> ORGANISM: Artificial Sequence
<220> FEATURE:
<223> OTHER INFORMATION: A322C reverse primer

<400> SEQUENCE: 96
ttcagcgtag ttcttacaaa cgtccttaga ttcaacg       37

<210> SEQ ID NO 97
<211> LENGTH: 36
<212> TYPE: DNA
<213> ORGANISM: Artificial Sequence
<220> FEATURE:
<223> OTHER INFORMATION: E333C reverse primer

<400> SEQUENCE: 97
gtacaagaac atacccaaga agacgtcctt agcttc       36

<210> SEQ ID NO 98

```
<211> LENGTH: 35
<212> TYPE: DNA
<213> ORGANISM: Artificial Sequence
<220> FEATURE:
<223> OTHER INFORMATION: D340C reverse primer

<400> SEQUENCE: 98
tgggtgtctt ctagcgtatt cgtacaagaa catac                          35

<210> SEQ ID NO 99
<211> LENGTH: 35
<212> TYPE: DNA
<213> ORGANISM: Artificial Sequence
<220> FEATURE:
<223> OTHER INFORMATION: E354C reverse primer

<400> SEQUENCE: 99
gtaggtctta gccaatctca acaacaagac aacgg                          35

<210> SEQ ID NO 100
<211> LENGTH: 35
<212> TYPE: DNA
<213> ORGANISM: Artificial Sequence
<220> FEATURE:
<223> OTHER INFORMATION: E358C reverse primer

<400> SEQUENCE: 100
gagggtagtt tcgtaggtct tagccaatct caaca                          35

<210> SEQ ID NO 101
<211> LENGTH: 34
<212> TYPE: DNA
<213> ORGANISM: Artificial Sequence
<220> FEATURE:
<223> OTHER INFORMATION: K359C reverse primer

<400> SEQUENCE: 101
ctcgagggta gtttcgtagg tcttagccaa tctc                           34

<210> SEQ ID NO 102
<211> LENGTH: 35
<212> TYPE: DNA
<213> ORGANISM: Artificial Sequence
<220> FEATURE:
<223> OTHER INFORMATION: A362C reverse primer

<400> SEQUENCE: 102
acaacacttc tcgagggtag tttcgtaggt cttag                          35

<210> SEQ ID NO 103
<211> LENGTH: 35
<212> TYPE: DNA
<213> ORGANISM: Artificial Sequence
<220> FEATURE:
<223> OTHER INFORMATION: E382C reverse primer

<400> SEQUENCE: 103
gaccaatggc ttgaattcat cgaaaacctt agcgt                          35

<210> SEQ ID NO 104
<211> LENGTH: 39
<212> TYPE: DNA
<213> ORGANISM: Artificial Sequence
<220> FEATURE:
<223> OTHER INFORMATION: L398C reverse primer
```

```
<400> SEQUENCE: 104
ttgttcgaac aattcacagt tttgcttgat caagttttg                                  39

<210> SEQ ID NO 105
<211> LENGTH: 585
<212> TYPE: PRT
<213> ORGANISM: Artificial Sequence
<220> FEATURE:
<223> OTHER INFORMATION: HSA C34A_L24C

<400> SEQUENCE: 105
```

| Asp | Ala | His | Lys | Ser | Glu | Val | Ala | His | Arg | Phe | Lys | Asp | Leu | Gly | Glu |
|---|---|---|---|---|---|---|---|---|---|---|---|---|---|---|---|
| 1 | | | | 5 | | | | | 10 | | | | | 15 | |

| Glu | Asn | Phe | Lys | Ala | Leu | Val | Cys | Ile | Ala | Phe | Ala | Gln | Tyr | Leu | Gln |
|---|---|---|---|---|---|---|---|---|---|---|---|---|---|---|---|
| | | | 20 | | | | 25 | | | | | 30 | | | |

| Gln | Ala | Pro | Phe | Glu | Asp | His | Val | Lys | Leu | Val | Asn | Glu | Val | Thr | Glu |
|---|---|---|---|---|---|---|---|---|---|---|---|---|---|---|---|
| | | 35 | | | | 40 | | | | | 45 | | | | |

| Phe | Ala | Lys | Thr | Cys | Val | Ala | Asp | Glu | Ser | Ala | Glu | Asn | Cys | Asp | Lys |
|---|---|---|---|---|---|---|---|---|---|---|---|---|---|---|---|
| | 50 | | | | | 55 | | | | | 60 | | | | |

| Ser | Leu | His | Thr | Leu | Phe | Gly | Asp | Lys | Leu | Cys | Thr | Val | Ala | Thr | Leu |
|---|---|---|---|---|---|---|---|---|---|---|---|---|---|---|---|
| 65 | | | | | 70 | | | | | 75 | | | | | 80 |

| Arg | Glu | Thr | Tyr | Gly | Glu | Met | Ala | Asp | Cys | Cys | Ala | Lys | Gln | Glu | Pro |
|---|---|---|---|---|---|---|---|---|---|---|---|---|---|---|---|
| | | | | 85 | | | | | 90 | | | | | 95 | |

| Glu | Arg | Asn | Glu | Cys | Phe | Leu | Gln | His | Lys | Asp | Asp | Asn | Pro | Asn | Leu |
|---|---|---|---|---|---|---|---|---|---|---|---|---|---|---|---|
| | | | 100 | | | | | 105 | | | | | 110 | | |

| Pro | Arg | Leu | Val | Arg | Pro | Glu | Val | Asp | Val | Met | Cys | Thr | Ala | Phe | His |
|---|---|---|---|---|---|---|---|---|---|---|---|---|---|---|---|
| | | 115 | | | | | 120 | | | | | 125 | | | |

| Asp | Asn | Glu | Glu | Thr | Phe | Leu | Lys | Lys | Tyr | Leu | Tyr | Glu | Ile | Ala | Arg |
|---|---|---|---|---|---|---|---|---|---|---|---|---|---|---|---|
| | 130 | | | | | 135 | | | | | 140 | | | | |

| Arg | His | Pro | Tyr | Phe | Tyr | Ala | Pro | Glu | Leu | Leu | Phe | Phe | Ala | Lys | Arg |
|---|---|---|---|---|---|---|---|---|---|---|---|---|---|---|---|
| 145 | | | | | 150 | | | | | 155 | | | | | 160 |

| Tyr | Lys | Ala | Ala | Phe | Thr | Glu | Cys | Cys | Gln | Ala | Ala | Asp | Lys | Ala | Ala |
|---|---|---|---|---|---|---|---|---|---|---|---|---|---|---|---|
| | | | | 165 | | | | | 170 | | | | | 175 | |

| Cys | Leu | Leu | Pro | Lys | Leu | Asp | Glu | Leu | Arg | Asp | Glu | Gly | Lys | Ala | Ser |
|---|---|---|---|---|---|---|---|---|---|---|---|---|---|---|---|
| | | | 180 | | | | | 185 | | | | | 190 | | |

| Ser | Ala | Lys | Gln | Arg | Leu | Lys | Cys | Ala | Ser | Leu | Gln | Lys | Phe | Gly | Glu |
|---|---|---|---|---|---|---|---|---|---|---|---|---|---|---|---|
| | | 195 | | | | | 200 | | | | | 205 | | | |

| Arg | Ala | Phe | Lys | Ala | Trp | Ala | Val | Ala | Arg | Leu | Ser | Gln | Arg | Phe | Pro |
|---|---|---|---|---|---|---|---|---|---|---|---|---|---|---|---|
| | 210 | | | | | 215 | | | | | 220 | | | | |

| Lys | Ala | Glu | Phe | Ala | Glu | Val | Ser | Lys | Leu | Val | Thr | Asp | Leu | Thr | Lys |
|---|---|---|---|---|---|---|---|---|---|---|---|---|---|---|---|
| 225 | | | | | 230 | | | | | 235 | | | | | 240 |

| Val | His | Thr | Glu | Cys | Cys | His | Gly | Asp | Leu | Leu | Glu | Cys | Ala | Asp | Asp |
|---|---|---|---|---|---|---|---|---|---|---|---|---|---|---|---|
| | | | | 245 | | | | | 250 | | | | | 255 | |

| Arg | Ala | Asp | Leu | Ala | Lys | Tyr | Ile | Cys | Glu | Asn | Gln | Asp | Ser | Ile | Ser |
|---|---|---|---|---|---|---|---|---|---|---|---|---|---|---|---|
| | | | 260 | | | | | 265 | | | | | 270 | | |

| Ser | Lys | Leu | Lys | Glu | Cys | Cys | Glu | Lys | Pro | Leu | Leu | Glu | Lys | Ser | His |
|---|---|---|---|---|---|---|---|---|---|---|---|---|---|---|---|
| | | 275 | | | | | 280 | | | | | 285 | | | |

| Cys | Ile | Ala | Glu | Val | Glu | Asn | Asp | Glu | Met | Pro | Ala | Asp | Leu | Pro | Ser |
|---|---|---|---|---|---|---|---|---|---|---|---|---|---|---|---|
| | 290 | | | | | 295 | | | | | 300 | | | | |

| Leu | Ala | Ala | Asp | Phe | Val | Glu | Ser | Lys | Asp | Val | Cys | Lys | Asn | Tyr | Ala |
|---|---|---|---|---|---|---|---|---|---|---|---|---|---|---|---|
| 305 | | | | | 310 | | | | | 315 | | | | | 320 |

| Glu | Ala | Lys | Asp | Val | Phe | Leu | Gly | Met | Phe | Leu | Tyr | Glu | Tyr | Ala | Arg |
|---|---|---|---|---|---|---|---|---|---|---|---|---|---|---|---|
| | | | | 325 | | | | | 330 | | | | | 335 | |

```
Arg His Pro Asp Tyr Ser Val Val Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
    435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
    515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 106
<211> LENGTH: 585
<212> TYPE: PRT
<213> ORGANISM: Artificial Sequence
<220> FEATURE:
<223> OTHER INFORMATION: HSA C34A_F49C

<400> SEQUENCE: 106

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Cys Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110
```

```
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
                180                 185                 190
Ser Ala Lys Gln Arg Leu Lys Cys Ala Ser Leu Gln Lys Phe Gly Glu
    195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
                260                 265                 270
Ser Lys Leu Lys Glu Cys Cys Glu Lys Pro Leu Leu Glu Lys Ser His
    275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
                340                 345                 350
Tyr Glu Thr Thr Leu Glu Lys Cys Cys Ala Ala Ala Asp Pro His Glu
    355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
                420                 425                 430
Val Gly Ser Lys Cys Cys Lys His Pro Glu Ala Lys Arg Met Pro Cys
    435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
                500                 505                 510
Ile Cys Thr Leu Ser Glu Lys Glu Arg Gln Ile Lys Lys Gln Thr Ala
    515                 520                 525
```

```
Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 107
<211> LENGTH: 585
<212> TYPE: PRT
<213> ORGANISM: Artificial Sequence
<220> FEATURE:
<223> OTHER INFORMATION: HSA C34A_V54C

<400> SEQUENCE: 107

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Phe Ala Lys Thr Cys Cys Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300
```

```
Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
            580                 585

<210> SEQ ID NO 108
<211> LENGTH: 585
<212> TYPE: PRT
<213> ORGANISM: Artificial Sequence
<220> FEATURE:
<223> OTHER INFORMATION: HSA C34A_D56C

<400> SEQUENCE: 108

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Cys Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80
```

```
Arg Glu Thr Tyr Gly Glu Met Ala Asp Cys Cys Ala Lys Gln Glu Pro
             85                  90                  95
Glu Arg Asn Glu Cys Phe Leu Gln His Lys Asp Asp Asn Pro Asn Leu
        100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
                180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
                260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
                340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
                420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
        450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
```

```
Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 109
<211> LENGTH: 585
<212> TYPE: PRT
<213> ORGANISM: Artificial Sequence
<220> FEATURE:
<223> OTHER INFORMATION: HSA C34A_L66C

<400> SEQUENCE: 109

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Cys His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270
```

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
                340                 345                 350

Tyr Glu Thr Thr Leu Glu Lys Cys Cys Ala Ala Ala Asp Pro His Glu
                355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
    515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 110
<211> LENGTH: 585
<212> TYPE: PRT
<213> ORGANISM: Artificial Sequence
<220> FEATURE:
<223> OTHER INFORMATION: HSA C34A_A92C

<400> SEQUENCE: 110

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

```
Phe Ala Lys Thr Cys Val Ala Asp Glu Ser Ala Glu Asn Cys Asp Lys
    50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Lys Gln Glu Pro
                85                  90                  95
Glu Arg Asn Glu Cys Phe Leu Gln His Lys Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
450                 455                 460
```

```
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 111
<211> LENGTH: 585
<212> TYPE: PRT
<213> ORGANISM: Artificial Sequence
<220> FEATURE:
<223> OTHER INFORMATION: HSA C34A_K93C

<400> SEQUENCE: 111

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Cys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240
```

```
Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 112
<211> LENGTH: 585
<212> TYPE: PRT
<213> ORGANISM: Artificial Sequence
<220> FEATURE:
<223> OTHER INFORMATION: HSA C34A_Q94C

<400> SEQUENCE: 112

Asp Ala His Lys Ser Glu Val Ala His Arg Phe Lys Asp Leu Gly Glu
1               5                   10                  15
```

```
Glu Asn Phe Lys Ala Leu Val Leu Ile Ala Phe Ala Gln Tyr Leu Gln
                 20                  25                  30

Gln Ala Pro Phe Glu Asp His Val Lys Leu Val Asn Glu Val Thr Glu
             35                  40                  45

Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Cys Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430
```

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 113
<211> LENGTH: 585
<212> TYPE: PRT
<213> ORGANISM: Artificial Sequence
<220> FEATURE:
<223> OTHER INFORMATION: HSA C34A_E97C

<400> SEQUENCE: 113

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Cys Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

```
Arg Ala Phe Lys Ala Trp Ala Val Ala Arg Leu Ser Gln Arg Phe Pro
            210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 114
<211> LENGTH: 585
<212> TYPE: PRT
<213> ORGANISM: Artificial Sequence
<220> FEATURE:
```

<223> OTHER INFORMATION: HSA C34A_H128C

<400> SEQUENCE: 114

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe Cys
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400
```

```
Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

<210> SEQ ID NO 115
<211> LENGTH: 585
<212> TYPE: PRT
<213> ORGANISM: Artificial Sequence
<220> FEATURE:
<223> OTHER INFORMATION: HSA C34A_F156C

<400> SEQUENCE: 115

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Cys Phe Ala Lys Arg
145                 150                 155                 160

Tyr Lys Ala Ala Phe Thr Glu Cys Cys Gln Ala Ala Asp Lys Ala Ala
                165                 170                 175
```

-continued

```
Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

<210> SEQ ID NO 116
<211> LENGTH: 585
<212> TYPE: PRT
<213> ORGANISM: Artificial Sequence
<220> FEATURE:
<223> OTHER INFORMATION: HSA C34A_A226C

<400> SEQUENCE: 116

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Cys Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365
```

| Cys | Tyr | Ala | Lys | Val | Phe | Asp | Glu | Phe | Lys | Pro | Leu | Val | Glu | Glu | Pro |
|---|---|---|---|---|---|---|---|---|---|---|---|---|---|---|---|
| | 370 | | | | 375 | | | | 380 | | | | | | |

Gln Asn Leu Ile Lys Gln Asn Cys Glu Leu Phe Glu Gln Leu Gly Glu
385　　　　　　390　　　　　　　395　　　　　　　400

Tyr Lys Phe Gln Asn Ala Leu Leu Val Arg Tyr Thr Lys Lys Val Pro
　　　　　405　　　　　　　410　　　　　　　415

Gln Val Ser Thr Pro Thr Leu Val Glu Val Ser Arg Asn Leu Gly Lys
　　　420　　　　　　　425　　　　　　　430

Val Gly Ser Lys Cys Cys Lys His Pro Glu Ala Lys Arg Met Pro Cys
　　435　　　　　　　440　　　　　　　445

Ala Glu Asp Tyr Leu Ser Val Val Leu Asn Gln Leu Cys Val Leu His
450　　　　　　　455　　　　　　　460

Glu Lys Thr Pro Val Ser Asp Arg Val Thr Lys Cys Cys Thr Glu Ser
465　　　　　　　470　　　　　　　475　　　　　　　480

Leu Val Asn Arg Arg Pro Cys Phe Ser Ala Leu Glu Val Asp Glu Thr
　　　　　485　　　　　　　490　　　　　　　495

Tyr Val Pro Lys Glu Phe Asn Ala Glu Thr Phe Thr Phe His Ala Asp
　　　　500　　　　　　　505　　　　　　　510

Ile Cys Thr Leu Ser Glu Lys Glu Arg Gln Ile Lys Lys Gln Thr Ala
　　　515　　　　　　　520　　　　　　　525

Leu Val Glu Leu Val Lys His Lys Pro Lys Ala Thr Lys Glu Gln Leu
530　　　　　　　535　　　　　　　540

Lys Ala Val Met Asp Asp Phe Ala Ala Phe Val Glu Lys Cys Cys Lys
545　　　　　　　550　　　　　　　555　　　　　　　560

Ala Asp Asp Lys Glu Thr Cys Phe Ala Glu Glu Gly Lys Lys Leu Val
　　　　　565　　　　　　　570　　　　　　　575

Ala Ala Ser Gln Ala Ala Leu Gly Leu
　　　　580　　　　　　　585

<210> SEQ ID NO 117
<211> LENGTH: 585
<212> TYPE: PRT
<213> ORGANISM: Artificial Sequence
<220> FEATURE:
<223> OTHER INFORMATION: HSA C34A_E227C

<400> SEQUENCE: 117

Asp Ala His Lys Ser Glu Val Ala His Arg Phe Lys Asp Leu Gly Glu
1　　　　　　5　　　　　　　10　　　　　　　15

Glu Asn Phe Lys Ala Leu Val Leu Ile Ala Phe Ala Gln Tyr Leu Gln
　　　　　20　　　　　　　25　　　　　　　30

Gln Ala Pro Phe Glu Asp His Val Lys Leu Val Asn Glu Val Thr Glu
　　　35　　　　　　　40　　　　　　　45

Phe Ala Lys Thr Cys Val Ala Asp Glu Ser Ala Glu Asn Cys Asp Lys
　　50　　　　　　　55　　　　　　　60

Ser Leu His Thr Leu Phe Gly Asp Lys Leu Cys Thr Val Ala Thr Leu
65　　　　　　　70　　　　　　　75　　　　　　　80

Arg Glu Thr Tyr Gly Glu Met Ala Asp Cys Cys Ala Lys Gln Glu Pro
　　　　　85　　　　　　　90　　　　　　　95

Glu Arg Asn Glu Cys Phe Leu Gln His Lys Asp Asp Asn Pro Asn Leu
　　　　100　　　　　　　105　　　　　　　110

Pro Arg Leu Val Arg Pro Glu Val Asp Val Met Cys Thr Ala Phe His
　　　115　　　　　　　120　　　　　　　125

Asp Asn Glu Glu Thr Phe Leu Lys Lys Tyr Leu Tyr Glu Ile Ala Arg
　　130　　　　　　　135　　　　　　　140

```
Arg His Pro Tyr Phe Tyr Ala Pro Glu Leu Leu Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Cys Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560
```

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 118
<211> LENGTH: 585
<212> TYPE: PRT
<213> ORGANISM: Artificial Sequence
<220> FEATURE:
<223> OTHER INFORMATION: HSA C34A_E230C

<400> SEQUENCE: 118

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Cys Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 119
<211> LENGTH: 585
<212> TYPE: PRT
<213> ORGANISM: Artificial Sequence
<220> FEATURE:
<223> OTHER INFORMATION: HSA C34A_D237C

<400> SEQUENCE: 119

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

```
Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Cys Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525
```

```
Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 120
<211> LENGTH: 585
<212> TYPE: PRT
<213> ORGANISM: Artificial Sequence
<220> FEATURE:
<223> OTHER INFORMATION: HSA C34A_K240C

<400> SEQUENCE: 120

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Cys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300
```

```
Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 121
<211> LENGTH: 585
<212> TYPE: PRT
<213> ORGANISM: Artificial Sequence
<220> FEATURE:
<223> OTHER INFORMATION: HSA C34A_D259C

<400> SEQUENCE: 121

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80
```

-continued

```
Arg Glu Thr Tyr Gly Glu Met Ala Asp Cys Cys Ala Lys Gln Glu Pro
            85                  90                  95
Glu Arg Asn Glu Cys Phe Leu Gln His Lys Asp Asp Asn Pro Asn Leu
           100                 105                 110
Pro Arg Leu Val Arg Pro Glu Val Asp Val Met Cys Thr Ala Phe His
           115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
               165                 170                 175
Cys Leu Leu Pro Lys Leu Asp Glu Leu Arg Asp Glu Gly Lys Ala Ser
           180                 185                 190
Ser Ala Lys Gln Arg Leu Lys Cys Ala Ser Leu Gln Lys Phe Gly Glu
           195                 200                 205
Arg Ala Phe Lys Ala Trp Ala Val Ala Arg Leu Ser Gln Arg Phe Pro
210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
               245                 250                 255
Arg Ala Cys Leu Ala Lys Tyr Ile Cys Glu Asn Gln Asp Ser Ile Ser
           260                 265                 270
Ser Lys Leu Lys Glu Cys Cys Glu Lys Pro Leu Leu Glu Lys Ser His
           275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
               325                 330                 335
Arg His Pro Asp Tyr Ser Val Val Leu Leu Leu Arg Leu Ala Lys Thr
           340                 345                 350
Tyr Glu Thr Thr Leu Glu Lys Cys Cys Ala Ala Ala Asp Pro His Glu
           355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
               405                 410                 415
Gln Val Ser Thr Pro Thr Leu Val Glu Val Ser Arg Asn Leu Gly Lys
           420                 425                 430
Val Gly Ser Lys Cys Cys Lys His Pro Glu Ala Lys Arg Met Pro Cys
           435                 440                 445
Ala Glu Asp Tyr Leu Ser Val Val Leu Asn Gln Leu Cys Val Leu His
450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
               485                 490                 495
```

```
Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
            580                 585

<210> SEQ ID NO 122
<211> LENGTH: 585
<212> TYPE: PRT
<213> ORGANISM: Artificial Sequence
<220> FEATURE:
<223> OTHER INFORMATION: HSA C34A_K262C

<400> SEQUENCE: 122

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Cys Tyr Ile Cys Glu Asn Gln Asp Ser Ile Ser
            260                 265                 270
```

```
Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

<210> SEQ ID NO 123
<211> LENGTH: 585
<212> TYPE: PRT
<213> ORGANISM: Artificial Sequence
<220> FEATURE:
<223> OTHER INFORMATION: HSA C34A_N267C

<400> SEQUENCE: 123

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45
```

```
Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Cys Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460
```

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 124
<211> LENGTH: 585
<212> TYPE: PRT
<213> ORGANISM: Artificial Sequence
<220> FEATURE:
<223> OTHER INFORMATION: HSA C34A_Q268C

<400> SEQUENCE: 124

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

```
Val His Thr Glu Cys Cys His Gly Asp Leu Leu Glu Cys Ala Asp Asp
                245                 250                 255

Arg Ala Asp Leu Ala Lys Tyr Ile Cys Glu Asn Cys Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 125
<211> LENGTH: 585
<212> TYPE: PRT
<213> ORGANISM: Artificial Sequence
<220> FEATURE:
<223> OTHER INFORMATION: HSA C34A_I271C

<400> SEQUENCE: 125

Asp Ala His Lys Ser Glu Val Ala His Arg Phe Lys Asp Leu Gly Glu
1               5                   10                  15
```

```
Glu Asn Phe Lys Ala Leu Val Leu Ile Ala Phe Ala Gln Tyr Leu Gln
                 20                  25                  30

Gln Ala Pro Phe Glu Asp His Val Lys Leu Val Asn Glu Val Thr Glu
             35                  40                  45

Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Cys Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
 370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430
```

```
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
450                     455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
                580                 585

<210> SEQ ID NO 126
<211> LENGTH: 585
<212> TYPE: PRT
<213> ORGANISM: Artificial Sequence
<220> FEATURE:
<223> OTHER INFORMATION: HSA C34A_L275C

<400> SEQUENCE: 126

Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
            20                  25                  30
Gln Ala Pro Phe Glu Asp His Val Lys Leu Val Asn Glu Val Thr Glu
        35                  40                  45
Phe Ala Lys Thr Cys Val Ala Asp Glu Ser Ala Glu Asn Cys Asp Lys
    50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
```

```
Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Cys Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 127
<211> LENGTH: 585
<212> TYPE: PRT
<213> ORGANISM: Artificial Sequence
<220> FEATURE:
<223> OTHER INFORMATION: HSA C34A_E277C
```

<400> SEQUENCE: 127

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

```
Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 128
<211> LENGTH: 585
<212> TYPE: PRT
<213> ORGANISM: Artificial Sequence
<220> FEATURE:
<223> OTHER INFORMATION: HSA C34A_L284C

<400> SEQUENCE: 128

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175
```

```
Cys Leu Leu Pro Lys Leu Asp Glu Leu Arg Asp Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Cys Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

<210> SEQ ID NO 129
<211> LENGTH: 585
<212> TYPE: PRT
<213> ORGANISM: Artificial Sequence
<220> FEATURE:
<223> OTHER INFORMATION: HSA C34A_E294C

<400> SEQUENCE: 129

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Cys Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365
```

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 130
<211> LENGTH: 585
<212> TYPE: PRT
<213> ORGANISM: Artificial Sequence
<220> FEATURE:
<223> OTHER INFORMATION: HSA C34A_E311C

<400> SEQUENCE: 130

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
                35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
                115                 120                 125

Asp Asn Glu Glu Thr Phe Leu Lys Lys Tyr Leu Tyr Glu Ile Ala Arg
130                 135                 140

-continued

```
Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Cys Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560
```

-continued

Ala Asp Asp Lys Glu Thr Cys Phe Ala Glu Glu Gly Lys Lys Leu Val
            565                 570                 575

Ala Ala Ser Gln Ala Ala Leu Gly Leu
            580                 585

<210> SEQ ID NO 131
<211> LENGTH: 585
<212> TYPE: PRT
<213> ORGANISM: Artificial Sequence
<220> FEATURE:
<223> OTHER INFORMATION: HSA C34A_K317C

<400> SEQUENCE: 131

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65              70                  75                  80

Arg Glu Thr Tyr Gly Glu Met Ala Asp Cys Cys Ala Lys Gln Glu Pro
            85                  90                  95

Glu Arg Asn Glu Cys Phe Leu Gln His Lys Asp Asp Asn Pro Asn Leu
        100                 105                 110

Pro Arg Leu Val Arg Pro Glu Val Asp Val Met Cys Thr Ala Phe His
    115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
            165                 170                 175

Cys Leu Leu Pro Lys Leu Asp Glu Leu Arg Asp Glu Gly Lys Ala Ser
        180                 185                 190

Ser Ala Lys Gln Arg Leu Lys Cys Ala Ser Leu Gln Lys Phe Gly Glu
    195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
            245                 250                 255

Arg Ala Asp Leu Ala Lys Tyr Ile Cys Glu Asn Gln Asp Ser Ile Ser
        260                 265                 270

Ser Lys Leu Lys Glu Cys Cys Glu Lys Pro Leu Leu Glu Lys Ser His
    275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Cys Asn Tyr Ala
305                 310                 315                 320

Glu Ala Lys Asp Val Phe Leu Gly Met Phe Leu Tyr Glu Tyr Ala Arg
            325                 330                 335

```
Arg His Pro Asp Tyr Ser Val Leu Leu Arg Leu Ala Lys Thr
            340             345             350

Tyr Glu Thr Thr Leu Glu Lys Cys Cys Ala Ala Ala Asp Pro His Glu
            355             360             365

Cys Tyr Ala Lys Val Phe Asp Glu Phe Lys Pro Leu Val Glu Glu Pro
            370             375             380

Gln Asn Leu Ile Lys Gln Asn Cys Glu Leu Phe Glu Gln Leu Gly Glu
385             390             395             400

Tyr Lys Phe Gln Asn Ala Leu Leu Val Arg Tyr Thr Lys Lys Val Pro
            405             410             415

Gln Val Ser Thr Pro Thr Leu Val Glu Val Ser Arg Asn Leu Gly Lys
            420             425             430

Val Gly Ser Lys Cys Cys Lys His Pro Glu Ala Lys Arg Met Pro Cys
            435             440             445

Ala Glu Asp Tyr Leu Ser Val Val Leu Asn Gln Leu Cys Val Leu His
            450             455             460

Glu Lys Thr Pro Val Ser Asp Arg Val Thr Lys Cys Cys Thr Glu Ser
465             470             475             480

Leu Val Asn Arg Arg Pro Cys Phe Ser Ala Leu Glu Val Asp Glu Thr
            485             490             495

Tyr Val Pro Lys Glu Phe Asn Ala Glu Thr Phe Thr Phe His Ala Asp
            500             505             510

Ile Cys Thr Leu Ser Glu Lys Glu Arg Gln Ile Lys Lys Gln Thr Ala
            515             520             525

Leu Val Glu Leu Val Lys His Lys Pro Lys Ala Thr Lys Glu Gln Leu
            530             535             540

Lys Ala Val Met Asp Asp Phe Ala Ala Phe Val Glu Lys Cys Cys Lys
545             550             555             560

Ala Asp Asp Lys Glu Thr Cys Phe Ala Glu Glu Gly Lys Lys Leu Val
            565             570             575

Ala Ala Ser Gln Ala Ala Leu Gly Leu
            580             585

<210> SEQ ID NO 132
<211> LENGTH: 585
<212> TYPE: PRT
<213> ORGANISM: Artificial Sequence
<220> FEATURE:
<223> OTHER INFORMATION: HSA C34A_A322C

<400> SEQUENCE: 132

Asp Ala His Lys Ser Glu Val Ala His Arg Phe Lys Asp Leu Gly Glu
1               5               10              15

Glu Asn Phe Lys Ala Leu Val Leu Ile Ala Phe Ala Gln Tyr Leu Gln
            20              25              30

Gln Ala Pro Phe Glu Asp His Val Lys Leu Val Asn Glu Val Thr Glu
            35              40              45

Phe Ala Lys Thr Cys Val Ala Asp Glu Ser Ala Glu Asn Cys Asp Lys
            50              55              60

Ser Leu His Thr Leu Phe Gly Asp Lys Leu Cys Thr Val Ala Thr Leu
65              70              75              80

Arg Glu Thr Tyr Gly Glu Met Ala Asp Cys Cys Ala Lys Gln Glu Pro
            85              90              95

Glu Arg Asn Glu Cys Phe Leu Gln His Lys Asp Asp Asn Pro Asn Leu
            100             105             110
```

```
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
        130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
                180                 185                 190
Ser Ala Lys Gln Arg Leu Lys Cys Ala Ser Leu Gln Lys Phe Gly Glu
            195                 200                 205
Arg Ala Phe Lys Ala Trp Ala Val Ala Arg Leu Ser Gln Arg Phe Pro
        210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
                260                 265                 270
Ser Lys Leu Lys Glu Cys Cys Glu Lys Pro Leu Leu Glu Lys Ser His
            275                 280                 285
Cys Ile Ala Glu Val Glu Asn Asp Glu Met Pro Ala Asp Leu Pro Ser
        290                 295                 300
Leu Ala Ala Asp Phe Val Glu Ser Lys Asp Val Cys Lys Asn Tyr Ala
305                 310                 315                 320
Glu Cys Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
                340                 345                 350
Tyr Glu Thr Thr Leu Glu Lys Cys Cys Ala Ala Ala Asp Pro His Glu
            355                 360                 365
Cys Tyr Ala Lys Val Phe Asp Glu Phe Lys Pro Leu Val Glu Glu Pro
        370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
                420                 425                 430
Val Gly Ser Lys Cys Cys Lys His Pro Glu Ala Lys Arg Met Pro Cys
            435                 440                 445
Ala Glu Asp Tyr Leu Ser Val Val Leu Asn Gln Leu Cys Val Leu His
        450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
                500                 505                 510
Ile Cys Thr Leu Ser Glu Lys Glu Arg Gln Ile Lys Lys Gln Thr Ala
            515                 520                 525
```

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 133
<211> LENGTH: 585
<212> TYPE: PRT
<213> ORGANISM: Artificial Sequence
<220> FEATURE:
<223> OTHER INFORMATION: HSA C34A_E333C

<400> SEQUENCE: 133

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Cys Tyr Ala Arg
            325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 134
<211> LENGTH: 585
<212> TYPE: PRT
<213> ORGANISM: Artificial Sequence
<220> FEATURE:
<223> OTHER INFORMATION: HSA C34A_D340C

<400> SEQUENCE: 134

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

-continued

```
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Cys Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
```

```
Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

<210> SEQ ID NO 135
<211> LENGTH: 585
<212> TYPE: PRT
<213> ORGANISM: Artificial Sequence
<220> FEATURE:
<223> OTHER INFORMATION: HSA C34A_E354C

<400> SEQUENCE: 135

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270
```

```
Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Cys Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 136
<211> LENGTH: 585
<212> TYPE: PRT
<213> ORGANISM: Artificial Sequence
<220> FEATURE:
<223> OTHER INFORMATION: HSA C34A_E358C

<400> SEQUENCE: 136

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45
```

```
Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Cys Lys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460
```

```
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
            580                 585

<210> SEQ ID NO 137
<211> LENGTH: 585
<212> TYPE: PRT
<213> ORGANISM: Artificial Sequence
<220> FEATURE:
<223> OTHER INFORMATION: HSA C34A_K359C

<400> SEQUENCE: 137

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240
```

Val His Thr Glu Cys Cys His Gly Asp Leu Leu Glu Cys Ala Asp Asp
            245                 250                 255

Arg Ala Asp Leu Ala Lys Tyr Ile Cys Glu Asn Gln Asp Ser Ile Ser
        260                 265                 270

Ser Lys Leu Lys Glu Cys Cys Glu Lys Pro Leu Leu Glu Lys Ser His
    275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Cys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 138
<211> LENGTH: 585
<212> TYPE: PRT
<213> ORGANISM: Artificial Sequence
<220> FEATURE:
<223> OTHER INFORMATION: HSA C34A_A362C

<400> SEQUENCE: 138

Asp Ala His Lys Ser Glu Val Ala His Arg Phe Lys Asp Leu Gly Glu
1               5                   10                  15

```
Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430
```

```
Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
        580                 585

<210> SEQ ID NO 139
<211> LENGTH: 585
<212> TYPE: PRT
<213> ORGANISM: Artificial Sequence
<220> FEATURE:
<223> OTHER INFORMATION: HSA C34A_E382C

<400> SEQUENCE: 139

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205
```

Arg Ala Phe Lys Ala Trp Ala Val Ala Arg Leu Ser Gln Arg Phe Pro
            210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Cys Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 140
<211> LENGTH: 585
<212> TYPE: PRT
<213> ORGANISM: Artificial Sequence
<220> FEATURE:

<223> OTHER INFORMATION: HSA C34A_L398C

<400> SEQUENCE: 140

| | | | | | | | | | | | | | | |
|---|---|---|---|---|---|---|---|---|---|---|---|---|---|---|
| Asp | Ala | His | Lys | Ser | Glu | Val | Ala | His | Arg | Phe | Lys | Asp | Leu | Gly | Glu |
| 1 | | | | 5 | | | | | 10 | | | | | 15 | |
| Glu | Asn | Phe | Lys | Ala | Leu | Val | Leu | Ile | Ala | Phe | Ala | Gln | Tyr | Leu | Gln |
| | | | 20 | | | | | 25 | | | | | 30 | | |
| Gln | Ala | Pro | Phe | Glu | Asp | His | Val | Lys | Leu | Val | Asn | Glu | Val | Thr | Glu |
| | | 35 | | | | 40 | | | | 45 | | | | | |
| Phe | Ala | Lys | Thr | Cys | Val | Ala | Asp | Glu | Ser | Ala | Glu | Asn | Cys | Asp | Lys |
| | 50 | | | | 55 | | | | 60 | | | | | | |
| Ser | Leu | His | Thr | Leu | Phe | Gly | Asp | Lys | Leu | Cys | Thr | Val | Ala | Thr | Leu |
| 65 | | | | 70 | | | | | 75 | | | | | 80 | |
| Arg | Glu | Thr | Tyr | Gly | Glu | Met | Ala | Asp | Cys | Cys | Ala | Lys | Gln | Glu | Pro |
| | | | 85 | | | | | 90 | | | | | 95 | | |
| Glu | Arg | Asn | Glu | Cys | Phe | Leu | Gln | His | Lys | Asp | Asp | Asn | Pro | Asn | Leu |
| | | 100 | | | | | 105 | | | | | 110 | | | |
| Pro | Arg | Leu | Val | Arg | Pro | Glu | Val | Asp | Val | Met | Cys | Thr | Ala | Phe | His |
| | 115 | | | | | 120 | | | | | 125 | | | | |
| Asp | Asn | Glu | Glu | Thr | Phe | Leu | Lys | Lys | Tyr | Leu | Tyr | Glu | Ile | Ala | Arg |
| 130 | | | | | 135 | | | | | 140 | | | | | |
| Arg | His | Pro | Tyr | Phe | Tyr | Ala | Pro | Glu | Leu | Leu | Phe | Phe | Ala | Lys | Arg |
| 145 | | | | 150 | | | | | 155 | | | | | 160 | |
| Tyr | Lys | Ala | Ala | Phe | Thr | Glu | Cys | Cys | Gln | Ala | Ala | Asp | Lys | Ala | Ala |
| | | | | 165 | | | | 170 | | | | 175 | | | |
| Cys | Leu | Leu | Pro | Lys | Leu | Asp | Glu | Leu | Arg | Asp | Glu | Gly | Lys | Ala | Ser |
| | | | 180 | | | | | 185 | | | | | 190 | | |
| Ser | Ala | Lys | Gln | Arg | Leu | Lys | Cys | Ala | Ser | Leu | Gln | Lys | Phe | Gly | Glu |
| | 195 | | | | | 200 | | | | | 205 | | | | |
| Arg | Ala | Phe | Lys | Ala | Trp | Ala | Val | Ala | Arg | Leu | Ser | Gln | Arg | Phe | Pro |
| 210 | | | | | 215 | | | | | 220 | | | | | |
| Lys | Ala | Glu | Phe | Ala | Glu | Val | Ser | Lys | Leu | Val | Thr | Asp | Leu | Thr | Lys |
| 225 | | | | | 230 | | | | | 235 | | | | | 240 |
| Val | His | Thr | Glu | Cys | Cys | His | Gly | Asp | Leu | Leu | Glu | Cys | Ala | Asp | Asp |
| | | | | 245 | | | | | 250 | | | | | 255 | |
| Arg | Ala | Asp | Leu | Ala | Lys | Tyr | Ile | Cys | Glu | Asn | Gln | Asp | Ser | Ile | Ser |
| | | | 260 | | | | | 265 | | | | | 270 | | |
| Ser | Lys | Leu | Lys | Glu | Cys | Cys | Glu | Lys | Pro | Leu | Leu | Glu | Lys | Ser | His |
| | | 275 | | | | | 280 | | | | | 285 | | | |
| Cys | Ile | Ala | Glu | Val | Glu | Asn | Asp | Glu | Met | Pro | Ala | Asp | Leu | Pro | Ser |
| | 290 | | | | | 295 | | | | | 300 | | | | |
| Leu | Ala | Ala | Asp | Phe | Val | Glu | Ser | Lys | Asp | Val | Cys | Lys | Asn | Tyr | Ala |
| 305 | | | | | 310 | | | | | 315 | | | | | 320 |
| Glu | Ala | Lys | Asp | Val | Phe | Leu | Gly | Met | Phe | Leu | Tyr | Glu | Tyr | Ala | Arg |
| | | | | 325 | | | | | 330 | | | | | 335 | |
| Arg | His | Pro | Asp | Tyr | Ser | Val | Val | Leu | Leu | Leu | Arg | Leu | Ala | Lys | Thr |
| | | | 340 | | | | | 345 | | | | | 350 | | |
| Tyr | Glu | Thr | Thr | Leu | Glu | Lys | Cys | Cys | Ala | Ala | Ala | Asp | Pro | His | Glu |
| | | | | 355 | | | | | 360 | | | | | 365 | |
| Cys | Tyr | Ala | Lys | Val | Phe | Asp | Glu | Phe | Lys | Pro | Leu | Val | Glu | Glu | Pro |
| | | 370 | | | | | 375 | | | | | 380 | | | |
| Gln | Asn | Leu | Ile | Lys | Gln | Asn | Cys | Glu | Leu | Phe | Glu | Gln | Cys | Gly | Glu |
| 385 | | | | | 390 | | | | | 395 | | | | | 400 |

```
Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 141
<211> LENGTH: 585
<212> TYPE: PRT
<213> ORGANISM: Artificial Sequence
<220> FEATURE:
<223> OTHER INFORMATION: HSA C34A_K93C_E294C

<400> SEQUENCE: 141

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Cys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175
```

```
Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Cys Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

```
<210> SEQ ID NO 142
<211> LENGTH: 585
<212> TYPE: PRT
<213> ORGANISM: Artificial Sequence
<220> FEATURE:
<223> OTHER INFORMATION: HSA K93C

<400> SEQUENCE: 142

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Cys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365
```

Cys Tyr Ala Lys Val Phe Asp Glu Phe Lys Pro Leu Val Glu Glu Pro
            370             375             380

Gln Asn Leu Ile Lys Gln Asn Cys Glu Leu Phe Glu Gln Leu Gly Glu
385             390             395             400

Tyr Lys Phe Gln Asn Ala Leu Leu Val Arg Tyr Thr Lys Lys Val Pro
                405             410             415

Gln Val Ser Thr Pro Thr Leu Val Glu Val Ser Arg Asn Leu Gly Lys
            420             425             430

Val Gly Ser Lys Cys Cys Lys His Pro Glu Ala Lys Arg Met Pro Cys
            435             440             445

Ala Glu Asp Tyr Leu Ser Val Val Leu Asn Gln Leu Cys Val Leu His
            450             455             460

Glu Lys Thr Pro Val Ser Asp Arg Val Thr Lys Cys Cys Thr Glu Ser
465             470             475             480

Leu Val Asn Arg Arg Pro Cys Phe Ser Ala Leu Glu Val Asp Glu Thr
                485             490             495

Tyr Val Pro Lys Glu Phe Asn Ala Glu Thr Phe Thr Phe His Ala Asp
            500             505             510

Ile Cys Thr Leu Ser Glu Lys Glu Arg Gln Ile Lys Lys Gln Thr Ala
            515             520             525

Leu Val Glu Leu Val Lys His Lys Pro Lys Ala Thr Lys Glu Gln Leu
            530             535             540

Lys Ala Val Met Asp Asp Phe Ala Ala Phe Val Glu Lys Cys Cys Lys
545             550             555             560

Ala Asp Asp Lys Glu Thr Cys Phe Ala Glu Glu Gly Lys Lys Leu Val
                565             570             575

Ala Ala Ser Gln Ala Ala Leu Gly Leu
            580             585

<210> SEQ ID NO 143
<211> LENGTH: 585
<212> TYPE: PRT
<213> ORGANISM: Artificial Sequence
<220> FEATURE:
<223> OTHER INFORMATION: HSA E294C

<400> SEQUENCE: 143

Asp Ala His Lys Ser Glu Val Ala His Arg Phe Lys Asp Leu Gly Glu
1               5               10              15

Glu Asn Phe Lys Ala Leu Val Leu Ile Ala Phe Ala Gln Tyr Leu Gln
                20              25              30

Gln Cys Pro Phe Glu Asp His Val Lys Leu Val Asn Glu Val Thr Glu
            35              40              45

Phe Ala Lys Thr Cys Val Ala Asp Glu Ser Ala Glu Asn Cys Asp Lys
        50              55              60

Ser Leu His Thr Leu Phe Gly Asp Lys Leu Cys Thr Val Ala Thr Leu
65              70              75              80

Arg Glu Thr Tyr Gly Glu Met Ala Asp Cys Cys Ala Lys Gln Glu Pro
                85              90              95

Glu Arg Asn Glu Cys Phe Leu Gln His Lys Asp Asp Asn Pro Asn Leu
            100             105             110

Pro Arg Leu Val Arg Pro Glu Val Asp Val Met Cys Thr Ala Phe His
        115             120             125

Asp Asn Glu Glu Thr Phe Leu Lys Lys Tyr Leu Tyr Glu Ile Ala Arg
130             135             140

```
Arg His Pro Tyr Phe Tyr Ala Pro Glu Leu Leu Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Cys Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560
```

Ala Asp Asp Lys Glu Thr Cys Phe Ala Glu Gly Lys Lys Leu Val
            565                 570                 575

Ala Ala Ser Gln Ala Ala Leu Gly Leu
        580                 585

<210> SEQ ID NO 144
<211> LENGTH: 585
<212> TYPE: PRT
<213> ORGANISM: Artificial Sequence
<220> FEATURE:
<223> OTHER INFORMATION: HSA K93C_E294C

<400> SEQUENCE: 144

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Cys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Cys Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 145
<211> LENGTH: 585
<212> TYPE: PRT
<213> ORGANISM: Artificial Sequence
<220> FEATURE:
<223> OTHER INFORMATION: HSA K573P

<400> SEQUENCE: 145

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

```
Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525
```

```
Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Pro Lys Leu Val
                565                 570                 575

Ala Ala Ser Gln Ala Ala Leu Gly Leu
            580                 585

<210> SEQ ID NO 146
<211> LENGTH: 585
<212> TYPE: PRT
<213> ORGANISM: Artificial Sequence
<220> FEATURE:
<223> OTHER INFORMATION: HSA C34A_K93C_K573P

<400> SEQUENCE: 146

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Cys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300
```

```
Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Pro Lys Leu Val
                565                 570                 575

Ala Ala Ser Gln Ala Ala Leu Gly Leu
            580                 585

<210> SEQ ID NO 147
<211> LENGTH: 585
<212> TYPE: PRT
<213> ORGANISM: Artificial Sequence
<220> FEATURE:
<223> OTHER INFORMATION: HSA C34A_E294C_K573P

<400> SEQUENCE: 147

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80
```

```
Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Cys Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495
```

```
Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Pro Lys Leu Val
                565                 570                 575

Ala Ala Ser Gln Ala Ala Leu Gly Leu
                580                 585

<210> SEQ ID NO 148
<211> LENGTH: 585
<212> TYPE: PRT
<213> ORGANISM: Artificial Sequence
<220> FEATURE:
<223> OTHER INFORMATION: HSA C34A_K93C_E294C_K573P

<400> SEQUENCE: 148

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Cys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270
```

```
Ser Lys Leu Lys Glu Cys Cys Glu Lys Pro Leu Leu Glu Lys Ser His
            275                 280                 285
Cys Ile Ala Glu Val Cys Asn Asp Glu Met Pro Ala Asp Leu Pro Ser
        290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Pro Lys Leu Val
                565                 570                 575
Ala Ala Ser Gln Ala Ala Leu Gly Leu
            580                 585

<210> SEQ ID NO 149
<211> LENGTH: 585
<212> TYPE: PRT
<213> ORGANISM: Artificial Sequence
<220> FEATURE:
<223> OTHER INFORMATION: HSA K93C_K573P

<400> SEQUENCE: 149

Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
                20                  25                  30
Gln Cys Pro Phe Glu Asp His Val Lys Leu Val Asn Glu Val Thr Glu
            35                  40                  45
```

```
Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Cys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460
```

```
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Pro Lys Leu Val
            565                 570                 575

Ala Ala Ser Gln Ala Ala Leu Gly Leu
            580                 585

<210> SEQ ID NO 150
<211> LENGTH: 585
<212> TYPE: PRT
<213> ORGANISM: Artificial Sequence
<220> FEATURE:
<223> OTHER INFORMATION: HSA E294C_K573P

<400> SEQUENCE: 150

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240
```

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Cys Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Pro Lys Leu Val
                565                 570                 575

Ala Ala Ser Gln Ala Ala Leu Gly Leu
            580                 585

<210> SEQ ID NO 151
<211> LENGTH: 585
<212> TYPE: PRT
<213> ORGANISM: Artificial Sequence
<220> FEATURE:
<223> OTHER INFORMATION: HSA K93C_E294C_K573P

<400> SEQUENCE: 151

Asp Ala His Lys Ser Glu Val Ala His Arg Phe Lys Asp Leu Gly Glu
1               5                   10                  15

-continued

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Cys Gln Glu Pro
            85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
            165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
            210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
            245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Cys Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
            485                 490                 495
Tyr Val Pro Lys Glu Phe Asn Ala Glu Thr Phe Thr Phe His Ala Asp
                500                 505                 510
Ile Cys Thr Leu Ser Glu Lys Glu Arg Gln Ile Lys Lys Gln Thr Ala
            515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Gly Pro Lys Leu Val
            565                 570                 575
Ala Ala Ser Gln Ala Ala Leu Gly Leu
                580                 585

<210> SEQ ID NO 152
<211> LENGTH: 585
<212> TYPE: PRT
<213> ORGANISM: Artificial Sequence
<220> FEATURE:
<223> OTHER INFORMATION: HSA C34A_L302C

<400> SEQUENCE: 152

Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
                20                  25                  30
Gln Ala Pro Phe Glu Asp His Val Lys Leu Val Asn Glu Val Thr Glu
            35                  40                  45
Phe Ala Lys Thr Cys Val Ala Asp Glu Ser Ala Glu Asn Cys Asp Lys
    50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
    115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
    195                 200                 205

-continued

```
Arg Ala Phe Lys Ala Trp Ala Val Ala Arg Leu Ser Gln Arg Phe Pro
    210             215                 220
Lys Ala Glu Phe Ala Glu Val Ser Lys Leu Val Thr Asp Leu Thr Lys
225             230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Cys Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
        450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585
```

ALBUMIN VARIANTS AND CONJUGATES

CROSS REFERENCE TO RELATED APPLICATIONS

This application is a continuation application of U.S. patent application Ser. No. 16/820,421, filed Mar. 16, 2020, which is a continuation application of U.S. patent application Ser. No. 15/753,947, filed on Feb. 20, 2018, and issued as U.S. Pat. No. 10,633,428 on Apr. 28, 2020, which is a U.S. National Phase Application of PCT International Application Number PCT/EP2016/069748, filed on Aug. 19, 2016, designating the United States of America and published in the English language, which is an International Application of and claims the benefit of priority to European Patent Application No. 15181822.6, filed on Aug. 20, 2015. The disclosures of the above-referenced applications are hereby expressly incorporated by reference in their entireties.

REFERENCE TO SEQUENCE LISTING

This application contains a Sequence Listing in computer readable form. The computer readable form is incorporated herein by reference.

FIELD OF THE INVENTION

The present invention relates to conjugation-competent albumins and albumin-related polypeptides, and their conjugates with at least one (e.g. several) moiety, and to polynucleotides encoding them.

BACKGROUND OF THE INVENTION

Serum albumins provide valuable scaffolds to which bioactive molecules may be fused, either through genetic fusions or chemical fusions to improve the properties of the fused molecule(s) (Leger, R. et al. (2004), Bioorg Med Chem Lett 14(17): 4395-8; Thibaudeau, K., et al. (2005). Bioconjug Chem 16(4): 1000-8; Balan, V. et al. (2006), Antivir Ther 11(1): 35-45; EP 0413622; WO 90/13653; EP 1681304; WO 1997/024445). Albumin has a long plasma half-life of about 19 days and because of this property it has been suggested for use in drug delivery.

The human serum albumin (HSA) polypeptide chain has 35 cysteine residues, which form 17 disulphide bonds and one unpaired (free) cysteine at position 34 of the mature protein (SEQ ID NO: 2). Cysteine-34 has been used for conjugation of molecules to albumin (Leger et al. (2004) Bioorg Med Chem Lett 14(17): 4395-8; Thibaudeau et al. (2005), Bioconjug Chem 16(4): 1000-8), and provides a precise, well defined site for conjugation. However, conjugation at cysteine-34 provides only one site for attachment of a single moiety and thus there is no choice of conjugation site. Also, the provision of a single conjugation site means that only one moiety can be conjugated to each albumin molecule. WO 2009/126920 and WO 2010/059315 propose the substitution for cysteine of one or more (e.g. several) selected surface-exposed threonine or serine residues in albumin. However, the actual production of such variants is not disclosed. WO 2010/092135 discloses albumin variants comprising three or more (several) conjugation-competent cysteine residues: cysteine-34 and at least two further cysteine residues; or variants in which another amino acid is substituted for the cysteine-34, and there are at least three further free cysteines.

Pharmaceutical agents, or their precursors, are generally prepared as homogeneous species, to allow for quality control. In HSA, the free cysteine at position 34 is located in a hydrophobic crevice with a depth of 9.5 Å (Cornell C N, Chang R, Kaplan L J. 1981. Arch. Biochem. Biophys. 209(1): 1-6.), and is not thought to be involved in homodimerization of HSA. However, surface-exposed cysteine residues in polypeptides may form stable inter-molecular disulphide bridges, as occur naturally for example between the heavy and light chains of immunoglobulin. It is desirable to provide albumin variants having introduced cysteine residues which have a low propensity to form dimers or oligomers.

WO 2000/69902 discloses conjugation of pharmaceutically beneficial compounds to HSA at cysteine-34, and it was found that the conjugates maintained the long plasma half-life of albumin. The resulting plasma half-life of the conjugate was generally considerably longer than the plasma half-life of the beneficial therapeutic compound alone. Further, albumin has been genetically fused to therapeutically beneficial peptides (WO 2001/79271A and WO 2003/59934) with the typical result that the fusion has the activity of the therapeutically beneficial peptide and a considerably longer plasma half-life than the plasma half-life of the therapeutically beneficial peptide alone.

Albumin binds in vivo to its receptor, the neonatal Fc receptor (FcRn) "Brambell" and this interaction is known to be important for the plasma half-life of albumin. FcRn is a membrane bound protein, expressed in many cell and tissue types. FcRn has been found to salvage albumin from intracellular degradation (Roopenian D. C. and Akilesh, S. (2007), Nat. Rev. Immunol 7, 715-725). FcRn is a bifunctional molecule that contributes to maintaining a high level of IgGs and albumin in plasma in mammals such as humans. Data indicate that IgG and albumin bind non-cooperatively to distinct sites on FcRn (Andersen et al. (2006), Eur. J. Immuno/36, 3044-3051; Chaudhury et al. (2006), Biochemistry 45, 4983-4990). Andersen et al. (2010), Journal of Biological Chemistry 285(7): 4826-36, describes the affinity of human and mouse FcRn for each of mouse and human albumin (all possible combinations). No binding of albumin from either species was observed at physiological pH to either receptor. At acidic pH, a 100-fold difference in binding affinity was observed.

The major FcRn receptor binding site in albumin is localized within Domain III (DIII, 381-585), (Andersen et al. (2010), Clinical Biochemistry 43, 367-372). A number of key amino acid residues have been shown to be important in binding, notably histidines H464, H510 and H536 and lysine K500 of human albumin (Andersen et al. (2010), Nat. Commun. 3:610. DOI:10.1038/ncomms1607). Generally, the higher the affinity of an albumin for FcRn, the longer is its plasma half-life. WO 2011/124718 discloses a class of variant albumins having modulated binding affinity to FcRn; the variants comprise domain III of an albumin with one or more (e.g. several) other domains of albumin and optionally include one or more (e.g. several) point mutations. WO 2012/059486 discloses variants of albumin in which a C-terminal portion of Domain III is swapped with a corresponding portion of an albumin of a different animal species. WO 2013/075066, WO 2011/103076, WO 2012/112188, WO 2011/051489 and WO 2014/072481 disclose point mutations within Domain III, or combinations of such point mutations, which alter the binding affinity of albumin to FcRn.

Various amino acid residues of albumin located in Domain I or Domain II have also recently been found to affect its interaction with FcRn. WO 2013/135896 discloses albumin variants having one or more (e.g. several) alterations in Domain I and one or more (e.g. several) alterations in Domain III. WO 2015/036579 discloses albumin variants having one or more (e.g. several) alterations in Domain II.

The listing or discussion of an apparently prior-published document in this specification should not necessarily be taken as an acknowledgement that the document is part of the state of the art or is common general knowledge.

It is desirable to provide albumin variants having one or more (e.g. several) introduced cysteine residues in which an introduced free cysteine residue does not itself have a major impact on FcRn binding of albumin, or be positioned such that conjugation of a partner molecule to the free cysteine will sterically hinder FcRn binding. Such considerations could reduce the risk of unpredictable effects when introducing combinations of more than one free cysteine in a single albumin variant. Such variant polypeptides may be further modified to include alterations known to affect the binding affinity of albumin for FcRn, so as to allow the plasma half-life of the polypeptide, or conjugates thereof, to be tailored for specific applications.

SUMMARY OF THE INVENTION

Based on an analysis of the three-dimensional structure of a human serum albumin (HSA) bound to FcRn, the inventors have designed variant polypeptides (muteins) of albumin which have one or more (e.g. several) conjugation-competent cysteine residues. The term 'thio-albumin' is used herein to describe an albumin variant which comprises one or more (e.g. several) unpaired cysteine residues, particularly an albumin variant in which one or more (e.g. several) of the unpaired cysteine residues does not occur in a naturally occurring variant of an albumin. Thus a thio-albumin is a 'conjugation-competent albumin'. A thio-albumin may be referred to as a 'cysteine variant of an albumin'. More particularly, the invention relates to a conjugation-competent polypeptide comprising an amino acid sequence which is at least 60% identical to human albumin, particularly residues 1 to 585 of the mature human albumin polypeptide sequence of SEQ ID NO: 2, or a fragment thereof; wherein at least one position equivalent to a position selected from K93, E294, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, E382, and L398 of SEQ ID NO: 2 comprises a conjugation-competent cysteine residue; and wherein the conjugation-competent polypeptide preferably has a tendency to exist as a monomer in solution which is at least 70% of the tendency of the polypeptide of SEQ ID NO: 2 to exist as a monomer in solution.

More preferably, the polypeptide has a tendency to exist as a monomer in solution which is at least 75% of the tendency of the polypeptide of SEQ ID NO: 2 to exist as a monomer in solution and at least one position equivalent to a position selected from K93, E294, A226, E230, I271, E358, L24, F49, V54, D56, A92, Q94, E97, H128, F156, E227, D237, K240, D259, K262, N267, Q268, L275, L284, K317, A322, E333, D340, E354, K359, A362, E382, and L398 comprises a conjugation-competent cysteine residue.

The invention also relates to a conjugation-competent polypeptide comprising an amino acid sequence as defined above, and at least one (e.g. several) further modification compared to SEQ ID NO: 2, such as a further modification which causes the polypeptide to have at least one (e.g. several) further conjugation-competent cysteine, or alters the binding affinity of the polypeptide for FcRn, or alters the plasma half-life of the polypeptide. The present invention also relates to isolated polynucleotides encoding the variants; nucleic acid constructs, vectors, and host cells comprising the polynucleotides; and methods of producing the variants.

The invention also relates to conjugates or associates comprising the variant albumin or fragment thereof according to the invention and a beneficial therapeutic moiety or to a fusion polypeptide comprising a variant albumin or fragment thereof of the invention and a fusion partner polypeptide.

The invention further relates to compositions comprising the variant albumin, fragment thereof, fusion polypeptide comprising variant albumin or fragment thereof or conjugates comprising the variant albumin or fragment thereof, according to the invention or associates comprising the variant albumin or fragment thereof, according to the invention. The compositions are preferably pharmaceutical compositions.

The invention further relates to a pharmaceutical composition comprising a variant albumin, fragment thereof, fusion polypeptide comprising variant albumin or fragment thereof or conjugates comprising the variant albumin or fragment thereof, or associates comprising the variant albumin or fragment thereof.

The invention also relates to the use of the variants, fragments, fusion polypeptides, conjugates, associates, nanoparticles and microparticles.

The invention also relates to a method for preparing a variant albumin, fragment thereof, fusion polypeptide comprising variant albumin or fragment thereof or conjugates comprising the variant albumin or fragment thereof, or associates comprising the variant albumin or fragment thereof.

BRIEF DESCRIPTION OF DRAWINGS

FIG. 1. Multiple alignment of amino acid sequences of (i) full length mature HSA (Hu_1_2_3) (SEQ ID NO: 2), (ii) an albumin variant comprising domain I and domain III of HSA (Hu_1_3) (SEQ ID NO: 24), (iii) an albumin variant comprising domain II and domain III of HSA (Hu_2_3) (SEQ ID NO: 25), (iv) full-length *Macaca mulatta* albumin (Mac_mul) (SEQ ID NO: 6), (v) full-length *Rattus norvegicus* albumin (Rat) (SEQ ID NO: 10) and (vi) full-length *Mus musculus* albumin (Mouse) (SEQ ID NO: 9). Positions 500, 550 and 573 (relative to full length HSA) are indicated by arrows.

FIG. 2. Multiple alignment of amino acid sequence of mature albumin from human (SEQ ID NO: 2), sheep (SEQ ID NO: 16), mouse (SEQ ID NO: 9), rabbit (SEQ ID NO: 14) and goat (SEQ ID NO: 15) and immature albumins from chimpanzee ("Chimp") (SEQ ID NO: 5), macaque (SEQ ID NO: 6), hamster (SEQ ID NO: 7), guinea pig (SEQ ID NO: 8), rat (SEQ ID NO: 10), cow (SEQ ID NO: 11), horse (SEQ ID NO: 12), donkey (SEQ ID NO: 13), dog (SEQ ID NO: 17), chicken (SEQ ID NO: 18), and pig (SEQ ID NO: 19). The Start and End amino acids of domains 1, 2 and 3 (as defined by Dockal et al (The Journal of Biological Chemistry, 1999, Vol. 274(41): 29303-29310)) are indicated with respect to mature human albumin.

FIG. 4. A: Reaction scheme for biotinylation of a protein comprising a free thiol group with maleimide-PEG2-biotin.

Figure 3:
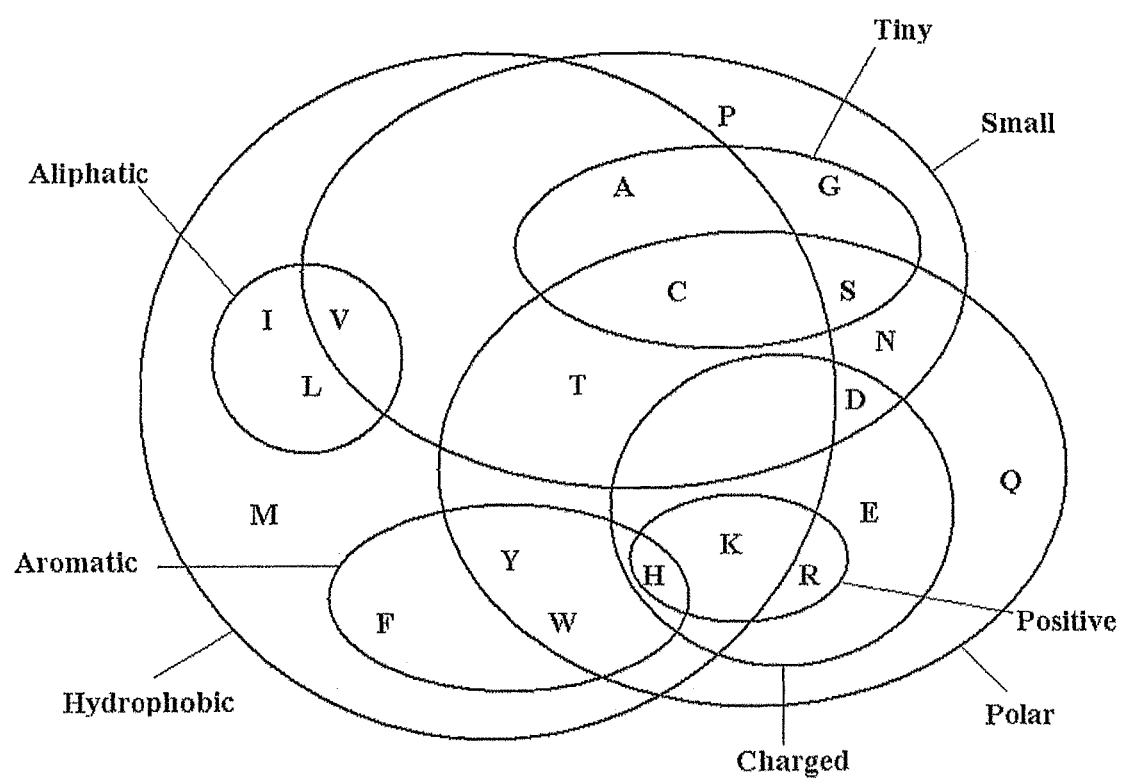
FIG. 3. Venn diagram showing the classes of and relationship between twenty amino acids.

B: Schematic illustrating potential retro-Michael and succinimide hydrolysis reactions of conjugates formed in scheme A.

In A, the maleimide forms an adduct with the thiol group, thus forming a succinimide moiety with a thio-ether bond.

B illustrates adduct formation. The adduct may revert back to maleimide and free thiol via a retro-Michael pathway. Alternatively, the succinimide moiety may undergo stabilizing ring opening to succinic acid, by hydrolysis at pH 9. The thio-ether bond of the conjugate is retained and the succinic acid moiety is unreactive to other thiol compounds which may be present. Free maleimide, when subjected to hydrolysis, also becomes thiol unreactive.

FIG. 5. MS spectra of purified variants (A: C34A+I271C variant; B: C34A+K93C variant) conjugated with maleimide-PEG2-biotin. A: The conjugate peak is 66924.1. The shorter peak is unconjugated protein. The relative peak heights indicate a conjugated proportion of 72%. +MS, 7.7-9.2 min, Baseline subtracted (0.50), Deconvoluted (MaxEnt), Smoothed (0.00, 1, GA). B: The conjugate peak is 66908.3, and there is no free proportion, indicating 100% conjugation. +MS, 7.6-9.4 min, Baseline subtracted (0.50), Deconvoluted (MaxEnt), Smoothed (0.00, 1, GA).

FIG. 6. MS spectra of purified albumins (A: wild type; B: C34A+E294C variant) conjugated with maleimide-PEG2-biotin and subjected to controlled hydrolysis. In A, 53% of the albumin is present as a thiol-stable conjugate with a peak of 66978.4; and 47% is present as a free albumin following retro-Michael deconjugation. +MS, 7.0-9.6 min, Baseline subtracted (0.50), Deconvoluted (MaxEnt), Smoothed (0.00, 1, GA). In B, 100% of the C34A+E294C variant is present as a thiol-stable conjugate with a peak of 66925.7. +MS, 7.6-9.5 min, Baseline subtracted (0.50), Deconvoluted (MaxEnt), Smoothed (0.00, 1, GA).

FIG. 7. MS spectra of purified albumin variants (A: K93C+E294C; B: K93C+E294C; C: C34A+K93C+E294C) conjugated with maleimide-PEG2-biotin and subjected to controlled hydrolysis (B and C). In A, a single peak of 67967.7 for K93C+E294C indicates 100% conjugation to each of the three free thiols. +MS, 1.6-2.6 min, Baseline subtracted (0.40), Deconvoluted (MaxEnt), Smoothed (0.00, 1, GA). In B, 20% of the triple conjugate of K93C+E294C is thiol stable after hydrolysis. The main peak, at 67476.2, is indicative of two thiol stable conjugate bonds, and the loss of one maleimide-PEG2-biotin through retro-Michael deconjugation. +MS, 1.8-2.9 min, Baseline subtracted (0.40), Deconvoluted (MaxEnt), Smoothed (0.00, 1, GA). In C, the double conjugate of C34A+K93C+E294C is the major species, at a peak of 67443.1, and the other species is the single conjugate at a peak of 66894.6. +MS, 1.7-2.8 min, Baseline subtracted (0.40), Deconvoluted (MaxEnt), Smoothed (0.00, 1, GA).

FIG. 8. MS spectra of purified albumin variant K93C+E294C+K573P (which includes native Cys34). A: indicates 100% conjugation to each of the three free thiols. +MS, 7.3-9.7 min, Baseline subtracted (0.50), Deconvoluted (MaxEnt), Smoothed (0.00, 1, GA). In B, 23% of the triple conjugate of K93C+E294C+K573P (which includes native Cys34) is thiol stable after hydrolysis. The main peak, at 67447.3, is indicative of two thiol stable conjugate bonds, and the loss of one maleimide-PEG2-biotin through retro-Michael deconjugation. +MS, 7.4-9.5 min, Baseline subtracted (0.50), Deconvoluted (MaxEnt), Smoothed (0.00, 1, GA).

FIG. 9. A: Schematic illustrating Alexa Fluor® 488-PEG4-Lys(monobromomaleimide)-NH2 dye. The MS spectra of purified albumin variants (B: K573P; C: K93C+E294C+K573P) conjugated with Alexa Fluor® 488-PEG4-Lys(monobromomaleimide)-NH2 dye are shown. In B, a single peak of 67468.5 for K573P indicates 100% conjugation to the single free thiol at Cys34. +MS, 7.6-9.7 min, Baseline subtracted (0.50), Deconvoluted (MaxEnt), Smoothed (0.00, 1, GA). In C, the triple conjugate of K93C+E294C+K573P (which includes native Cys34) is the major species, at a peak of 69535.8. The shorter peak is double conjugate. The relative peak heights indicate 58% triple conjugate and 42% double conjugate respectively. +MS, 7.6-9.3 min, Baseline subtracted (0.50), Deconvoluted (MaxEnt), Smoothed (0.00, 1, GA).

FIG. 10. A: Schematic illustrating 5-carboxyfluorescein-PEG4-Lys(monobromomaleimide)-NH2 dye. The MS spectra of purified albumin variants (B: K573P; C: C34A+K93C+E294C+K573P) conjugated with 5-carboxyfluorescein-PEG4-Lys(monobromomaleimide)-NH2 dye are shown. In B, a single peak of 67310.6 for K573P indicates 100% conjugation to the single free thiol at Cys34. +MS, 7.2-9.3 min, Baseline subtracted (0.50), Deconvoluted (MaxEnt), Smoothed (0.00, 1, GA). In C, the double conjugate of C34A+K93C+E294C+K573P is the major species, at a peak of 68129.7. The shorter peak is single conjugated protein. The relative peak heights indicate 91% double conjugate and 9% single conjugated protein respectively. +MS, 7.3-9.3 min, Baseline subtracted (0.50), Deconvoluted (MaxEnt), Smoothed (0.00, 1, GA).

FIG. 11. A: Schematic illustrating monobromomaleimide-paclitaxel. The MS spectra of purified albumin variants (B: K573P; C: K93C+E294C+K573P) conjugated with monobromomaleimide-paclitaxel are shown. In B, a peak of 67412.2 for K573P indicates conjugation to the single free thiol at Cys34. The shorter peak is unconjugated protein. The relative peak heights indicate 77% single conjugate and 23% unconjugated protein respectively +MS, 7.1-8.9 min, Baseline subtracted (0.50), Deconvoluted (MaxEnt), Smoothed (0.00, 1, GA). In C, the double conjugate of K93C+E294C+K573P is the major species which is at a peak of 68364.2. The shorter peak is triple conjugated protein. The relative peak heights indicate 60% double conjugated and 30% triple conjugate protein respectively. +MS, 7.2-9.0 min, Baseline subtracted (0.50), Deconvoluted (MaxEnt), Smoothed (0.00, 1, GA).

FIG. 12. A: Schematic illustrating monobromomaleimide-PEG2-exenatide peptide. The MS spectra of purified albumin variants (B: K573P; C: C34A+K93C+E294C+K573P) conjugated with monobromomaleimide-PEG2-exenatide peptide are shown. In B, a peak of 71018.7 for K573P indicates conjugation to the single free thiol at Cys34. The main peak, at 66409.2 is unconjugated protein. The relative peak heights indicate single 33% conjugate and 67% unconjugated protein respectively. +MS, 7.2-8.8 min, Baseline subtracted (0.50), Deconvoluted (MaxEnt), Smoothed (0.00, 1, GA). In C, the double conjugate of C34A+K93C+E294C+K573P is 75557.3. The main peak, at 70941.7 is single conjugate. The shortest peak at 66322.4 is unconjugated protein. The relative peak heights indicate 33% double conjugate, 45% single conjugate and 22% unconjugated protein respectively. +MS, 7.2-9.2 min, Baseline subtracted (0.50), Deconvoluted (MaxEnt), Smoothed (0.00, 1, GA).

FIG. 13. A: Schematic illustrating maleimide-propyl-FLAG peptide. The MS spectra of purified albumin variants (B: K573P; C: K93C+E294C+K573P) conjugated with maleimide-propyl-FLAG peptide are shown. In B, a peak of 67573.4 for K573P indicates conjugation to the single free thiol at Cys34. The main peak is unconjugated protein. The relative peak heights indicate 29% single conjugate and 71% unconjugated protein respectively. +MS, 7.3-8.7 min, Baseline subtracted (0.50), Deconvoluted (MaxEnt), Smoothed (0.00, 1, GA). In C, the triple conjugate of K93C+E294C+ K573P (which includes native Cys34) is 69850.5. The main peak, at 68685.5 is double conjugate. The peak at 67520.3 is single conjugate. The shortest peak, at 66350.2 is unconjugated protein. The relative peak heights indicate 29% triple conjugate, 50% double conjugate, 20% single conjugate and 2% unconjugated protein respectively. +MS, 7.2-8.8 min, Baseline subtracted (0.50), Deconvoluted (MaxEnt), Smoothed (0.00, 1, GA).

DEFINITIONS

Variant: The term "variant" means a polypeptide derived from a parent albumin by one or more (e.g. several) alteration(s), i.e. a substitution, insertion, and/or deletion, at one or more (e.g. several) positions. A substitution means a replacement of an amino acid occupying a position with a different amino acid; a deletion means removal of an amino acid occupying a position; and an insertion means adding 1 or more (e.g. several), such as 1, 2, 3, 4, 5, 6, 7, 8, 9 or 10, preferably 1-3 amino acids immediately adjacent an amino acid occupying a position. In relation to insertion, 'immediately adjacent' may be to the N-side ('upstream') or C-side ('downstream') of the amino acid occupying a position ('the named amino acid'). Therefore, for an amino acid named/numbered 'X', the insertion may be at position 'X+1' ('downstream') or at position 'X-1' ('upstream').

Mutant: The term "mutant" means a polynucleotide encoding a variant.

Wild-Type Albumin: The term "wild-type" (WT) albumin means albumin having the same amino acid sequence as naturally found in an animal or in a human being.

Parent Albumin: The term "parent" or "parent albumin" means an albumin to which an alteration is made by the hand of man to produce the albumin variants of the invention. The parent may be a naturally occurring (wild-type) polypeptide or an allele thereof, or even a variant thereof.

Albumin: Albumins are proteins and constitute the most abundant protein in plasma in mammals and albumins from a long number of mammals have been characterized by biochemical methods and/or by sequence information. Several albumins, e.g. HSA, have also been characterized crystallographically and the structure determined (HSA: He X M, Carter D C (July 1992), "Atomic structure and chemistry of human serum albumin", Nature 358 (6383): 209-15; horse albumin: Ho, J. X. et al. (2001). X-ray and primary structure of horse serum albumin (*Equus caballus*) at 0.27-nm resolution. Eur J Biochem. 215(1):205-12). The invention relates to all albumins and their structures.

The term "albumin" means a protein having the same and/or very similar three dimensional (tertiary) structure as HSA or HSA domains and having similar properties to HSA or to the relevant domains. Similar three dimensional structures are for example the structures of the albumins from the species mentioned herein. Some of the major properties of albumin are i) its ability to regulate plasma volume (oncotic activity), ii) a long plasma half-life of around 19 days±5 days, iii) binding to FcRn, iv) ligand-binding, e.g. binding of endogenous molecules such as acidic, lipophilic compounds including bilirubin, fatty acids, hemin and thyroxine (see also Table 1 of Kragh-Hansen et al., 2002, Biol. Pharm. Bull. 25, 695, hereby incorporated by reference), v) binding of small organic compounds with acidic or electronegative features e.g. drugs such as warfarin, diazepam, ibuprofen and paclitaxel (see also Table 1 of Kragh-Hansen et al., 2002, Biol. Pharm. Bull. 25, 695, hereby incorporated by reference), vi) binding to gp60, also known as albondin. Not all of these properties need to be fulfilled in order to characterize a protein or fragment as an albumin. If a fragment, for example, does not comprise a domain responsible for binding of certain ligands or organic compounds the variant of such a fragment will not be expected to have these properties either.

Albumins have generally a long plasma half-life of approximately 20 days or longer, e.g. HSA has a plasma half-life of 19 days. It is known that the long plasma half-life of HSA is mediated via interaction with its receptor FcRn, however, an understanding or knowledge of the exact mechanism behind the long half-life of HSA is not essential for the invention.

As examples of albumin proteins as starting parent "backbones" for making albumin variants according to the invention can be mentioned HSA (e.g. AAA98797 or P02768-1, SEQ ID NO: 2 (mature), SEQ ID NO: 3 (immature)), primate serum albumin, (such as chimpanzee serum albumin (e.g. predicted sequence XP_517233.2 SEQ ID NO: 4), gorilla serum albumin or macaque serum albumin (e.g. NP_001182578, SEQ ID NO: 5), rodent serum albumin (such as hamster serum albumin (e.g. A6YF56, SEQ ID NO: 6), guinea pig serum albumin (e.g. Q6WDN9-1, SEQ ID NO: 7), mouse serum albumin (e.g. AAH49971 or P07724-1 Version 3, SEQ ID NO: 8) and rat serum albumin (e.g. AAH85359 or P02770-1 Version 2, SEQ ID NO: 9), bovine serum albumin (e.g. cow serum albumin P02769-1, SEQ ID NO: 10), equine serum albumin such as horse serum albumin (e.g. P35747-1, SEQ ID NO: 11) or donkey serum albumin (e.g. Q5XLE4-1, SEQ ID NO: 12), rabbit serum albumin (e.g. P49065-1 Version 2, SEQ ID NO: 13), goat serum albumin (e.g. ACF10391, SEQ ID NO: 14), sheep serum albumin (e.g. P14639-1, SEQ ID NO: 15), dog serum albumin (e.g. P49822-1, SEQ ID NO: 16), chicken serum albumin (e.g. P19121-1 Version 2, SEQ ID NO: 17) and pig serum albumin (e.g. P08835-1 Version 2, SEQ ID NO: 18) or a polypeptide having at least 70, 75, 80, 85, 90, 91, 92, 93, 94, 95, 96, 97, 98, 99, 99.2, 99.4, 99.6, or at least 99.8% amino acid identity to such an albumin. Other examples of albumin, which are also included in the scope of this application, include ovalbumin (e.g. P01012.pro: chicken ovalbumin; O73860.pro: turkey ovalbumin). A mature albumin sequence can be identified from an immature albumin sequence using techniques known to the skilled person, for example alignment with HSA (for which the mature and immature regions are known). For example, immature HSA is 609 amino acids long in which amino acids 1 to 19 are a signal sequence (also known as a leader sequence or pre sequence), amino acids 20 to 24 are a pro sequence and amino acids 25 to 609 are the mature protein. The alignment in FIG. 2 allows the skilled person to predict mature sequences for several animal albumins (see "D1 Start").

HSA as disclosed in SEQ ID NO: 2, or any naturally occurring allele thereof, is the preferred parent albumin according to the invention. HSA is a protein consisting of 585 amino acid residues and has a molecular weight of 67 kDa. In its natural form it is not glycosylated. The skilled person will appreciate that natural alleles may exist having essentially the same properties as HSA but having one or more (e.g. several) amino acid changes compared to SEQ ID NO: 2, and the inventors also contemplate the use of such natural alleles as parent albumins according to the invention.

The parent albumin, a fragment thereof, or conjugation-competent albumin variant, or albumin part of a fusion polypeptide or conjugate comprising albumin or a fragment thereof according to the invention preferably has a sequence identity to the sequence of HSA shown in SEQ ID NO: 2 of at least 60%, preferably at least 70%, preferably at least 80%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, more preferred at least 96%, more preferred at least 97%, more preferred at least 98% and most preferred at least 99%, at least 99.2%, at least 99.4%, at least 99.6% or at least 99.8% or 100%. It is preferred that the parent albumin maintains at least one of the major properties of albumin or a similar tertiary structure as an albumin, such as HSA. The sequence identity may be over the full-length of SEQ ID NO: 2 or over a molecule consisting or comprising of a fragment such as one or more (e.g. several) domains of SEQ ID NO: 2, such as a molecule consisting of or comprising Domain III (e.g. SEQ ID NO: 19), a molecule consisting of or comprising Domain II and Domain III (e.g. SEQ ID NO: 20), a molecule consisting of or comprising Domain I and Domain III (e.g. SEQ ID NO: 21), a molecule consisting of or comprising two copies of Domain III (e.g. SEQ ID NO: 22), a molecule consisting of or comprising three copies of Domain III (e.g. SEQ ID NO: 23) or a molecule consisting of or comprising Domain I and two copies of Domain III (e.g. SEQ ID NO: 24).

The parent albumin, a fragment thereof, or conjugation-competent albumin variant, or albumin part of a fusion polypeptide or conjugate comprising albumin or a fragment thereof according to the invention, when folded, may have several, for example at least 1, 2, 3, 4, 5, 6, 7, 8, 9, 10, 11, 12, 13, 14, 15, 16 and suitably all 17, of the native disulphide bonds of the polypeptide of SEQ ID NO: 2.

The parent preferably comprises or consists of the amino acid sequence of SEQ ID NO: 3 (immature sequence of HSA) or SEQ ID NO: 2 (mature sequence of HSA).

In another embodiment, the parent is an allelic variant of the mature polypeptide of SEQ ID NO: 2.

The parent albumin may be encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 2, or (ii) the full-length complementary strand of (i) (J. Sambrook, E. F. Fritsch, and T. Maniatis, 1989, *Molecular Cloning, A Laboratory Manual*, 2d edition, Cold Spring Harbor, New York).

The polynucleotide of SEQ ID NO: 1 or a subsequence thereof, as well as the amino acid sequence of SEQ ID NO: 2 or SEQ ID NO: 3 or a fragment thereof, may be used to design nucleic acid probes to identify and clone DNA encoding a parent from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g. at least 25, at least 35, or at least 70 nucleotides in length. Preferably, the nucleic acid probe is at least 100 nucleotides in length, e.g. at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labelled for detecting the corresponding gene (for example, with 32P, 3H, 35S, biotin, or avidin). Such probes are encompassed by the invention.

A genomic DNA or cDNA library prepared from such other organisms may be screened for DNA that hybridizes with the probes described above and encodes a parent. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or a subsequence thereof, the carrier material is used in a Southern blot.

For purposes of the invention, hybridization indicates that the polynucleotide hybridizes to a labelled nucleotide probe corresponding to the polynucleotide shown in SEQ ID NO: 1, its complementary strand, or a subsequence thereof, under low to very high stringency conditions. Molecules to which the probe hybridizes can be detected using, for example, X-ray film or any other detection means known in the art.

The nucleic acid probe may comprise or consist of the mature polypeptide coding sequence of SEQ ID NO: 1, i.e. nucleotides 1 to 1785 of SEQ ID NO: 1. The nucleic acid probe may comprise or consist of a polynucleotide of SEQ ID NO: 25 (nucleotide sequence encoding HSA, the nucleotide sequence has been engineered to introduce restriction enzyme sites) or a fragment thereof.

For long probes of at least 100 nucleotides in length, very low to very high stringency conditions are defined as pre-hybridization and hybridization at 42° C. in 5×SSPE, 0.3% SDS, 200 micrograms/mL sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° ° C. (very low stringency), 50° C. (low stringency), 55° C. (medium stringency), 60° C. (medium-high stringency), 65° C. (high stringency), or 70° C. (very high stringency).

For short probes that are about 15 nucleotides to about 70 nucleotides in length, stringency conditions are defined as pre-hybridization and hybridization at about 5° C. to about 10° C. below the calculated $T_m$ using the calculation according to Bolton and Mccarthy (1962, Proc. Natl. Acad. Sci. USA 48: 1390) in 0.9 M NaCl, 0.09 M Tris-HCl PH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per mL following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The parent or conjugation-competent albumin may be encoded by a polynucleotide with a sequence identity to the mature polypeptide coding sequence of SEQ ID NO: 1 of at least 60%, e.g. at least 65%, at least 70%, at least 75%, at least 80%, at least 85%, at least 90%, at least 95%, at least 96%, at least 97%, at least 98%, at least 99%, or 100%, which encodes a polypeptide which is able to function as an albumin. In an embodiment, the parent is encoded by a polynucleotide comprising or consisting of SEQ ID NO 1.

Three Dimensional (3D) Models

The present disclosure makes reference to the crystal structure of HSA from the RCSB Protein Databank (PDB, which can be viewed at www.rcsb.org/pdb/) with the entry with PDB identity 1AO6 or 1ao6 (Sugio, S., A. Kashima, et al. (1999), Protein Eng 12(6): 439-46). Compared to the mature HSA sequence (SEQ ID NO: 2), the 1A06 structure starts at residue S5 (with the first 4 amino acids absent from the structure) and finishes at A582 of SEQ ID NO: 2 (with the last 3 amino acids absent from the structure). The amino acid positions used herein to describe positions to alter to generate conjugation-competent cysteines are referring to the positions in SEQ ID NO: 2, not 1ao6. Further structures of albumin are available to the skilled person, for example the atomic coordinates for the tertiary structure of human albumin are available at the GenBank DNA database which can be viewed at www.ncbi.nlm.nih.gov.

Structures may be viewed using suitable software such as RasM.1 Chime (Sayle, TIBS 20, 374, 1995). Available albumin coordinates include:

1AO6, 1BMO (Sugio et al. (1999), *Protein Eng* 12(6): 439-46), which was among the top 17 requested proteins.
1UOR, He & Carter (1992), *Nature* 358(6383): 209-15.
1bj5 and 1bke, Curry et al. (1998), *Nat Struct Biol* 5(9): 827-35.
1e7a, 1e7b, 1e7c, Bhattacharya et al. (2000), *J Biol Chem* 275(49): 38731-8.
1e7e, 1e7f, 1e7g, 1e7h and 1e7i, Bhattacharya et al. (2000), *J Mol Biol* 303(5): 721-32.
1GNJ, Petitpas et al. (2001), *J Mol Biol* 314(5): 955-60.
1HA2 and 1H9Z Petitpas et al. (2001), *J Biol Chem* 276(25): 22804-9.
4K71, Schmidt et al. (2013), *Structure* 21:1966-1978
4N0F and 4N0U, Oganesyan et al. (2014), *J Biol Chem* 289(11): 7812-24.

Albumin moiety: The albumin part of a fusion polypeptide, conjugate, associate, nanoparticle or composition comprising the albumin variant or fragment thereof according to the invention, may be referred to as an 'albumin moiety' or 'albumin component'. A polypeptide according to the invention may comprise or consist of an albumin moiety.

Isolated variant: The term "isolated variant" means a variant in a form or environment which does not occur in nature. Non-limiting examples of isolated variants include (1) any non-naturally occurring variant; (2) any variant that is at least partially removed from one or more (e.g. several) or all of the naturally occurring constituents with which it is associated in nature; (3) any variant modified by the hand of man relative to the polypeptide from which it is derived (e.g. the polypeptide from which it is derived as found in nature); or (4) any variant modified by increasing the amount of the variant relative to other components with which it is naturally associated (e.g. multiple copies of a gene encoding the substance; use of a stronger promoter than the promoter naturally associated with the gene encoding the substance). An isolated variant may be present in a fermentation broth sample. Isolated variants may be recombinant or synthetic.

Substantially pure variant: The term "substantially pure variant" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the variant is at least 92% pure, e.g. at least 94% pure, at least 95% pure, at least 96% pure, at least 97% pure, at least 98% pure, at least 99%, at least 99.5% pure, and 100% pure by weight of the total polypeptide material present in the preparation. Purity may be determined by SDS-PAGE or GP-HPLC. The variants of the invention are preferably in a substantially pure form. This can be accomplished, for example, by preparing the variant by well-known recombinant methods and by purification methods.

Mature polypeptide: The term "mature polypeptide" means a polypeptide in its final form following translation and any post-translational modifications, such as N-terminal processing, C-terminal truncation, glycosylation, phosphorylation, etc. The mature polypeptide may be amino acids 1 to 585 of SEQ ID NO: 2, e.g. with the inclusion of alterations according to the invention and/or any post-translational modifications.

Mature polypeptide coding sequence: The term "mature polypeptide coding sequence" means a polynucleotide that encodes a mature albumin polypeptide. The mature polypeptide coding sequence may be nucleotides 1 to 1758 of SEQ ID NO: 1 e.g. with the alterations required to encode a variant according to the invention.

Sequence Identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later, more preferably version 5.0.0 or later. The parameters used are gap open penalty of 10, gap extension penalty of 0.5, and the EBLOSUM62 (EMBOSS version of BLOSUM62) substitution matrix. The output of Needle labelled "longest identity" (obtained using the −nobrief option) is used as the percent identity and is calculated as follows:

(Identical Residues×100)/(Length of Alignment −Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later, more preferably version 5.0.0 or later. The parameters used are gap open penalty of 10, gap extension penalty of 0.5, and the EDNAFULL (EMBOSS version of NCBI NUC4.4) substitution matrix. The output of Needle labelled "longest identity" (obtained using the −nobrief option) is used as the percent identity and is calculated as follows:

(Identical Deoxyribonucleotides×100)/(Length of Alignment −Total Number of Gaps in Alignment)

Fragment: The term "fragment" as used herein includes any fragment of full-length albumin or a variant thereof, so long as at least one (e.g. several) basic property, for example binding activity (type of and specific activity e.g. binding to bilirubin), osmolarity (oncotic pressure, colloid osmotic pressure), behaviour in a certain pH-range (pH-stability) has not significantly been changed. "Significantly" in this context means that one skilled in the art would say that the properties of the variant may still be different but would not be unobvious over the ones of the original protein. A fragment may consist of one uninterrupted sequence derived from HSA or it may comprise two or more (e.g. several) sequences derived from HSA. The fragments according to the invention have a size of more than approximately 20 amino acid residues, preferably more than 30 amino acid residues, more preferred more than 40 amino acid residues, more preferred more than 50 amino acid residues, more preferred more than 75 amino acid residues, more preferred more than 100 amino acid residues, more preferred more than 200 amino acid residues, more preferred more than 300 amino acid residues, even more preferred more than 400 amino acid residues and most preferred more than 500 amino acid residues. A fragment may comprise or consist of at least 50, 60, 70, 75, 80, 85, 90, 95, 96, 97, 98, or 99% of an albumin or of a domain of an albumin. Preferred albumin domains of the invention are domains having at least 70, 75, 80, 85, 90, 95, 96, 97, 98, 99, 99.5% or 100% identity to HSA domain I consisting of amino acid residues 1 to 194±1 to 15 amino acids of SEQ ID NO: 2; at least 70, 75, 80, 85, 90, 95, 96, 97, 98, 99, 99.5% or 100% identity to HSA domain II consisting of amino acid residues 192 to 387±1 to 15 amino acids of SEQ ID NO: 2 and at least 70, 75, 80, 85, 90, 95, 96, 97, 98, 99, 99.5% or 100% identity to HSA domain III consisting of amino acid residues 381 to 585±1 to 15 amino acids of SEQ ID NO: 2.

Domains I, II and III may be defined with reference to HSA (SEQ ID NO: 2). For example, HSA Domain I may consist of or comprise amino acids 1 to 194 (±1 to 15 amino acids) of SEQ ID NO: 2, HSA Domain II may consist of or comprise amino acids 192 (±1 to 15 amino acids) to 387 (±1 to 15 amino acids) of SEQ ID NO: 2 and Domain III may consist of or comprise amino acid residues 381 (±1 to 15 amino acids) to 585 (±1 to 15 amino acids) of SEQ ID NO: 2. "±1 to 15 amino acids" means that the residue number may deviate by 1, 2, 3, 4, 5, 6, 7, 8, 9, 10, 11, 12, 13, 14, or 15 amino acids to the C-terminus and/or to the N-terminus of the stated amino acid position. Examples of domains I, II and III are described by Dockal et al. (The Journal of Biological Chemistry, 1999, Vol. 274(41): 29303-29310) and Kjeldsen et al. (Protein Expression and Purification, 1998, Vol 13: 163-169) and are tabulated below.

TABLE 1

| Amino acid residues of HSA domains I, II and III with reference to SEQ ID NO. 2 | Dockal et al | Kjeldsen et al |
|---|---|---|
| Domain I | 1 to 197 | 1 to 192 |
| Domain II | 189 to 385 | 193 to 382 |
| Domain III | 381 to 585 | 383 to 585 |

A fragment may comprise or consist of one or more (e.g. several) domains of albumin described herein such as DI+DII, DI+DIII, DII+DIII, DIII+DIII, DI+DIII+DIII, DIII+DIII+DIII, or fragments of such domains or combinations of domains.

The skilled person can identify domains I, II and III in non-human albumins by amino acid sequence alignment with HSA, for example using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later, more preferably version 5.0.0 or later. The optional parameters used are gap open penalty of 10, gap extension penalty of 0.5, and the EBLOSUM62 (EMBOSS version of BLOSUM62) substitution matrix. Other suitable software includes MUSCLE ((Multiple sequence comparison by log-expectation, Robert C. Edgar, Version 3.6, www.drive5.com/muscle; Edgar (2004) Nucleic Acids Research 32(5), 1792-97 and Edgar (2004) BMC Bioinformatics, 5(1):113) which may be used with the default settings as described in the User Guide (Version 3.6, September 2005). Versions of MUSCLE later than 3.6 may also be used for any aspect of the invention). Examples of suitable alignments are provided in FIGS. 1 and 2.

It is preferred that domains have at least 70, 75, 80, 85, 90, 95, 96, 97, 98, 99, 99.5% identity or 100% identity to Domain I, II or III of HSA (SEQ ID NO: 2).

Additionally, single or multiple heterologous fusions comprising any of the above; or single or multiple heterologous fusions to albumin, or a variant or fragment of any of these may be used. Such fusions include albumin N-terminal fusions, albumin C-terminal fusions and co-N-terminal and C-terminal albumin fusions as exemplified by WO 01/79271 (incorporated herein by reference).

Equivalent amino acid positions: Throughout this specification amino acid positions are defined in relation to full-length mature HSA (i.e. without leader sequence, SEQ ID NO: 2). However, the skilled person understands that the invention also relates to variants of non-human albumins (e.g. those disclosed herein) and/or fragments of a human or non-human albumin. For clarity, for albumins other than HSA (SEQ ID NO: 2), equivalent residues are favoured for mutation. Equivalent positions can be identified in fragments of HSA, in animal albumins and in fragments, fusions and other derivatives or variants thereof by comparing amino acid sequences using pairwise (e.g. ClustalW) or multiple (e.g. MUSCLE) alignments. For example, FIG. 1 shows that positions equivalent to 500, 550 and 573 in full length HSA are easily identified in fragments of HSA and in albumins of other species. Positions 500, 550 and 573 are indicated by arrows. Further details are provided in Table 2 below.

TABLE 2

Example of identification of equivalent positions in HSA, animal albumins and albumin fragments

| Organism (accession number of protein) | Albumin | | Total length of mature protein | Position equivalent to HSA (native amino acid): | | |
|---|---|---|---|---|---|---|
| | Full length or fragment | Fragment details | | 500 (K) | 550 (D) | 573 (K) |
| Homo sapiens (AAA98797) | Full length | — | 585 | 500 (K) | 550 (D) | 573 (K) |
| Homo sapiens | Fragment | DI, DIII | 399 | 314 (K) | 364 (D) | 387 (K) |
| Homo sapiens | Fragment | DI, DIII | 403 | 318 (K) | 368 (D) | 391 (K) |
| Macaca mulatta (NP_001182578) | Full length | — | 584 | 500 (K) | 550 (N) | 573 (P) |
| Rattus norvegicus (AAH85359) | Full length | — | 584 | 500 (K) | 550 (D) | 573 (P) |
| Mus musculus (AAH49971) | Full length | — | 584 | 500 (K) | 550 (D) | 573 (P) |

FIG. 1 was generated by MUSCLE using the default parameters including output in ClustalW 1.81 format. The raw output data was shaded using BoxShade 3.21 (which can be accessed at www.ch.embnet.org/software/BOX_form.html) using Output Format: RTF_new; Font Size: 10; Consensus Line: no consensus line; Fraction of sequences (that must agree for shading): 0.5; Input sequence format: ALN. Therefore, throughout this specification amino acid positions defined in HSA also apply to equivalent positions in fragments, derivatives or variants and fusions of HSA, albumins from other species and fragments and fusions thereof. Such equivalent positions may have (i) a different residue number in its native protein and/or (ii) a different native amino acid in its native protein. Likewise, FIG. 2 shows that equivalent positions can be identified in fragments (e.g. domains) of an albumin with reference to SEQ ID NO: 2 (HSA).

Conservative substitution: As used herein, the term "conservative" amino acid substitutions refers to substitutions made within the same group, and which typically do not substantially affect protein function. By "conservative substitutions" is intended combinations such as Gly, Ala; Val, Ile, Leu; Asp, Glu; Asn, Gln; Ser, Thr; Lys, Arg; and Phe, Tyr. Such variants may be made by techniques well known in the art, such as by site-directed mutagenesis as disclosed in U.S. Pat. No. 4,302,386 issued 24 Nov. 1981 to Stevens, incorporated herein by reference.

In one embodiment, the Venn diagram of FIG. 3 may be used to determine conservative amino acid substitutions: Using FIG. 3, a conservation mutation score (ranging from 0 to 5) may be calculated. A score of 0 is the highest conservation, which, for cysteine, is only assigned for substitution of a cysteine residue with another cysteine residue. For changes from any other amino acid to a cysteine (or for a cysteine to any other amino acid), the score may be 1, 2, 3, 4, 5. A score of 1 is a more conservative substitution than a score of 2, 3, 4 or 5. A score of 5 is assigned to the lowest conservation between a substituted amino acid and the cysteine. The score of 0 to 5 is calculated from FIG. 3 as the number of boundaries (i.e. lines) crossed to go from cysteine to the appropriate amino acid. Thus the score for cysteine is 0 as no boundaries are crossed. Likewise, the score of aspartic acid (D) is 3, since 3 boundaries are crossed. The conservation mutation score (with respect to FIG. 3) for the 20 different amino acids are defined as (using one-letter codes for the amino acids): A=1, C=0, D=3, E=4, F=4, G=2, H=5, I=4, K=4, L=4, M=3, N=2, P=3, Q=3, R=5, S=1, T=1, V=3, W=3, Y=3.

Alternatively, or in addition, "conservative" amino acid substitutions refers to substitutions made within the same group such as within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

For example, a conservative substitution of alanine-2 in SEQ ID NO: 2 can include glycine or serine. Non-conservative substitutions encompass substitutions of amino acids in one group by amino acids in another group. For example, a non-conservative substitution could include the substitution of a polar amino acid for a hydrophobic amino acid.

Conventions for Designation of Variants

For purposes of the present invention, the mature polypeptide disclosed in SEQ ID NO: 2 is used to determine the corresponding amino acid residue in another albumin. The amino acid sequence of another albumin is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later, more preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another albumin can be determined or confirmed by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other polypeptide (or protein) has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Altschul et al., 1997, *Nucleic Acids Res.* 25: 3389-3402). Even greater sensitivity can be achieved if the family or superfamily for the polypeptide has one or more (e.g. several) representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more (e.g. several) protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g. Holm and Park, 2000, *Bioinformatics* 16: 566-567).

In describing the albumin variants of the present invention, the nomenclature described below is adapted for ease of reference. The accepted IUPAC single letter or three letter amino acid abbreviation is employed. The term 'point mutation' and/or 'alteration' includes deletions, insertions and substitutions.

Substitutions. For an amino acid substitution, the following nomenclature is used: Original amino acid, position, substituted amino acid. Accordingly, the substitution of threonine at position 226 with alanine is designated as "Thr326Ala" or "T326A". Multiple mutations (or alterations) are separated by addition marks ("+"), e.g. "Gly205Arg+Ser411Phe" or "G205R+S411F", representing substitutions at positions 205 and 411 of glycine (G) with arginine (R) and serine (S) with phenylalanine (F), respectively. The Figures also use ("/"), e.g. "E492T/N503D" this should be viewed as interchangeable with ("+").

Deletions. For an amino acid deletion, the following nomenclature is used: Original amino acid, position*. Accordingly, the deletion of glycine at position 195 is designated as "Gly195*" or "G195*". Multiple deletions are separated by addition marks ("+"), e.g. "Gly195*+Ser411*" or "G195*+S411*".

Insertions. As disclosed above, an insertion may be to the N-side ('upstream', 'X−1') or C-side ('downstream', 'X+1') of the amino acid occupying a position ('the named (or original) amino acid', 'X').

For an amino acid insertion to the C-side ('downstream', 'X+1') of the original amino acid ('X'), the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G - K - A |

For an amino acid insertion to the N-side ('upstream', 'X-1') of the original amino acid (X), the following nomenclature is used: Original amino acid, position, inserted amino acid, original amino acid. Accordingly the insertion of lysine (K) before glycine (G) at position 195 is designated "Gly195LysGly" or "G195KG". An insertion of multiple amino acids is designated [Original amino acid, position, inserted amino acid #1, inserted amino acid #2; etc., original amino acid]. For example, the insertion of lysine (K) and alanine (A) before glycine at position 195 is indicated as "Gly195LysAlaGly" or "G195KAG". In such cases the inserted amino acid residue(s) are numbered by the addition of lower case letters with 'prime' to the position number of the amino acid residue following the inserted amino acid residue(s). In the above example, the sequence would thus be:

| Parent: | Variant: |
|---------|----------|
| 195     | 195a' 195b' 195 |
| G       | K - A - G |

Multiple alterations. Variants comprising multiple alterations are separated by addition marks ("+"), e.g. "Arg170Tyr+Gly195Glu" or "R170Y+G195E" representing a substitution of arginine and glycine at positions 170 and 195 tyrosine and glutamic acid, respectively.

Different alterations. Where different alterations can be introduced at a position, the different alterations are separated by a comma, e.g. "Arg170Tyr, Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

Conjugation competence: A conjugation-competent cysteine is a cysteine residue which is capable of forming an intermolecular bond with a conjugation partner, particularly a conjugation partner that is not an albumin. A conjugation-competent polypeptide, i.e. thio-albumin, is capable of forming an intermolecular bond with a conjugation partner by virtue of the conjugation-competent cysteine residue. The thio-albumin may or may not have a high level of conjugation competence, for example at least 50, 60, 70, 80, 90, 95, 96, 97, 98, 99 or 100% relative to the conjugation competence of an albumin consisting of SEQ ID NO: 2 having only one conjugation competent cysteine at Cys-34. Conjugation competence may be determined relative to any conjugatable molecule (conjugation partner) of interest, for example a bioactive molecule or a fluorescent dye. Determination may be through mass spectrometry (MS) analysis or quantification of the activity of the bioactive compound such as its fluorescence. Conjugation competence of albumin and biotin or HRP may be determined by assaying the mass of the resultant conjugate and/or the enzyme activity of the conjugated compound. Determination by fluorescent labelling and cellular uptake is described by McGraw et al., (1987), *The Journal of Cell Biology*, 105, 207-214; and Presley et al., (1993), *The Journal of Cell Biology*, 122, 1231-1241. An advantage of a thio-albumin having a high conjugation competence is that it may allow efficient conjugation of molecules to the thio-albumin. Conjugation competence may be measured with respect to time. Favoured thio-albumins may be (a) those which achieve maximal conjugation quickly or (b) slowly. The conjugation competence of a specific cysteine may be determined by methods known to those skilled in the art—for example, the protein may be digested post-conjugation and peptide mapping performed to determine the degree of conjugation at the specific cysteine.

A bioactive agent or bioactive compound is one which has the ability to interact with a living organism, system or cell. It may, for example, be a biological or chemical agent or compound.

Ligand binding: The ligand binding properties of albumin include binding to anionic and neutral ligands such as long-chain fatty acids, bilirubin and other miscellaneous ligands. The long-chain fatty acids, oleic (C18:1), palmitic (C16:0), linoleic (C18:2), stearic (C18:0), arachidonic (C20:4) and palmitoleic (C16:1) are known to bind HSA. Ligand binding studies can be performed on HSA and thio-albumins using an isothermal titration calorimetry method that had been suitably qualified for this purpose. Samples can be pre-treated by defatting (Sogami, M. and J. F. Foster (1968). Biochemistry 7(6): 2172-82, incorporated herein by reference) followed by thiol blocking (Sogami, M., H. A. Petersen, et al. (1969). Biochemistry 8(1): 49-58, incorporated herein by reference) and subsequent gel permeation chromatography. The binding curves generated for thio-albumins and HSA with octanoate, for example, may subsequently be compared, and functional similarity established. Conjugated- and/or non-conjugated thio-albumin may have at least 5%, 10%, 15%, 20%, 30%, 40% or 50%, 60%, 70%, at least 80%, 90%, 95%, 100%, 105% or more of HSA's receptor binding activity, mole for mole, to bilirubin and/or a fatty acid.

FcRn and shFcRn: The term "FcRn" means the neonatal Fc receptor (FcRn), particularly the human neonatal Fc receptor. shFcRn is a soluble recombinant form of FcRn. shFcRn is a heterodimer of SEQ ID NO: 26 (truncated heavy chain of the major histocompatibility complex class I-like Fc receptor (FCGRT)) and SEQ ID NO: 27 (beta-2-microglobulin). Together, SEQ ID NO: 26 and 27 form hFcRn.

The conjugated- and/or non-conjugated thio-albumin may or may not have an altered binding affinity to FcRn.

The thio-albumin or conjugate thereof may have a binding to FcRn that is stronger or weaker (and, preferably, is stronger) than that of the parent albumin or conjugate thereof.

The thio-albumin or conjugate thereof may have a KD to FcRn (e.g. shFcRn) that is lower than the corresponding KD for HSA or conjugate thereof to. Preferably, the KD for the thio-albumin or conjugate is less than 0.9×KD for HSA to FcRn, more preferred less than 0.5×KD for HSA to FcRn, more preferred less than 0.1×KD for HSA to FcRn, even more preferred less than 0.05×KD for HSA to FcRn, even more preferred less than 0.02×KD for HSA to FcRn, even more preferred less than 0.01×KD for HSA to FcRn and most preferred less than 0.001×KD for HSA to FcRn (where × means 'multiplied by').

For a conjugate comprising a thio-albumin, preferably the KD for the conjugate is less than 0.9×KD for the corresponding conjugate comprising HSA to FcRn, more preferred less than 0.5×KD for the corresponding conjugate to FcRn, more preferred less than 0.1×KD for the corresponding conjugate to FcRn, even more preferred less than 0.05× KD for the corresponding conjugate to FcRn, even more preferred less than 0.02×KD for the corresponding conjugate to FcRn, even more preferred less than 0.01×KD for the corresponding conjugate to FcRn and most preferred less than 0.001×KD for the corresponding conjugate to FcRn (where × means 'multiplied by'). 'Corresponding conjugate' means a conjugate comprising HSA (e.g. SEQ ID NO: 2) instead of the thio-albumin (i.e. albumin variant).

The thio-albumin or conjugate thereof may have a KD to FcRn that is higher than the corresponding KD for HSA or conjugate thereof to FcRn. Preferably, the KD for the thio-albumin or conjugate is more than 2×KD for HSA to FcRn, more preferred more than 5×KD for HSA to FcRn, more preferred more than 10×KD for HSA to FcRn, even more preferred more than 25×KD for HSA to FcRn, most preferred more than 50×KD for HSA to FcRn. The thio-albumin or conjugate may be a null binder to FcRn.

For a conjugate comprising a thio-albumin, preferrably the KD for the conjugate, Preferably, the KD for the corresponding conjugate comprising HSA is more than 2×KD for the corresponding conjugate to FcRn, more preferred more than 5×KD for the corresponding conjugate to FcRn, more preferred more than 10×KD for the corresponding conjugate to FcRn, even more preferred more than 25×KD for the corresponding conjugate to FcRn, most preferred more than 50×KD for the corresponding conjugate to FcRn. Corresponding conjugate' means a conjugate comprising HSA (e.g. SEQ ID NO: 2) instead of the thio-albumin (i.e. albumin variant).

When determining and/or comparing KD, one or more (e.g. several) (and preferably all) of the following parameters may be used:

Instrument: Biacore 3000 instrument (GE Healthcare)
Flow cell: CM5 sensor chip
FcRn: human FcRn, preferably soluble human FcRn, optionally coupled to a tag such as Glutathione S Transferase (GST) or Histidine (His), most preferably His such as 6 histidine residues at the C-terminus of the beta-2-microglobulin.
Quantity of FcRn: 1200-2500 RU
Coupling chemistry: amine coupling chemistry (e.g. as described in the protocol provided by the manufacturer of the instrument).
Coupling method: The coupling may be performed by injecting 20 µg/mL of the protein in mM sodium acetate pH 5.0 (GE Healthcare). Phosphate buffer (67 mM phosphate buffer, 0.15 M NaCl, 0.005% Tween 20) at pH 5.5 may be used as running buffer and dilution buffer. Regeneration of the surfaces may be done using injections of HBS-EP buffer (0.01 M HEPES, 0.15 M NaCl, 3 mM EDTA, 0.005% surfactant P20) at pH 7.4 (Biacore AB).
Quantity of injection of test molecule (e.g. HSA or variant) 20-0.032 µM
Flow rate of injection: constant, e.g. 30 µL/mL
Temperature of injection: 25° C.
Data evaluation software: BIAevaluation 4.1 software (BIAcore AB).

Plasma half-life: Plasma half-life is ideally determined in vivo in suitable individuals. However, since it is time consuming and expensive and inevitably there are ethical concerns connected with doing experiments in animals or man, it is desirable to use an in vitro assay for determining whether plasma half-life is extended or reduced. It is known that the binding of albumin to its receptor (FcRn) is important for plasma half-life and the correlation between receptor binding and plasma half-life is that a higher affinity of albumin to its receptor leads to longer plasma half-life. Thus for the invention a higher affinity of albumin to FcRn is considered indicative of an increased plasma half-life and a lower affinity of albumin to its receptor is considered indicative of a reduced plasma half-life.

The binding of albumin to its receptor FcRn may be described using the term affinity and the expressions "stronger" or "weaker". Thus, it should be understood that a molecule having a higher affinity to FcRn than HSA is considered to bind more strongly to FcRn than HSA and a molecule having a lower affinity to FcRn than HSA is considered to bind more weakly to FcRn than HSA. The term 'binding coefficient' can be used instead of the term 'binding affinity'.

The terms "longer plasma half-life" or "shorter plasma half-life" and similar expressions are understood to be in relationship to the corresponding parent or reference or corresponding albumin molecule. Thus, a longer plasma half-life with respect to a variant albumin of the invention means that the variant has longer plasma half-life than that of the corresponding albumin having the same sequences except for the alteration(s) described herein.

Reference: a reference is an albumin, fusion, conjugate, composition, associate, nanoparticle or microparticle to which an albumin variant, fusion, conjugate, composition, associate, nanoparticle or microparticle is compared. The reference may comprise or consist of full length albumin (such as HSA or a natural allele thereof) or a fragment thereof. A reference may also be referred to as a 'corresponding' albumin, fusion, conjugate, composition, associate or nanoparticle to which an albumin variant, fusion, conjugate, composition, associate or nanoparticle is compared. A reference may comprise or consist of HSA (SEQ ID NO: 2) or a fragment, fusion, conjugate, associate, nanoparticle or microparticle thereof. Preferably, the reference is identical to the polypeptide, fusion polypeptide, conjugate, composition, associate, nanoparticle or microparticle according to the invention ("being studied") with the exception of the albumin moiety. Preferably the albumin moiety of the reference comprises or consists of an albumin (e.g. HSA, SEQ ID NO: 2) or a fragment thereof. The amino acid sequence of the albumin moiety of the reference may be longer than, shorter than or, preferably, the same (±1 to 15 amino acids) length as the amino sequence of the albumin moiety of the polypeptide, fusion polypeptide, conjugate, composition, associate, nanoparticle or microparticle according to the invention ("being studied").

Allelic variant: The term "allelic variant" means any of two or more (several) alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene. Polymorphisms known for HSA (SEQ ID NO: 2) are discussed in Minchiotti et al. (2008). Hum Mutat 29(8): 1007-16 and at www.uniprot.org/uniprot/P02768.

Coding sequence: The term "coding sequence" means a polynucleotide, which directly specifies the amino acid sequence of its translated polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the invention.

Control sequences: The term "control sequences" means all nucleic acid sequences necessary for the expression of a polynucleotide encoding a variant of the invention. Each control sequence may be native (i.e. from the same gene) or foreign (i.e. from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the variant including, but not limited to, transcription, post-transcriptional modification, translation, post-translational modification, and secretion. The thio-albumin may or may not be capable of being expressed at a level of at least 10, 20, 30, 40, 50, 60, 70, 80, 90 or 100% relative to the expression of an unmodified albumin (such as SEQ ID NO: 2) from a suitable expression system, such as yeast (e.g. *Saccharomyces*, e.g. *S. cerevisiae*) or an *Aspergillus*. Relative expression levels can be determined, for example, by expression of the protein followed by quantification by SDS-PAGE, GP-HPLC or Western Blotting.

Expression vector: The term "expression vector" means a linear or circular DNA molecule that comprises a polynucleotide encoding a variant and is operably linked to control sequences that provide for its expression.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

DETAILED DESCRIPTION OF THE INVENTION

Conjugation-Competent Polypeptides I

A first aspect of the invention provides a conjugation-competent polypeptide comprising an amino acid sequence which is at least 60% identical to human albumin, particularly residues 1 to 585 of the mature human albumin polypeptide sequence of SEQ ID NO: 2, or a fragment thereof;

wherein at least one (e.g. several) position equivalent to a position selected from K93, E294, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, E382, and L398 of SEQ ID NO: 2 comprises a conjugation-competent cysteine residue;

preferably wherein the conjugation-competent polypeptide has a tendency to exist as a monomer in solution which is at least 70% of the tendency of the parent polypeptide (such as the polypeptide of SEQ ID NO: 2) to exist as a monomer in solution, more preferably at least 75, 80, 85, 90, 95, 96, 97, 98, at least 99 or 100% of the tendency of the polypeptide of SEQ ID NO: 2 to exist as a monomer in solution. Preferably the parent polypeptide does not contain the conjugation-competent Cys residue or residues described herein. Preferably the parent polypeptide does not contain the additional mutation or mutations described herein. That is, preferably the parent polypeptide is identical to the conjugation-competent polypeptide with the exception of the introduced cysteine residue or residues and, if present, the introduced other mutation or mutations.

Suitably, the at least one (e.g. several) position is selected from K93, E294, A226, E230, I271, and E358, particularly from K93, E294, A226, E230, and I271.

Preferably the conjugation-competent polypeptide has at least 70, 75, 80, 85, 90, 95, 96, 97, 98, 99, 99.2, 99.4, 99.6, 99.8% sequence identity to SEQ ID NO: 2. For example, in addition to the introduced Cys residue or Cys residues, the conjugation-competent polypeptide may have at least 1, 2, 3, 4, 5, 6, 7, 8, 9, 10 (e.g. several) other mutations relative to SEQ ID NO: 2. Alternatively, in addition to the introduced Cys residue or Cys residues, the conjugation-competent polypeptide may have zero other mutations relative to SEQ ID NO: 2.

Preferably, the conjugation-competent polypeptide has a tendency to exist as a monomer in solution which is at least 75% of the tendency of the polypeptide of SEQ ID NO: 2 to exist as a monomer in solution and at least one position equivalent to a position selected from K93, E294, A226, E230, I271, E358, L24, F49, V54, D56, A92, Q94, E97, H128, F156, E227, D237, K240, D259, K262, N267, Q268, L275, L284, K317, A322, E333, D340, E354, K359, A362, E382, and L398 comprises a conjugation-competent cysteine residue.

Preferably the polypeptide is a recombinant polypeptide. Preferably the polypeptide is an isolated and/or purified polypeptide. Preferably the polypeptide is synthetic and/or does not naturally occur in nature.

A conjugation-competent cysteine at the position defined above may or may not be created in an albumin by insertion, for example by adding a cysteine with or without one or more (e.g. several) additional residues and without removal of an amino acid residue from the albumin sequence; or by substituting one or more (e.g. several) adjacent amino acids with a larger number of residues containing at least one (e.g. several) cysteine, thus extending the overall length of the polypeptide. For example, a cysteine residue may be introduced immediately adjacent an albumin residue identified herein. The cysteine residue may be introduced as a single cysteine residue or within a polypeptide. The polypeptide may be from 2 to 50 amino acids long, preferably from 2, 10, 20, 30, or 40 to 10, 20, 30, 40 or 50 amino acids long.

Suitably, the polypeptide comprises one or more (e.g. several) of:
a) substitution of an amino acid, other than cysteine, with a cysteine at a position corresponding to a position equivalent to any of residues K93, E294, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, E382, and L398, particularly from K93, E294, A226, E230, and I271, of SEQ ID NO: 2; and/or
b) insertion of a cysteine at a position adjacent the N- or C-side of an amino acid corresponding to a position equivalent to any of residues K93, E294, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, E382, and L398, particularly from K93, E294, A226, E230, and I271, of SEQ ID NO: 2.

Substitutions are preferred, and the following disclosure of selected positions should be understood to specifically encompass substitutions, without limitation.

Suitably 2, 3, 4, 5 or more (e.g. several) positions equivalent to positions selected from K93, E294, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, E382, and L398, particularly from K93, E294, A226, E230, and I271, of SEQ ID NO: 2 comprise a conjugation-competent cysteine residue. Suitably the 2, 3, 4, 5 or more (e.g. several) positions are selected from K93, E294, A226, E230, I271, and E358, particularly from K93, E294, A226, E230 and I271.

For a polypeptide comprising a Cys at a position equivalent to position E294 of SEQ ID NO: 1, preferably the polypeptide also comprises a Cys at a position equivalent to one or more of K93, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, or E382.

The inventors have found that variants of HSA in which cysteine has been substituted at a position selected from K93, E294, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, and E382 have the beneficial property of a tendency to exist as a monomer in solution which is at least 70% of the tendency of the HSA polypeptide of SEQ ID NO: 2 to exist as a monomer in solution. A cysteine introduced at one of the selected positions therefore has a low tendency to cause the variant to form dimers or higher order oligomers in solution. This beneficial effect is also noted in variants in which there are cysteines at more than one selected position. Without wishing to be bound by theory, the inventors ascribe the monomer tendencies of the polypeptides of the invention to the flexibility of the polypeptide chain in the region of, and surface exposure at, the site of cysteine substitution. This reflects an exercise of inventive skill, based on years of experience in protein structural biology, in the choices applied by the inventors in selecting positions within HSA for substitution with cysteine.

The tendency of albumin or variants thereof to exist as a monomer, rather than a dimer or higher order oligomer, can be determined based on measurement of monomer, dimer and higher order oligomer quantities in solutions of the albumin or variant under similar conditions.

Suitable techniques for performing such measurements include Gel Permeation High Pressure Liquid Chromatography, as described in the Examples. Results are typically expressed as "percentage monomer", which is calculated as:

amount of monomeric albumin by mass×100/
(amount of monomeric albumin by mass+
amount of dimeric albumin by mass+amount of
higher order oligomer by mass).

Alternatively, the tendency to form non-monomers in solution, that is dimers and/or higher order oligomers, may be expressed. The "percentage non-monomer" is 100% minus percentage monomer.

Samples may be tested shortly after purification (for example, within 24 hours after purification) following production in shake flasks or 10 L bioreactors, or following storage at 2-8° C., e.g. 5° C., for time periods of up to or including 1 week, 1 month, 2 months, 3 months or 6 months. Samples are typically tested, and optionally stored, in a solution of one or more (e.g. several) salts and at a pH of about 7.0±0.5. The solution may comprise a buffer comprising 50 mM ammonium acetate, 10 mM sodium octanoate, pH 7.0, preferably at a polypeptide concentration of from about 0.2 to about 2.5 mg/mL. The solution may comprise a buffer comprising 25 mM sodium phosphate, 215 mM sodium chloride, pH 6.5, preferably at a polypeptide concentration of from about 5 to about 50 mg/mL.

The percentage monomer for a given albumin may differ depending on the albumin purity and concentration. Albumin produced in shake flask culture is typically purified using a single AlbuPure® (Prometic Life Sciences Inc. or Albumedix Ltd (formerly Novozymes Biopharma UK Ltd)) chromatography step, and typically is obtained at a concentration of about 0.2 to 2.0 mg/mL, more preferably 1±0.5 mg/ml and a protein purity of >95% by SDS reducing PAGE. AlbuPure® is a high-performance affinity capture adsorbent designed for albumin fusion protein purification, which comprises a synthetic triazine ligand coupled to a base matrix. Under these conditions, percentage monomer of HSA was found to be about 87%, rising to about 89% upon storage at 6 months at 2-8° C. e.g. 5° C. Albumin produced in 10 L bioreactor culture is typically purified by an AlbuPure® chromatography step followed by an ion exchange chromatography, is ultrafiltered, and then formulated at 50 mg/mL, and has a protein purity of >99% by SDS reducing PAGE. Under these conditions, percentage monomer of HSA was found to be about 94%, and was stable at two months of storage at 2-8° C. and at 6 months storage at 2-8° C. A variant having at least 70% of the tendency of HSA to exist as a monomer in solution may therefore be found to be at least 60% monomer, preferably at least 69% monomer (less than 40% non-monomer, preferably less than 31% non-monomer) when tested after typical shake flask production and purification as described above, for samples tested shortly after purification or stored for up to two or up to six months. For a variant having at least 80% of the tendency of HSA to exist as a monomer in solution, the percentage monomer should be at least 70% preferably at least 79% monomer, and the percentage non-monomer less than 30%, preferably less than 21%. A variant having at least 70% of the tendency of HSA to exist as a monomer in solution may be found to be at least 65% monomer, preferably at least 69% monomer, when tested after typical 10 L bioreactor production and purification as described above, for samples tested shortly after purification or stored for up to two months. For a variant having at least 80% of the tendency of HSA to exist as a monomer in solution, the percentage monomer should be at least 75% preferably at least 79%. The tendency is preferably measured at day 0, e.g. the day that the variant is produced, however it may also be measured later e.g. at day 1, 2, 3, 4, 5, 6, 7 or after 2, 3, 4, 5, 6, 7 weeks or after 1 or 2 months storage e.g. at 2-8° C. e.g. 5° C. Suitably, the percentage monomer should be stable upon storage for up to seven weeks or two months, meaning that it does not reduce by more than 10, more than 9, 8, 7, 6, 5, 4, 3, 2 or 1 percentage points between testing shortly after purification and testing after two months of storage e.g. at 2-8° C. e.g. 5° C. Preferably the percentage monomer should not reduce by more than 5 percentage points between testing shortly after purification and testing after 7 weeks of storage at 2-8° C. e.g. 5° C.

The variant may or may not have a tendency to exist as a monomer in solution which is at least 75%, at least 80%, at least 85%, at least 90%, at least 95%, at least 96%, at least 97%, at least 98%, at least 99%, or at least 100% of the tendency of the polypeptide of SEQ ID NO: 2 to exist as a monomer in solution. This tendency may be tested shortly after purification or after storage for up to six months e.g. at 2-8° C. e.g. 5° C.

The tendency of the polypeptide to exist as monomer in solution may be measured following storage for at least 7 weeks at a temperature from 2 to 8° C. such as 5° C., at least 8 weeks at a temperature from 2 to 8° C. such as 5° C., at least 3 months at a temperature from 2 to 8° C. such as 5° C., at least 4 months at a temperature from 2 to 8° C. such as 5° C., at least 6 months storage at a temperature from 2 to 8° C. such as 5° C., or at least 3 months storage at a temperature of about 40° C. Most preferably the tendency of the polypeptide to exist as monomer in solution is measured following storage for at least 3 months at a temperature from 2 to 8° C. such as 5° C.

The tendency of the polypeptide to exist as a monomer in solution may be measured at a polypeptide concentration of from 0.2 to 50 mg/mL, for example at about 5 mg/mL.

The tendency of the polypeptide to exist as a monomer in solution may be measured at a pH from about 6.0, 6.1, 6.2, 6.3, 6.4, 6.5, 6.6, 6.7, 6.8, 6.9, 7.0, 7.1, 7.2, 7.3, or 7.4 to about 6.1, 6.2, 6.3, 6.4, 6.6, 6.7, 6.8, 6.9, 7.0, 7.1, 7.2, 7.3, 7.4 or 7.5, preferably about pH 7.

The tendency of the polypeptide to exist as a monomer in solution may be measured in a buffer comprising 50 mM ammonium acetate, 10 mM sodium octanoate, pH 7.0, preferably at a polypeptide concentration of from about 0.5 to about 5 mg/mL.

The tendency of the polypeptide to exist as a monomer in solution may be measured in a buffer comprising 25 mM sodium phosphate, 215 mM sodium chloride, pH 6.5, preferably at a polypeptide concentration of from about 5 to about 50 mg/mL.

The conjugation-competent polypeptide may, prior to storage, be purified for example using a triazine (such as AlbuPure®) chromatography matrix or DE-FF chromatography matrix, more preferably by triazine (such as AlbuPure®) chromatography matrix followed by DE-FF chromatography matrix. Suitable methods are disclosed in Example 10

The polypeptide sample storage may be static. The polypeptide sample storage may be vertical.

Where a variant comprises more than one conjugation-competent cysteine as provided above, the tendency to exist as a monomer may be reduced compared to the variant which differs only by virtue of having one fewer such cysteines. For example, a variant albumin having the substitutions E294C+K93C has a lower tendency to exist as a monomer than a variant albumin having either substitution alone. Suitably, the variant comprises a conjugation-competent cysteine residue at two positions selected from K93, E294, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, E382, and L398, particularly from K93, E294, A226, E230, and I271, of SEQ ID NO: 2, wherein the variant has a tendency to exist as a monomer in solution which is at least 75% of the tendency of a variant which differs only by virtue of comprising a conjugation-competent cysteine residue at only one of the two positions.

Suitably, the variant comprises a conjugation-competent cysteine residue at two positions selected from K93, E294, A226, E230, I271, E358, particularly from K93, E294, A226, E230, and I271, of SEQ ID NO: 2, wherein the variant has a tendency to exist as a monomer in solution which is at least 75% of the tendency of a variant which differs only by virtue of comprising a conjugation-competent cysteine residue at only one of the two positions.

Higher monomer tendencies are preferred, such as at least 80%, at least 85%, at least 90%, at least 95%, at least 96%, at least 97%, at least 98%, at least 99%, or at least 100%. For example, HSA comprising the substitution E294C+K93C has a tendency to exist as a monomer in solution which is at least 90% of the tendency of HSA comprising the substitution K93C, or at least 85% of the tendency of HSA comprising the substitution E294C, to exist as a monomer in solution. These results are illustrated in the Examples, with material purified from 10 L bioreactor preparations, and tested shortly after purification, or after storage for seven weeks or two months at 2-8° C. e.g. 5° C. The same samples were also stable following storage for 6 months. Albumin variants having more than one conjugation-competent cysteine can be prepared by introducing a further conjugation-competent cysteine residue into a variant which already has at least one (e.g. several) conjugation-competent cysteine residue. Variants comprising a further conjugation-competent cysteine residue which have at least 75% of the tendency of the reference albumin lacking the further conjugation-competent cysteine residue to exist as a monomer in solution may be preferred.

Suitable variants may comprise a conjugation-competent cysteine residue at one or two or more (e.g. several) positions selected from K93, E294, A226, E230, I271 and E358 of SEQ ID NO: 2. Suitable combinations of positions are (i) K93+E294, A226, E230, I271, or E358; (ii) E294+K93, A226, E230, I271, or E358; (iii) A226+K93, E294, E230, I271, or E358; (iv) E230+K93, E294, A226, I271, or E358; (v) I271+K93, E294, A226, E230, or E358; (vi) K93+E294+A226, E230, I271, or E358 of SEQ ID NO: 2. Suitable variants may comprise a conjugation-competent cysteine residue at one or two or more (e.g. several) positions selected from L24, F49, V54, D56, L66, A92, K93, Q94, E97, H128, F156, A226, E227, D237, E230, K240, D259, K262, N267, Q268, I271, L275, E277, L284, E294, E311, K317, A322, E333, D340, E354, E358, K359, A362, E382, L398 of SEQ ID NO: 2. Suitable combinations of positions are: (1) L24+F49, V54, D56, L66, A92, K93, Q94, E97, H128, F156, E227, E230, D237, K240, D259, K262, N267, Q268, I271, L275, E277, L284, E294, E311, K317, A322, E333, D340, E354, E358, K359, A362, E382, or L398; (2) F49+L24, V54, D56, L66, A92, K93, Q94, E97, H128, F156, A226, E227, E230, D237, K240, D259, K262, N267, Q268, I271, L275, E277, L284, E294, E311, K317, A322, E333, D340, E354, E358, K359, A362, E382, or L398; (3) V54+L24, F49, D56, L66, A92, K93, Q94, E97, H128, F156, A226, E227, E230, D237, K240, D259, K262, N267, Q268, I271, L275, E277, L284, E294, E311, K317, A322, E333, D340, E354, E358, K359, A362, E382, or L398; (4) D56+L24, F49, V54, L66, A92, K93, Q94, E97, H128, F156, A226, E227, E230, D237, K240, D259, K262, N267, Q268, I271, L275, E277, L284, E294, E311, K317, A322, E333, D340, E354, E358, K359, A362, E382, or L398; (5) L66+L24, F49, V54, D56, A92, K93, Q94, E97, H128, F156, A226, E227, E230, D237, K240, D259, K262, N267, Q268, I271, L275, E277, L284, E294, E311, K317, A322, E333, D340, E354, E358, K359, A362, E382, or L398; (6) A92+L24, F49, V54, D56, L66, K93, Q94, E97, H128, F156, A226, E227, E230, D237, K240, D259, K262, N267, Q268, I271, L275, E277, L284, E294, E311, K317, A322, E333, D340, E354, E358, K359, A362, E382, or L398; (7) Q94+L24, F49, V54, D56, L66, A92, K93, E97, H128, F156, A226, E227, E230, D237, K240, D259, K262, N267, Q268, I271, L275, E277, L284, E294, E311, K317, A322, E333, D340, E354, E358, K359, A362, E382, or L398; (8) E97+L24, F49, V54, D56, L66, A92, K93, Q94, H128, F156, A226, E227, E230, D237, K240, D259, K262, N267, Q268, I271, L275, E277, L284, E294, E311, K317, A322, E333, D340, E354, E358, K359, A362, E382, or L398; (9) H128+L24, F49, V54, D56, L66, A92, K93, Q94, E97, F156, A226, E227, E230, D237, K240, D259, K262, N267, Q268, I271, L275, E277, L284, E294, E311, K317, A322, E333, D340, E354, E358, K359, A362, E382, or L398; (10) F156+L24, F49, V54, D56, L66, A92, K93, Q94, E97, H128, A226, E227, E230, D237, K240, D259, K262, N267, Q268, I271, L275, E277, L284, E294, E311, K317, A322, E333, D340, E354, E358, K359, A362, E382, or L398; (11) E227+L24, F49, V54, D56, L66, A92, K93, Q94, E97, H128, F156, A226, E230, D237, K240, D259, K262, N267, Q268, I271, L275, E277, L284, E294, E311, K317, A322, E333, D340, E354, E358, K359, A362, E382, or L398; (12) D237+L24, F49, V54, D56, L66, A92, K93, Q94, E97, H128, F156, A226, E230, E227, K240, D259, K262, N267, Q268, I271, L275, E277, L284, E294, E311, K317, A322, E333, D340, E354, E358, K359, A362, E382, or L398; (13) K240+L24, F49, V54, D56, L66, A92, K93, Q94, E97, H128, F156, A226, E230, E227, D237, D259, K262, N267, Q268, I271, L275, E277, L284, E294, E311, K317, A322, E333, D340, E354, E358, K359, A362, E382, or L398; (14) D259+L24, F49, V54, D56, L66, A92, K93, Q94, E97, H128, F156, A226, E230, E227, D237, K240, K262, N267, Q268, I271, L275, E277, L284, E294, E311, K317, A322, E333, D340, E354, E358, K359, A362, E382, or L398; (15) K262+L24, F49, V54, D56, L66, A92, K93, Q94, E97, H128, F156, A226, E230, E227, D237, K240, D259, N267, Q268, I271, L275, E277, L284, E294, E311, K317, A322, E333, D340, E354, E358, K359, A362, E382, or L398; (16) N267+L24, F49, V54, D56, L66, A92, K93, Q94, E97, H128, F156, A226, E230, E227, D237, K240, D259, K262, Q268, I271, L275, E277, L284, E294, E311, K317, A322, E333, D340, E354, E358, K359, A362, E382, or L398; (17) Q268+L24, F49, V54, D56, L66, A92, K93, Q94, E97, H128, F156, A226, E227, E230, D237, K240, D259, K262, N267, I271, L275, E277, L284, E294, E311, K317, A322, E333, D340, E354, E358, K359, A362, E382, or L398; (18) L275+L24, F49, V54, D56, L66, A92, K93, Q94, E97, H128, F156, A226, E227, E230, D237, K240, D259, K262, N267, Q268, I271, L284, E294, E311, K317, A322, E333, D340, E354, E358, K359, A362, E382, or L398; (19) E277+L24, F49, V54, D56, L66, A92, K93, Q94, E97, H128, F156, A226, E227, E230, D237, K240, D259, K262, N267, Q268, I271, L275, L284, E294, E311, K317, A322, E333, D340, E354, E358, K359, A362, E382, or L398; (20) L284+L24, F49, V54, D56, L66, A92, K93, Q94, E97, H128, F156, A226, E227, E230, D237, K240, D259, K262, N267, Q268, I271, L275, E277, E294, E311, K317, A322, E333, D340, E354, E358, K359, A362, E382, or L398; (21) E311+L24, F49, V54, D56, L66, A92, K93, Q94, E97, H128, F156, A226, E227, E230, D237, K240, D259, K262, N267, Q268, I271, L275, E277, L284, E294, K317, A322, E333, D340, E354, E358, K359, A362, E382, or L398; (22) K317+L24, F49, V54, D56, L66, A92, K93, Q94, E97, H128, F156, A226, E227, E230, D237, K240, D259, K262, N267, Q268, I271, L275, E277, L284, E294, E311, A322, E333, D340, E354, E358, K359, A362, E382, or L398; (23) A322+L24, F49, V54, D56, L66, A92, K93, Q94, E97, H128, F156, A226, E227, E230, D237, K240, D259, K262, N267, Q268, I271, L275, E277, L284, E294, E311, K317, E333, D340, E354, E358, K359, A362, E382, or L398; (24) E333+L24, F49, V54, D56, L66, A92, K93, Q94, E97, H128, F156, A226, E227, E230, D237, K240, D259, K262, N267, Q268, I271, L275, E277, L284, E294, E311, K317, A322, D340, E354, E358, K359, A362, E382, or L398; (25) D340+L24, F49, V54, D56, L66, A92, K93, Q94, E97, H128, F156, E227, D237, E230, K240, D259, K262, N267, Q268, I271, L275, E277, L284, E294, E311, K317, A322, E333, E354, E358, K359, A362, E382, or L398; (26) E354+L24, F49, V54, D56, L66, A92, K93, Q94, E97, H128, F156, A226, E227, E230, D237, K240, D259, K262, N267, Q268, I271, L275, E277, L284, E294, E311, K317, A322, E333, D340, E358, K359, A362, E382, or L398; (27) K359+L24, F49, V54, D56, L66, A92, K93, Q94, E97, H128, F156, A226, E227, E230, D237, K240, D259, K262, N267, Q268, I271, L275, E277, L284, E294, E311, K317, A322, E333, D340, E354, E358, A362, E382, or L398; (28) A362+L24, F49, V54, D56, L66, A92, K93, Q94, E97, H128, F156, A226, E227, E230, D237, K240, D259, K262, N267, Q268, I271, L275, E277, L284, E294, E311, K317, A322, E333, D340, E354, E358, K359, E382, or L398; (29) E382+L24, F49, V54, D56, L66, A92, K93, Q94, E97, H128, F156, A226, E227, E230, D237, K240, D259, K262, N267, Q268, I271, L275, E277, L284, E294, E311, K317, A322, E333, D340, E354, E358, K359, A362, or L398; (30) L398+L24, F49, V54, D56, L66, A92, K93, Q94, E97, H128, F156, A226, E227, E230, D237, K240, D259, K262, N267, Q268, I271, L275, E277, L284, E294, E311, K317, A322, E333, D340, E354, E358, K359, A362, or E382; (31) K93+L24, F49, V54, D56, L66, A92, Q94, E97, H128, F156, A226, E227, E230, D237, K240, D259, K262, N267, Q268, I271, L275, E277, L284, E294, E311, K317, A322, E333, D340, E354, E358, K359, A362, E382 or L398; (32) E294+L24, F49, V54, D56, L66, A92, K93, Q94, E97, H128, F156, A226, E227, E230, D237, K240, D259, K262, N267, Q268, I271, L275, E277, L284, E311, K317, A322, E333, D340, E354, E358, K359, A362, E382 or L398; (33) A226+L24, F49, V54, D56, L66, A92, K93, Q94, E97, H128, F156, E227, E230, D237, K240, D259, K262, N267, Q268, I271, L275, E277, L284, E294, E311, K317, A322, E333, D340, E354, E358, K359, A362, E382 or L398; (34) E230+L24, F49, V54, D56, L66, A92, K93, Q94, E97, H128, F156, A226, E227, D237, K240, D259, K262, N267, Q268, I271, L275, E277, L284, E294, E311, K317, A322, E333, D340, E354, E358, K359, A362, E382 or L398; (35) I271+L24, F49, V54, D56, L66, A92, K93, Q94, E97, H128, F156, A226, E227, E230, D237, K240, D259, K262, N267, Q268, L275, E277, L284, E294, E311, K317, A322, E333, D340, E354, E358, K359, A362, E382 or L398; and (36) E358+L24, F49, V54, D56, L66, A92, K93, Q94, E97, H128, F156, A226, E227, E230, D237, K240, D259, K262, N267, Q268, I271, L275, E277, L284, E294, E311, K317, A322, E333, D340, E354, K359, A362, E382 or L398.

A preferred polypeptide may have at least 90% identity to SEQ ID NO: 2 and a cysteine provided at a position equivalent to K93 in SEQ ID NO: 2.

A preferred polypeptide may have at least 90% identity to SEQ ID NO: 2 and a cysteine at a position equivalent to E294 in SEQ ID NO: 2.

A preferred polypeptide may have at least 90% identity to SEQ ID NO: 2 and a cysteine at a position equivalent to A226 in SEQ ID NO: 2.

A preferred polypeptide may have at least 90% identity to SEQ ID NO: 2 and a cysteine at a position equivalent to E230 in SEQ ID NO: 2.

A preferred polypeptide may have at least 90% identity to SEQ ID NO: 2 and a cysteine at a position equivalent to I271 in SEQ ID NO: 2.

A preferred polypeptide may have at least 90% identity to SEQ ID NO: 2 and a cysteine at a position equivalent to E358 in SEQ ID NO: 2.

A particularly preferred polypeptide may have at least 90% identity to SEQ ID NO: 2, a cysteine at a position equivalent to K93 in SEQ ID NO: 2 and a cysteine at a position equivalent to E294 in SEQ ID NO: 2.

A preferred polypeptide may have at least 90% identity to SEQ ID NO: 2 and a cysteine at a position equivalent to L24 in SEQ ID NO: 2.

A preferred polypeptide may have at least 90% identity to SEQ ID NO: 2 and a cysteine at a position equivalent to F49 in SEQ ID NO: 2.

A preferred polypeptide may have at least 90% identity to SEQ ID NO: 2 and a cysteine at a position equivalent to V54 in SEQ ID NO: 2.

A preferred polypeptide may have at least 90% identity to SEQ ID NO: 2 and a cysteine at a position equivalent to D56 in SEQ ID NO: 2.

A preferred polypeptide may have at least 90% identity to SEQ ID NO: 2 and a cysteine at a position equivalent to L66 in SEQ ID NO: 2.

A preferred polypeptide may have at least 90% identity to SEQ ID NO: 2 and a cysteine at a position equivalent to A92 in SEQ ID NO: 2.

A preferred polypeptide may have at least 90% identity to SEQ ID NO: 2 and a cysteine at a position equivalent to Q94 in SEQ ID NO: 2.

A preferred polypeptide may have at least 90% identity to SEQ ID NO: 2 and a cysteine at a position equivalent to E97 in SEQ ID NO: 2.

A preferred polypeptide may have at least 90% identity to SEQ ID NO: 2 and a cysteine at a position equivalent to H128 in SEQ ID NO: 2.

A preferred polypeptide may have at least 90% identity to SEQ ID NO: 2 and a cysteine at a position equivalent to F156 in SEQ ID NO: 2.

A preferred polypeptide may have at least 90% identity to SEQ ID NO: 2 and a cysteine at a position equivalent to E227 in SEQ ID NO: 2.

A preferred polypeptide may have at least 90% identity to SEQ ID NO: 2 and a cysteine at a position equivalent to D237 in SEQ ID NO: 2.

A preferred polypeptide may have at least 90% identity to SEQ ID NO: 2 and a cysteine at a position equivalent to K240 in SEQ ID NO: 2.

A preferred polypeptide may have at least 90% identity to SEQ ID NO: 2 and a cysteine at a position equivalent to D259 in SEQ ID NO: 2.

A preferred polypeptide may have at least 90% identity to SEQ ID NO: 2 and a cysteine at a position equivalent to K262 in SEQ ID NO: 2.

A preferred polypeptide may have at least 90% identity to SEQ ID NO: 2 and a cysteine at a position equivalent to N267 in SEQ ID NO: 2.

A preferred polypeptide may have at least 90% identity to SEQ ID NO: 2 and a cysteine at a position equivalent to Q268 in SEQ ID NO: 2.

A preferred polypeptide may have at least 90% identity to SEQ ID NO: 2 and a cysteine at a position equivalent to L275 in SEQ ID NO: 2.

A preferred polypeptide may have at least 90% identity to SEQ ID NO: 2 and a cysteine at a position equivalent to E277 in SEQ ID NO: 2.

A preferred polypeptide may have at least 90% identity to SEQ ID NO: 2 and a cysteine at a position equivalent to L284 in SEQ ID NO: 2.

A preferred polypeptide may have at least 90% identity to SEQ ID NO: 2 and a cysteine at a position equivalent to E311 in SEQ ID NO: 2.

A preferred polypeptide may have at least 90% identity to SEQ ID NO: 2 and a cysteine at a position equivalent to K317 in SEQ ID NO: 2.

A preferred polypeptide may have at least 90% identity to SEQ ID NO: 2 and a cysteine at a position equivalent to A322 in SEQ ID NO: 2.

A preferred polypeptide may have at least 90% identity to SEQ ID NO: 2 and a cysteine at a position equivalent to E333 in SEQ ID NO: 2.

A preferred polypeptide may have at least 90% identity to SEQ ID NO: 2 and a cysteine at a position equivalent to D340 in SEQ ID NO: 2.

A preferred polypeptide may have at least 90% identity to SEQ ID NO: 2 and a cysteine at a position equivalent to E354 in SEQ ID NO: 2.

A preferred polypeptide may have at least 90% identity to SEQ ID NO: 2 and a cysteine at a position equivalent to K359 in SEQ ID NO: 2.

A preferred polypeptide may have at least 90% identity to SEQ ID NO: 2 and a cysteine at a position equivalent to A362 in SEQ ID NO: 2.

A preferred polypeptide may have at least 90% identity to SEQ ID NO: 2 and a cysteine at a position equivalent to E382 in SEQ ID NO: 2.

A preferred polypeptide may have at least 90% identity to SEQ ID NO: 2 and a cysteine at a position equivalent to L398 in SEQ ID NO: 2.

A preferred polypeptide may have at least 90% identity to SEQ ID NO: 2, a cysteine provided at a position equivalent to K93 and a cysteine at a position equivalent to C34 in SEQ ID NO: 2.

A particularly preferred polypeptide may have at least 90% identity to SEQ ID NO: 2 a cysteine at a position equivalent to E294 in SEQ ID NO: 2 and a cysteine at a position equivalent to C34 in SEQ ID NO: 2.

A preferred polypeptide may have at least 90% identity to SEQ ID NO: 2, a cysteine at a position equivalent to A226 in SEQ ID NO: 2 and a cysteine at a position equivalent to C34 in SEQ ID NO: 2.

A preferred polypeptide may have at least 90% identity to SEQ ID NO: 2, a cysteine at a position equivalent to E230 in SEQ ID NO: 2 and a cysteine at a position equivalent to C34 in SEQ ID NO: 2.

A preferred polypeptide may have at least 90% identity to SEQ ID NO: 2, a cysteine at a position equivalent to I271 in SEQ ID NO: 2 and a cysteine at a position equivalent to C34 in SEQ ID NO: 2.

A preferred polypeptide may have at least 90% identity to SEQ ID NO: 2, a cysteine at a position equivalent to E358 in SEQ ID NO: 2 and a cysteine at a position equivalent to C34 in SEQ ID NO: 2.

A preferred polypeptide may have at least 90% identity to SEQ ID NO: 2, a cysteine at a position equivalent to K93 in SEQ ID NO: 2 and a cysteine at a position equivalent to C34 in SEQ ID NO: 2, a cysteine at a position equivalent to E294 in SEQ ID NO: 2.

A preferred polypeptide may have at least 90% identity to SEQ ID NO: 2, a cysteine at a position equivalent to L24 in SEQ ID NO: 2 and a cysteine at a position equivalent to C34 in SEQ ID NO: 2.

A preferred polypeptide may have at least 90% identity to SEQ ID NO: 2, a cysteine at a position equivalent to F49 in SEQ ID NO: 2 and a cysteine at a position equivalent to C34 in SEQ ID NO: 2.

A preferred polypeptide may have at least 90% identity to SEQ ID NO: 2, a cysteine at a position equivalent to V54 in SEQ ID NO: 2 and a cysteine at a position equivalent to C34 in SEQ ID NO: 2.

A preferred polypeptide may have at least 90% identity to SEQ ID NO: 2, a cysteine at a position equivalent to D56 in SEQ ID NO: 2 and a cysteine at a position equivalent to C34 in SEQ ID NO: 2.

A preferred polypeptide may have at least 90% identity to SEQ ID NO: 2, a cysteine at a position equivalent to L66 in SEQ ID NO: 2 and a cysteine at a position equivalent to C34 in SEQ ID NO: 2.

A preferred polypeptide may have at least 90% identity to SEQ ID NO: 2, a cysteine at a position equivalent to A92 in SEQ ID NO: 2 and a cysteine at a position equivalent to C34 in SEQ ID NO: 2.

A preferred polypeptide may have at least 90% identity to SEQ ID NO: 2, a cysteine at a position equivalent to Q94 in SEQ ID NO: 2 and a cysteine at a position equivalent to C34 in SEQ ID NO: 2.

A preferred polypeptide may have at least 90% identity to SEQ ID NO: 2, a cysteine at a position equivalent to E97 in SEQ ID NO: 2 and a cysteine at a position equivalent to C34 in SEQ ID NO: 2.

A preferred polypeptide may have at least 90% identity to SEQ ID NO: 2, a cysteine at a position equivalent to H128 in SEQ ID NO: 2 and a cysteine at a position equivalent to C34 in SEQ ID NO: 2.

A preferred polypeptide may have at least 90% identity to SEQ ID NO: 2, a cysteine at a position equivalent to F156 in SEQ ID NO: 2 and a cysteine at a position equivalent to C34 in SEQ ID NO: 2.

A preferred polypeptide may have at least 90% identity to SEQ ID NO: 2, a cysteine at a position equivalent to E227 in SEQ ID NO: 2 and a cysteine at a position equivalent to C34 in SEQ ID NO: 2.

A preferred polypeptide may have at least 90% identity to SEQ ID NO: 2, a cysteine at a position equivalent to D237 in SEQ ID NO: 2 and a cysteine at a position equivalent to C34 in SEQ ID NO: 2.

A preferred polypeptide may have at least 90% identity to SEQ ID NO: 2, a cysteine at a position equivalent to K240 in SEQ ID NO: 2 and a cysteine at a position equivalent to C34 in SEQ ID NO: 2.

A preferred polypeptide may have at least 90% identity to SEQ ID NO: 2, a cysteine at a position equivalent to D259 in SEQ ID NO: 2 and a cysteine at a position equivalent to C34 in SEQ ID NO: 2.

A preferred polypeptide may have at least 90% identity to SEQ ID NO: 2, a cysteine at a position equivalent to K262 in SEQ ID NO: 2 and a cysteine at a position equivalent to C34 in SEQ ID NO: 2.

A preferred polypeptide may have at least 90% identity to SEQ ID NO: 2, a cysteine at a position equivalent to N267 in SEQ ID NO: 2 and a cysteine at a position equivalent to C34 in SEQ ID NO: 2.

A preferred polypeptide may have at least 90% identity to SEQ ID NO: 2, a cysteine at a position equivalent to Q268 in SEQ ID NO: 2 and a cysteine at a position equivalent to C34 in SEQ ID NO: 2.

A preferred polypeptide may have at least 90% identity to SEQ ID NO: 2, a cysteine at a position equivalent to L275 in SEQ ID NO: 2 and a cysteine at a position equivalent to C34 in SEQ ID NO: 2.

A preferred polypeptide may have at least 90% identity to SEQ ID NO: 2, a cysteine at a position equivalent to E277 in SEQ ID NO: 2 and a cysteine at a position equivalent to C34 in SEQ ID NO: 2.

A preferred polypeptide may have at least 90% identity to SEQ ID NO: 2, a cysteine at a position equivalent to L284 in SEQ ID NO: 2 and a cysteine at a position equivalent to C34 in SEQ ID NO: 2.

A preferred polypeptide may have at least 90% identity to SEQ ID NO: 2, a cysteine at a position equivalent to E311 in SEQ ID NO: 2 and a cysteine at a position equivalent to C34 in SEQ ID NO: 2.

A preferred polypeptide may have at least 90% identity to SEQ ID NO: 2, a cysteine at a position equivalent to K317 in SEQ ID NO: 2 and a cysteine at a position equivalent to C34 in SEQ ID NO: 2.

A preferred polypeptide may have at least 90% identity to SEQ ID NO: 2, a cysteine at a position equivalent to A322 in SEQ ID NO: 2 and a cysteine at a position equivalent to C34 in SEQ ID NO: 2.

A preferred polypeptide may have at least 90% identity to SEQ ID NO: 2, a cysteine at a position equivalent to E333 in SEQ ID NO: 2 and a cysteine at a position equivalent to C34 in SEQ ID NO: 2.

A preferred polypeptide may have at least 90% identity to SEQ ID NO: 2, a cysteine at a position equivalent to D340 in SEQ ID NO: 2 and a cysteine at a position equivalent to C34 in SEQ ID NO: 2.

A preferred polypeptide may have at least 90% identity to SEQ ID NO: 2, a cysteine at a position equivalent to E354 in SEQ ID NO: 2 and a cysteine at a position equivalent to C34 in SEQ ID NO: 2.

A preferred polypeptide may have at least 90% identity to SEQ ID NO: 2, a cysteine at a position equivalent to K359 in SEQ ID NO: 2 and a cysteine at a position equivalent to C34 in SEQ ID NO: 2.

A preferred polypeptide may have at least 90% identity to SEQ ID NO: 2, a cysteine at a position equivalent to A362 in SEQ ID NO: 2 and a cysteine at a position equivalent to C34 in SEQ ID NO: 2.

A preferred polypeptide may have at least 90% identity to SEQ ID NO: 2, a cysteine at a position equivalent to E382 in SEQ ID NO: 2 and a cysteine at a position equivalent to C34 in SEQ ID NO: 2.

A preferred polypeptide may have at least 90% identity to SEQ ID NO: 2, a cysteine at a position equivalent to L398 in SEQ ID NO: 2 and a cysteine at a position equivalent to C34 in SEQ ID NO: 2.

A preferred polypeptide may have at least 90% identity to SEQ ID NO: 2, a cysteine provided at a position equivalent to K93 and no cysteine at a position equivalent to C34 in SEQ ID NO: 2.

A particularly preferred polypeptide may have at least 90% identity to SEQ ID NO: 2 a cysteine at a position equivalent to E294 in SEQ ID NO: 2 and no cysteine at a position equivalent to C34 in SEQ ID NO: 2.

A preferred polypeptide may have at least 90% identity to SEQ ID NO: 2, a cysteine at a position equivalent to A226 in SEQ ID NO: 2 and no cysteine at a position equivalent to C34 in SEQ ID NO: 2.

A preferred polypeptide may have at least 90% identity to SEQ ID NO: 2, a cysteine at a position equivalent to E230 in SEQ ID NO: 2 and no cysteine at a position equivalent to C34 in SEQ ID NO: 2.

A preferred polypeptide may have at least 90% identity to SEQ ID NO: 2, a cysteine at a position equivalent to I271 in SEQ ID NO: 2 and no cysteine at a position equivalent to C34 in SEQ ID NO: 2.

A preferred polypeptide may have at least 90% identity to SEQ ID NO: 2, a cysteine at a position equivalent to E358 in SEQ ID NO: 2 and no cysteine at a position equivalent to C34 in SEQ ID NO: 2.

A preferred polypeptide may have at least 90% identity to SEQ ID NO: 2, a cysteine at a position equivalent to K93 in SEQ ID NO: 2 and no cysteine at a position equivalent to C34 in SEQ ID NO: 2, a cysteine at a position equivalent to E294 in SEQ ID NO: 2.

A preferred polypeptide may have at least 90% identity to SEQ ID NO: 2, a cysteine at a position equivalent to L24 in SEQ ID NO: 2 and no cysteine at a position equivalent to C34 in SEQ ID NO: 2.

A preferred polypeptide may have at least 90% identity to SEQ ID NO: 2, a cysteine at a position equivalent to F49 in SEQ ID NO: 2 and no cysteine at a position equivalent to C34 in SEQ ID NO: 2.

A preferred polypeptide may have at least 90% identity to SEQ ID NO: 2, a cysteine at a position equivalent to V54 in SEQ ID NO: 2 and no cysteine at a position equivalent to C34 in SEQ ID NO: 2.

A preferred polypeptide may have at least 90% identity to SEQ ID NO: 2, a cysteine at a position equivalent to D56 in SEQ ID NO: 2 and no cysteine at a position equivalent to C34 in SEQ ID NO: 2.

A preferred polypeptide may have at least 90% identity to SEQ ID NO: 2, a cysteine at a position equivalent to L66 in SEQ ID NO: 2 and no cysteine at a position equivalent to C34 in SEQ ID NO: 2.

A preferred polypeptide may have at least 90% identity to SEQ ID NO: 2, a cysteine at a position equivalent to A92 in SEQ ID NO: 2 and no cysteine at a position equivalent to C34 in SEQ ID NO: 2.

A preferred polypeptide may have at least 90% identity to SEQ ID NO: 2, a cysteine at a position equivalent to Q94 in SEQ ID NO: 2 and no cysteine at a position equivalent to C34 in SEQ ID NO: 2.

A preferred polypeptide may have at least 90% identity to SEQ ID NO: 2, a cysteine at a position equivalent to E97 in SEQ ID NO: 2 and no cysteine at a position equivalent to C34 in SEQ ID NO: 2.

A preferred polypeptide may have at least 90% identity to SEQ ID NO: 2, a cysteine at a position equivalent to H128 in SEQ ID NO: 2 and no cysteine at a position equivalent to C34 in SEQ ID NO: 2.

A preferred polypeptide may have at least 90% identity to SEQ ID NO: 2, a cysteine at a position equivalent to F156 in SEQ ID NO: 2 and no cysteine at a position equivalent to C34 in SEQ ID NO: 2.

A preferred polypeptide may have at least 90% identity to SEQ ID NO: 2, a cysteine at a position equivalent to E227 in SEQ ID NO: 2 and no cysteine at a position equivalent to C34 in SEQ ID NO: 2.

A preferred polypeptide may have at least 90% identity to SEQ ID NO: 2, a cysteine at a position equivalent to D237 in SEQ ID NO: 2 and no cysteine at a position equivalent to C34 in SEQ ID NO: 2.

A preferred polypeptide may have at least 90% identity to SEQ ID NO: 2, a cysteine at a position equivalent to K240 in SEQ ID NO: 2 and no cysteine at a position equivalent to C34 in SEQ ID NO: 2.

A preferred polypeptide may have at least 90% identity to SEQ ID NO: 2, a cysteine at a position equivalent to D259 in SEQ ID NO: 2 and no cysteine at a position equivalent to C34 in SEQ ID NO: 2.

A preferred polypeptide may have at least 90% identity to SEQ ID NO: 2, a cysteine at a position equivalent to K262 in SEQ ID NO: 2 and no cysteine at a position equivalent to C34 in SEQ ID NO: 2.

A preferred polypeptide may have at least 90% identity to SEQ ID NO: 2, a cysteine at a position equivalent to N267 in SEQ ID NO: 2 and no cysteine at a position equivalent to C34 in SEQ ID NO: 2.

A preferred polypeptide may have at least 90% identity to SEQ ID NO: 2, a cysteine at a position equivalent to Q268 in SEQ ID NO: 2 and no cysteine at a position equivalent to C34 in SEQ ID NO: 2.

A preferred polypeptide may have at least 90% identity to SEQ ID NO: 2, a cysteine at a position equivalent to L275 in SEQ ID NO: 2 and no cysteine at a position equivalent to C34 in SEQ ID NO: 2.

A preferred polypeptide may have at least 90% identity to SEQ ID NO: 2, a cysteine at a position equivalent to E277 in SEQ ID NO: 2 and no cysteine at a position equivalent to C34 in SEQ ID NO: 2.

A preferred polypeptide may have at least 90% identity to SEQ ID NO: 2, a cysteine at a position equivalent to L284 in SEQ ID NO: 2 and no cysteine at a position equivalent to C34 in SEQ ID NO: 2.

A preferred polypeptide may have at least 90% identity to SEQ ID NO: 2, a cysteine at a position equivalent to E311 in SEQ ID NO: 2 and no cysteine at a position equivalent to C34 in SEQ ID NO: 2.

A preferred polypeptide may have at least 90% identity to SEQ ID NO: 2, a cysteine at a position equivalent to K317 in SEQ ID NO: 2 and no cysteine at a position equivalent to C34 in SEQ ID NO: 2.

A preferred polypeptide may have at least 90% identity to SEQ ID NO: 2, a cysteine at a position equivalent to A322 in SEQ ID NO: 2 and no cysteine at a position equivalent to C34 in SEQ ID NO: 2.

A preferred polypeptide may have at least 90% identity to SEQ ID NO: 2, a cysteine at a position equivalent to E333 in SEQ ID NO: 2 and no cysteine at a position equivalent to C34 in SEQ ID NO: 2.

A preferred polypeptide may have at least 90% identity to SEQ ID NO: 2, a cysteine at a position equivalent to D340 in SEQ ID NO: 2 and no cysteine at a position equivalent to C34 in SEQ ID NO: 2.

A preferred polypeptide may have at least 90% identity to SEQ ID NO: 2, a cysteine at a position equivalent to E354 in SEQ ID NO: 2 and no cysteine at a position equivalent to C34 in SEQ ID NO: 2.

A preferred polypeptide may have at least 90% identity to SEQ ID NO: 2, a cysteine at a position equivalent to K359 in SEQ ID NO: 2 and no cysteine at a position equivalent to C34 in SEQ ID NO: 2.

A preferred polypeptide may have at least 90% identity to SEQ ID NO: 2, a cysteine at a position equivalent to A362 in SEQ ID NO: 2 and no cysteine at a position equivalent to C34 in SEQ ID NO: 2.

A preferred polypeptide may have at least 90% identity to SEQ ID NO: 2, a cysteine at a position equivalent to E382 in SEQ ID NO: 2 and no cysteine at a position equivalent to C34 in SEQ ID NO: 2.

A preferred polypeptide may have at least 90% identity to SEQ ID NO: 2, a cysteine at a position equivalent to L398 in SEQ ID NO: 2 and no cysteine at a position equivalent to C34 in SEQ ID NO: 2.

The 'no cysteine' at a position equivalent to C34 in SEQ ID NO: 2 may be provided, for example, by a substitution of C34 to an amino acid, such as a natural amino acid, for example, A, D, E, F, G, H, I, K, L, M, N, P, Q, R, S, T, V, W, or Y. Such a substitution may be described as C34X. The substitution C34A is preferred. The 'no cysteine' at a position equivalent to C34 in SEQ ID NO: 2 may be provided, for example, by deletion of the cysteine at this position.

A thio-albumin may or may not include a polypeptide where one or more (e.g. several) naturally occurring free-thiol group(s), such as cysteine-34 in HSA (SEQ ID NO: 2), is modified to an amino acid which is not cysteine. For example, cysteine may or may not be replaced by an amino acid which has a relatively high conservation score (e.g. 1, 2 or 3 as calculated according to FIG. 3) such as alanine or serine. A thio-albumin may or may not include a polypeptide where one or more (e.g. several) naturally occurring free-thiol group(s), such as cysteine-34 in HSA (SEQ ID NO: 2) are present. Thus, the conjugation-competent polypeptide of any of the above embodiments may comprise, at a position equivalent to position 34 of SEQ ID NO: 2, a conjugation-competent cysteine. Alternatively, there may not be a conjugation-competent cysteine at a position equivalent to position 34 of SEQ ID NO: 2.

For a polypeptide comprising two or more (several) conjugation competent cysteine residues, when the polypeptide is folded, the conjugation competent cysteine residues may or may not be relatively evenly distributed over the surface of the folded protein. The term 'folded' includes folding of a polypeptide/protein into its natural configuration, for example the most thermodynamically stable folded configuration. An advantage of relatively even distribution is that it allows conjugation of two or more (several) moieties to the thio-albumin with minimal steric hindrance or without steric hindrance between two or more (several) of the conjugated moieties. This has the advantage of minimising, and optionally eliminating, potential loss of activity due to issues such as steric hindrance between adjacent moieties (conjugation partners) which may be conjugated to the thio-albumin. Such moieties, for example bioactive molecules, may be relatively bulky.

Preferably the two or more (several) conjugation-competent cysteines are distributed over the surface of the thio-albumin molecule such that they are spaced as far from each other as possible, for example geometrically possible. Preferably the distance between two or more (several) conjugation-competent cysteines is at least 5, 10, 20, 30, 40, 50, 60, 70, or 80 Angstroms. Preferably each conjugation competent cysteine is at least 5, 10, 20, 30, 40, 50, 60, 70, or 80 Angstroms distant from one or several or all other conjugation-competent cysteines in the molecule. The distance between two conjugation-competent cysteines is preferably a distance which is at least 5, 10, 20, 30, 40, 50, 60, 70, 80, 90, or 95% and most preferably 100% of the length of the longest axis of the folded albumin molecule, for example as shown in a model of an albumin. For example, the longest axis of SEQ ID NO: 2 as shown in protein structure 1AO6 is approximately 85 Angstroms. Therefore, it is preferred that the two or more (several) of the cysteine residues are at least 65, 70, 75 or most preferably 80 Angstroms apart. Most preferably each conjugation-competent cysteine residue is at a distance of at least 80, 90, or 95% and most preferably 100% of the length of the longest axis of the folded albumin molecule.

Preferably the side chains of conjugation-competent cysteines are directed away from each other and/or directed so that a moiety conjugated to the cysteine will be directed away from the centre of the albumin structure. This provides the advantage of preventing interactions between the conjugated moieties and/or the albumin moiety itself.

With reference to an amino acid sequence, candidate amino acid residues may be visually inspected using software such as Yasara (Krieger and Vriend, 2014, Bioinformatics 30(20) 2981-2982; and described at www.yasara.org/).

Suitably, the polypeptide comprises substitution of an amino acid, other than cysteine, with a cysteine at one or both positions corresponding to a position equivalent to residues K93 or E294 of SEQ ID NO: 2. The Cα-Cα distance between C34 and K93 is 20.3 Å, between C34 and E294 is 39.9 Å and K93 and E294 45.9 Å in WT HSA (SEQ ID NO: 2).

Maleimide conjugation is a convenient means of conjugating a conjugation partner to an albumin. Capability to form a conjugate with maleimide-polyethylenglycol2-biotin is believed to be indicative of capability to form a conjugate with other conjugation partners containing a maleimide group. Conversely, if a conjugation-competent polypeptide has a low efficiency of conjugation with maleimide-polyethylenglycol2-biotin, or fails to conjugate, this is not indicative that it is poorly capable or not capable of conjugating with a different chemical group. Maleimide conjugates form a thio-ether bond, which may or may not be capable of stabilisation upon controlled hydrolysis. Stable conjugate formation may be preferred, such that the conjugate does not release a reactive maleimide conjugation partner during storage or use. The latter could potentially form unwanted conjugates with thiol-reactive species encountered in vivo.

As shown in the Examples, native HSA having a single free thiol at cysteine 34 forms approximately 50% stable conjugate upon maleimide conjugation and controlled hydrolysis. In contrast, polypeptides of the invention may form stable conjugates at higher efficiencies. In particular, albumins comprising a free thiol group at a position selected from those equivalent to K93, E294, and E358 of SEQ ID NO: 2 form stable maleimide conjugates at high efficiency, as shown in the Examples. Albumins comprising two or more (several) such thiols also may also form stable maleimide conjugates.

A conjugation-competent polypeptide of the invention may or may not be capable of forming a conjugate with maleimide-polyethylenglycol2-biotin (maleimide-PEG2-biotin) at a conjugation efficiency of at least 90%, preferably at least 95%, which conjugate may or may not be at least 90%, preferably at least 95% stable upon controlled hydrolysis. FIG. 4 illustrates the conjugation of maleimide-PEG2-biotin to a free thiol of a protein, and reactions which may occur to the formed conjugate.

A conjugation efficiency of a particular percentage indicates that the specified percentage of free thiol groups in the albumin form an adduct with the maleimide moiety, under suitable reaction conditions. The maleimide group reacts with thiols in the pH range 6.5-7.5 to form a thio-ether linkage with very little cross-reactivity with amines at this pH. The use of 20 mM sodium phosphate, 150 mM sodium chloride, pH 7.2 works well for this reaction. The concentration of protein should ideally be in the range of 1-10 mg/mL. Lower concentrations of protein may result in the need to increase the molar excess of reagent to obtain an acceptable level of modification (Hermanson, Greg T. (2008), Bioconjugate Techniques. Second Edition, Academic Press, San Diego, CA). The formation of the adduct results in an increase in mass which can be measured, for example by mass spectrometry, as in the Examples. Conveniently, the percentage conjugation efficiency is in relation to all free thiols of the albumin. Where the albumin has more than one such free thiol, a different percentage conjugation efficiency may pertain to each free thiol, and may be expressed in relation either to each individual free thiol, or collectively to all free thiols. Thus, if an albumin has two free thiols, one having 50% conjugation efficiency and the other having 100% conjugation efficiency, the overall conjugation efficiency for the albumin is the average of the two conjugation efficiencies, in this case 75%.

A stability of a particular percentage upon controlled hydrolysis indicates that the specified percentage of thiol-maleimide adduct undergoes ring-opening stabilisation, that is, the succinimide ring moiety is hydrolysed to a succinic acid moiety, and the thio-ether bond of the conjugate is maintained, as illustrated in FIG. 4. The percentage stability may be expressed in relation either to each individual free thiol or the albumin, or collectively to all free thiols. Controlled hydrolysis may be performed at alkaline pH and above ambient temperature. Suitably, adducts are incubated at pH 9.0 and 37° C. for at least 18 hours, preferably 24 hours in a buffered salts solution, such as phosphate buffered saline. The hydrolysis of the succinimide moiety to a succinic acid moiety by the addition of $H_2O$ has the effect of increasing the mass of the conjugate, which can be measured, for example by mass spectrometry, as in the Examples. Where conjugation efficiency is incomplete, this must be taken into account in determining the percentage stability. For example, if 50% of an albumin having one free thiol forms a conjugate, and 40% of the albumin is conjugated following controlled hydrolysis, this represents a stability of 80%. In these circumstances, 50% of the albumin is initially unconjugated, and therefore has a mass indicative of free albumin. The mass does not change upon controlled hydrolysis. Of the 50% of the albumin that is initially conjugated, a portion, 40% of the total albumin, has an increased mass of 18 Da due to the addition of $H_2O$. The other portion, 10% of the total albumin, does not undergo hydrolysis and therefore its mass does not change. Although this albumin is still conjugated, it may be unstable during storage or use, because it can undergo de-conjugation via the retro-Michael pathway, as illustrated in FIG. 4. In contrast, the stably hydrolysed conjugate can be expected to remain stable during storage or use (Fontaine, S. et al, *Bioconjugate Chem.* 2015, 26, 145-152).

Suitably conjugation efficiencies for a polypeptide of the invention may be at least 50%, at least 60%, at least 70%, at least 80%, at least 90%, at least 95%, at least 96%, at least 97%, at least 98%, at least 99%, or substantially 100%. Suitably conjugation efficiencies for an individual free thiol of a polypeptide of the invention may be at least 50%, at least 60%, at least 70%, at least 80%, at least 90%, at least 95% at least 96%, at least 97%, at least 98%, at least 99%, or substantially 100%. Suitable stabilities of a polypeptide conjugate upon controlled hydrolysis may be at least 50%, at least 60%, at least 70%, at least 80%, at least 90%, at least 95%, at least 96%, at least 97%, at least 98%, at least 99%, or substantially 100%.

As shown in the Examples, native HSA having a single free thiol at cysteine 34 forms greater than about 90% conjugate. Albumins comprising a free thiol group at a position selected from those equivalent to K93, E294, E358, L24, V54, H128, E227, K240, K262, Q268, E277, K317, A322, K359, and A362 of SEQ ID NO: 2 form maleimide conjugates greater than about 90% efficiency, those with a free thiol group at a position selected from those equivalent to L24, V54, H128, E227, K240, K262, K359, and A362 form maleimide conjugates greater than about 95% efficiency.

Suitable stabilities of a particular thiol-ether conjugate bond of a polypeptide conjugate upon controlled hydrolysis may be at least 50%, at least 60%, at least 70%, at least 80%, at least 90%, at least 95%, at least 96%, at least 97%, at least 98%, at least 99%, or substantially 100%.

The polypeptide may or may not further comprise a further linker to which a conjugation partner, such as a bioactive compound, radiopharmaceutical or imaging agent, may be linked. For example a linker may comprise a primary amine such as a lysine.

It is preferred that the conjugation-competent polypeptide has an acceptable immunogenicity, particularly in humans. More preferably the conjugation-competent polypeptide has an immunogenicity that is comparable to or lower than that of a parent albumin such as WT HSA (SEQ ID NO: 2). Therefore, preferably the alteration(s) to provide a conjugation competent cysteine residue(s) do not adversely affect the immunogenicity of the polypeptide relative to the parent albumin such as WT HSA.

Preferably, the alteration(s) made to provide the conjugation competent cysteine residue(s) do not adversely affect the immunogenicity of the polypeptide in human, e.g. relative to the immunogenicity of wild-type HSA (SEQ ID NO: 2).

The immunogenicity of the polypeptide may be determined or predicted by screening for T-cell epitopes and/or for B-cell epitopes. Screening may be in silico, in vitro or ex vivo. For example, the immunogenicity of the polypeptide may be determined or predicted by an ex vivo T cell activation assay. The T cell activation assay may comprise measuring T cell responses using a proliferation assay, e.g. [3H]-thymidine uptake. Preferably, the polypeptide has less than 10% reactivity in the T cell proliferation assay, preferably less than 8, 6, 4, or 2% reactivity, most preferably 0%. 'Reactivity' means that a positive response was observed. Therefore 10% reactivity means that a positive response was observed in 10% of the donor samples.

The T cell activation assay may comprise measuring T cell responses using a cytokine secretion assay, e.g. IL-2 ELISpot. Preferably the polypeptide has less than 10% reactivity in the cytokine secretion assay, preferably less than 8, 6, 4, or 2% reactivity, most preferably 0%. 'Reactivity' means that a positive response was observed. Therefore 10% reactivity means that a positive response was observed in 10% of the donor samples.

More preferred, the conjugation-competent polypeptide has less than 10% reactivity in a T cell proliferation assay and in a cytokine secretion assay, e.g. an EpiScreen™ assay (Abzena, Cambridge, UK).

The T cell assays may comprise CD4+ T cells.

The T cell assays may use peripheral blood mononuclear cells from a cohort of 50 healthy donors representing the European and North American population (based on HLA allotypes).

Preferably, the polypeptide does not stimulate an adverse antibody response in human, such as a specific antibody response.

For a conjugate comprising the conjugation-competent polypeptide, preferably the conjugate has an immunogenicity that is comparable to or lower than that of a corresponding conjugate comprising a parent albumin such as WT HSA (SEQ ID NO: 2) instead of the conjugation-competent polypeptide. Consequently, the properties mentioned for the conjugation-competent polypeptide also apply to a conjugate comprising the conjugation-competent polypeptide, however the 'control' may be a parent albumin such as WT HSA or a corresponding conjugate comprising a parent albumin such as WT HSA.

Conjugation-Competent polypeptides II

A second aspect of the invention provides a conjugation-competent polypeptide comprising an amino acid sequence according to the first aspect of the invention, and at least one (e.g. several) further modification compared to SEQ ID NO: 2, such as a further modification which causes the polypeptide to have at least one (e.g. several) further conjugation-competent cysteine, or alters the binding affinity of the polypeptide for FcRn, or alters the plasma half-life of the polypeptide.

The second aspect of the invention allows for the favoured conjugation-competent cysteines as defined in relation to the first aspect of the invention to be combined with other modifications in an albumin background, and provides the option to further tailor the albumin for specific applications.

Further Conjugation-Competent Cysteines

The at least one (e.g. several) further modification may or may not cause the polypeptide to have at least one (e.g. several) further conjugation-competent cysteine. The polypeptide may or may not comprise a total of 2, 3, 4, 5, 6, 7, 8, 9, 10, 11, 12, 13, 14, 15, 16, 17, 18, 19 or 20 conjugation competent cysteine residues. The polypeptide may or may not comprise at least one (e.g. several) further conjugation-competent cysteine as defined in relation to the first aspect of the invention.

The polypeptide may or may not comprise at least one (e.g. several) further conjugation-competent cysteine, other than at a position corresponding to least one position equivalent to a position selected from K93, E294, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, E382, and L398, particularly from K93, E294, A226, E230, and I271, of SEQ ID NO: 2. Suitable conjugation-competent cysteines are disclosed in WO 2010/092135 (incorporated by reference, particularly FIGS. 5 and 6). Suitably, at least one (e.g. several) position equivalent to a position selected from D1, A2, H3, S5, A55, S58, C75, T76, T79, E82, T83, E86, C91, D121, V122, C124, T125, D129, C169, C177, A229, T236, E266, D269, S270, S273, S304, K313, D314, C316, N318, A320, C361, A364, C369, A371, N386, Q390, Q397, S435, T478, T496, A504, E505, T506, T508, D549, C558, D562, C567, A581, L585 and A578 of SEQ ID NO: 2 may comprise a conjugation-competent cysteine. Suitably, the polypeptide may comprise one or more (e.g. several) of: (a) substitution of an amino acid, other than cysteine, with a cysteine at a position corresponding to a position equivalent to any of residues D1, A2, H3, S5, A55, S58, C75, T76, T79, E82, T83, E86, C91, D121, V122, C124, T125, D129, C169, C177, A229, T236, E266, D269, S270, S273, S304, K313, D314, C316, N318, A320, C361, A364, C369, A371, N386, Q390, Q397, S435, T478, T496, A504, E505, T506, T508, D549, C558, D562, C567, A581, L585 and A578 of SEQ ID NO: 2; (b) insertion of a cysteine at a position adjacent the N- or C-side of an amino acid corresponding to a position equivalent to any of residues D1, A2, H3, S5, A55, S58, C75, T76, T79, E82, T83, E86, C91, D121, V122, C124, T125, D129, C169, C177, A229, T236, E266, D269, S270, S273, S304, K313, D314, C316, N318, A320, C361, A364, C369, A371, N386, Q390, Q397, S435, T478, T496, A504, E505, T506, T508, D549, C558, D562, C567, A581, L585 and A578 of SEQ ID NO: 2 so as to generate a conjugation competent cysteine at any of C369, C361, C91, C177, C567, C316, C75, C169, C124 and C558; and (c) addition of a cysteine to the N-side of the N-terminal residue of an albumin sequence or to the C-side of the C-terminal residue of an albumin sequence. Exemplary combinations include conjugation-competent cysteines located at: (a) A2+L585, (b) A2+A364+D562+L585C, (c) A2 and adjacent the C-side of the C-terminus of the albumin (d) T79+A364; (e) A364+D1; (f) T79+D562+A364; (g) D562+A364+D1; (h) T79+D562+A364+A504; (i) T79+D562+A364+L585; (j) T79+D562+A364+D1; (k) T79+D562+A364+L585+D1; (l) E86+D562+A364+A504+A2; (m) S270+A581; (n) S270+D129; (0) S270+A581+E82; (p) S270+A581+D129; (q) S270+A581+E82+D129; (r) S270+A581+E82+D129+Q397; (s) C369+C177; (t) A364+A581; (u) T79+A364+A581; (v) A364+A581+D129; (w) A364+C177; (x) D562+C369; (y) D129+C369; (z) A581+C369; or (aa) D562+D129+C369.

Further suitable cysteine residues may be introduced as disclosed in WO 2009/126920 or WO 2010/059315 (incorporated herein by reference). Specifically, one or more (e.g. several) surface-exposed amino acid residues may be substituted for a cysteine residue, corresponding to one or more (e.g. several) positions corresponding S58, T76, T79, T83, T125, T236, S270, S273, S304, S435, T478, T496, T506 and T508 of SEQ ID NO: 2.

As noted in relation to the first aspect of the invention, increasing the number of conjugation-competent cysteine residues in an albumin variant may reduce its tendency to exist as a monomer in solution. It is preferred that the conjugation-competent polypeptide of the second aspect of the invention has a tendency to exist as a monomer in solution which is at least 70% of the tendency of the polypeptide of SEQ ID NO: 2 to exist as a monomer in solution, and optionally at least 75%, at least 80%, at least 90%, at least 91%, at least 92%, at least 93%, at least 94%, at least 95%, at least 96%, at least 97%, at least 98%, at least 99%, or at least 100%. This preference applies whether or not the polypeptide comprises a further conjugation-competent cysteine as defined in relation to the second aspect. Nevertheless, useful conjugation-competent polypeptides may still be provided which have a lower tendency to exist as a monomer in solution. Because the conjugation-competent cysteine residues defined in relation to the first aspect of the invention themselves contribute relatively minimally to non-monomer formation, combining one or more (e.g. several) of them with one or more (e.g. several) other conjugation-competent cysteine residues can be expected to result in a variant having increased monomer percentage compared to a variant having the same number of conjugation-competent cysteine residues selected from the prior art.

Albumin Variants with Altered Binding to FcRn and/or Altered Plasma Half-Life

The at least one (e.g. several) further modification may or may not alter the binding affinity of the albumin variant to FcRn and/or alter the plasma half-life. Preferably the albumin variant may have at least 70, 75, 80, 85, 90, 95, 96, 97, 98, 99, 99.2, 99.4, 99.6, 99.8% sequence identity to SEQ ID NO: 2. For example, in addition to the introduced Cys residue or Cys residues, the albumin variant may have at least 1, 2, 3, 4, 5, 6, 7, 8, 9, 10 (e.g. several) other mutations relative to SEQ ID NO: 2. Alternatively, in addition to the introduced Cys residue or Cys residues, the albumin variant may have zero other mutations relative to SEQ ID NO: 2.

The thio-albumin or conjugate may have a plasma half-life that is either longer or shorter, preferably longer, than that of the parent albumin or conjugate thereof, or a binding to FcRn that is stronger or weaker, preferably stronger. Preferably the thio-albumin or conjugate has a plasma half-life that is longer than that of HSA or the corresponding conjugate thereof.

Alternatively, this may be expressed as the thio-albumin or conjugate having a KD to FcRn (e.g. shFcRn) that is lower than the corresponding KD for HSA or conjugate thereof to. Preferably, the KD for the thio-albumin or conjugate is less than 0.9×KD for HSA to FcRn, more preferred less than 0.5×KD for HSA to FcRn, more preferred less than 0.1×KD for HSA to FcRn, even more preferred less than 0.05×KD for HSA to FcRn, even more preferred less than 0.02×KD for HSA to FcRn, even more preferred less than 0.01×KD for HSA to FcRn and most preferred less than 0.001×KD for HSA to FcRn (where × means 'multiplied by').

For a conjugate comprising a thio-albumin, preferrably the KD for the conjugate is less than 0.9×KD for the corresponding conjugate comprising HSA to FcRn, more preferred less than 0.5×KD for the corresponding conjugate to FcRn, more preferred less than 0.1×KD for the corresponding conjugate to FcRn, even more preferred less than 0.05×KD for the corresponding conjugate to FcRn, even more preferred less than 0.02×KD for the corresponding conjugate to FcRn, even more preferred less than 0.01×KD for the corresponding conjugate to FcRn and most preferred less than 0.001×KD for the corresponding conjugate to FcRn (where × means 'multiplied by'). 'Corresponding conjugate' means a conjugate comprising HSA (e.g. SEQ ID NO: 2) instead of the thio-albumin (i.e. albumin variant).

Alternatively, the thio-albumin or conjugate may have a plasma half-life that is shorter than that of HSA or the conjugate thereof.

This may be expressed as the thio-albumin or conjugate having a KD to FcRn that is higher than the corresponding KD for HSA or conjugate thereof to FcRn. Preferably, the KD for the thio-albumin or conjugate is more than 2×KD for HSA to FcRn, more preferred more than 5×KD for HSA to FcRn, more preferred more than 10×KD for HSA to FcRn, even more preferred more than 25×KD for HSA to FcRn, most preferred more than 50×KD for HSA to FcRn. The thio-albumin or conjugate may be a null binder to FcRn.

For a conjugate comprising a thio-albumin, preferrably the KD for the conjugate, Preferably, the KD for the corresponding conjugate comprising HSA is more than 2×KD for the corresponding conjugate to FcRn, more preferred more than 5×KD for the corresponding conjugate to FcRn, more preferred more than 10×KD for the corresponding conjugate to FcRn, even more preferred more than 25×KD for the corresponding conjugate to FcRn, most preferred more than 50×KD for the corresponding conjugate to FcRn. Corresponding conjugate' means a conjugate comprising HSA (e.g. SEQ ID NO: 2) instead of the thio-albumin (i.e. albumin variant).

The half-life of the thio-albumin or conjugate or product made from associate, nanoparticle, microparticle or liposome may be tailored in order to achieve a binding affinity or half-life which meets the needs of the user.

When determining and/or comparing KD, one or more (e.g. several) (and preferably all) of the following parameters may be used:
Instrument: Biacore 3000 instrument (GE Healthcare)
Flow cell: CM5 sensor chip
FcRn: human FcRn, preferably soluble human FcRn, optionally coupled to a tag such as Glutathione S Transferase (GST) or Histidine (His), most preferably His such as 6 histidine residues at the C-terminus of the beta-2-microglobulin.
Quantity of FcRn: 1200-2500 RU
Coupling chemistry: amine coupling chemistry (e.g. as described in the protocol provided by the manufacturer of the instrument).
Coupling method: The coupling may be performed by injecting 20 μg/mL of the protein in 10 mM sodium acetate pH 5.0 (GE Healthcare). Phosphate buffer (67 mM phosphate buffer, 0.15 M NaCl, 0.005% Tween 20) at pH 5.5 may be used as running buffer and dilution buffer. Regeneration of the surfaces may be done using injections of HBS-EP buffer (0.01 M HEPES, 0.15 M NaCl, 3 mM EDTA, 0.005% surfactant P20) at pH 7.4 (Biacore AB).
Quantity of injection of test molecule (e.g. HSA or variant) 20-0.032UM
Flow rate of injection: constant, e.g. 30 μL/mL
Temperature of injection: 25° C.
Data evaluation software: BIAevaluation 4.1 software (BIAcore AB).

Domain III of albumin is primarily responsible for binding FcRn. The conjugation-competent polypeptide may or may not comprise or consist of albumin domain III or a variant thereof and at least one (e.g. several) additional albumin domain or fragment thereof, such as a second albumin domain III or a variant thereof, as disclosed in WO 2011/124718 (incorporated herein by reference). Suitably, the polypeptide comprises or consists of at least one (e.g. several) albumin domain III or variant or fragment thereof, wherein at least one (e.g. several) albumin domain III comprises one or more (e.g. several) substitutions in positions corresponding to the positions in SEQ ID NO: 2 selected among: 573, 500, 550, 417, 440, 464, 490, 492, 493, 494, 495, 496, 499, 501, 503, 504, 505, 506, 510, 535, 536, 537, 538, 540, 541, 542, 574, 575, 577, 578, 579, 580, 581, 582 and 584, as disclosed in WO 2011/051489 (incorporated herein by reference). Suitable substitutions include one or more (e.g. several) substitutions in positions corresponding to the positions in SEQ ID NO: 2 selected among: K573Y, W, P, H, F, V, I, T, N, S, G, M, C, A, E, Q, R, L, D, K500E, G, D, A, S, C, P, H, F, N, W, T, M, Y, V, Q, L, I, R, Q417A, H440A, H464Q, E492G, D494N,Q,A, E495Q,A, T496A, D494E+Q417H, D494N+T496A, E492G+V493P, P499A, E501A,Q, N503H,K, H510Q, H535Q, K536A, P537A, K538A, K541G,D, D550E,N, E492G+K573P,A, or E492G/N503H/K573P.

In an alternative embodiment, the polypeptide may comprise alterations at two or more (several) positions selected from positions corresponding to positions (a) 492 and 580; (b) 492 and 574; (c) 492 and 550; (d) 550 and 573; (e) 550 and 574; (f) 550 and 580 in SEQ ID NO: 2, as disclosed in WO 2014/072481 (incorporated herein by reference).

In an alternative embodiment, the conjugation-competent polypeptide may comprise: (i) an N-terminal region comprising a first albumin which is a human albumin variant, in which the N-terminal of the first albumin comprises all amino acids of the human albumin variant except the C-terminal 2 to 30 amino acids; and (ii) a C-terminal region of a second albumin, which is selected from macaque albumin, mouse albumin, rabbit albumin, sheep albumin, human albumin, goat albumin, chimpanzee albumin, hamster albumin, guinea pig albumin, rat albumin, cow albumin, horse albumin, donkey albumin, dog albumin, chicken albumin, or pig albumin, or a variant thereof, in which the C-terminal of the second albumin or albumin variant comprises the C-terminal 2 to 30 amino acids of the second albumin or albumin variant; wherein the polypeptide has (i) an altered plasma half-life compared with the human albumin variant and/or (ii) an altered binding affinity to FcRn compared with the human albumin variant, as disclosed in WO 2012/059486 (incorporated herein by reference).

In an alternative embodiment, the polypeptide may comprise one or more (e.g. several) alterations in Domain I of the mature human albumin polypeptide sequence of SEQ ID NO: 2; and one or more (e.g. several) alterations in Domain III of the mature human albumin polypeptide sequence of SEQ ID NO: 2, wherein the one or more (e.g. several) alterations cause the polypeptide to have an altered binding affinity to FcRn, as disclosed in WO 2013/135896 (incorporated herein by reference). Suitably, the alteration(s) in Domain I are selected from positions corresponding to any of positions 78 to 120 of SEQ ID NO: 2, such as any of positions 78 to 88 and/or from any of 105 to 120; and the alteration(s) in Domain III are selected from positions corresponding to any of positions 425, 505, 510, 512, 524, 527, 531, 534, 569, 573, 575 of SEQ ID NO: 2. Suitably, the alteration at the position corresponding to positions 78 to 120 or 425, 505, 510, 512, 524, 527, 531, 534, 569, 573, and/or 575 of SEQ ID NO: 2 is a substitution; and the alteration is optionally a substitution selected from (i) 83N, K or S; (ii) 111D, G, H, R, Q or E; or (iii) 573P, Y, W, H, F, T, I or V.

In an alternative embodiment, the polypeptide may comprise one or more (e.g. several) alterations in Domain II of the mature human albumin polypeptide sequence of SEQ ID NO: 2 selected from the group consisting of positions corresponding to positions 349, 342, 381, 345, 384, 198, 206, 340, 341, 343, 344, 352, 382, 348, and/or 383 in SEQ ID NO: 2; wherein the one or more (e.g. several) alterations causes the conjugation-competent polypeptides to have (i) an altered plasma half-life and/or (ii) an altered binding affinity to FcRn, as disclosed in WO 2015/036579 (incorporated herein by reference). Suitably, the alteration at the position corresponding to position 349, 342, 381, 345, 384, 198, 206, 340, 341, 343, 344, 352, 382, 348, and/or 383 is a substitution; and the alteration is optionally a substitution selected from (i) 349F, W, Y, H, P, K or Q, preferably F; (ii) 342Y, W, F, H, T, N, Q, A, C, I, L, P, V, preferably Y; (iii) 381G or A, preferably G; or (iv) 345E, H, I or Q.

In an alternative embodiment, the polypeptide may comprise a variant Domain III of an albumin, or fragment thereof, comprising a mutation, such as a substitution, corresponding to one or more (e.g. several) positions corresponding to V418, T420, V424, E505 and V547 of SEQ ID NO: 2. These mutations are disclosed in WO 2013/075066 (incorporated herein by reference). Substitutions may be at one, two or more (several, e.g. at two, three, four, or five) of the positions corresponding to V418, T420, V424, E505 and V547; for example, there may be one or more (e.g. several) substitutions selected from V418M, T420A, V424I, E505(R/K/G) and V547A. In a particular embodiment, the albumin comprises the substitutions V418M, T420A and E505R; or V418M, T420A, E505G and V547A. The albumin may comprise one or more (e.g. several) additional substitutions at positions selected from N429, M446, A449, T467, and A552; such as selected from N429D, M446V, A449V, T467M, and A552T.

In an alternative embodiment, the variant may comprise a variant Domain III of an albumin, or fragment thereof, comprising one to eighteen amino acid substitutions to increase one or both of affinity for FcRn and serum half-life of the polypeptide, as disclosed in WO 2011/103076 (incorporated herein by reference). Substitutions may be at any one or more (e.g. several) of positions corresponding to positions 381, 383, 391, 401, 402, 407, 411, 413, 414, 415, 416, 424, 426, 434, 442, 445, 447, 450, 454, 455, 456, 457, 459, 463, 495, 506, 508, 509, 511, 512, 515, 516, 517, 519, 521, 523, 524, 525, 526, 527, 531, 535, 538, 539, 541, 557, 561, 566 or 569 of SEQ ID NO: 2. Suitable substitutions may be selected from V381N, V381Q, E383A, E383G, E383I, E383L, E383V, N391A, N391G, N391I, N391L, N391V, Y401D, Y401E, K402A, K402G, K402I, K402L, K402V, L407F, L407N, L407Q, L407W, L407Y, Y411Q, Y411N, K413C, K413S, K413T, K414S, K414T, V415C, V415S, V415T, Q416H, Q416P, V424A, V424G, V424I, V424L, V424N, V424Q, V426D, V426E, V426H, V426P, G434C, G434S, G434T, E442K, E442R, R445F, R445W, R445Y, P447S, P447T, E450D, E450E, S454C, S454M, S454T, V455N, V455Q, V456N, V456Q, L457F, L457W, L457Y, Q459K, Q459R, L463N, L463Q, E495D, T506F, T506W, T506Y, T508K, T508R, T508S, F509C, F509I, F509L, F509M, F509V, F509W, F509Y, A511F, A511W, A511Y, D512F, D512W, D512Y, T515C, T515H, T515N, T515P, T515Q, T515S, L516F, L516S, L516T, L516W, L516Y, S517C, S517F, S517M, S517T, S517W, S517Y, K519A, K519G, K519I, K519L, K519V, R521F, R521W, R521Y, I523A, I523D, I523E, I523F, I523G, I523K, I523L, I523N, I523Q, I523R, I523V, I523W, I523Y, K524A, K524G, K524I, K524L, K524V, K525A, K525G, K525I, K525L, K525V, Q526C, Q526M, Q526S, Q526T, Q526Y, T527F, T527W, T527Y, E531A, E531G, E531I, E531L, E531V, H535D, H535E, H535P, K538F, K538W, K538Y, A539I, A539L, A539V, K541F, K541W, K541Y, K557A, K557G, K557I, K557L, K557V, A561F, A561W, A561Y, T566F, T566W, T566Y, A569H, and A569P; such as selected from L407N, L407Y, V415T, V424I, V424Q, V426E, V426H, P447S, V455N, V456N, L463N, E495D, T506Y, T508R, F509M, F509W, A511F, D512Y, T515Q, L516T, L516W, S517W, R521W, I523D, I523E, I523G, I523K, I523R, K524L, Q526M, T527Y, H535P and K557G.

The variant may comprise a variant Domain III of an albumin, or fragment thereof, comprising amino acid substitutions at positions corresponding to the following positions of SEQ ID NO: 2: (a) residues 383 and 413; (b) residues 401 and 523; (c) residues 407 and 447; (d) residues 407 and 447 and 539; (e) residues 407 and 509; (f) residues 407 and 526; (g) residues 411 and 535; (h) residues 414 and 456; (i) residues 415 and 569; (j) residues 426 and 526; (k) residues 442 and 450 and 459; (l) residues 463 and 508; (m) residues 508 and 519 and 525; (n) residues 509 and 527; (o) residues 523 and 538; (p) residues 526 and 557; (q) residues 541 and 561; (r) residues 463 and 523; (s) residues 508 and 523; (t) residues 508 and 524; (u) residues 463, 508 and 523; (v) residues 463, 508 and 524; (w) residue 508, 523 and 524; (x) residue 463, 508, 523 and 524; (y) residues 463 and 524; (z) residues 523 and 524; and (aa) residues 463, 523, and 524, wherein the substitutions increase one or both of affinity for FcRn and serum half-life of the polypeptide, as disclosed in WO 2012/112188 (incorporated herein by reference). Suitable substitutions may be selected from (a) L463C, F, G, H, I, N, S or Q; (b) T508C, E, I, K, R or S; (c) I523A, C, D, E, F, G, H, I, K, L, M, N, P, Q, R, S, T, V, W or Y; (d) K524A, F, G, H, I, L, M, Q, T or V; (e) L463F or N; (f) T508R or S; (g) I523D, E, F, G, K or R; and (h) K524L.

The variant albumin may comprise one or more (e.g. several) alterations in the mature human albumin polypeptide sequence of SEQ ID NO: 2 selected from the group consisting of positions corresponding to positions V418, T420, V424, E505, V547, K573 in SEQ ID NO: 2; wherein the one or more (several) alterations causes the conjugation-competent polypeptides to have (i) an altered plasma half-life and/or (ii) an altered binding affinity to FcRn.

The variant albumin may comprise one or more (e.g. several) alterations in the mature human albumin polypeptide sequence of SEQ ID NO: 2 selected from the group consisting of positions corresponding to positions V381, preferably V381N or Q; E383, preferably E383A, G, I, L, or V; N391, preferably N391A, G, I, L or V; Y401 preferably Y401D or E; K402, preferably K402A, G, I, L, or V; L407, preferably L407F, N, Q, W, or Y; Y411, preferably Y411Q, or N; K413, preferably K413C, S, or T; K414, preferably K414S or T; V415C, preferably V415C, S, or T; Q416, preferably Q416H or P; V424, preferably V424A, G, I, L, N, or Q; V426D, preferably V426D, E, H, or P; G434, preferably G434C, S, or T; E442, preferably E442K or R; R445, preferably R445F, W or Y; P447, preferably P447S or T; E450, preferably E450D or E; S454, preferably S454C, M or T; V455, preferably V455N or Q; V456, preferably V456N or Q; L457, preferably L457F, W or Y; Q459, preferably Q459K or R; L463, preferably L463N or Q; E495, preferably E495D; T506, preferably T506F, W or Y; T508, preferably T508K, R, or S; F509, preferably F509C, I, L, M, V, W or Y; A511, preferably A511F, W, or Y; D512, preferably D512F, W or Y; T515, preferably T515C, H, N, P, Q or S; L516, preferably L516F, S, T, W or Y; S517, preferably S517C, F, M, T, W or Y; K519, preferably K519A, G, I, L, or V; R521, preferably R521F, W or Y; I523, preferably I523A, D, E, F, G, K, L, N, Q, R, V, W or Y; K524, preferably K524A, G, I, L or V; K525, preferably K525A, G, I, L or V; Q526, preferably Q526C, M, S, T or Y; T527, preferably T527F, W or Y; E531, preferably E531A, G, I, L or V; H535, preferably H535D, E or P; K538, preferably K538F, W or Y; A539, preferably A539I, L or V; K541, preferably K541F, W or Y; K557, preferably K557A, G, I, L or V; A561, preferably A561F, W or Y; T566, preferably T566F, W or Y; A569, preferably A569H or P in SEQ ID NO: 2; wherein the one or more (e.g. several) alterations causes the conjugation-competent polypeptides to have (i) an altered plasma half-life and/or (ii) an altered binding affinity to FcRn.

The variant albumin may comprise one or more (e.g. several) alterations in the mature human albumin polypeptide sequence of SEQ ID NO: 2 selected from the group consisting of positions corresponding to positions V547, preferably V457A; K573, preferably K573P or Y; I523, preferably I523A or G, T527, preferably T527M, K500, preferably K500A; or E505, preferably E505Q in SEQ ID NO: 2; wherein the one or more (e.g. several) alterations causes the conjugation-competent polypeptides to have (i) an altered plasma half-life and/or (ii) an altered binding affinity to FcRn.

The variant albumin may comprise one or more (e.g. several) alterations in the mature human albumin polypeptide sequence of SEQ ID NO: 2 selected from the group consisting of positions corresponding to positions 573, 523, 527 or 505 of SEQ ID NO: 2, preferably K573Y; I523G; I523A; T527M; E505Q; or K573P, for example K573Y and I523G; K573Y, I523G and T527M; K573Y, E505Q and T527M; K573Y and T527M; K573P and I523G; K573P, I523G and T527M; K573P, E505Q and T527M; K573P and T527M; V547A; V547A and K573P; V547A, E505Q, K573P and T527M; or K500A and H510Q of SEQ ID NO: 2.

Other Modifications

The second aspect of the invention encompasses other modifications. For example, the polypeptide may or may not comprise at least one (e.g. several) mutation that reduces glycosylation.

Fusion Polypeptide

A third aspect of the invention provides a fusion polypeptide comprising a conjugation-competent polypeptide of either the first or the second aspect of the invention.

Polypeptides of the invention may be fused with a non-albumin polypeptide fusion partner. The fusion partner may in principle be any polypeptide but generally it is preferred that the fusion partner is a polypeptide having bioactive, therapeutic, prophylactic (including vaccine), diagnostic, imaging or other beneficial properties. Such properties may be referred to as 'pharmaceutically beneficial properties'. Fusion polypeptides comprising albumin or fragments thereof are known in the art. It has been found that such fusion polypeptides comprising albumin or a fragment thereof and a fusion partner polypeptide have a longer plasma half-life compared to the unfused fusion partner polypeptide alone.

One or more (e.g. several) bioactive, therapeutic, prophylactic (including vaccine), diagnostic, imaging or other beneficial polypeptides may be fused to the N-terminus, the C-terminus of albumin, inserted into a loop in the albumin structure or any combination thereof. It may or it may not comprise linker sequences separating the various components of the fusion polypeptide. By way of non-limiting examples, a fusion may comprise N'-partner-albumin-C', N'-albumin-partner-C', N'-albumin-partner-albumin-C', N'-partner-albumin-partner-C' where 'partner' is the fusion partner.

Teachings relating to fusions of albumin or a fragment thereof are known in the art and the skilled person will appreciate that such teachings can also be applied to the invention. WO 2001/79271A (particularly page 9 and/or Table 1), WO 2003/59934 (particularly Table 1), WO 03/060071 (particularly Table 1) and WO 01/079480 (particularly Table 1) (each incorporated herein by reference in their entirety) also contain examples of bioactive, therapeutic, prophylactic (including vaccine), diagnostic, imaging or other beneficial polypeptides that may be fused to albumin or fragments thereof, and these examples apply also to the invention.

An advantage of using a genetically or chemically fused albumin is that either or all of the molecules which contribute to the fusion may have improved properties relative to the unfused molecule(s) (Balan et al. (2006), Antivir Ther 11(1): 35-45). Albumins and albumin particles are also important for carrying and delivering drugs and prodrugs to their sites of action (Kratz, F. (2008), Journal of Controlled Release, 132 (3), p. 171-183). Fusion and particle technologies offer improved dosing regimens due to improved pharmacokinetic properties, such as half-life extension, and may improve bioavailability and protect the fused conjugation partner, for example bioactive molecule, radiopharmaceutical or imaging agent, from inactivation.

The polypeptide may also be fused to one or more (e.g. several) purification tags such as (Ala-Trp-Trp-Pro)$_n$, avidin/streptavidin/Strep-tag, FLAG™ peptide (DYKDDDDK), His-tag.

Further preferences for the third aspect of the invention include those of the first and second aspects of the invention. The skilled person understands that any aspect of the invention may be combined with another aspect or aspects of the invention and/or with one or more (e.g. several) of the preferences for the aspects of the invention and/or other disclosures made herein.

Polynucleotides

A fourth aspect of the invention provides a polynucleotide which encodes the polypeptide according to the first, second or third aspects of the invention.

The polynucleotide may be an isolated polynucleotide. The polynucleotide may be comprised in a vector (such as a plasmid) and/or in a host cell.

The polynucleotide may or may not be codon-optimised relative to the host from which it is to be expressed. SEQ ID NO: 1 provides the usual coding sequence of HSA (SEQ ID NO: 2). SEQ ID NO: 28 provides a coding sequence of HSA (SEQ ID NO: 1) which is codon-optimised for expression from *S. cerevisiae*. SEQ ID NO: 1 or SEQ ID NO: 28 may be mutated in order to provide a polynucleotide which encodes a polypeptide according to the invention. Preferably the polynucleotide is synthetic and/or recombinant. Preferably the polynucleotide is an isolated polynucleotide. The polynucleotide may encode an HSA with or without a leader sequence. For example, the polynucleotide may encode an HSA with the natural leader sequence of HSA (amino acids 1 to 24 of SEQ ID NO: 3) or an HSA with a fusion leader sequence (amino acids 1 to 24 of SEQ ID NO: 29).

The polypeptide may be provided as a nucleic acid construct comprising a polynucleotide encoding a polypeptide of the invention operably linked to one or more (e.g. several) control sequences that direct the expression of the coding sequence in a suitable host cell under conditions compatible with the control sequences.

A polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, which is recognized by a host cell for expression of the polynucleotide. The promoter sequence contains transcriptional control sequences that mediate the expression of the variant. The promoter may be any nucleic acid sequence that shows transcriptional activity in the host cell including mutant, truncated, and hybrid promoters, and may be obtained from genes encoding extracellular or intracellular polypeptides either homologous or heterologous to the host cell.

In a yeast host, useful promoters are obtained from the genes for *Saccharomyces cerevisiae* enolase (ENO-1), *Saccharomyces cerevisiae* protease A (PRA1), *Saccharomyces cerevisiae* protease B (PRB1), *Saccharomyces cerevisiae* translation elongation factor (TEF1), *Saccharomyces cerevisiae* translation elongation factor (TEF2), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae*

3-phosphoglycerate kinase. Other useful promoters for yeast host cells are described by Romanos et al., 1992, Yeast 8: 423-488.

The skilled person knows useful promoters for use in rice and mammalian cells, such as CHO or HEK. In a rice host, useful promoters are obtained from cauliflower mosaic virus 35S RNA gene (CaMV35S), maize alcohol dehydrogenase (Adh1) and alpha Amy3.

In a mammalian host cell, such as CHO or HEK, useful promoters are obtained from Cytomegalovirus (CMV) and CAG hybrid promoter (hybrid of CMV early enhancer element and chicken beta-actin promoter), Simian vacuolating virus 40 (SV40).

The control sequence may also be a suitable transcription terminator sequence, which is recognized by a host cell to terminate transcription. The terminator sequence is operably linked to the 3'-terminus of the polynucleotide encoding the variant. Any terminator that is functional in the host cell may be used.

Preferred terminators for yeast host cells are obtained from the genes for *Saccharomyces cerevisiae* enolase, *Saccharomyces cerevisiae* cytochrome C (CYC1), *Saccharomyces cerevisiae* alcohol dehydrogenase (ADH1) and *Saccharomyces cerevisiae* glyceraldehyde-3-phosphate dehydrogenase. Other useful terminators for yeast host cells are described by Romanos et al., 1992, supra. The skilled person knows useful terminators for use in rice and mammalian cells, such as CHO or HEK. For example, in a rice host, preferred terminators are obtained from *Agrobacterium tumefaciens* nopaline synthase (Nos) and cauliflower mosaic virus 35S RNA gene (CaMV35S).

The control sequence may also be a suitable leader sequence, a nontranslated region of an mRNA that is important for translation by the host cell. The leader sequence is operably linked to the 5'-terminus of the polynucleotide encoding the variant. Any leader sequence that is functional in the host cell may be used.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding region naturally linked in translation reading frame with the segment of the coding region that encodes the variant. Alternatively, the 5'-end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the variant. However, any signal peptide coding region that directs the expressed variant into the secretory pathway of a host cell may be used.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra. The skilled person knows useful signal peptides for use in rice and mammalian cells, such as CHO or HEK.

Where both signal peptide and propeptide regions are present at the N-terminus of a variant, the propeptide region is positioned next to the N-terminus of the variant and the signal peptide region is positioned next to the N-terminus of the propeptide region.

Plasmids

A fifth aspect of the invention provides a plasmid comprising the polynucleotide of the fourth aspect of the invention. The plasmid may be a 2 micron based plasmid such as those described in WO 2005/061719, WO 2005/061718 and WO 2006/067511 (all incorporated herein by reference). The plasmid may exhibit enhanced chaperone activity, for example through over expression of a chaperone, particularly PDI. Preferred helper proteins include PDI1, AHA1, ATP11, CCT2, CCT3, CCT4, CCT5, CCT6, CCT7, CCT8, CNS1, CPR3, CPR6, DER1, DER3, DOA4, ERO1, EUG1, ERV2, EPS1, FKB2, FMO1, HCH1, HRD3, HSP10, HSP12, HSP104, HSP26, HSP30, HSP42, HSP60, HSP78, HSP82, KAR2, JEM1, MDJ1, MDJ2, MPD1, MPD2, PDI1, PFD1, ABC1, APJ1, ATP11, ATP12, BTT1, CDC37, CPR7, HSC82, KAR2, LHS1, MGE1, MRS11, NOB1, ECM10, SCJ1, SSA1, SSA2, SSA3, SSA4, SSB1, SSB2, SSC1, SSE2, SIL1, SLS1, ORM1, ORM2, PER1, PTC2, PSE1, UBC7, UBI4 and HAC1 or a truncated intronless HAC1 (Valkonen et al. 2003, Applied Environ. Micro., 69, 2065). Such helper proteins are disclosed in WO 2005/061718, WO 2006/067511 and WO 2006/136831 (all incorporated herein by reference).

Host Cells

A sixth aspect of the invention provides an expression system such as a host cell comprising a polynucleotide according to the fourth aspect of the invention and/or a plasmid of the fifth aspect of the invention. Preferably the host cell is a mammalian cell such as a human or bovine cell, or a fungal cell such as a yeast cell. Alternatively, the host cell may be a bacterial cell such as a *Bacillus* or *Escherichia coli* or a viral cell such as Baculovirus or a plant cell such as a rice e.g. *Oryza sativa*. Most preferably, the cell is a yeast cell such as a *Saccharomyces* (e.g. *S. cerevisiae*), a *Pichia* or an *Aspergillus* cell.

Conjugates

A seventh aspect of the invention provides a conjugate which comprises a conjugation partner, such as a bioactive compound, radiopharmaceutical or imaging agent, and a polypeptide according to the first, second or third aspect of the invention, wherein the conjugation partner is linked to the polypeptide through a conjugation-competent cysteine residue of the polypeptide. The conjugation partner may be a bioactive, therapeutic, diagnostic or imaging compound such as those mentioned herein. The conjugate may comprise 2 or more, (several, for example 2, 3, 4, 5, 6, 7, 8, 9 or 10), conjugation partners which may each be different and/or may be multiple copies of the same compound. Preferably, each conjugation partner is linked to the polypeptide through a conjugation-competent cysteine residue of the polypeptide, however conjugation partners may be linked by other means for example by a genetic fusion or covalent bonds to non-cysteine amino acids such as lysine.

A related aspect provides a use of a polypeptide according to the invention for the production of a thio-albumin-conjugate.

Conjugation Partner

The term 'conjugation partner' includes bioactive agents, imaging agents, diagnostic agents, contrast agents, radiopharmaceuticals and therapeutic compounds such as chemotherapeutic drugs and radiopharmaceuticals. A thio-albumin of the invention may be conjugated to one or more (e.g. several) conjugation partners.

Imaging Agents, Diagnostic Compounds, Contrast Agents and Therapeutic Compounds

The use of diagnostic agents, imaging agents and biological "contrast" agents are well known to the art. A diagnostic agent is any pharmaceutical product used as part of a diagnostic test (i.e. together with the equipment and procedures that are needed to assess the test result). The diagnostic agent may be used in vivo, ex vivo or in vitro.

The ability of albumin to accumulate in damaged muscle fibres of dystrophic muscle has been well described. For example, a Gadolinium-DTPA-albumin conjugate may be used as a combined diagnostic and therapeutic tool to visualize and monitor, for example, dystrophic muscle by magnetic resonance imaging (MRI) and for the delivery of putative therapeutics bound to albumin for effective targeting to dystrophic muscle (Amthor et al. (2004), Neuromuscular Disorders 14912: 791-796). Malignant tumours often show an increased uptake and metabolism of albumin. The use of gadolinium-albumin conjugate has also been described for improved imaging of malignant tumours and to determine by MRI tumours sensitive to a therapy with drug-conjugated albumin (Kiessling et al. (2002), Investigative Radiology 37(4): 93-198).

Current imaging agents often degrade quickly whilst longer-lasting agents are often toxic. The use of albumin conjugates may be especially useful to increase the half-life of imaging agents and would therefore permit imaging over an extended period of time. WO 2005/082423 (incorporated herein by reference) describes the use of serum albumin conjugated to fluorescent substances for imaging.

A thio-albumin of this invention may be conjugated to two or more (several) molecules selected from bioactive, imaging agents, diagnostic agents, therapeutic compounds and contrast agents.

Tumours (and muscle degeneration) show enhanced uptake of albumin (EPR: Enhanced Permeation and Retention). Albumin conjugates may be used for enhanced imaging, and also to assess whether tumours (or other tissues and organs) would be suitable for albumin conjugated drugs.

Bioactive Compounds

The bioactive compound may be a therapeutic or diagnostic compound. The therapeutic compound may be a chemotherapy drug for use in cancer chemotherapy. It may be cytostatic or cytotoxic; it may be a tumor-inhibiting agent.

The bioactive compound may already contain a free thiol group, e.g. a polypeptide containing a Cysteine residue with a free thiol group. Alternatively, the bioactive compound may be modified so as to contain a free thiol group. Thus, the amino acid sequence of a polypeptide may be altered so as to include a Cysteine residue with a free thiol group, or the bioactive compound may be chemically derivatized to include a free thiol group.

The bioactive compound may be a polypeptide (protein), particularly a recombinant protein pharmaceutical. It may be a chemotherapy or radiotherapy drug used to treat cancers and other related diseases.

The free thiol containing albumin mutein of the invention (thio-albumin) can be conjugated via the free thiol group, or groups if the albumin mutein of the invention contains more than one free thiol, to at least one (e.g. several) bioactive compound by methods know to the art. The bioactive compound includes but is not limited to, peptides, polypeptides or proteins (either natural, recombinant, or synthetic) (Debinski, (2002) Cancer Investigation 20, 801-809, O'Keefe and Draper et al., (1985) JBC 260, 932-937, Xia et al., (2000) J. Pharmacology Experimental Therapeutics 295, 594-600, Kavimandan et al., (2006), Bioconjugate Chem. 17, 1376-1384, Humphries, et al., (1994) J. Tissue Culture Methods 16, 239-242, Wenning et al., (1998) Biotech. Bioeng. 57, 484-496, Yazdi and Murphy, (1994), Cancer Research 54, 6387-6394, Weaver and Laske (2003) J. Neuro-Oncology 65, 3-13, Widera et al., (2003) Pharmaceutical Research 20, 1231-1238, Daniels, T. R. et al. (2006) Clinical Immunology 121, 159-176 and the references included therein); therapeutic and diagnostic drugs or compounds (Mishra et al., (2006) J. Drug Targeting 14, 45-53, Lim and Shen, (2004) Pharmaceutical Research 21, 1985-1992, Fritzer et al., (1996) Biochemical Pharmacology 51, 489-493, Lubgan and Jozwiak (2002) Cell. Mol. Biol. Lett. 7, 98, Daniels, T. R. et al. (2006) Clinical Immunology 121, 159-176 and the references included therein); high molecular weight complexes including but not limited to liposomes, viruses and nanoparticles (Mishra et al., (2006) J. Drug Targeting 14, 45-53, Daniels, T. R. et al. (2006) Clinical Immunology 121, 159-176 and the references included therein); nucleic acids and radionuclides, including DNA, RNA (including siRNA) and their analogs (Lee et al., (2005), Arch. Pharm. Res. 28, 722-729, Huang et al., (2007) FASEB J. 21, 1117-1125, Daniels, T. R. et al. (2006) Clinical Immunology 121, 159-176 and the references included therein) and devices (Humphries, et al., (1994) J. Tissue Culture Methods 16, 239-242 and the references included therein). Additionally the entity can itself be modified by methods known to the art.

Therapeutic Compounds

Examples of therapeutic compounds include: 4-1BB ligand, 5-helix, A human C-C chemokine, A human L105 chemokine, A human L105 chemokine designated huL105_3, A monokine induced by gamma-interferon (MIG), A partial CXCR4B protein, A platelet basic protein (PBP), α1-antitrypsin, ACRP-30 Homologue, Complement Component C1q C, Adenoid-expressed chemokine (ADEC), aFGF, FGF-1, AGF, AGF Protein, albumin, an etoposide, angiostatin, Anthrax vaccine, Antibodies specific for collapsin, antistasin, Anti-TGF beta family antibodies, antithrombin III, APM-1, ACRP-30, Famoxin, apo-lipoprotein species, Arylsulfatase B, b57 Protein, BCMA, Beta-thromboglobulin protein (beta-TG), bFGF, FGF2, Blood coagulation factors, BMP Processing Enzyme Furin, BMP-10, BMP-12, BMP-15, BMP-17, BMP-18, BMP-2B, BMP-4, BMP-5, BMP-6, BMP-9, Bone Morphogenic Protein-2, calcitonin, Calpain-10a, Calpain-10b, Calpain-10c, Cancer Vaccine, Carboxypeptidase, C-C chemokine, MCP2, CCR5 variant, CCR7, CCR7, CD11a Mab, CD137, 4-1BB Receptor Protein, CD20 Mab, CD27, CD27L, CD30, CD30 ligand, CD33 immunotoxin, CD40, CD40L, CD52 Mab, Cerebus Protein, Chemokine Eotaxin, Chemokine hIL-8, Chemokine hMCP1, Chemokine hMCP1a, Chemokine hMCP1b, Chemokine hMCP2, Chemokine hMCP3, Chemokine hSDF1b, Chemokine MCP-4, chemokine TECK and TECK variant, Chemokine-like protein IL-8M1 Full-Length and Mature, Chemokine-like protein IL-8M10 Full-Length and Mature, Chemokine-like protein IL-8M3, Chemokine-like protein IL-8M8 Full-Length and Mature, Chemokine-like protein IL-8M9 Full-Length and Mature, Chemokine-like protein PF4-414 Full-Length and Mature, Chemokine-like protein PF4-426 Full-Length and Mature, Chemokine-like protein PF4-M2 Full-Length and Mature, Cholera vaccine, Chondromodulin-like protein, c-kit ligand, SCF, Mast cell growth factor, MGF, Fibrosarcoma-derived stem cell factor, CNTF and fragment thereof (such as CNTFAx15'(Axokine™)), coagulation factors in both pre and active forms, collagens, Complement C5 Mab, Connective tissue activating protein-III, CTAA16.88 Mab, CTAP-III, CTLA4-Ig, CTLA-8, CXCR3, CXC chemokine receptor 3, cyanovirin-N, Darbepoetin, designated exodus, designated huL105_7, DIL-40, Dnase, EDAR, EGF Receptor Mab, ENA-78, Endostatin, Eotaxin, Epithelial neutrophil activating protein-78, EPO receptor, EPOR, erythropoietin (EPO) and EPO mimics, Eutropin, Exodus protein, Factor IX, Factor VII, Factor VIII, Factor X and Factor XIII, FAS Ligand Inhibitory Protein (DcR3), FasL, FGF, FGF-12, Fibroblast growth factor homologous factor-1, FGF-15, FGF-16, FGF-18, FGF-3, INT-2, FGF-4, gelonin, HST-1, HBGF-4, FGF-5, FGF-6, Heparin binding secreted transforming factor-2, FGF-8, FGF-9, Glia activating factor, fibrinogen, flt-1, flt-3 ligand, Follicle stimulating hormone Alpha subunit, Follicle stimulating hormone Beta subunit, Follitropin, Fractalkine, fragment. myofibrillar protein Troponin I, FSH, Galactosidase, Galectin-4, G-CSF, GDF-1, Gene therapy, Glioma-derived growth factor, glucagon, glucagon-like peptides, Glucocerebrosidase, glucose oxidase, Glucosidase, Glycodelin-A, Progesterone-associated endometrial protein, GM-CSF, gonadotropin, Granulocyte chemotactic protein-2 (GCP-2), Granulocyte-macrophage colony stimulating factor, growth hormone, Growth related oncogene-alpha (GRO-alpha), Growth related oncogene-beta (GRO-beta), Growth related oncogene-gamma (GRO-gamma), hAPO-4, TROY, hCG, Hepatitus B surface Antigen, Hepatitus B Vaccine, HER2 Receptor Mab, hirudin, HIV gp120, HIV gp41, HIV Inhibitor Peptide, HIV Inhibitor Peptide, HIV Inhibitor Peptide, HIV protease inhibiting peptides, HIV-1 protease inhibitors, HPV vaccine, Human 6CKine protein, Human Act-2 protein, Human adipogenesis inhibitory factor, human B cell stimulating factor-2 receptor, Human beta-chemokine H1305 (MCP-2), Human C-C chemokine DGWCC, Human CC chemokine ELC protein, Human CC type chemokine interleukin C, Human CCC3 protein, Human CCF18 chemokine, Human CC-type chemokine protein designated SLC (secondary lymphoid chemokine), Human chemokine beta-8 short forms, Human chemokine C10, Human chemokine CC-2, Human chemokine CC-3, Human chemokine CCR-2, Human chemokine Ckbeta-7, Human chemokine ENA-78, Human chemokine eotaxin, Human chemokine GRO alpha, Human chemokine GROalpha, Human chemokine GRObeta, Human chemokine HCC-1, Human chemokine HCC-1, Human chemokine I-309, Human chemokine IP-10, Human chemokine L105_3, Human chemokine L105_7, Human chemokine MIG, Human chemokine MIG-beta protein, Human chemokine MIP-1alpha, Human chemokine MIP1beta, Human chemokine MIP-3alpha, Human chemokine MIP-3beta, Human chemokine PF4, Human chemokine protein 331D5, Human chemokine protein 61164, Human chemokine receptor CXCR3, Human chemokine SDF1alpha, Human chemokine SDF1beta, Human chemokine ZSIG-35, Human Chr19Kine protein, Human CKbeta-9, Human CX3C 111 amino acid chemokine, Human DNAX interleukin-40, Human DVic-1 C-C chemokine, Human EDIRF I protein sequence, Human EDIRF II protein sequence, Human eosinocyte CC type chemokine eotaxin, Human eosinophil-expressed chemokine (EEC), Human fast twitch skeletal muscle troponin C, Human fast twitch skeletal muscle troponin I, Human fast twitch skeletal muscle Troponin subunit C, Human fast twitch skeletal muscle Troponin subunit I Protein, Human fast twitch skeletal muscle Troponin subunit T, Human fast twitch skeletal muscle troponin T, Human foetal spleen expressed chemokine, FSEC, Human GM-CSF receptor, Human gro-alpha chemokine, Human gro-beta chemokine, Human gro-gamma chemokine, Human IL-16 protein, Human IL-1RD10 protein sequence, Human IL-1RD9, Human IL-5 receptor alpha chain, Human IL-6 receptor, Human IL-8 receptor protein hIL8RA, Human IL-8 receptor protein hIL8RB, Human IL-9 receptor protein, Human IL-9 receptor protein variant #3, Human IL-9 receptor protein variant fragment, Human IL-9 receptor protein variant fragment #3, Human interleukin 1 delta, Human interleukin 10, Human interleukin 18, Human interleukin 18 derivatives, Human interleukin-1 beta precursor, Human interleukin-1 beta precursor, Human interleukin-1 receptor accessory protein, Human interleukin-1 receptor antagonist beta, Human interleukin-1 type-3 receptor, Human interleukin-10 (precursor), Human interleukin-11 receptor, Human interleukin-12 40 kD subunit, Human interleukin-12 beta-1 receptor, Human interleukin-12 beta-2 receptor, Human interleukin-12 p35 protein, Human interleukin-12 p40 protein, Human interleukin-12 receptor, Human interleukin-13 alpha receptor, Human interleukin-13 beta receptor, Human interleukin-15, Human interleukin-15 receptor from clone P1, Human interleukin-17 receptor, Human interleukin-18 protein (IL-18), Human interleukin-3, human interleukin-3 receptor, Human interleukin-3 variant, Human interleukin-4 receptor, Human interleukin-5, Human interleukin-6, Human interleukin-7, Human interleukin-7, Human interleukin-8 (IL-8), Human intracellular IL-1 receptor antagonist, Human IP-10 and HIV-1 gp120 hypervariable region fusion protein, Human IP-10 and human Muc-1 core epitope (VNT) fusion protein, human liver and activation regulated chemokine (LARC), Human Lkn-1 Full-Length and Mature protein, Human mammary associated chemokine (MACK) protein Full-Length and Mature, Human mature chemokine Ckbeta-7, Human mature gro-alpha, Human mature gro-gamma polypeptide used to treat sepsis, Human MCP-3 and human Muc-1 core epitope (VNT) fusion protein, Human MI10 protein, Human MI1A protein, Human monocyte chemoattractant factor hMCP-1, Human monocyte chemoattractant factor hMCP-3, Human monocyte chemotactic proprotein (MCPP) sequence, Human neurotactin chemokine like domain, Human non-ELR CXC chemokine H174, Human non-ELR CXC chemokine IP10, Human non-ELR CXC chemokine Mig, Human PAI-1 mutants, Human protein with IL-16 activity, Human protein with IL-16 activity, Human secondary lymphoid chemokine (SLC), Human SISD protein, Human STCP-1, Human stromal cell-derived chemokine, SDF-1, Human T cell mixed lymphocyte reaction expressed chemokine (TMEC), Human thymus and activation regulated cytokine (TARC), Human thymus expressed, Human TNF-alpha, Human TNF-beta (LT-alpha), Human type CC chemokine eotaxin 3 protein sequence, Human type II interleukin-1 receptor, Human wild-type interleukin-4 (hIL-4) protein, Human ZCHEMO-8 protein, Humanized Anti-VEGF Antibodies, and fragments thereof, Humanized Anti-VEGF Antibodies, and fragments thereof, Hyaluronidase, ICE 10 kD subunit, ICE 20 kD subunit, ICE 22 kD subunit, Iduronate-2-sulfatase, Iduronidase, IL-1 alpha, IL-1 beta, IL-1 inhibitor (IL-1i), IL-1 mature, IL-10 receptor, IL-11, IL-11, IL-12 p40 subunit, IL-13, IL-14, IL-15, IL-15 receptor, IL-17, IL-17 receptor, IL-19, IL-1i fragments, IL1-receptor antagonist, IL-21 (TIF), IL-3 containing fusion protein, IL-3 mutant proteins, IL-3 variants, IL-4, IL-4 muteins, IL-4 mutein Y124G, IL-4 mutein Y124X, IL-5, IL-5 muteins, Il-5 receptor, IL-6, 11-6 receptor, IL-7 receptor clone, IL-8 receptor, IL-9 mature protein variant (Met117 version), immunoglobulins or immunoglobulin-based molecules or fragment of either (e.g. a Small Modular ImmunoPharmaceutical™ ("SMIP") or dAb, Fab' fragments, F(ab')2, scAb, scFv or scFv fragment), including but not limited to plasminogen, Influenza Vaccine, Inhibin alpha, Inhibin beta, insulin, insulin-like growth factor, Integrin Mab, inter-alpha trypsin inhibitor, inter-alpha trypsin inhibitor, Interferon gamma-inducible protein (IP-10), interferons (such as interferon alpha species and sub-species, interferon beta species and sub-species, interferon gamma species and sub-species), interleukin 6, interleukin 8 (IL-8) receptor, interleukin 8 receptor B, interleukin-1alpha, interleukin-2 receptor associated protein p43, interleukin-3, interleukin-4 muteins, interleukin-8 (IL-8) protein, interleukin-9, interleukin-9 (IL-9) mature protein (Thr117 version), interleukins (such as IL10, IL11 and IL2), Japanese encephalitis vaccine, Kalikrein Inhibitor, Keratinocyte growth factor, Kunitz domain protein (such as aprotinin, amyloid precursor protein and those described in WO 03/066824, with or without albumin fusions), LACI, lactoferrin, Latent TGF-beta binding protein II, leptin, Liver expressed chemokine-1 (LVEC-1), Liver expressed chemokine-2 (LVEC-2), LT-alpha, LT-beta, Luteinization Hormone, Lyme Vaccine, Lymphotactin, Macrophage derived chemokine analogue MDC (n+1), Macrophage derived chemokine analogue MDC-eyfy, Macrophage derived chemokine analogue MDC-yl, Macrophage-derived chemokine (MDC), Maspin, Protease Inhibitor 5, MCP-1 receptor, MCP-1a, MCP-1b, MCP-3, MCP-4 receptor, M-CSF, Melanoma inhibiting protein, Membrane-bound proteins, Met117 human interleukin 9, MIP-3 alpha, MIP-3 beta, MIP-Gamma, MIRAP, Modified Rantes, monoclonal antibody, MP52, Mutant interleukin 6 S176R, myofibrillar contractile protein Troponin I, Natriuretic Peptide, Nerve Growth Factor-beta, Nerve Growth Factor-beta2, Neuropilin-1, Neuropilin-2, Neurotactin, Neurotrophin-3, Neurotrophin-4, Neurotrophin-4a, Neurotrophin-4b, Neurotrophin-4c, Neurotrophin-4d, Neutrophil activating peptide-2 (NAP-2), NOGO-66 Receptor, NOGO-A, NOGO-B, NOGO-C, Novel beta-chemokine designated PTEC, N-terminal modified chemokine GroHEK/hSDF-1alpha, N-terminal modified chemokine GroHEK/hSDF-1beta, N-terminal modified chemokine met-hSDF-1 alpha, N-terminal modified chemokine met-hSDF-1 beta, OPGL, Osteogenic Protein-1 (OP-1), BMP-7, Osteogenic Protein-2, OX40, ACT-4, OX40L, Oxytocin (Neurophysin I), parathyroid hormone, Patched, Patched-2, PDGF-D, Pertussis toxoid, Pituitary expressed chemokine (PGEC), Placental Growth Factor, Placental Growth Factor-2, Plasminogen Activator Inhibitor-1 (PAI-1), Plasminogen Activator Inhibitor-2 (PAI-2), Platelet derived growth factor, Platelet derived growth factor Bv-sis, Platelet derived growth factor precursor A, Platelet derived growth factor precursor B, Platelet Mab, platelet-derived endothelial cell growth factor (PD-ECGF), Platelet-Derived Growth Factor A chain, Platelet-Derived Growth Factor B chain, polypeptide used to treat sepsis, Preproapolipoprotein "milano" variant, Preproapolipoprotein "paris" variant, pre-thrombin, Primate CC chemokine "ILINCK", Primate CXC chemokine "IBICK", proinsulin, Prolactin, Prolactin2, prosaptide, Protease inhibitor peptides, Protein C, Protein S, pro-thrombin, prourokinase, RANTES, RANTES 8-68, RANTES 9-68, RANTES peptide, RANTES receptor, Recombinant interleukin-16, Resistin, restrictocin, Retroviral protease inhibitors, ricin, Rotavirus Vaccine, RSV Mab, saporin, sarcin, Secreted and Transmembrane polypeptides, serum cholinesterase, serum protein (such as a blood clotting factor), Soluble BMP Receptor Kinase Protein-3, Soluble VEGF Receptor, Stem Cell Inhibitory Factor, Straphylococcus Vaccine, Stromal Derived Factor-1 alpha, Stromal Derived Factor-1 beta, Substance P (tachykinin), T1249 peptide, T20 peptide, T4 Endonuclease, TACI, Tarc, TGF-beta 1, TGF-beta 2, Thr117 human interleukin 9, thrombin, thrombopoietin, thrombopoietin derivative 1, thrombopoietin derivative 2, thrombopoietin derivative 3, thrombopoietin derivative 4, thrombopoietin derivative 5, thrombopoietin derivative 6, thrombopoietin derivative 7, Thymus expressed chemokine (TECK), Thyroid stimulating Hormone, tick anticoagulant peptide, Tim-1 protein, TNF-alpha precursor, TNF-R, TNF-RII, TNF p75 Receptor, Death Receptor, tissue plasminogen activator (tPA), transferrin, transforming growth factor beta, Troponin peptides, Truncated monocyte chemotactic protein 2 (6-76), Truncated RANTES protein (3-68), tumour necrosis factor, Urate Oxidase, urokinase, Vasopressin (Neurophysin II), VEGF R-3, flt-4, VEGF Receptor, KDR, flk-1, VEGF-110, VEGF-121, VEGF-138, VEGF-145, VEGF-162, VEGF-165, VEGF-182, VEGF-189, VEGF-206, VEGF-D, VEGF-E, VEGF-X, von Willebrand's factor, Wild type monocyte chemotactic protein 2, ZTGF-beta 9.

Chemotherapy Drugs

Examples of chemotherapy drugs include: 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bevacizumab, Bexarotene, BEXXAR®, Bicalutamide, BICNU, Blenoxane®, Bleomycin, Bortezomib, Busulfan, Busulfex®, C225, Calcium Leucovorin, Campath®, Camptosar® Camptothecin-11, Capecitabine, Carac™, Carboplatin, Carmustine, Carmustine Wafer, Casodex®, CC-5013, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-UR, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin diftitox, DepoCyt™, Dexamethasone, Dexamethasone acetate, Dexamethasone Sodium Phosphate, Dexasone, Dexrazoxane, DHAD, DIC, Diodex, Docetaxel, Doxil®, Doxorubicin, Doxorubicin liposomal, Droxia, DTIC, DTIC-Dome®, Duralone®, Efudex®, Eligard™, Ellence™, Eloxatin™, Elspar®, Emcyt®, Epirubicin, Epoetin alfa, Erbitux™, Erlotinib, *Erwinia* L-asparaginase, Estramustine, Ethyol, Etopophos®, Etoposide, Etoposide Phosphate, Eulexin®, Evista®, Exemestane, Fareston®, Faslodex®, Femara®, Filgrastim, Floxuridine, Fludara®, Fludarabine, Fluoroplex®, Fluorouracil, Fluoxymesterone, Flutamide, Folinic Acid, FUDR®, Fulvestrant, G-CSF, Gefitinib, Gemcitabine, Gemtuzumab ozogamicin, Gemzar®, Gleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), interleukin-2, interleukin-11, Intron A® (interferon alfa-2b), Iressa®, Irinotecan, Isotretinoin, Kidrolase®, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar® Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar® Temozolomide, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Tositumomab, Trastuzumab, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, Zometa®.

Radiopharmaceuticals

Examples of radiopharmaceuticals include: Carbon-11, Carbon-14, Chromium-51, Cobalt-57, Cobalt-58, Erbium-169, Fluorine-18, Gallium-67, Gold-198, Indium-111, Indium-113m, Iodine-123, Iodine-125, Iodine-131, Iron-59, Krypton-81m, Nitrogen-13, Oxygen-15, Phosphorous-32, Rhenium-186, Rubidium-82, Samarium-153, Selenium-75, Strontium-89, Technetium-99m, Thallium-201, Tritium, Xenon-127, Xenon-133, Yttrium-90.

Imaging Agents

Examples of imaging agents include: Gadolinium, magnetite, manganese, technetium, I125, I131, P32, Tl201, Iopamidol, PET-FDG.

Preparation of a Polynucleotide

An eighth aspect of the invention provides a method of producing a polynucleotide comprising:
(a) providing a nucleic acid molecule encoding a parent albumin or fragment thereof; and
(b) modifying the nucleic acid sequence of the nucleic acid molecule to encode a conjugation-competent polypeptide which is at least 60% identical to human albumin, particularly residues 1 to 585 of the mature human albumin polypeptide sequence of SEQ ID NO: 2, or a fragment thereof, wherein at least one (e.g. several) position equivalent to a position selected from K93, E294, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, E382, and L398, particularly from K93, E294, A226, E230, and I271, of SEQ ID NO: 2 comprises a conjugation-competent cysteine residue.

Suitably, modifying the nucleic acid sequence comprises introducing an alteration such that at least one (e.g. several) conjugation-competent cysteine as provided for in step (b) is introduced into the encoded polypeptide. Preferred alterations are as described in relation to the first and second aspects of the invention.

It is preferred that the parent albumin comprises or consists of:
(a) a polypeptide having at least 70% sequence identity to the mature polypeptide of SEQ ID NO: 2;
(b) a polypeptide encoded by a polynucleotide that hybridizes under low stringency conditions with (i) the mature polypeptide coding sequence of SEQ ID NO: 2, or (ii) the full-length complement of (i);
(c) a polypeptide encoded by a polynucleotide having at least 60% identity to the mature polypeptide coding sequence of SEQ ID NO: 2; and/or
(d) a fragment of the mature polypeptide of SEQ ID NO: 2.

Suitably, the parent albumin comprises or consists of the HSA polypeptide sequence of SEQ ID NO: 2 or a variant or fragment thereof.

The variant polynucleotides can be prepared by those skilled persons using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g. several) mutations (alterations) are created at one or more (e.g. several) defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests at the plasmid and the oligonucleotide is the same, permitting ligation of the plasmid and insert to one another. See, e.g. Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art, see, e.g. U.S. Patent Application Publication: 2004/0171154; Storici et al., 2001, Nature Biotechnol. 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g. Lowman et al., 1991, Biochemistry 30: 10832-10837; U.S. Pat. No. 5,223,409; WO 92/06204) and region-directed mutagenesis (Derbyshire et al., 1986, *Gene* 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide sub sequences may then be shuffled.

Method of Producing a Polypeptide

A ninth aspect of the invention provides a method of producing a polypeptide of the invention comprising:
  (a) culturing a host cell according to the invention under conditions that allow expression of the polypeptide; and
  (b) recovering the polypeptide from the host cell and/or from host cell growth medium.

The method may or may not further comprise determining the receptor binding capacity and/or the conjugation competence of the polypeptide and/or the tendency to exist as a monomer in solution, and optionally selecting a polypeptide which does or does not have a receptor binding capacity and/or conjugation competence and/or selected range of percentage monomer tendency.

The variants of the invention can be prepared using techniques well known to the skilled person. One convenient way is by cloning a nucleic acid molecule encoding a parent albumin or a fragment thereof and modifying the sequence of the nucleic acid molecule according to the method of the eighth aspect of the invention, preparing a suitable genetic construct where the modified nucleic acid molecule is placed in operative connection with suitable regulatory genetic elements, such as promoter, terminator, activation sites, ribosome binding sites etc., introducing the genetic construct into a suitable host organism, culturing the transformed host organism under conditions leading to expression of the variant and recovering the variant. All these techniques are known in the art and it is within the skills of the average practitioner to design a suitable method for preparing a particular variant according to the invention.

The variant polypeptide of the invention may also be connected to a signal sequence in order to have the variant polypeptide secreted into the growth medium during culturing of the transformed host organism. It is generally advantageous to have the variant polypeptide secreted into the growth medium in order to ease recovery and purification. The polypeptide may be prepared as a fusion polypeptide as described in relation to the third aspect of the invention. Techniques for preparing variant polypeptides have been disclosed in WO 2009/019314 (included by reference) and these techniques may also be applied to the invention.

Albumins have been successfully expressed as recombinant proteins in a range of hosts including fungi (including but not limited to *Aspergillus* (WO 06066595), *Kluyveromyces* (Fleer 1991, *Bio/technology* 9, 968-975), *Pichia* (Kobayashi 1998 Therapeutic Apheresis 2, 257-262) and *Saccharomyces* (Sleep 1990, *Bio/technology* 8, 42-46)), bacteria (Pandjaitab 2000, *J. Allergy Clin. Immunol.* 105, 279-285)), animals (Barash 1993, *Transgenic Research* 2, 266-276) and plants (including but not limited to potato and tobacco (Sijmons 1990, *Bio/technology* 8, 217 and Farran 2002, *Transgenic Research* 11, 337-346) and rice e.g. *Oryza sativa*) and mammalian cells such as CHO and HEK. The variant polypeptide of the invention is preferably produced recombinantly in a suitable host cell. In principle any host cell capable of producing a polypeptide in suitable amounts may be used and it is within the skills of the average practitioner to select a suitable host cell according to the invention. A preferred host organism is yeast, preferably selected among Saccharomycesae, more preferred *Saccharomyces cerevisiae*.

The variant polypeptides of the invention may be recovered and purified from the growth medium using a combination of known separation techniques such as filtration, centrifugation, chromatography, and affinity separation techniques etc. It is within the skills of the average practitioner to purify the variants of the invention using a particular combination of such known separation steps. As an example of purification techniques that may be applied to the variants of the invention can be mentioned the teaching of WO 00/44772.

In the method of the invention, the host cell may or may not exhibit enhanced chaperone activity. Accordingly, the present invention also provides a method for producing a polypeptide (or protein) of the invention, the method comprising: (a) providing a host cell of the invention comprising a polynucleotide encoding protein product of choice as defined above; and (b) growing the host cell (for example, culturing the host cell in a culture medium); thereby to produce a cell culture or recombinant organism comprising an increased level of the protein product of choice compared to the level of production of the protein product of choice achieved by growing (for example, culturing), under the same conditions, the same host cell that has not been genetically modified to cause over-expression of one or more (e.g. several) helper proteins.

The step of growing the host cell may or may not involve allowing a host cell derived from a multicellular organism to be regrown into a multicellular recombinant organism (such as a plant or animal) and, optionally, producing one or more (e.g. several) generations of progeny therefrom.

The thio-albumin may or may not be capable of being expressed at a level of at least 10, 20, 30, 40, 50, 60, 70, 80, 90 or 100% relative to the expression of an unmodified albumin (such as SEQ ID NO: 2) from a suitable expression system, such as yeast (e.g. *Saccharomyces*, e.g. *S. cerevisiae*) or an *Aspergillus*. Relative expression levels can be determined, for example, by expression of the protein followed by quantification by SDS-PAGE, HPLC or Western Blotting. Relative expression levels may be determined in at least 10 liter scale.

The method may or may not further comprise the step of purifying the thus expressed protein product of choice from the cultured host cell, recombinant organism or culture medium.

The production method may comprise linking a conjugation partner to the polypeptide of the invention through a conjugation competent cysteine residue of the polypeptide. Suitable conjugation methods and conjugation partners are described herein.

The thio-albumin or fusions of thio-albumin and another protein or proteins can be expressed as variants with reduced N-linked glycosylation. Accordingly, in case of HSA, it may be particularly advantageous to use a yeast deficient in one or more (e.g. several) protein mannosyl transferases involved in O-glycosylation of proteins, for instance by disruption of the gene coding sequence. Recombinantly expressed proteins can be subject to undesirable post-translational modifications by the producing host cell. The mannosylated albumin would be able to bind to the lectin Concanavalin A. The amount of mannosylated albumin produced by the yeast can be reduced by using a yeast strain deficient in one or more (e.g. several) of the PMT genes (WO 94/04687). The most convenient way of achieving this is to create a yeast which has a defect in its genome such that a reduced level of one of the Pmt proteins is produced. For example, there may or may not be a deletion, insertion or transposition in the coding sequence or the regulatory regions (or in another gene regulating the expression of one of the PMT genes) such that little or no Pmt protein is produced. Alternatively, the yeast could be transformed to produce an anti-Pmt agent, such as an anti-Pmt antibody. Alternatively, the yeast could be cultured in the presence of a compound that inhibits the activity of one of the PMT genes (Duffy et al, "Inhibition of protein mannosyltransferase 1 (PMT1) activity in the pathogenic yeast *Candida albicans*", International Conference on Molecular Mechanisms of Fungal Cell Wall Biogenesis, 26-31 Aug. 2001, Monte Verita, Switzerland, Poster Abstract P38). If a yeast other than *S. cerevisiae* is used, disruption of one or more (e.g. several) of the genes equivalent to the PMT genes of *S. cerevisiae* is also beneficial, e.g. in *Pichia pastoris* or *Kluyveromyces lactis*. The sequence of PMT1 (or any other PMT gene) isolated from *S. cerevisiae* may be used for the identification or disruption of genes encoding similar enzymatic activities in other fungal species. The cloning of the PMT1 homologue of *Kluyveromyces lactis* is described in WO 94/04687.

The variant polypeptides of the invention may be used for delivering a therapeutically beneficial compound (including prophylactically beneficial compound such as a vaccine) to an animal or a human individual in need thereof. Such therapeutically beneficial compounds include, but are not limited to, labels and readily detectable compounds for use in diagnostics, such as various imaging techniques; pharmaceutical active compounds such as drugs, or specifically binding moieties such as antibodies. The variants of the invention may even be connected to two or more (several) different therapeutically beneficial compounds, e.g. an antibody and a drug, which gives the combined molecule the ability to bind specifically to a desired target and thereby provide a high concentration of the connected drug at that particular target.

The method may further comprise the step of purifying the polypeptide recovered from the host cell and/or from the host cell growth medium. The purification step optionally comprises cell immobilisation, cell separation and/or cell breakage, but always comprises at least one (e.g. several) other purification step different from the step or steps of cell immobilisation, separation and/or breakage.

Thio-albumin of the invention may be purified from the culture medium by any technique that has been found to be useful for purifying such proteins. Similarly, cell separation techniques, such as centrifugation, filtration (e.g. cross-flow filtration, expanded bed chromatography and the like) are well known in the art. Likewise, methods of cell breakage, including beadmilling, sonication, enzymatic exposure and the like are well known in the art.

The "at least one (e.g. several) other purification step" may be any other step suitable for protein purification known in the art. For example purification techniques for the recovery of recombinantly expressed albumin have been disclosed in: WO 92/04367, removal of matrix-derived dye; EP 464590, removal of yeast-derived colorants; EP 319067, alkaline precipitation and subsequent application of the albumin to a lipophilic phase; and WO 96/37515, U.S. Pat. No. 5,728,553 and WO 00/44772, which describe complete purification processes; all of which are incorporated herein by reference. Suitable methods include ammonium sulphate or ethanol precipitation, acid or solvent extraction, anion or cation exchange chromatography, phosphocellulose chromatography, hydrophobic interaction chromatography, affinity chromatography, hydroxyapatite chromatography, lectin chromatography, concentration, dilution, pH adjustment, diafiltration, ultrafiltration, high performance liquid chromatography ("HPLC"), reverse phase HPLC, conductivity adjustment and the like.

The polypeptide may be purified to a commercially or industrially acceptable level of purity. By commercially or industrially acceptable level of purity, we include the provision of the thio-albumin and/or thio-albumin-conjugate in which other material (for example, one or more (e.g. several) contaminants) are present at a level of less than 50%, 40%, 30%, 20%, 10%, 5%, 4%, 3%, 2%, 1%, 0.5%, 0.1%, 0.01%, 0.001%, 0.0001%, 0.00001%, or 0.000001% and, most preferably at a level of 0%.

A commercially or industrially acceptable level of purity may be obtained by a relatively crude purification method by which the protein product of choice is put into a form suitable for its intended purpose. A protein preparation that has been purified to a commercially or industrially acceptable level of purity may, in addition to the protein product of choice, also comprise, for example, cell culture components such as host cells or debris derived therefrom. Alternatively, high molecular weight components (such as host cells or debris derived therefrom) may or may not be removed (such as by filtration or centrifugation) to obtain a composition comprising the protein product of choice and, optionally, a functionally acceptable level of low molecular weight contaminants derived from the cell culture process.

The protein may or may not be purified to achieve a pharmaceutically acceptable level of purity. A protein has a pharmaceutically acceptable level of purity if it is essentially pyrogen free and can be used for its intended purpose and hence be administered in a pharmaceutically efficacious amount without causing medical effects not associated with the activity of the protein.

The thio-albumin and/or thio-albumin-conjugate may be provided at a concentration of at least $10^{-4}$ g·L$^{-1}$, $10^{-3}$ g·L$^{-1}$, 0.01 g·L$^{-1}$, 0.02 g·L$^{-1}$, 0.03 g·L$^{-1}$, 0.04 g·L$^{-1}$, 0.05 g·L$^{-1}$, 0.06 g·L$^{-1}$, 0.07 g·L$^{-1}$, 0.08 g·L$^{-1}$, 0.09 g·L$^{-1}$, 0.1 g·L$^{-1}$, 0.2 g·L$^{-1}$, 0.3 g·L$^{-1}$, 0.4 g·L$^{-1}$, 0.5 g·L$^{-1}$, 0.6 g·L$^{-1}$, 0.7 g·L$^{-1}$, 0.8 g·L$^{-1}$, 0.9 g·L$^{-1}$, 1 g·L$^{-1}$, 2 g·L$^{-1}$, 3 g·L$^{-1}$, 4 g·L$^{-1}$, 5 g·L$^{-1}$, 6 g·L$^{-1}$, 7 g·L$^{-1}$, 8 g·L$^{-1}$, 9 g·L$^{-1}$, 10 g·L$^{-1}$, 15 g·L$^{-1}$, 20 g·L$^{-1}$, 25 g·L$^{-1}$, 30 g·L$^{-1}$, 40 g·L$^{-1}$, 50 g·L$^{-1}$, 60 g·L$^{-1}$, 70 g·L$^{-1}$, 80 g·L$^{-1}$, 90 g·L$^{-1}$, 100 g·L$^{-1}$, 150 g·L$^{-1}$, 200 g·L$^{-1}$, 250 g·L$^{-1}$, 300 g·L$^{-1}$, 350 g·L$^{-1}$, 400 g·L$^{-1}$, 500 g·L$^{-1}$, 600 g·L$^{-1}$, 700 g·L$^{-1}$, 800 g·L$^{-1}$, 900 g·L 1, 1000 g·L$^{-1}$.

A method of the present invention may or may not further comprise the step of formulating the purified protein product of choice with a carrier or diluent and optionally presenting the thus formulated protein in a unit dosage form.

Although it is possible for a therapeutically useful protein obtained by a process of the invention to be administered alone, it is preferable to present it as a pharmaceutical formulation, together with one or more (e.g. several) acceptable carriers or diluents. The carrier(s) or diluent(s) must be "acceptable" in the sense of being compatible with the desired protein. Typically, the carriers or diluents will be water or saline which will be sterile and pyrogen free. Alternatively, a method of the present invention may or may not further comprise the step of lyophilising the thus purified protein product of choice.

The thio-albumin may be formulated by strategies given in "Protein Formulation and Delivery", E. J. McNally (Ed.), published by Marcel Dekker Inc. New York 2000 and "Rational Design of Stable Protein Formulations—Theory and Practice"; J. F. Carpenter and M. C. Manning (Ed.) Pharmaceutical Biotechnology Vol 13. Kluwer Academic/Plenum Publishers, New York 2002, Yazdi and Murphy, (1994), Cancer Research 54, 6387-6394, Widera et al., (2003) Pharmaceutical Research 20, 1231-1238; Lee et al., (2005), Arch. Pharm. Res. 28, 722-729. Examples of formulation methods are as follows:

Method #1: Following purification the free thiol containing albumin mutein of the invention or the conjugate can be stored at 4° C., −20° C. or −80° C. in 0.01 M-0.1 M phosphate buffered saline (pH 7.0-8.0) containing 0.01 M-0.25 M NaCl.

Method #2: Following purification the free thiol containing albumin mutein of the invention or the conjugate can be stored at 4° C., −20° C. or −80° C. in 0.01 M-0.1 M phosphate buffered saline (pH 7.0-8.0) containing 0.01 M-0.25 M NaCl and containing $10^{-20}$ mg/L Polysorbate 80.

Method #3: Following purification the free thiol containing albumin mutein of the invention or the conjugate can be stored at 4° C., −20° C. or −80° C. in 0.01 M-0.25 M NaCl (pH 7.0-8.0).

Method #4: Following purification the free thiol containing albumin mutein of the invention or the conjugate can be stored at 4° C., −20° C. or −80° C. in 0.01 M-0.25 M NaCl (pH 7.0-8.0) containing $10^{-20}$ mg/L Polysorbate 80.

Freeze-Dried Formulations

Method #5: Following purification the free thiol containing albumin mutein of the invention or the conjugate can be dialysed against water, freeze dried and stored at 4° C., −20° C. or −80° C.

Method #6: Following purification the free thiol containing albumin mutein of the invention or the conjugate can be dialysed against 0.01 M-0.25 M NaCl (pH 7.0-8.0), freeze dried and stored at 4° C., −20° C. or −80° C.

Conjugation Methods

A tenth aspect of the invention provides a method of producing the conjugate of the seventh aspect of the invention, the method comprising linking a polypeptide of the first, second or third aspect of the invention, or produced by the method of the ninth aspect of the invention, to a bioactive compound through a conjugation-competent cysteine residue of the polypeptide. The linking may be carried out using a linker.

The albumin mutein (thio-albumin) of the invention can be covalently linked to one or more (e.g. several) conjugation partners such as bioactive compounds by methods known in the art (for example those provided by Pierce, Thermo Fisher Scientific, Rockford, IL, USA; tools.lifetechnologies.com/content/sfs/brochures/1602163-Crosslinking-Reagents-Handbook.pdf). These include, but are not limited to incorporating or engineering a thiol reactive group into or onto the conjugation partner, for example by incorporating or engineering another free thiol present on the conjugation partner; or by incorporating or engineering a pyridyl disulphide group on the conjugation partner; or by incorporating or engineering an haloacetyl group on the bioactive compound or by incorporating or engineering a maleimide group on the conjugation partner, or by incorporating or engineering a thiosulfonate group on the conjugation partner, or by incorporating or engineering vinylsulfone group on the conjugation partner. For example, but not limited to, N-ethylmaleimide (NEM, Pierce), 2-amino-2'-aminoethanethiolsulfonate (Pierce), N-beta-maleimidoprpionic acid (BMPA Pierce), methyl methane thiosulfonate (MMTS, Pierce), fluorescein-5-maleimide (Pierce), 5-iodoacetamido-fluorescein (5-IAF, Pierce) or N-[6-7-amino-4-methylcoumarin-3-acetamido) hexyl]-3'-[2'-pyridyldithio] propionamide (AMCA-HPDP, Pierce).

If the conjugation partner contains at least one (e.g. several) thiol group, then the conjugation partner may be cross-linked to the albumin mutein of the invention by methods known to the art such as, but not limited to, oxidation or by the use of cross-linking reagents such as, but not limited to, 1,4-Bis-maleimidibutane (BMB, Pierce); 1,4-Bis-maleimidyl-2,3-dihydroxybutane (BMDB, Pierce); Bis-maleimidohexane (BMH, Pierce), Bis-maleimidoethane (BMOE, Pierce); 1,8-Bis-Maleimidotriethyleneglycol (BM[PEO]3 Pierce); 1,11-Bis-Maleimidotetraethyleneglycol (BM[PEO]4 Pierce); 1,4-Di-[3'-(2'-pyridyldithio)-propionamido]butane (DPDPB, Pierce); dithio-bis-maleimidoethane (DTME Pierce); 1,6-Hexane-bis-vinylsulfone (HBVS, Pierce) and Tris-[2-maleimimidoethyl]amine (TMEA, Pierce).

If the conjugation partner does not contain a thiol reactive group then it may be modified to incorporate one or more (e.g. several) such groups by either chemical modification or genetic engineering by methods know to the art (Chapman, A. P. (2002) Adv. Drug Deliv. Rev., 54 531-545: Humphreys, D. P. et al. Protein Engineering, Design & Selection vol. 20 no. 5 pp. 227-234, 2007). While these two references describe methodologies to cross-link PEG to an engineered free thiol within an antibody or antibody fragment, the techniques may be used to cross-link a conjugation partner to an engineered free thiol within the albumin mutein of the invention. Alternatively the Drug Affinity Complex (DAC™) technology developed by ConjuChem Inc. (Montreal, Quebec, Canada, H2X 3Y8) may be used, e.g. as described in WO 200069902. There are three parts of each DAC™ construct: 1) the drug component (the portion responsible for biologic activity); 2) a linker attached to the drug component, and 3) a reactive chemistry group at the opposite end of the linker, usually a soft electrophile selective for thiols; a maleimide is the most useful embodiment. Other applicable conjugation methods are described in WO 2007/071068 incorporated herein by reference.

If the conjugation partner does not contain a thiol reactive group but does contain one or more (e.g. several) amino groups then it may be modified to incorporate one or more (e.g. several) thiol reactive groups by chemical modification by methods known to the art such as the use of cross-linking reagents such as, but not limited to, N-5-azido-2-nitrobenzoyloxysuccinimide (AMAS, Pierce), N-[beta-maleimidopropyloxy] succinimide ester (BMPS, Pierce), N-eta-maleimidocaproic acid (EMCA, Pierce), N-[eta-maleimidocaproyloxy]succinimide ester (EMCS, Pierce), N-[eta-maleimidocaproyloxy]sulfosuccinimide ester (sulfo-EMCS, Pierce), N-[gamma-maleimidobutyryloxy]succinimide ester (GMBS, Pierce), N-[gamma-maleimidobutyryloxy]sulfosuccinimide ester (sulfo-GMBS, Pierce), N-kappa-maleimidoundecanoic acid (KMUA, Pierce), N-[kappa-maleimidoundecanoyloxy]sulfosuccinimide ester (sulfo-KMUS, Pierce), m-maleimidobenzoyl-N-hydroxysuccinimide (MBS, Pierce), m-maleimidobenzoyl-N-hydroxysulfosuccinimide ester (sulfo-MBS, Pierce), N-succinimidyl S-acetylthio-acetate (SATA, Pierce), N-succinimidyl S-acetylthiopropionate (SATP, Pierce), succinimidyl 3-[bromoacetamido]propionate (SBAP, Pierce), N-succinimidyl iodoacetate (SIA, Pierce), N-succinimidyl[4-iodoacetyl] aminobenzoate (SIAB, Pierce), sulfosuccinimidyl[4-iodoacetyl]aminobenzoate (sulfo-SIAB, Pierce), succinimidyl [4-[N-maleimidomethyl]cyclohexane-1-carboxylate (SMCC, Pierce), sulfosuccinimidyl [4-[N-maleimidomethyl]cyclohexane-1-carboxylate (sulfo-SMCC, Pierce), succinimidyl-[4-[N-maleimidomethyl]cyclohexane-1-carboxy-[6-amidocaproate (LC-SMCC, Pierce), 4-succinimidyloxycarbonyl-methyl-alpha[2-pyridyldithio]toluene (SMPT, Pierce), sulfosuccinimidyl6-[alpha-methyl-alpha-(2-pyridyldithio)toluamido]hexanoate (sulfo-LC-SMPT, Pierce), succinimidyl 4-[p-maleimidophenyl]-butyrate (SMPB, Pierce), sulfosuccinimidyl 4-[p-maleimidophenyl]-butyrate (sulfo-SMPB, Pierce), succinimidyl-6-[(beta-maleimidopropionamido)hexanoate] (SMPH, Pierce), N-succinimidyl 3-[2-pyridyldithio]propionate (SPDP, Pierce), succinimidyl [3-(2-pyridyldithio)propionamido]hexanoate (LC-SPDP, Pierce), sulfosuccinimidyl [3'-(2-pyridyldithio) propionamido]hexanoate (sulfo-LC-SPDP, Pierce) and N-succinimidyl-[4-vinylsulfonyl]benzoate (SVSB Pierce). It may be advantageous to block certain amine residue as described by Kavimandan et al., (2006), Bioconjugate Chem. 17, 1376-1384.

Suitable linkers include bromomaleimide linkers such as monobromomaleimide linkers. Monobromomaleimides are next generation maleimides for the construction of stable conjugates, as described in Smith et al Organic & Biomolecular Chemistry, (2015), 13, pages 7946-7949. Preferred monobromomaleimide linkers include those described in WO 2011/018611 (incorporated herein by reference).

If the conjugation partner does not contain a thiol reactive group but does contain one or more (e.g. several) carbonyl (oxidised carbohydrate) groups then it can be modified to incorporate one or more (e.g. several) thiol reactive groups by chemical modification by methods known to the art such as the use of cross-linking reagents such as, but not limited to, (N-β-maleimidopropionic acid hydrazide (BMPH, Pierce)N-[eta-maleimidocaproic acid]hydrazide (EMCH, Pierce), 4-[N-maleimidomethyl]cyclohexane-1carboxylhydrazide·HCl·½ dioxane (MMCCH, Pierce), 3-maleimidophenyl boronic acid (MPBH, Pierce), N-[kappa-maleimidoundecanoic acid]hydrazide (KMUH, Pierce) and 3-[2-pyridyldithio]propionyl hydrazide (PDPH, Pierce).

If the conjugation partner does not contain a thiol reactive group but does contain one or more (e.g. several) hydroxyl groups then it may be modified to incorporate one or more (e.g. several) thiol reactive groups by chemical modification by methods known to the art such as the use of cross-linking reagents such as, but not limited to, N-[p-maleimidophenyl] isocyanate (PMPI, Pierce).

Associates

An eleventh aspect of the invention provides an associate comprising the conjugate of the seventh aspect of the invention and a bioactive, therapeutic, prophylactic, diagnostic, imaging or other beneficial moiety.

The conjugates may further be used in the form of "associates". In this connection the term "associate" is intended to mean a compound comprising a conjugate of a variant of albumin or a fragment thereof and another compound bound or associated to the conjugate by non-covalent binding. As an example of such an associate can be mentioned an associate consisting of a variant albumin conjugate and a lipid associated to albumin by a hydrophobic interaction. Such associates are known in the art and they may be prepared using well known techniques. As an example of a preferred associate according to the invention can be mentioned, an associate comprising a variant albumin conjugate and a taxane, a taxol or taxol derivative (e.g. paclitaxel). Further examples of associates comprise a bioactive, therapeutic, prophylactic (including vaccine), diagnostic, imaging or other beneficial moiety.

Methods for the preparation of associates are well-known to the skilled person, for example, formulation (by association) of HSA with lipo-compounds is described in Hussain, R. and Siligardi, G. (2006), International Journal of Peptide Research and Therapeutics, Vol. 12, NO: 3, pp. 311-315.

Nanoparticle, Microparticle or Liposome

A twelfth aspect of the invention provides a nanoparticle, a microparticle or a liposome comprising the polypeptide or the first, second or third aspect of the invention, the conjugate of the seventh aspect of the invention or the associate of the eleventh aspect of the invention.

Albumins and albumin particles are important for carrying and delivering drugs and prodrugs to their sites of action (Kratz (2008), Journal of Controlled Release, 132 (3), p. 171-183). Fusion and particle technologies offer improved dosing regimens due to improved pharmacokinetic properties, such as plasma half-life extension, and may improve bioavailability and protect the fused bioactive molecule from inactivation.

Techniques for incorporation of a molecule into nano- or microparticles are known in the art. Preferred methods for preparing nano- or microparticles that may be applied to the variant albumin conjugate or associate thereof according to the invention are disclosed in WO 2004/071536 or WO 2008/007146 or Oner & Groves (Pharmaceutical Research, Vol 10(9), 1993, pages 1387 to 1388) which are incorporated herein by reference. Preferably the average diameter of a nano-particle is from 5 to 1000 nm, more preferably from 5, 10, 20, 30, 40, 50, 80, 100, 130, 150, 200, 300, 400, 500, 600, 700, 800, 900, or 999 to 5, 10, 20, 30, 40, 50, 80, 100, 130, 150, 200, 300, 400, 500, 600, 700, 800, 900, or 1000 nm. An advantage of a microparticle less than 200 nm diameter, and more particularly less than 130 nm, is that is amenable to sterilization by filtration through a 0.2 μm (micron) filter. Preferably, the average diameter of a microparticle is from 1000 nm (1 μm (micron)) to 100 μm (micron), more preferably from 1, 2, 5, 10, 20, 30, 40, 50, 60, 70, 80, 90, 100 to 1, 2, 5, 10, 20, 30, 40, 50, 60, 70, 80, 90, 100 μm (micron).

The thio-albumin of the invention (and/or its conjugated form) may be used to produce nanoparticles and/or be entrapped within a nanoparticle or liposome.

The thio-albumin of the invention may be used with and/or in and/or as a nanoparticle and/or liposome. A problem of current conjugation strategies is maintaining both the pharmacological and immunological activity of the conjugation partner, such as a bioactive-targeting ligand conjugate. There is likely to be a maximum number of protein targeting ligand or bioactive moieties (conjugation partners) possible for conjugation to a protein and if this number is exceeded the targeting ligand does not retain its biological activity. Preferably the biological activity of the conjugation partner is not reduced by conjugation to an albumin of the invention.

Liposomes and nanoparticles may be used to entrap bioactive compounds. They provide a mechanism for enhanced delivery of drugs such as bioactive compounds, or uptake by target cells and/or a reduction in the toxicity of the free bioactive to non-target organs which may result in an increased therapeutic index and/or reduced side effects. In addition, many solvent-based formulations required for the delivery of some bioactive compounds (e.g. taxanes) are associated with toxicity which limits the maximum dose which can be given to a patient. Liposome and nanoparticle delivery may also be advantageous for such bioactive compounds, since they would allow larger amounts of the bioactive compound to be delivered whilst avoiding some of the toxicities of solvent-based formulations (Hawkins et al (2008), Advanced Drug Delivery Reviews, 60, 8, p876-885).

Methods for attaching targeting ligands to liposomes and nanoparticles are known in the art (reviewed in Nobs et al (2004), Journal of Pharmaceutical Sciences Vol 93 p1980-1992) and may be used in accordance with the invention. Attachment methods may be non-covalent or covalent. Covalent reactions appear to be favourable, because covalent linkage is more stable than noncovalent methods. Lipids for the covalent or non-covalent attachment of proteins, peptides, or drugs to the liposome surface are available commercially (for example Avanti Polar Lipids Inc Alabaster, Alabama, USA). There are 3 major classes of functionality: conjugation through disulphide or thioether formation, amide bond formation, or biotin/streptavidin binding, any of these may be used in the invention.

A number of methods relying on covalent coupling ligands to the surface of liposomes via thioether bonds have been described, most commonly utilizing the highly efficient reaction of maleimide with thiol groups. Functionalized lipid anchors commonly added to liposomes, and which may be used in or with the invention, include, but are not limited to those containing maleimide such as N-[4-(p-maleimidophenyl) butyramide]-PE (N-MPB]-PE) or N-[4-(p-maleimidomethyl) cyclohexane-carboxamide) (MCC-PE) which allow convenient covalent coupling of the targeting moiety via a stable thioether bond (Martin & Papahadjopoulos (1982), J. Biol. Chem. 257, 286-288).

Method #7: Following purification the free thiol containing albumin mutein of the invention or the conjugate can be formulated into nanoparticles prepared according to known procedures for preparing nanoparticles, such as procedures disclosed in WO 2004/071536 A1 and WO 2008/007146 A1, both incorporated herein by reference.

Similarly materials for the formation of nanoparticles, including but are not limited to poly(lactic acid) (PLA), poly(lactic-co-glycolic acid) (PLGA), and COOH-PLA are commercially available and may be functionalized with maleimide or other known chemistries according to known literature for nanoparticle formation. Any of these may be used in or with the invention.

Another convenient way for covalent coupling of ligands to liposomes involves conjugation of two thiols to form a disulphide; however under the reductive conditions in serum more stable conjugation chemistries involving one free thiol group may be preferred. Chemistries such as (PDP-PE) allow covalent coupling via a disulphide bond. Modification of the ligand to introduce a free thiol group or a functionalized linker may be used. An advantage of the thio-albumin of the invention is that no ligand modification is required. However, ligand modification may optionally be used in addition to the invention.

Frequently thiol groups are not present in proteins, or are not present in sufficient amounts or at the desired location. Thus, most cases of covalent coupling of one of more ligands to a liposome via thioether or disulphide bonds requires the use of heterobifunctional cross linking agents (described herein with reference to conjugation). Some heterobifunctional cross linking agents (such as SPDP and SATA) require a de-protection step. The thio-albumin of the invention overcomes the requirement for this additional processing.

Alternatively thio-albumin could be conjugated to liposomes or nanoparticles by other chemistries, known to the art. For example, thio-albumin could be attached by an amide bond using a functionalised lipid anchor with either amine or carboxyl functional groups (examples include DSPE-PEG-COOH) which reacts with the primary amine of the ligand. Direct cross linking between primary amines and the surface of liposomes may also be used. The one or more (e.g. several) free thiol groups of thio-albumin would then be available for conjugation to another conjugation partner.

Following conjugation, a conjugation partner (e.g. bioactive molecule) may show a reduction in its activity (e.g. bioactivity). Thio-albumin described in this invention may overcome this problem by providing a conjugate, nanoparticle and/or liposome in which the conjugation partner is located and/or orientated with respect to a thio-albumin such that the conjugation partner retains at least 10, 20, 30, 40, 50, 60, 70, 80, 90 or 100% of its unconjugated activity.

Nanoparticles may be used, for example, in angiogenic applications, anti-angiogenic applications and to coat a medical device such as a stent. Nanoparticles are effective at targeting, for example to non tight-junctions, and therefore can be useful for targeting tumours such as cancerous tumours. Nanoparticles can also be useful to target antigen in order to provoke an immune response since nanoparticles are particularly susceptible to engulfment and presentation by phagocytes. The invention provides nanoparticles consisting only of thio-albumin according to the invention which may or may not be conjugated to a moiety (conjugation partner). The invention also provides nanoparticles comprising thio-albumin according to the invention, which may or may not be conjugated to a moiety, and one or more (e.g. several) other constituents of a nanoparticle which may or may not be albumin related. In a preferred embodiment, a thio-albumin according to the invention comprises at least two conjugation competent cysteine residues located on the surface of the polypeptide. Such a thio-albumin may be used for the preparation of nanoparticles in which one or more (e.g. several) conjugation competent cysteine residues may be used in the formation of a nanoparticle and one or more (e.g. several) conjugation competent residues is used for conjugation to a conjugation partner, for example to a bioactive molecule.

Compositions

A thirteenth aspect of the invention provides a composition comprising a polypeptide, fusion polypeptide, conjugate, associate, nanoparticle, microparticle or liposome according to the invention and at least one (e.g. several) pharmaceutically acceptable carrier and/or diluent.

Various formulations are described herein in relation to the corresponding products.

A related aspect of the invention provides a method for making a pharmaceutical ingredient and/or a pharmaceutical product comprising making a thio-albumin according to the present invention, optionally conjugating a further molecule to the thio-albumin, optionally formulating the resultant conjugate with a pharmaceutically acceptable diluent and/or carrier and optionally preparing the product in unit dosage form.

Medical Uses

A fourteenth aspect of the invention provides use of a polypeptide, fusion polypeptide, conjugate according to the invention and/or produced by a method according to the invention, or an associate, nanoparticle, microparticle or liposome for treatment of disease, treatment of illness and/or diagnosis.

Various medical uses are described herein in relation to the corresponding products.

In addition, in some embodiments, the thio-albumin or conjugate has a binding affinity to FcRn and/or plasma half-life that is altered compared to the parent or reference albumin or conjugate. This has the advantage that the binding affinity to FcRn and/or plasma half-life of conjugates, associates, nanoparticle, microparticle or liposome according to the invention can be selected in accordance with the particular therapeutic purpose. An increased half-life could have the benefit that the administration would be needed less frequently or at a reduced dose (and consequently with fewer side effects) compared to the situation where the reference molecule or composition was used. Alternatively, a shorter plasma half-life than the reference molecule or composition would have the benefit that the administration can be carried out at a higher dose compared to the situation where the reference molecule or composition was used with the benefit that the administered compound clears from the recipient more quickly than if the reference molecule or composition was used.

For example for a conjugate, associate or fusion polypeptide used for imaging purposes in animals or humans, where the imaging moiety has a very short half-life and a conjugate or a fusion polypeptide comprising HSA has a plasma half-life that is far longer than needed for the imaging purposes it would be advantageous to use a variant albumin or fragment thereof of the invention having a shorter plasma half-life than the parent or reference albumin or fragment thereof, to provide conjugates or fusion polypeptides having a plasma half-life that is sufficiently long for the imaging purpose but sufficiently short to be cleared form the body of the particular patient on which it is applied.

In another example for a conjugate, an associate or fusion polypeptide comprising a therapeutic compound effective to treat or alleviate a particular condition in a patient in need for such a treatment it would be advantageous to use the variant albumin or fragment thereof having a longer plasma half-life than the parent or reference albumin or fragment thereof, to provide associates or conjugates or fusion polypeptides having longer plasma half-lives which would have the benefit that the administration of the associate or conjugate or fusion polypeptide of the invention would be needed less frequently or at reduced dose with less side effects compared to the situation where the parent or reference albumin or associates thereof or fragment thereof was used. For example, the invention provides a method of treating a proliferative disease in an individual, comprising administering the individual an effective amount of an associate according to the invention in which the associate comprises a taxane, a taxol or taxol derivative (e.g. paclitaxel).

Use to Increase Half-Life

A fifteenth aspect of the invention provides for use of a polypeptide as defined in any previous aspect of the invention to increase the half-life of a molecule such as a bioactive agent, an imaging agent, a diagnostic agent, a contrast agent or a therapeutic compound such as a chemotherapeutic drug or radiopharmaceutical. Preferably, the half-life is increased by at least 10, 20, 30, 40, 50, 60, 70, 80, 90 or at least 100% relative to the half-life of the molecule alone. Preferably, the half-life is increased by at least 2, 4, 6, 8, 10, 12, 14, 16, 18, 20, 22 hours or by at least 1, 2, 3, 4, 5, 6, 7, 8, 9, 10, 11, 12, 13 or at least 14 days relative to the half-life of the molecule alone.

For example, the half-life of a molecule may be increased by conjugating it to the polypeptide as defined in any previous aspect of the invention for example via a conjugatable cysteine residue; by genetically fusing the molecule to the polypeptide, by associating the molecule with the polypeptide and/or by incorporating it into a particle according to any previous aspect of the invention.

Embodiments of the Invention

The invention is further described with reference to the following numbered paragraphs:

1. A conjugation-competent polypeptide comprising an amino acid sequence which is at least 70% identical to human albumin, particularly residues 1 to 585 of the mature human albumin polypeptide sequence of SEQ ID NO: 2, or a fragment thereof;
   wherein at least one (e.g. several) position equivalent to a position selected from K93, E294, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, E382, and L398, particularly from K93, E294, A226, E230, and I271, of SEQ ID NO: 2 comprises a conjugation-competent cysteine residue; and
   preferably wherein the conjugation-competent polypeptide has a tendency to exist as a monomer in solution which is at least 70% of the tendency of the polypeptide of SEQ ID NO: 2 to exist as a monomer in solution.
2. The conjugation-competent polypeptide of Paragraph 1, wherein the polypeptide comprises one or more (e.g. several) of:

substitution of an amino acid, other than cysteine, with a cysteine at a position corresponding to a position equivalent to any of residues K93, E294, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, E382, and L398, particularly from K93, E294, A226, E230, and I271, of SEQ ID NO: 2; and/or insertion of a cysteine at a position adjacent the N- or C-side of an amino acid corresponding to a position equivalent to any of residues K93, E294, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, E382, and L398, particularly from K93, E294, A226, E230, and I271, of SEQ ID NO: 2.

3. The conjugation-competent polypeptide of Paragraph 1 or 2 wherein two, three, four, five or more (e.g. several) positions equivalent to positions selected from K93, E294, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, E382, and L398, particularly from K93, E294, A226, E230, and I271, of SEQ ID NO: 2 comprise a conjugation-competent cysteine residue.

4. The conjugation-competent polypeptide of any preceding Paragraph, wherein the polypeptide has a tendency to exist as a monomer in solution which is at least 75%, at least 80%, at least 85%, at least 90%, at least 95% or at least 100% of the tendency of the polypeptide of SEQ ID NO: 2 to exist as a monomer in solution.

5. The conjugation-competent polypeptide of any preceding Paragraph wherein the tendency of the polypeptide to exist as monomer in solution is measured following storage for at least 7 weeks at a temperature from 2 to 8° C. such as 5° C., at least 8 weeks at a temperature from 2 to 8° C. such as 5° C., at least 3 months at a temperature from 2 to 8° C. such as 5° C., at least 4 months at a temperature from 2 to 8° C. such as 5° C., at least 6 months storage at a temperature from 2 to 8° C. such as 5° C., or at least 3 months storage at a temperature of about 40° C.

6. The conjugation-competent polypeptide of Paragraph 5 wherein the tendency of the polypeptide to exist as monomer in solution is measured following storage for at least 3 months at a temperature from 2 to 8° C., such as 5° C. 7. The conjugation-competent polypeptide of paragraph 5 or 6, prior to storage, wherein the polypeptide is purified using triazine (such as AlbuPure®) chromatography matrix or DE-FF chromatography matrix prior to storage.

8. The conjugation-competent polypeptide of any of paragraphs 5, 6 or 7 wherein, prior to storage, the polypeptide is purified using triazine (such as AlbuPure®) chromatography matrix followed by DE-FF chromatography matrix.

9. The conjugation-competent polypeptide of any of paragraphs 5 to 8 wherein, prior to storage, the polypeptide is purified using triazine (such as AlbuPure®) chromatography matrix followed by DE-FF chromatography matrix followed by size exclusion (e.g size exclusion limit (Mr) of about $5 \times 10^3$ to $2.5 \times 10^5$ such as Sephacryl S-200 HR) chromatography.

10. The conjugation-competent polypeptide of any of Paragraphs 5 to 9 wherein the storage uses a polypeptide concentration of from 0.5 to 50 mg/mL.

11. The conjugation-competent polypeptide of any of Paragraphs 5 to 10 wherein the storage uses a polypeptide concentration of about 5 mg/mL.

12. The conjugation-competent polypeptide of any of Paragraphs 5 to 11 wherein the storage is at a pH between about 6.0 and about 7.5.

13. The conjugation-competent polypeptide of any of Paragraphs 5 to 12 wherein the storage is at a pH about 7.

14. The conjugation-competent polypeptide of any of Paragraphs 5 to 13 wherein the storage uses a buffer comprising 50 mM ammonium acetate, 10 mM sodium octanoate, pH 7.0, preferably at a polypeptide concentration of from about 0.2 to about 2.5 mg/mL.

15. The conjugation-competent polypeptide of any of Paragraphs 5 to 14 wherein the storage uses a buffer comprising 25 mM sodium phosphate, 215 mM sodium chloride, pH 6.5, preferably at a polypeptide concentration of from about 5 to about 50 mg/mL.

16. The conjugation-competent polypeptide of any preceding Paragraph, wherein at least one (e.g. several) position equivalent to a position selected from K93, E294, A226, E230, I271, E358, L24, F49, V54, D56, A92, Q94, E97, H128, F156, E227, D237, K240, D259, K262, N267, Q268, L275, L284, K317, A322, E333, D340, E354, K359, A362, E382, and L398, particularly from K93, E294, A226, E230, and I271, of SEQ ID NO: 2 comprises a conjugation-competent cysteine residue; and wherein the tendency to exist as monomer in solution is at least 75% of the tendency of the polypeptide of SEQ ID NO: 2 to exist as a monomer in solution.

17. The conjugation-competent polypeptide of any preceding Paragraph wherein the amino acid sequence is at least 95% identical to human albumin, particularly residues 1 to 585 of the mature human albumin polypeptide sequence of SEQ ID NO: 2, or a fragment thereof and the conjugation-competent polypeptide has a tendency to exist as a monomer in solution which is at least 80% of the tendency of the polypeptide of SEQ ID NO: 2 to exist as a monomer in solution.

18. The conjugation-competent polypeptide of any preceding Paragraph, wherein at a position equivalent to position 34 of SEQ ID NO: 2 there is a conjugation-competent cysteine.

19. The conjugation-competent polypeptide of any of Paragraphs 1 to 18, wherein at a position equivalent to position 34 of SEQ ID NO: 2 there is not a conjugation-competent cysteine.

20. The conjugation-competent polypeptide of any preceding Paragraph in which the polypeptide comprises two or more (several) conjugation-competent cysteine residues wherein, when the polypeptide is folded, there is a distance of at least 5 Å between at least one pair of the conjugation-competent cysteine residues.

21. The conjugation-competent polypeptide of any preceding Paragraph, wherein the polypeptide comprises substitution of an amino acid, other than cysteine, with a cysteine at one or both positions corresponding to a position equivalent to residues K93 or E294 of SEQ ID NO: 2.

22. The conjugation-competent polypeptide of any preceding Paragraph which is capable of forming a conjugate with maleimide-polyethylenglycol2-biotin, at a conjugation efficiency of at least 90%, preferably at least 95%, suitably wherein the conjugate is at 90%, preferably at least 95% stable upon controlled hydrolysis.

23. The conjugation-competent polypeptide of Paragraph 22 wherein the capability of forming a conjugate with maleimide-polyethylenglycol2-biotin is determined by incubating at ambient temperature overnight in phosphate buffered saline buffer pH 7.4.

24. The conjugation-competent polypeptide of Paragraph 22 or 23 wherein stability is determined by incubating at pH 9.0 and 37° C. for at least 18 hours, preferably 24 hours, in a buffered salts solution, such as phosphate buffered saline.

25. A conjugation-competent polypeptide comprising an amino acid sequence which is at least 70% identical to human albumin (SEQ ID NO: 2), or a fragment thereof; wherein at least one (e.g. several) position equivalent to
a position selected from K93, E294, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, E382, and L398, particularly from K93, E294, A226, E230, and I271, of SEQ ID NO: 2 comprises a conjugation-competent cysteine residue; and
comprising at least one (e.g. several) further conjugation-competent cysteine, or at least one (e.g. several) modification that alters the binding affinity of the polypeptide for FcRn, or alters the plasma half-life of the polypeptide.

26. The conjugation-competent polypeptide of Paragraph 25 wherein the at least one (e.g. several) further modification comprises at least one (e.g. several) further conjugation-competent cysteine as defined in any one of Paragraphs 1, 2, 3 or 21.

27. The conjugation-competent polypeptide of any preceding Paragraph wherein at least one (e.g. several) position equivalent to a position selected from D1, A2, H3, S5, A55, S58, C75, T76, T79, E82, T83, E86, C91, D121, V122, C124, T125, D129, C169, C177, A229, T236, E266, D269, S270, S273, S304, K313, D314, C316, N318, A320, C361, A364, C369, A371, N386, Q390, Q397, S435, T478, T496, A504, E505, T506, T508, D549, C558, D562, C567, A581, L585 and A578 of SEQ ID NO: 2 comprises a conjugation-competent cysteine.

28. The conjugation-competent polypeptide of any preceding Paragraph in which the polypeptide comprises one or more (e.g. several) of:
substitution of an amino acid, other than cysteine, with a cysteine at a position corresponding to a position equivalent to any of residues D1, A2, H3, S5, A55, S58, C75, T76, T79, E82, T83, E86, C91, D121, V122, C124, T125, D129, C169, C177, A229, T236, E266, D269, S270, S273, S304, K313, D314, C316, N318, A320, C361, A364, C369, A371, N386, Q390, Q397, S435, T478, T496, A504, E505, T506, T508, D549, C558, D562, C567, A581, L585 and A578 of SEQ ID NO: 2; and/or
insertion of a cysteine at a position adjacent the N- or C-side of an amino acid corresponding to a position equivalent to any of residues D1, A2, H3, S5, A55, S58, C75, T76, T79, E82, T83, E86, C91, D121, V122, C124, T125, D129, C169, C177, A229, T236, E266, D269, S270, S273, S304, K313, D314, C316, N318, A320, C361, A364, C369, A371, N386, Q390, Q397, S435, T478, T496, A504, E505, T506, T508, D549, C558, D562, C567, A581, L585 and A578 of SEQ ID NO: 2; and/or
deletion or substitution of a cysteine at a position corresponding to any of C360, C316, C75, C168, C558, C361, C91, C124, C169 and C567 of SEQ ID NO: 2 so as to generate a conjugation competent cysteine at any of C369, C361, C91, C177, C567, C316, C75, C169, C124 and C558; and/or
addition of a cysteine to the N-side of the N-terminal residue of an albumin sequence or to the C-side of the C-terminal residue of an albumin sequence.

29. The conjugation-competent polypeptide of any preceding Paragraph in which the polypeptide comprises conjugation-competent cysteines located at: (a) A2+L585, (b) A2+A364+D562+L585C, (c) A2 and adjacent the C-side of the C-terminus of the albumin (d) T79+A364; (e) A364+D1; (f) T79+D562+A364; (g) D562+A364+D1; (h) T79+D562+A364+A504; (i) T79+D562+A364+L585; (j) T79+D562+A364+D1; (k) T79+D562+A364+L585+D1; (l) E86+D562+A364+A504+A2; (m) S270+A581; (n) S270+D129; (o) S270+A581+E82; (p) S270+A581+D129; (q) S270+A581+E82+D129; (r) S270+A581+E82+D129+Q397; (s) C369+C177; (t) A364+A581; (u) T79+A364+A581; (v) A364+A581+D129; (w) A364+C177; (x) D562+C369; (y) D129+C369; (z) A581+C369; or (aa) D562+D129+C369.

30. The conjugation-competent polypeptide of any preceding Paragraph which comprises or consists of albumin domain III or a variant thereof and at least one (e.g. several) additional albumin domain or fragment thereof, such as a second albumin domain III or a variant thereof.

31. The conjugation-competent polypeptide of any preceding Paragraph which comprises or consists of at least one (e.g. several) albumin domain III or variant or fragment thereof wherein at least one (e.g. several) albumin domain III comprises one or more (e.g. several) substitutions in positions corresponding to the positions in SEQ ID NO: 2 selected among: 573, 500, 550, 417, 440, 464, 490, 492, 493, 494, 495, 496, 499, 501, 503, 504, 505, 506, 510, 535, 536, 537, 538, 540, 541, 542, 574, 575, 577, 578, 579, 580, 581, 582 and 584.

32. The conjugation-competent polypeptide of Paragraph 31, wherein the one or more (e.g. several) substitutions in positions corresponding to the positions in SEQ ID NO: 2 is selected among: K573Y, W, P, H, F, V, I, T, N, S, G, M, C, A, E, Q, R, L, D, K500E, G, D, A, S, C, P, H, F, N, W, T, M, Y, V, Q, L, I, R, Q417A, H440A, H464Q, E492G, D494N, Q,A, E495Q,A, T496A, D494E+Q417H, D494N+T496A, E492G+V493P, P499A, E501A,Q, N503H,K, H510Q, H535Q, K536A, P537A, K538A, K541G,D, D550E,N, E492G+K573P, A, or E492G/N503H/K573P.

33. The conjugation-competent polypeptide of any preceding Paragraph wherein the polypeptide comprises alterations at two or more (e.g. several) positions selected from positions corresponding to positions (a) 492 and 580; (b) 492 and 574; (c) 492 and 550; (d) 550 and 573; (e) 550 and 574; (f) 550 and 580 in SEQ ID NO: 2.

34. The conjugation-competent polypeptide of any preceding Paragraph comprising: (i) an N-terminal region comprising a first albumin which is a human albumin variant, in which the N-terminal of the first albumin comprises all amino acids of the human albumin variant except the C-terminal 2 to 30 amino acids; and (ii) a C-terminal region of a second albumin, which is selected from macaque albumin, mouse albumin, rabbit albumin, sheep albumin, human albumin, goat albumin, chimpanzee albumin, hamster albumin, guinea pig albumin, rat albumin, cow albumin, horse albumin, donkey albumin, dog albumin, chicken albumin, or pig albumin, or a variant thereof, in which the C-terminal of the second albumin or albumin variant comprises the C-terminal 2 to 30 amino acids of the second albumin or albumin variant;

wherein the polypeptide has (i) an altered plasma half-life compared with the human albumin variant and/or (ii) an altered binding affinity to FcRn compared with the human albumin variant.

35. The conjugation-competent polypeptide of any preceding Paragraph comprising one or more (e.g. several) alterations in Domain I of the mature human albumin polypeptide sequence of SEQ ID NO: 2; and one or more (e.g. several) alterations in Domain III of the mature human albumin polypeptide sequence of SEQ ID NO: 2, wherein the one or more (e.g. several) alterations cause the polypeptide to have an altered binding affinity to FcRn.

36. The conjugation-competent polypeptide of Paragraph 35 wherein the alteration(s) in Domain I are selected from positions corresponding to any of positions 78 to 120 of SEQ ID NO: 2, such as any of positions 78 to 88 and/or from any of 105 to 120; and the alteration(s) in Domain III are selected from positions corresponding to any of positions 425, 505, 510, 512, 524, 527, 531, 534, 569, 573, or 575 of SEQ ID NO: 2.

37. The conjugation-competent polypeptide of Paragraph 36 wherein the alteration at the position corresponding to positions is selected among 78 to 120 or 425, 505, 510, 512, 524, 527, 531, 534, 569, 573, and/or 575 of SEQ ID NO: 2 is a substitution; and the alteration is optionally a substitution selected from (i) 83N, K or S; (ii) 111D, G, H, R, Q or E; or (iii) 573P, Y, W, H, F, T, I or V.

38. The conjugation-competent polypeptide of any preceding Paragraph comprising one or more (e.g. several) alterations in Domain II of the mature human albumin polypeptide sequence of SEQ ID NO: 2 selected from the group consisting of positions corresponding to positions 349, 342, 381, 345, 384, 198, 206, 340, 341, 343, 344, 352, 382, 348, and/or 383 in SEQ ID NO: 2; wherein the one or more (e.g. several) alterations causes the conjugation-competent polypeptides to have (i) an altered plasma half-life and/or (ii) an altered binding affinity to FcRn.

39. The conjugation-competent polypeptide of Paragraph 38 wherein the alteration at the position corresponding to position 349, 342, 381, 345, 384, 198, 206, 340, 341, 343, 344, 352, 382, 348, and/or 383 is a substitution; and the alteration is optionally a substitution selected from (i) 349F, W, Y, H, P, K or Q, preferably F; (ii) 342Y, W, F, H, T, N, Q, A, C, I, L, P, V, preferably Y; (iii) 381G or A, preferably G; or (iv) 345E, H, I or Q.

40. The conjugation-competent polypeptide of any preceding Paragraph comprising one or more (e.g. several) alterations in the mature human albumin polypeptide sequence of SEQ ID NO: 2 selected from the group consisting of positions corresponding to positions V418, T420, V424, E505, V547, K573 in SEQ ID NO: 2; wherein the one or more (e.g. several) alterations causes the conjugation-competent polypeptides to have (i) an altered plasma half-life and/or (ii) an altered binding affinity to FcRn.

41. The conjugation-competent polypeptide of any preceding Paragraph comprising one or more (e.g. several) alterations in the mature human albumin polypeptide sequence of SEQ ID NO: 2 selected from the group consisting of positions corresponding to positions V381, preferably V381N or Q; E383, preferably E383A, G, I, L, or V; N391, preferably N391A, G, I, L or V; Y401 preferably Y401D or E; K402, preferably K402A, G, I, L, or V; L407, preferably L407F, N, Q, W, or Y; Y411, preferably Y411Q, or N; K413, preferably K413C, S, or T; K414, preferably K414S or T; V415C, preferably V415C, S, or T; Q416, preferably Q416H or P; V424, preferably V424A, G, I, L, N, or Q; V426D, preferably V426D, E, H, or P; G434, preferably G434C, S, or T; E442, preferably E442K or R; R445, preferably R445F, W or Y; P447, preferably P447S or T; E450, preferably E450D or E; S454, preferably S454C, M or T; V455, preferably V455N or Q; V456, preferably V456N or Q; L457, preferably L457F, W or Y; Q459, preferably Q459K or R; L463, preferably L463N or Q; E495, preferably E495D; T506, preferably T506F, W or Y; T508, preferably T508K, R, or S; F509, preferably F509C, I, L, M, V, W or Y; A511, preferably A511F, W, or Y; D512, preferably D512F, W or Y; T515, preferably T515C, H, N, P, Q or S; L516, preferably L516F, S, T, W or Y; S517, preferably S517C, F, M, T, W or Y; K519, preferably K519A, G, I, L, or V; R521, preferably R521F, W or Y; I523, preferably I523A, D, E, F, G, K, L, N, Q, R, V, W or Y; K524, preferably K524A, G, I, L or V; K525, preferably K525A, G, I, L or V; Q526, preferably Q526C, M, S, T or Y; T527, preferably T527F, W or Y; E531, preferably E531A, G, I, L or V; H535, preferably H535D, E or P; K538, preferably K538F, W or Y; A539, preferably A5391, L or V; K541, preferably, K541F, W or Y; K557, preferably K557A, G, I, L or V; A561, preferably A561F, W or Y; T566, preferably T566F, W or Y; A569, preferably A569H or P in SEQ ID NO: 2; wherein the one or more (e.g. several) alterations causes the conjugation-competent polypeptides to have (i) an altered plasma half-life and/or (ii) an altered binding affinity to FcRn.

42. The conjugation-competent polypeptide of any preceding Paragraph comprising one or more (e.g. several) alterations in the mature human albumin polypeptide sequence of SEQ ID NO: 2 selected from the group consisting of positions corresponding to positions V547, preferably V457A; K573, preferably K573P or Y; I523, preferably I523A or G, T527, preferably T527M, K500, preferably K500A; or E505, preferably E505Q in SEQ ID NO: 2; wherein the one or more (e.g. several) alterations causes the conjugation-competent polypeptides to have (i) an altered plasma half-life and/or (ii) an altered binding affinity to FcRn.

43. The conjugation-competent polypeptide of any preceding Paragraph comprising one or more (e.g. several) alterations in the mature human albumin polypeptide sequence of SEQ ID NO: 2 selected from the group consisting of positions corresponding to positions 573, 523, 527 or 505 of SEQ ID NO: 2, preferably K573Y; I523G; I523A; T527M; E505Q; or K573P.

44. The conjugation-competent polypeptide of Paragraph 43 comprising one or more (e.g. several) alterations in the mature human albumin polypeptide sequence of SEQ ID NO: 2 selected from the group consisting of positions corresponding to positions K573Y and I523G; K573Y, I523G and T527M; K573Y, E505Q and T527M; K573Y and T527M; K573P and I523G; K573P, I523G and T527M; K573P, E505Q and T527M; K573P and T527M; V547A; V547A and K573P; V547A, E505Q, K573P and T527M; or K500A and H510Q.

45. The conjugation-competent polypeptide of any of Paragraphs 25 to 44 wherein the conjugation-competent polypeptide has a tendency to exist as a monomer in solution which is at least 70% of the tendency of the polypeptide of SEQ ID NO: 2 to exist as a monomer in solution, and optionally at least 75%, at least 80%, at least 90%, at least 95% or at least 100%.

46. The conjugation-competent polypeptide of any preceding Paragraph, in which the polypeptide has at least 70, 75, 80, 85, 90, 95, 96, 97, 98, 99, 99.2, 99.4, 99.6, 99.8% sequence identity to SEQ ID NO: 2.

47. The conjugation-competent polypeptide of any preceding Paragraph wherein, when the polypeptide is folded, there are at least 1, 2, 3, 4, 5, 6, 7, 8, 9, 10, 11, 12, 13, 14, 15, 16, and preferably all 17 of the native disulphide bonds of the polypeptide of SEQ ID NO: 2.

48. The conjugation-competent polypeptide of any preceding Paragraph in which the polypeptide further comprises a further linker to which a bioactive compound, radiopharmaceutical or imaging agent may be linked.

49. The conjugation-competent polypeptide of any preceding Paragraph wherein the alteration(s) to provide a conjugation competent cysteine residue(s) result in a polypeptide with acceptable immunogenicity in human, preferably an immunogenicity which is comparable to or lower than that of wild-type HSA (SEQ ID NO: 2).

50. The conjugation-competent polypeptide of any preceding Paragraph wherein the alteration(s) to provide a conjugation competent cysteine residue(s) does not adversely affect the immunogenicity of the polypeptide in human, e.g. relative to the immunogenicity of wild-type HSA (SEQ ID NO: 2).

51. The conjugation-competent polypeptide of Paragraph 49 or 50 wherein the immunogenicity of the polypeptide is determined or predicted by screening for T-cell epitopes and/or for B-cell epitopes.

52. The conjugation-competent polypeptide of any of Paragraphs 50 to 51 wherein the immunogenicity of the polypeptide is determined or predicted by an ex vivo T cell activation assay.

53. The conjugation-competent polypeptide of Paragraph 52 wherein the T cell activation assay comprises measuring T cell responses using a proliferation assay, e.g. [3H]-thymidine uptake.

54. The conjugation-competent polypeptide of Paragraph 52 or 53 wherein the polypeptide has less than 10% reactivity in the T cell proliferation assay, preferably less than 8, 6, 4, or 2% reactivity, most preferably 0%.

55. The conjugation-competent polypeptide of any of Paragraphs 52 to 54 wherein the T cell activation assay comprises measuring T cell responses using a cytokine secretion assay, e.g. IL-2 ELISpot.

56. The conjugation-competent polypeptide of Paragraph 55 wherein the polypeptide has less than 10% reactivity in the cytokine secretion assay, preferably less than 8, 6, 4, or 2% reactivity, most preferably 0%.

57. The conjugation-competent polypeptide of any of Paragraphs 49 to 56 wherein the polypeptide has less than 10% reactivity in a T cell proliferation assay and in a cytokine secretion assay.

58. The conjugation-competent polypeptide of any preceding Paragraph wherein the polypeptide does not stimulate an adverse antibody response in human.

59. A fusion polypeptide comprising a conjugation-competent polypeptide of any preceding Paragraph and a fusion partner polypeptide.

60. A polynucleotide which encodes the polypeptide of any of Paragraphs 1 to 59.

61. A plasmid comprising the polynucleotide of Paragraph 60.

62. A host cell comprising a polynucleotide of Paragraph 60 and/or a plasmid of Paragraph 61.

63. The host cell of Paragraph 62, which is a yeast cell, particularly a *Saccharomyces cerevisiae* cell.

64. A conjugate which comprises a bioactive compound, radiopharmaceutical or imaging agent, and a polypeptide according to any of Paragraphs 1 to 59, wherein the bioactive compound is radiopharmaceutical or imaging agent, linked to the polypeptide through a conjugation-competent cysteine residue of the polypeptide.

65. The conjugate of Paragraph 64 further comprising one or more (e.g. several) further bioactive compounds radiopharmaceuticals or imaging agents, each bioactive compound, radiopharmaceutical or imaging agent, being linked to the polypeptide through a conjugation-competent cysteine residue of the polypeptide.

66. A method of producing the polynucleotide of Paragraph 60 comprising:
(a) providing a nucleic acid molecule encoding a parent albumin or fragment thereof; and
(b) modifying the nucleic acid sequence of the nucleic acid molecule to encode a conjugation-competent polypeptide which is at least 70% identical to human albumin, particularly residues 1 to 585 of the mature human albumin polypeptide sequence of SEQ ID NO: 2, or a fragment thereof, wherein at least one position equivalent to a position selected from K93, E294, A226, E230, I271, E358, L24, F49, V54, D56, L66, A92, Q94, E97, H128, F156, E227, D237, K240, D259, K262, N267, Q268, L275, E277, L284, E311, K317, A322, E333, D340, E354, K359, A362, E382, and L398, particularly from K93, E294, A226, E230, and I271, of SEQ ID NO: 2 comprises a conjugation-competent cysteine residue.

67. A method of producing the polypeptide of any of Paragraphs 1 to 59, comprising:
(a) culturing the host cell of Paragraph 62 or 63 under conditions that allow expression of the polypeptide; and
(b) recovering the polypeptide from the host cell and/or from host cell growth medium.

68. The method of paragraph 67 in which the host cell exhibits enhanced chaperone activity.

69. The method of Paragraph 67 or 68 further comprising purifying the polypeptide obtained in step (b).

70. A method of producing the conjugate of Paragraph 64 or 65 which comprises linking a polypeptide of any one of Paragraphs 1 to 59, or produced by the method of any one of Paragraphs 67 to 69, to a bioactive compound, radiopharmaceutical or imaging agent, through a conjugation-competent cysteine residue of the polypeptide.

71. An associate comprising the conjugate of Paragraph 64 or 65 and a bioactive, therapeutic, prophylactic, diagnostic, imaging or other beneficial moiety.
72. A nanoparticle or a microparticle or a liposome comprising the polypeptide of any one of Paragraphs 1 to 59, the conjugate of Paragraph 64 or 65 or the associate of Paragraph 71.
73. A composition comprising the conjugate of Paragraph 64 or 65, the associate of Paragraph 71 or the nanoparticle or microparticle or liposome of Paragraph 72 and at least one (e.g. several) pharmaceutically acceptable carrier or diluent.
74. The conjugate of Paragraph 64 or 65, the associate of Paragraph 71, the nanoparticle or microparticle or liposome of Paragraph 72, or the composition of Paragraph 73, wherein the bioactive molecule, radiopharmaceutical or imaging agent, is selected from those described herein.
75. The conjugate of Paragraph 64, 65 or 74, or the associate of Paragraph 71, the nanoparticle or microparticle or liposome of Paragraph 72 for treatment of disease, treatment of illness and/or for diagnosis.
76. Use of a polypeptide as defined in any of Paragraphs 1 to 59 to increase half-life of a bioactive molecule, radiopharmaceutical or imaging agent.

The invention is further described by the following examples that should not be construed as limiting the scope of the invention.

EXAMPLES

Example 1. Preparation of Variants

Preparation of Specific HSA Variant Expression Plasmids.

Methods for the expression of HSA variants were performed using several techniques, employing standard molecular biology techniques throughout, such as described in Sambrook, J. and D. W. Russell, 2001 (Molecular Cloning: a laboratory manual, 3rd ed. Cold Spring Harbor Laboratory Press, Cold Spring Harbor, N.Y).
Method 1.

Single amino acid mutations (K93C, A226C, E230C, I271C, E294C, and E358C) were introduced into the pDB5155 plasmid (encoding mutated C34A HSA, SEQ ID NO: 30) using a mutagenic forward primer and non-mutagenic reverse primer (Table 3). pDB5155, encoding a C34A mutant, based on the plasmid pDB5102 was made using a mutagenic forward primer and a non-mutagenic reverse primer (Table 3). pDB5102 is described in WO 2015/036579. Methylated template DNA was prepared by mixing about 1.7 µg of plasmid DNA with 5 µL 10× buffer (50 mM Tris-HCl mM β-mercaptoethanol, 10 mM EDTA PH 7.5 at 25° C.—New England Biolabs), 1 µL dam methyltransferase (New England Biolabs), 12.5 µL s-adenosylmethionine (New England Biolabs 80 µM final concentration) and water to 50 µl final volume and incubating at 37° C. for 1.5 hours. Reaction mixtures were then purified using a QIAquick PCR purification kit (Qiagen) according to the manufacturer's instructions. The relevant primers were employed in the PCR reaction (described in Tables 4 and 5) using dam-methylated pDB5102 as template and Q5 DNA polymerase (New England Biolabs). Amplification of the plasmid was confirmed by analysis of 5 µl of PCR product on a 1% TBE agarose gel. The remaining PCR product was supplemented with 5 µl buffer 4 (50 mM potassium acetate, 20 mM Tris-acetate, 10 mM magnesium acetate, 1 mM DTT, pH 7.9 at 25° C.—New England Biolabs) and 1 µl DpnI enzyme, followed by incubation at 37° C. for two hours. The reaction mixtures were then purified using a QIAquick PCR purification kit (Qiagen) according to the manufacturer's instructions. 1 µl of purified plasmid was transformed into E. coli 10-beta cells (New England Biolabs) and plated onto LB plates (5 g/L yeast extract, 10 g/L peptone from casein, 10 g/L NaCl, 12 g/L agar agar (Millers LB agar, Merck Millipore)) supplemented with 50 µg/mL ampicilin. Plasmids were isolated using a Qiagen Plasmid Plus Kit (Qiagen—according to manufacturer's instructions) and sequenced to confirm the presence of the desired mutation within the HSA sequence and the plasmid named pDB5155.

Methylated pDB5155 template DNA was prepared by mixing about 3.0 µg of plasmid DNA with 5 µL 10× buffer (50 mM Tris-HCl mM β-mercaptoethanol, 10 mM EDTA PH 7.5 at 25° C. —New England Biolabs), 1 µL dam methyltransferase (New England Biolabs), 12.5 µL 80 UM s-adenosylmethionine (New England Biolabs 80 UM final concentration) and water to 50 µl final volume and incubating at 37° C. for two hours. Reaction mixtures were then purified using a QIAquick PCR purification kit (Qiagen) according to the manufacturer's instructions.

The relevant primers were employed in the PCR reaction (described in Tables 4 and 5) using dam-methylated pDB5155 as template and Q5 DNA polymerase (New England Biolabs).

TABLE 3

Oligonucleotides for mutagenic amplification with mutated codons underlined (R = reverse, F = Forward) and the resultant protein.

| Oligo | Sequence (5' to 3') | SEQ ID NO. |
|---|---|---|
| C34A R | TTGTTGCAAGTATTGAGCGAAAGCGATCAAGACCAA | 31 |
| C34A F | TTCGCTCAATACTTGCAACAAGCTCCATTCGAAGAT CACGTCAAG | 32 |
| L24C F | GAAGAAAACTTCAAGGCTTTGGTCTGTATCGCTTTC GCTCAATACTTGCA | 33 |
| F49C F | AGTTGGTCAACGAAGTTACCGAATGTGCTAAGACTT GTGTTGCTGACG | 34 |
| V54C F | GTTACCGAATTCGCTAAGACTTGTTGTGCTGACGAA TCCGCGGAAAAC | 35 |
| D56C F | GAATTCGCTAAGACTTGTGTTGCTTGTGAATCCGCG GAAAACTGTGACA | 36 |
| L66C F | CGCGGAAAACTGTGACAAGTCCTGTCACACCTTGTT CGGTGATAAGTT | 37 |
| A92C F | CGGTGAAATGGCTGACTGTTGTTGTAAGCAAGAACC AGAAAGAAACGAA | 38 |
| K93C F | GTGAAATGGCTGACTGTTGTGCTTGTCAAGAACCAG AAAGAAACGAATGT | 39 |
| Q94C F | AAATGGCTGACTGTTGTGCTAAGTGTGAACCAGAAA GAAACGAATGTTTC | 40 |
| E97C F | ACTGTTGTGCTAAGCAAGAACCATGTAGAAACGAAT GTTTCTTGCAACAC | 41 |
| H128C F | TTGACGTCATGTGTACTGCTTTCTGTGACAACGAAG AAACCTTCTTGAAG | 42 |
| F156C F | ACTTCTACGCTCCAGAATTGTTGTGTTTCGCTAAGA GATACAAGGCTGC | 43 |

TABLE 3-continued

Oligonucleotides for mutagenic amplification with mutated codons underlined (R = reverse, F = Forward) and the resultant protein.

| Oligo | Sequence (5' to 3') | SEQ ID NO. |
|---|---|---|
| A226C F | AGATTGTCTCAAAGATTCCCAAAGTGTGAATTCGCTGAAGTTTCTAAGTTG | 44 |
| E227C F | TGTCTCAAAGATTCCCAAAGGCTTGTTTCGCTGAAGTTTCTAAGTTGGTT | 45 |
| E230C F | GATTCCCAAAGGCTGAATTCGCTTGTGTTTCTAAGTTGGTTACTGACTTG | 46 |
| D237C F | GCTGAAGTTTCTAAGTTGGTTACTTGTTTGACTAAGGTTCACACTGAATGT | 47 |
| K240C F | TCTAAGTTGGTTACTGACTTGACTTGTGTTCACACTGAATGTTGTCACGG | 48 |
| D259C F | GGAATGTGCTGATGACAGAGCTTGTTTGGCTAAGTACATCTGTGAAAAC | 49 |
| K262C F | TGATGACAGAGCTGACTTGGCTTGTTACATCTGTGAAAACCAAGACTCT | 50 |
| N267C F | GACTTGGCTAAGTACATCTGTGAATGTCAAGACTCTATCTCTTCCAAGTTG | 51 |
| Q268C F | TTGGCTAAGTACATCTGTGAAAACTGTGACTCTATCTCTTCCAAGTTGAAG | 52 |
| I271C F | TACATCTGTGAAAACCAAGACTCTTGTTCTTCCAAGTTGAAGGAATGTTGT | 53 |
| L275C F | ACCAAGACTCTATCTCTTCCAAGTGTAAGGAATGTTGTGAAAAGCCATTG | 54 |
| E277C F | GACTCTATCTCTTCCAAGTTGAAGTGTTGTTGTGAAAAGCCATTGTTGGAA | 55 |
| L284C F | AAGGAATGTTGTGAAAAGCCATTGTGTGAAAAGTCTCACTGTATTGCTGAA | 56 |
| E294C F | AAGTCTCACTGTATTGCTGAAGTTTGTAACGATGAAATGCCAGCTGACTT | 57 |
| E311C F | CATCTTTGGCTGCTGACTTCGTTTGTTCTAAGGACGTTTGTAAGAACTAC | 58 |
| K317C F | TTCGTTGAATCTAAGGACGTTTGTTGTAACTACGCTGAAGCTAAGGACG | 59 |
| A322C F | GACGTTTGTAAGAACTACGCTGAATGTAAGGACGTCTTCTTGGGTATGTT | 60 |
| E333C F | GTCTTCTTGGGTATGTTCTTGTACTGTTACGCTAGAAGACACCCAGACT | 61 |
| D340C F | CGAATACGCTAGAAGACACCCATGTTACTCCGTTGTCTTGTTGTTGAG | 62 |
| E354C F | TGTTGAGATTGGCTAAGACCTACTGTACTACCCTCGAGAAGTGTTGTG | 63 |
| E358C F | CTAAGACCTACGAAACTACCCTCTGTAAGTGTTGTGCTGCTGACC | 64 |
| K359C F | GACCTACGAAACTACCCTCGAGTGTTGTTGTGCTGCTGCTGACCCA | 65 |
| A362C F | AAACTACCCTCGAGAAGTGTTGTTGTGCTGCTGACCCACACGAATGT | 66 |
| E382C F | TCGATGAATTCAAGCCATTGGTCTGTGAACCACAAACTTGATCAAGCAA | 67 |

TABLE 3-continued

Oligonucleotides for mutagenic amplification with mutated codons underlined (R = reverse, F = Forward) and the resultant protein.

| Oligo | Sequence (5' to 3') | SEQ ID NO. |
|---|---|---|
| L398G F | GCAAAACTGTGAATTGTTCGAACAATGTGGTGAATACAAGTTCCAAAACGC | 68 |
| L24C R | GACCAAAGCCTTGAAGTTTTCTTCACCCAAGTCCT | 69 |
| F49C R | TTCGGTAACTTCGTTGACCAACTTGACGTGATCTT | 70 |
| V54C R | ACAAGTCTTAGCGAATTCGGTAACTTCGTTGACCAA | 71 |
| D56C R | AGCAACACAAGTCTTAGCGAATTCGGTAACTTCGTT | 72 |
| L66C R | GGACTTGTCACAGTTTTCCGCGGATTCGTCAGC | 73 |
| A92C R | ACAACAGTCAGCCATTTCACCGTAGGTTTCTCTC | 74 |
| K93C R | AGCACAACAGTCAGCCATTTCACCGTAGGTTTCTC | 75 |
| Q94C R | CTTAGCACAACAGTCAGCCATTTCACCGTAGGTT | 76 |
| E97C R | TGGTTCTTGCTTAGCACAACAGTCAGCCATTTCAC | 77 |
| H128C R | GAAAGCAGTACACATGACGTCAACTTCTGGTCTAA | 78 |
| F156C R | CAACAATTCTGGAGCGTAGAAGTATGGGTGTCTTC | 79 |
| A226C R | CTTTGGGAATCTTTGAGACAATCTAGCGACAGCC | 80 |
| E227C R | AGCCTTTGGGAATCTTTGAGACAATCTAGCGACAG | 81 |
| E230C R | AGCGAATTCAGCCTTTGGGAATCTTTGAGACAATCT | 82 |
| D237C R | AGTAACCAACTTAGAAACTTCAGCGAATTCAGCCTT | 83 |
| K240C R | AGTCAAGTCAGTAACCAACTTAGAAACTTCAGCGAA | 84 |
| D259C R | AGCTCTGTCATCAGCACATTCCAACAAGTCACCG | 85 |
| K262C R | AGCCAAGTCAGCTCTGTCATCAGCACATTCCAAC | 86 |
| N267C R | TTCACAGATGTACTTAGCCAAGTCAGCTCTGTCATC | 87 |
| Q268C R | GTTTTCACAGATGTACTTAGCCAAGTCAGCTCTGT | 88 |
| I271C R | AGAGTCTTGGTTTTCACAGATGTACTTAGCCAAGTC | 89 |
| L275C R | CTTGGAAGAGATAGAGTCTTGGTTTTCACAGATGTA | 90 |
| E277C R | CTTCAACTTGGAAGAGATAGAGTCTTGGTTTTCACAG | 91 |
| L284C R | CAATGGCTTTTCACAACATTCCTTCAACTTGGAAGA | 92 |
| E294C R | AACTTCAGCAATACAGTGAGACTTTTCCAACAATGG | 93 |
| E311C R | AACGAAGTCAGCAGCCAAAGATGGCAAGTCAGCT | 94 |
| K317C R | ACAAACGTCCTTAGATTCAACGAAGTCAGCAGCC | 95 |
| A322C R | TTCAGCGTAGTTCTTACAAACGTCCTTAGATTCAACG | 96 |
| E333C R | GTACAAGAACATACCCAAGAAGACGTCCTTAGCTTC | 97 |
| D340C R | TGGGTGTCTTCTAGCGTATTCGTACAAGAACATAC | 98 |
| E354C R | GTAGGTCTTAGCCAATCTCAACAACAAGACAACGG | 99 |
| E358C R | GAGGGTAGTTTCGTAGGTCTTAGCCAATCTCAACA | 100 |
| K359C R | CTCGAGGGTAGTTTCGTAGGTCTTAGCCAATCTC | 101 |

TABLE 3-continued

Oligonucleotides for mutagenic amplification with mutated codons underlined (R = reverse, F = Forward) and the resultant protein.

| Oligo | Sequence (5' to 3') | SEQ ID NO. |
|---|---|---|
| A362C R | ACAACACTTCTCGAGGGTAGTTTCGTAGGTCTTAG | 102 |
| E382C R | GACCAATGGCTTGAATTCATCGAAAACCTTAGCGT | 103 |
| L398C R | TTGTTCGAACAATTCACAGTTTTGCTTGATCAAGTTTTG | 104 |

TABLE 4

PCR reaction components

| Template (5 ng/μL) | 1 μL | Forward primer (10 μM) | 2.5 μL |
|---|---|---|---|
| 5x buffer | 10 μL | Reverse primer (10 μM) | 2.5 μL |
| dNTP (2.5 mM) | 1 μL | Q5 polymerase | 0.5 μL |
| Sterile water | 32.5 μL | | |

TABLE 5

PCR reaction conditions

| Temperature | Cycle Length | Number of cycles |
|---|---|---|
| 98° C. | 2 min | 1 |
| 98° C. | 10 sec | 30 |
| 60° C. | 30 sec | |
| 72° C. | 5 min | |
| 72° C. | 7 min | 1 |

Amplification of the plasmid was confirmed by analysis of 5 μl of PCR product on a 1% TBE agarose gel. The remaining PCR product was supplemented with 4 μl buffer 4 (50 mM potassium acetate, 20 mM Tris-acetate, 10 mM magnesium acetate, 1 mM DTT, PH 7.9 at 25° ° C. —New England Biolabs) and 1 μl DpnI enzyme, followed by incubation at 37° C. for one hour. The reaction mixtures were then purified using a QIAquick 96 PCR purification kit (Qiagen) according to the manufacturer's instructions. 2 μl of purified plasmid was transformed into competent E. coli DH5-alpha cells and grown in a 96 deep well block in 1.2 mL LB media (1% w/v bacteriological tryptone, 0.5% w/v yeast extract, 0.5% w/v NaCl) supplemented with 50 μg/mL ampicillin to repair nicks in the DNA backbone. Plasmids were isolated using a QiaPrep 96 turbo miniprep kit (Qiagen—according to manufacturer's instructions). The thioalbumin constructs are detailed in Table 6.

Plasmid DNA was prepared for transformation into S. cerevisiae as described in WO 2015/036579 (incorporated herein by reference), Method 4, except that 9723 bp Acc651-BamHI fragment from pDB4164 was used as the gapped vector fragment instead of the 9721 bp fragment from pDB3936, which has two additional bases GC next to the BamHI site to create a NotI restriction site GCGGCCGC (additional bases in bold). pDB3936 is described in WO 2011/124718 (incorporated herein by reference). pDB4164 also differs from pDB3936 in containing a 1368 bp sequence between the Acc651 and BamHI sites containing an apramycin resistance selectable marker which was excised by the Acc651 and BamHI digestion and was not used in the gap-repair transformation. The host strain for the constructs was S. cerevisiae BXP10 cir⁰ (WO 2015/036759, incorporated herein by reference). Transformed cells were grown as single colonies on selective agar plates (BMMD+CSM-Leu or BMMD) from which isolated colonies were patched out, also on selective agar plates, for the preparation of cryopreserved yeast stocks and samples for analysis. Cryopreserved stocks were made from 5 mL of a 48 hour BMMD+CSM-Leu shake flask culture mixed with an equal volume of 40% [w/v] trehalose and 1 mL aliquots transferred to cryovials for storage at −80° C. 0.5 mL BMMD in 48-well microtitre plate wells was inoculated with yeast from the patch plates and grown for 4-days at 30° C. with shaking as described in WO 2015/036579, Method 4 (incorporated herein by reference). Shake flask cultures were inoculated from trehalose stocks. Purification of these variants from shake flask was performed as described in WO 2012/150319 (incorporated herein by reference).

Preparation of the expression plasmids for the L24C, F49C, V54C, D56C, L66C, A92C, Q94C, E97C, H128C, F156C, E227C, D237C, K240C, D259C, K262C, N267C, Q268C, L275C, E277C, L284C, E311C, K317C, A322C, E333C, D340C, E354C, K359C, A362C, E382C, and L398C (all in C34A background) was slightly different to that described above:

Single amino acid mutations were introduced into the pDB5155 plasmid (encoding mutated C34A HSA, SEQ ID NO: 30) using a mutagenic forward primer and non-mutagenic reverse primer (Table 3).

Methylated template DNA was prepared by mixing about 2.5 μg of plasmid DNA with 5 μL 10× buffer (50 mM Tris-HCl mM β-mercaptoethanol, 10 mM EDTA PH 7.5 at 25° C.—New England Biolabs), 1 μL dam methyltransferase (New England Biolabs), 12.5 μL 80 M s-adenosylmethionine (New England Biolabs 80 μM final concentration) and water to 50 μl final volume and incubating at 37° C. for one hour. Reaction mixtures were then purified using a QIAquick PCR purification kit (Qiagen) according to the manufacturer's instructions.

The relevant primers were employed in the PCR reaction (described in Tables 4 and 5, above) using dam-methylated pDB5155 as template and Q5 DNA polymerase (New England Biolabs).

Amplification of the plasmid was confirmed by analysis of 5 μl of PCR product on a 1% TBE agarose gel. The remaining PCR product was supplemented with 4 μl buffer 4 (50 mM potassium acetate, 20 mM Tris-acetate, 10 mM magnesium acetate, 1 mM DTT, PH 7.9 at 25° ° C. —New England Biolabs) and 1 μl DpnI enzyme, followed by incubation at 37° C. for one hour. The reaction mixtures were then purified using a QIAquick 96 PCR purification kit (Qiagen) according to the manufacturer's instructions. 1 μl of purified plasmid was transformed into competent E. coli DH5-alpha cells and grown in a 96 deep well block in 1.2 mL LB media (1% w/v bacteriological tryptone, 0.5% w/v yeast extract, 0.5% w/v NaCl) supplemented with 50 μg/mL ampicillin to repair nicks in the DNA backbone. Plasmids were isolated using a QiaPrep 96 turbo miniprep kit (Qiagen—according to manufacturer's instructions). The thioalbumin constructs are detailed in Table 6.

Plasmid DNA was prepared for transformation into S. cerevisiae as described in WO 2015/036579, Method 4 (incorporated herein by reference). The host strain for the constructs was S. cerevisiae DYB7 (Payne et al. (2008) Applied and Environmental Microbiology Vol 74(24): 7759-7766). The yeast microtitre plate growth diverged from the method as described in WO 2015/036579 in that transformations were performed in duplicate and the initial growth was for two days. Stocks were produced from the two days growth by transfer of 50 µl culture to a fresh microtitre plate containing 50 µl 40% (w/v) trehalose. 50 µl of the two day culture was also added to a fresh microtitre plate containing 450 µL of BMMD+CSM-leu and incubated at 30° C. with shaking (200 rpm, 2.5 cm orbit at in a sealed chamber at 100% humidity in an Eppendorf Innova 44 incubated shaker) for a further four days. Culture supernatants were harvested by centrifugation at 3000 rpm for 5 minutes and 375 µl of supernatant was transferred to a fresh 48-well microtitre plate.

Production of Expression Plasmid and Yeast Stocks.

Preparation of the expression plasmids and transformation of S. cerevisiae was performed as described in WO 2011/051489 and WO 2012/150319 (incorporated herein by reference) by the 48-hour stocking method, using equal volumes of culture and trehalose. The host strain for the constructs was S. cerevisiae BXP10 Cir⁰ (WO 2015/036759, incorporated herein by reference). Purification of variants from shake flask was performed as described in WO 2012/150319 unless otherwise stated.

The resultant albumin variants are summarized in Table 6.

TABLE 6

| Albumin variant | SEQ ID NO. |
|---|---|
| C34A | 30 |
| C34A + L24C | 105 |
| C34A + F49C | 106 |
| C34A + V54C | 107 |
| C34A + D56C | 108 |
| C34A + L66C | 109 |
| C34A + A92C | 110 |
| C34A + K93C | 111 |
| C34A + Q94C | 112 |
| C34A + E97C | 113 |
| C34A + H128C | 114 |
| C34A + F156C | 115 |
| C34A + A226C | 116 |
| C34A + E227C | 117 |
| C34A + E230C | 118 |
| C34A + D237C | 119 |
| C34A + K240C | 120 |
| C34A + D259C | 121 |
| C34A + K262C | 122 |
| C34A + N267C | 123 |
| C34A + Q268C | 124 |
| C34A + I271C | 125 |
| C34A + L275C | 126 |
| C34A + E277C | 127 |
| C34A + L284C | 128 |
| C34A + E294C | 129 |
| C34A + E311C | 130 |
| C34A + K317C | 131 |
| C34A + A322C | 132 |
| C34A + E333C | 133 |
| C34A + D340C | 134 |
| C34A + E354C | 135 |
| C34A + E358C | 136 |
| C34A + K359C | 137 |
| C34A + A362C | 138 |
| C34A + E382C | 139 |
| C34A + L398C | 140 |

Example 2. Thiol Determination of DTNB Incubated Thio-Albumin Variants

The free thiol content of thiol albumin variants was determined at small scale using microtitre plate (MTP) grown cultures. The tested thiol albumin variants included the C34A substitution, and thus should lack the thiol group of native albumin. As such, they were each expected to have only one free thiol.

The number of free thiols on a protein can be determined spectrophotometrically using Ellman's reagent. Ellman's reagent (5'5'-dithio-bis(2-nitrobenzoic acid) (DTNB)) is an aromatic disulphide which reacts with thiol groups to form a mixed disulphide of the protein and one mole of 5-thio-2-nitrobenzoic acid (TNB) (per mole of protein sulfhydryl group). This reaction also results in a yellow colour from free TNB being released in solution. Alternatively the number of free thiols on a protein can be determined using mass spectrometric analysis of protein sample treated with DTNB reagent. 5-thio-2-nitrobenzoic acid (TNB) has a molecular weight of 199 Da, thus an increase in mass of 197 Da (TNB minus H2 lost during disulphide bond formation with the free thiol group on the test protein) indicates the presence of one free thiol group on the protein sample.

4 µl Buffer 2 (4 mg/mL DTNB, 500 mM sodium phosphate, pH 7.0) was added to 200 µL of the test protein culture sample in a 96-well MTP format. The preparation was allowed to incubate for 25 minutes at ambient temperature (20±5° C.) to allow TNB labelling. Protein intact mass was determined by UltraPerformance Liquid Chromatography Mass Spectrometry (UPLC-MS). UPLC separation was carried out on 10 µL of sample using a Waters Acquity on a BEH 50×2.1 mm ACQUITY BEH 1.7 µm 300 Å C4 column and a 5 min analytical gradient of buffer A 0.1% formic acid and Buffer B 100% acetonitrile 0.1% formic acid. Eluted proteins were directly introduced to a Bruker MicrOTOF II mass spectrometer via an Electrospray Ionisation (ESI) source. All instrument control and sample tables were controlled using BioPharma Compass™. All data were manually processed over the leading edge of the protein peak between 2.9-3.0 minutes in Data Analysis. This included spectral smoothing using a Gauss smoothing algorithm set at 0.0765 Da and a baseline correction setting of 0.8 flatness. Deconvoluted intact mass spectra were obtained using the Max. Entropy algorithm, all methods and parameters were set within BioPharma Compass™.

The results of the above thiol analysis of the thio-albumin samples are summarised in Table 7. An increase in mass of 197 Da upon DTNB incubation is predicted to be indicative of the presence of one free thiol group on the protein in the sample. A mass increase of 197±15 Da as actually measured by MS was taken as indicative of the correct mass. All variants successfully bound a molecule of TNB.

TABLE 7

Mass Spectrometry DTNB thiol screening results

| | Molecular weight (Da) | | | |
|---|---|---|---|---|
| | | Post DTNB treatment | | |
| Variant description (all C34A) | Variant Theoretical | Theoretical | Actual measured | Difference (Actual minus theoretical) |
| L24C | 66397 | 66594 | 66599 | 5 |
| F49C | 66363 | 66560 | 66568 | 8 |
| V54C | 66411 | 66608 | 66613 | 5 |
| D56C | 66395 | 66592 | 66600 | 8 |
| L66C | 66397 | 66594 | 66599 | 5 |
| A92C | 66439 | 66636 | 66641 | 5 |
| K93C | 66382 | 66579 | 66588 | 9 |
| Q94C | 66382 | 66579 | 66581 | 2 |
| E97C | 66381 | 66578 | 66580 | 2 |
| H128C | 66373 | 66570 | 66572 | 2 |
| F156C | 66363 | 66560 | 66564 | 4 |
| A226C | 66439 | 66636 | 66637 | 1 |
| E227C | 66381 | 66578 | 66584 | 6 |
| E230C | 66381 | 66578 | 66582 | 4 |

TABLE 7-continued

Mass Spectrometry DTNB thiol screening results

| | | Molecular weight (Da) | | |
| --- | --- | --- | --- | --- |
| | | | Post DTNB treatment | |
| Variant description (all C34A) | Variant Theoretical | Theoretical | Actual measured | Difference (Actual minus theoretical) |
| D237C | 66395 | 66592 | 66593 | 1 |
| K240C | 66382 | 66579 | 66584 | 5 |
| D259C | 66395 | 66592 | 66594 | 2 |
| K262C | 66382 | 66579 | 66584 | 5 |
| N267C | 66396 | 66593 | 66592 | −1 |
| Q268C | 66382 | 66579 | 66584 | 5 |
| I271C | 66397 | 66594 | 66596 | 2 |
| L275C | 66397 | 66594 | 66597 | 3 |
| E277C | 66381 | 66578 | 66583 | 5 |
| L284C | 66397 | 66594 | 66592 | −2 |
| E294C | 66381 | 66578 | 66581 | 3 |
| E311C | 66381 | 66578 | 66589 | 11 |
| K317C | 66382 | 66579 | 66582 | 3 |
| A322C | 66439 | 66636 | 66640 | 4 |
| E333C | 66381 | 66578 | 66582 | 4 |
| D340C | 66395 | 66592 | 66602 | 10 |
| E354C | 66381 | 66578 | 66583 | 5 |
| E358C | 66381 | 66578 | 66583 | 5 |
| K359C | 66382 | 66579 | 66583 | 4 |
| A362C | 66439 | 66636 | 66641 | 5 |
| E382C | 66381 | 66578 | 66586 | 8 |
| L398C | 66397 | 66594 | 66597 | 3 |

Example 3. Aggregation Screening of Thio-Albumin Variants

Variants were tested for tendency to remain as a monomer in solution. Each variant has a single free thiol group. Therefore, they were tested in comparison with wild-type HSA, which also has a single free thiol group.

Shake flask culturing of *S. cerevisiae* and purification was performed as described in WO 2012/150319 (incorporated herein by reference) with the following modifications. BMMS media (10 mL) was inoculated with *S. cerevisiae* and grown for 2 days at 30° C. with orbital shaking at 200 rpm. An aliquot of each starter culture (5 mL) was used to inoculate 2×200 ml BMMS media and grown for 5 days at 30° C. with orbital shaking at 200 rpm. Cells were harvested by filtration through a 0.2 μm vacuum filter membrane (Nalgene Sterile Top Filter) and the supernatant retained for purification.

A single step chromatography procedure was used to prepare purified material from the thio-albumin variants. The purification step used a column (bed volume approximately 2 mL) packed with AlbuPure® matrix (ProMetic BioSciences Ltd, Cambridge UK or Albumedix Ltd (formerly Novozymes Biopharma UK Ltd)). This was equilibrated with 50 mM sodium acetate, pH 5.3, and loaded with neat shake flask culture supernatants, at approximately pH 5.5-6.5, to approximately 20 mg protein/mL matrix. The column was washed with approximately 10 column volumes each of 50 mM sodium acetate, pH 5.3, and 50 mM ammonium acetate, pH 8.0, respectively. Bound protein was eluted using approximately 10 column volumes of 50 mM ammonium acetate, 10 mM octanoate, pH 7.0. The flow rate throughout was 240 cm/h using an AKTA Explorer system (GE Healthcare). Eluate samples were approximately 20 mL in volume. The concentration and percentage monomer of the eluate samples was determined by Gel Permeation High Pressure Liquid Chromatography (GP-HPLC). Protein concentrations were determined using a LC2010 HPLC system (Shimadzu) equipped with UV detection under Shimadzu VP7.3 client server software control. Injections of 25 μL were made onto a 7.8 mm internal diameter×300 mm length TSK G3000SWXL column (Tosoh Bioscience), with a 6.0 mm internal diameter×40 mm length TSK SW guard column (Tosoh Bioscience). Samples were chromatographed in 25 mM sodium phosphate, 100 mM sodium sulphate, 0.05% (w/V) sodium azide, pH 7.0 at 1 mL·min$^{-1}$, with a run time of 15 minutes. Samples were quantified by UV detection at 280 nm, by peak area, relative to a recombinant human albumin standard of known concentration (10 mg/mL).

The samples were reanalysed to determine the change in percentage monomer post seven weeks storage at 2-8° C., and post 6 months storage at 2-8° C. The percentage monomer (in brackets) was determined for each sample relative to its wild type control under the same storage conditions. The results are summarised in Table 8A. Final eluate concentrations were in the range of 0.6-1.2 mg/mL, resulting in 12-24 mg protein recovered post purification. All variants had a monomer percentage equivalent to or higher than that of the wild type control at T=0, which had a monomer percentage of 87%. The variants maintained their monomeric protein percentage over 7 weeks' storage at 2-8° C., with no significant evidence of aggregation propensity during 6 months storage at 2-8° C. observed for at least four variants.

TABLE 8A

GPHPLC aggregation screening results

| | GPHPLC conc. (mg/mL) | % Monomer | | | Δ% Monomer | |
| --- | --- | --- | --- | --- | --- | --- |
| Sample | | T = 0 | T = 7 week | T = 6 month | 0-7 week | 0-6 month |
| WT albumin control | 1.1 | 87 (100) | 88 (100) | 89 (100) | 1 | 2 |
| C34A + K93C | 0.7 | 91 (105) | 92 (105) | 92 (103) | 1 | 1 |
| C34A + A226C | 1.1 | 93 (107) | 93 (106) | 93 (105) | 0 | 0 |
| C34A + E230C | 0.6 | 90 (103) | 91 (103) | ND (ND) | 1 | ND |
| C34A + I271C | 1.2 | 91 (105) | 91 (103) | 91 (102) | 0 | 0 |
| C34A + E294C | 0.9 | 96 (110) | 96 (109) | 96 (108) | 0 | 0 |
| C34A + E358C | 1.0 | 89 (102) | 83 (94) | 80 (90) | −6 | −9 |

ND: Not determined

Further variants were analysed using the method previously described in Example 3, or alternatively using an Agilent 1260 isocratic UHPLC (Ultra-High Performance Liquid Chromatography) instrument. For the UHPLC method, injections of 4 μL were made onto a 4.6 mm id×150 mm length BEH 200 Å, 1.7 μm column (Waters), using the mobile phase described in Example 3, at 0.5 mL·min$^{-1}$, with a run time of 5 minutes. Samples were quantified by UV detection at 280 nm, by peak height relative to a recombinant human albumin standard of known concentration (10 mg/mL).

The samples were reanalysed post eight weeks storage at 2-8° C., and post 4 months storage at 2-8° C. to determine the change in percentage monomer. The percentage monomer (in brackets) was determined for each sample relative to its wild type control under the same storage conditions. The results are summarised in Table 8B. Final eluate concentrations were in the range of 0.1-1.0 mg/mL, resulting in 2-20 mg protein recovered post purification. The majority of variants had a monomer percentage equivalent to or higher than that of the wild type control at T=0, which had a monomer percentage of 86%. These variants maintained their monomeric protein over 8 weeks' storage at 2-8° C., with no significant evidence of aggregation propensity during 4 months storage at 2-8° C. observed. However, it was evident that variants C34A+L66C, C34A+E277C, and C34A+E311C had a relatively low percentage monomer at T=0, and consequently had a propensity to form aggregates.

TABLE 8B

GPHPLC aggregation screening results

| Sample | GPHPLC conc. (mg/mL) | % Monomer T = 0 | T = 8 week | T = 4 month | Δ% Monomer 0-8 week | Δ% Monomer 0-4 month |
|---|---|---|---|---|---|---|
| WT albumin control | 0.6 | 86 (100) | 88 (100) | 87 (100) | 2 | 1 |
| C34A + L24C | 0.7 | 94 (109) | 96 (109) | 97 (112) | 2 | 3 |
| C34A + F49C | 0.5 | 94 (109) | 95 (108) | 94 (108) | 1 | 0 |
| C34A + V54C | 0.5 | 93 (108) | 94 (107) | 93 (107) | 1 | 0 |
| C34A + D56C | 0.3 | 85 (99) | 77 (88) | 75 (86) | -8 | -10 |
| C34A + L66C | 0.2 | 7 (8) | 12 (14) | 6 (7) | 5 | -1 |
| C34A + A92C | 0.9 | 93 (108) | 94 (107) | 94 (108) | 1 | 1 |
| C34A + Q94C | 0.1 | 95 (111) | 96 (109) | 95 (109) | 1 | 0 |
| C34A + E97C | 0.5 | 88 (102) | 85 (97) | 85 (98) | -3 | -3 |
| C34A + H128C | 0.6 | 92 (107) | 93 (106) | 93 (107) | 1 | 1 |
| C34A + F156C | 1.0 | 92 (107) | 94 (107) | 94 (108) | 2 | 2 |
| C34A + E227C | 0.5 | 86 (100) | 88 (100) | 88 (101) | 2 | 2 |
| C34A + D237C | 0.5 | 93 (108) | 95 (108) | 94 (108) | 2 | 1 |
| C34A + K240C | 0.6 | 93 (108) | 94 (107) | 94 (108) | 1 | 1 |
| C34A + D259C | 0.5 | 93 (108) | 95 (108) | 94 (108) | 2 | 1 |
| C34A + K262C | 0.6 | 92 (107) | 93 (106) | 93 (107) | 1 | 1 |
| C34A + N267C | 0.6 | 94 (109) | 95 (108) | 95 (109) | 1 | 1 |
| C34A + Q268C | 0.8 | 95 (111) | 96 (109) | 96 (110) | 1 | 1 |
| C34A + L275C | 0.5 | 94 (109) | 95 (108) | 94 (108) | 1 | 0 |
| C34A + E277C | 0.7 | 65 (76) | 60 (68) | 59 (68) | -5 | -6 |
| C34A + L284C | 0.7 | 92 (107) | 94 (107) | 94 (108) | 2 | 2 |
| C34A + E311C | 0.7 | 54 (63) | 48 (55) | 46 (53) | -6 | -8 |
| C34A + K317C | 0.6 | 83 (97) | 82 (93) | 82 (94) | -1 | -1 |
| C34A + A322C | 0.8 | 81 (94) | 84 (96) | 83 (95) | 3 | 2 |
| C34A + E333C | 0.3 | 94 (109) | 97 (110) | 95 (109) | 3 | 1 |
| C34A + D340C | 0.6 | 93 (108) | 94 (107) | 94 (108) | 1 | 1 |
| C34A + E354C | 0.7 | 89 (104) | 90 (102) | 90 (103) | 1 | 1 |
| C34A + K359C | 0.6 | 86 (100) | 87 (99) | 87 (100) | 1 | 1 |
| C34A + A362C | 0.6 | 89 (104) | 89 (101) | 88 (101) | 0 | -1 |
| C34A + E382C | 0.6 | 86 (100) | 84 (96) | 84 (97) | -2 | -2 |
| C34A + L398C | 0.7 | 90 (105) | 92 (105) | 87 (100) | 2 | -3 |

Example 4. Conjugation Efficiency and Controlled Hydrolysis of Thio-Albumin Variants Thio-albumin variants from Example 3 were conjugated with biotin (Thermo Scientific, EZ-Link Maleimide-PEG2-Biotin) using a 3.2 fold molar excess of maleimide-PEG2-biotin to protein. A reaction schematic is shown in FIG. 4. The thio-albumin AlbuPure® eluates were diluted with phosphate buffered saline (PBS buffer), pH 7.4 to give 10 mL solutions at 0.3 mg/ml (45.15 nmol) and conjugated as described below Table 9A.

The MS spectrum for the thio-albumin variant C34A+A226C indicated that no conjugation had occurred post an overnight incubation with maleimide-PEG2-biotin. The results are summarised in Table 9A. The MS spectra for the thio-albumin variants C34A+E230C, and C34A+I271C indicated that conjugation had occurred post an overnight incubation, giving approximately 72% or 72% monoconjugate respectively (i.e. the same level of monoconjugate) when comparing the relative peak heights of conjugated and unconjugated species. The MS spectrum for C34A+I271C is shown in FIG. 5A. The MS spectrum for thio-albumin variant C34A+K93C shown in FIG. 5B, exhibited a single species at 66908 Da indicating the correct molecular weight for the thio-albumin variant plus a single addition of maleimide-PEG2-biotin (±525 Da). This confirmed the variant had a single free thiol available for conjugation. Comparable results were obtained for thio-albumin variants C34A+E294C and C34A+E358C.

TABLE 9A

Conjugation efficiency results

| Sample Description | Reference Mr unconjugated (Da) | Theoretical conjugate mass (Da) | Conjugate intact mass result (Da) | % conjugation |
|---|---|---|---|---|
| WT control | 66439 | 66964 | * | * |
| C34A + K93C | 66382 | 66907 | 66908 | 100 |
| C34A + A226C | 66439 | 66964 | 66440 | 0 |
| C34A + E230C | 66381 | 66906 | 66908 | 72 |
| C34A + I271C | 66397 | 66922 | 66924 | 72 |
| C34A + E294C | 66381 | 66906 | 66909 | >95 |
| C34A + E358C | 66381 | 66906 | 66909 | 100 |

* WT control sample failed to inject on MS during sequence run.

Further variants were analysed and the results are shown in Table 9B. For samples C34A+L66C and C34A+Q94C the protein concentrations were low, hence 10 mL solutions at 0.15 mg/mL (22.58 nmol) were used. Stock solutions of 2 mg/mL biotin were prepared by the addition of 5×200 µL aliquots of PBS buffer, pH 7.4, to each of two 2 mg pre-weighed EZ-Link microtubes, the vials were rinsed to maximise recovery of the lyophilised product. The two 1 mL volumes were pooled into a 7 mL container with a lid. From the biotin stock solution, 38 µL (144.5 nmol) was added to the 10 mL albumin samples to give approximately a 3.2-fold molar excess of biotin over albumin. However, for the C34A+L66C and C34A+Q94C samples only 19 µL biotin was added to maintain a 3.2 fold excess of maleimide-PEG2-biotin to protein. Samples were gently mixed and incubated at ambient temperature overnight. Post incubation, the samples were subjected to mass spectrometry to determine the intact protein mass post conjugation according to the method described in Example 2, but using a 15 minute analytical gradient, and processing data for the protein peak between approximately 7 and 10 minutes. The MS spectra results summarised in Table 9B indicated that thio-albumin variants C34A+L66C, C34A+A92C, C34A+Q94C, C34A+D259C, C34A+L275C, and C34A+L284C did not conjugate post an overnight incubation with maleimide-PEG2-biotin. The MS spectra for the WT control, and the thio-albumin variants C34A+L24C, C34A+V54C, C34A+H128C, C34A+E227C, C34A+K240C, C34A+K262C, C34A+Q268C, C34A+E277C, C34A+K317C, C34A+A322C, C34A+K359C and C34A+A362C indicated 90% conjugation or greater with maleimide-PEG2-biotin.

TABLE 9B

Conjugation efficiency results

| Sample Description | Reference Mr unconjugated (Da) | Theoretical conjugate mass (Da) | Conjugate intact mass result (Da) | % conjugation |
|---|---|---|---|---|
| WT control | 66439 | 66964 | 66966 | 93 |
| C34A + L24C | 66397 | 66922 | 66924 | 96 |
| C34A + F49C | 66363 | 66888 | 66889 | 84 |
| C34A + V54C | 66411 | 66936 | 66938 | 100 |
| C34A + D56C | 66395 | 66920 | 66922 | 79 |
| C34A + L66C | 66397 | 66922 | 66400 | 0 |
| C34A + A92C | 66439 | 66964 | 66407 | 0 |
| C34A + Q94C | 66382 | 66907 | 66409 | 0 |
| C34A + E97C | 66381 | 66906 | 66907 | 9 |
| C34A + H128C | 66373 | 66898 | 66899 | 100 |
| C34A + F156C | 66363 | 66888 | 66890 | 76 |
| C34A + E227C | 66381 | 66906 | 66907 | 95 |
| C34A + D237C | 66395 | 66920 | 66921 | 73 |
| C34A + K240C | 66382 | 66907 | 66908 | 100 |
| C34A + D259C | 66395 | 66920 | 67424 | 0 |
| C34A + K262C | 66382 | 66907 | 66908 | 100 |
| C34A + N267C | 66396 | 66921 | 66922 | 47 |
| C34A + Q268C | 66382 | 66907 | 66908 | 92 |
| C34A + L275C | 66397 | 66922 | 66897 | 0 |
| C34A + E277C | 66381 | 66906 | 66908 | 90 |
| C34A + L284C | 66397 | 66922 | 67427 | 0 |
| C34A + E311C | 66381 | 66906 | 66909 | 76 |
| C34A + K317C | 66382 | 66907 | 66909 | 91 |
| C34A + A322C | 66439 | 66964 | 66965 | 94 |
| C34A + E333C | 66381 | 66906 | 66907 | 83 |
| C34A + D340C | 66395 | 66920 | 66923 | 12 |
| C34A + E354C | 66381 | 66906 | 66908 | 32 |
| C34A + K359C | 66382 | 66907 | 66908 | 95 |
| C34A + A362C | 66439 | 66964 | 66966 | 94 |
| C34A + E382C | 66381 | 66906 | 66909 | 83 |
| C34A + L398C | 66397 | 66922 | 66925 | 36 |

The stability of maleimide conjugate bonds is not robust. The succinimide can revert back to maleimide and free thiol via a retro-Michael pathway (FIG. 4). Thus, highly undesirably, the released maleimide may react with other thiol reactive species and the released thiol may react with other compounds in vivo. To avoid retro-Michael reactivity, the succinimide may be hydrolysed to succinic acid, effectively taking on $H_2O$ (+18 Da) and locking the conjugate to be thiol-stable. The property of thiol-stability by hydrolysis is desirable as it would ensure that there was no unwanted thiol transfer taking place in various environments in vivo. Therefore, controlled hydrolysis of the succinimide was performed by increasing the pH and temperature. Post conjugation the samples were transferred to Vivaspin 20 centrifugal concentrators (Sartorius) and balanced with PBS buffer pH 7.4. The samples were centrifuged at 4,500×g for 15 minutes to reduce the volume to approximately 200 μL. A diafiltration cup was fitted to the Vivaspin 20 vessels and subsequently filled with 15 ml of PBS buffer pH 9.0. The samples were centrifuged at 4,500×g for 15 minutes a second time. A further 15 mL PBS buffer pH 9.0 was added and the samples centrifuged a third time to ensure that all the free maleimide-PEG2-biotin was removed from solution. The remaining retentate was removed and made up to a final volume of 10 mL with PBS buffer pH 9.0 (i.e. assuming no losses then to a concentration of 0.3 mg/mL). The samples were incubated at 37° C. for at least 24 hours for controlled hydrolysis to occur to determine the stability of the thio ether conjugate bond. The results are summarised in Table 10.

The yield of the hydrolysed thiol stable wild type control conjugate was in the order of 53%, likely due to the competing retro-Michael deconjugation during hydrolysis (FIG. 6A). Also observed was an average conjugate mass shift of +14 Da indicating that partial hydrolysis had occurred. It was apparent that the thio-albumin variants that had the highest conjugation efficiency also had improved conjugate stability upon controlled hydrolysis. Specifically the reaction favoured the hydrolysis of the succinimide rather than the retro-Michael deconjugation pathway. An example of C34A+E294C is shown in FIG. 6B indicating no conjugate losses following incubation at pH 9.0, 37° C. Comparable results were obtained for thio-albumin variants C34A+K93C, C34A+E294C and C34A+E358C with no significant losses during controlled hydrolysis.

TABLE 10

Controlled hydrolysis stability results

| Sample Description | Reference Mr unconjugated (Da) | Theoretical conjugate mass (Da) | Conjugate intact mass result (Da) | Conjugate mass increase (Da) | % conjugation post hydrolysis |
|---|---|---|---|---|---|
| WT control | 66439 | 66964 | 66978 | 14 | 53 |
| C34A + K93C | 66382 | 66907 | 66911 | 4 | 100 |
| C34A + A226C | 66439 | 66964 | 66441 | 2 | 0 |
| C34A + E230C | 66381 | 66906 | 66926 | 20 | 63 |
| C34A + I271C | 66397 | 66922 | 66939 | 6 | 61 |
| C34A + E294C | 66381 | 66906 | 66926 | 20 | 100 |
| C34A + E358C | 66381 | 66906 | 66927 | 21 | 100 |

The combined aggregation results and conjugation results are summarised together in Table 11. It was apparent that the variants C34A+K93C and C34A+E294C had improved aggregation profiles compared to wild type albumin, conjugated to a high percentage with maleimide-PEG2-biotin, and had minimal loss of conjugate following controlled hydrolysis at pH 9.0, 37° C. These variants were selected for further evaluation.

TABLE 11

Thio-albumin variant aggregation screen and conjugation results summary

| Sample Description | Improved aggregation profile | Conjugation efficiency >95% | No losses during controlled hydrolysis | Variant selected |
|---|---|---|---|---|
| WT control | | | | |
| C34A + K93C | ✓ | ✓ | ✓ | ✓ |
| C34A + A226C | ✓ | | | |
| C34A + E230C | ✓ | | | |
| C34A + I271C | ✓ | | | |
| C34A + E294C | ✓ | ✓ | ✓ | ✓ |
| C34A + E358C | | ✓ | ✓ | |

TABLE 12

Summary information for combination variants

| Variant | Number of thiols | Plasmid | Protein SEQ ID NO. |
|---|---|---|---|
| C34A + K93C | 1 | pDB5623 | 111 |
| C34A + E294C | 1 | pDB5624 | 129 |
| C34A + K93C + E294C | 2 | pDB5625 | 141 |
| K93C | 2 | pDB5626 | 142 |
| E294C | 2 | pDB5627 | 143 |
| K93C + E294C | 3 | pDB5628 | 144 |

Example 5. Combination Variants

Method 2.

Combination variants (Table 12) were produced to combine the mutations K93C and E294C described both with and without the HSA C34A mutation. Briefly, plasmids comprising the individual mutations were prepared, and the mutations combined by restriction enzyme digestion and ligation.

1 µl of purified plasmid produced in Method 1 corresponding to the mutations K93C or E294C was transformed into E. coli NEB 5-alpha (New England Biolabs) and plated onto LB plates (as described above) supplemented with 50 µg/mL ampicillin. Plasmids were isolated using a Qiagen Plasmid Plus Kit (Qiagen—according to manufacturer's instructions) and sequenced to confirm the presence of the desired mutation within the HSA sequence. These plasmids were named pDB5623 (C34A+K93C) and pDB5624 (C34A+E294C).

A fragment was removed from plasmid pDB5624 using the NheI and SphI restriction sites and was purified using a QIAquick Gel Extraction Kit (Qiagen) and ligated into pDB5623 digested with the same enzymes to produce construct pDB5625. pDB5626 and pDB5627 were constructed by insertion of the fragment produced by digestion of pDB5102 with SacII and PstI restriction enzymes into similarly digested pDB5623 and pDB5624. pDB5102 is described in WO 2015/036579 (incorporated herein by reference). The ligated plasmids were all transformed into E. coli NEB 5-alpha and plated onto LB plates (as described above) supplemented with 50 µg/mL ampicillin. Plasmids were isolated using a Qiagen Plasmid Plus Kit (Qiagen—according to manufacturer's instructions) and sequenced to confirm the presence of the desired mutation within the HSA sequence.

To produce pDB5628 a fragment was removed from plasmid pDB5102 using the SacII and PstI restriction sites and was purified using a QIAquick Gel Extraction Kit (Qiagen) and ligated into pDB5625 digested with the same enzymes. The ligated plasmids were all transformed into E. coli NEB 5-alpha and plated onto LB plates supplemented with 50 µg/mL ampicillin. Plasmids were isolated using a Qiagen Plasmid Plus Kit (Qiagen—according to manufacturer's instructions) and sequenced to confirm the presence of the desired mutation within the HSA sequence.

Production of Expression Plasmid and Yeast Stocks.

Preparation of the expression plasmids and transformation of S. cerevisiae was performed as described in WO 2012/150319 by the 48-hour stocking method (incorporated herein by reference). The host strain for the constructs was S. cerevisiae BXP10 Cir⁰ (WO 2015/036579, incorporated herein by reference). Purification of variants from shake flask was performed as described in WO 2012/150319 (incorporated herein by reference) unless otherwise stated.

Example 6. Production, Purification and Conjugation of Thio-Albumin Variants

Cryopreserved yeast stocks each in 1 mL aliquots were inoculated into separate shake flasks containing 100 mL BMMS growth medium (yeast nitrogen base without amino acids or $(NH4)_2SO_4$, Difco 1.7 g/L; citric acid monohydrate 6.09 g/L; $Na_2HPO_4 \cdot 2H_2O$ 25.27 g/L; $(NH_4)_2SO_4$ 5.0 g/L; pH 6.5±0.2; sucrose added to 20 g/L). Cells were transferred from the shake flask to the fermenter (10 L working volume, Sartorius Biostat C 10-3 fermenter) when the concentration of cells in the shake flask reached 0.8-1.2 mg/mL achieving a cell inoculum concentration of ≥10 mg/L (greater than or equal to 10 mg/L) in the fermenter.

The thio-albumin variants were produced by axenic culture of each of the yeast strains in high cell density (HCD) fed-batch fermentation. The aim of the fermentation was to achieve maximum biomass and productivity by controlling feed rate addition so that formation of by-products such as ethanol and acetate were avoided. Further details of the fermentation process are described in WO 96/37515 (incorporated herein by reference). The temperature and pH were controlled at 30° C. and pH 6.2 respectively. Culture supernatant was harvested by centrifugation using a Sorvall RC 3C centrifuge (DuPont) to provide materials for immediate purification and the remaining materials were frozen (−20° C.) for storage, before being thawed for subsequent purifications. Final product concentrations were determined by GP-HPLC using a LC2010 HPLC system (Shimadzu) equipped with UV detection under Shimadzu VP7.3 client server software control as described in Example 3. Table 13 provides the yields of each thio-albumin variant (in mg/mL culture supernatant) and shows that high product titres of greater than 1 mg/mL culture supernatant were obtained in all cases.

TABLE 13

Thio-albumin variant protein concentration by GP-HPLC

| Sample Description | Number of thiols | Concentration by GPHPLC (mg/mL) | SEQ ID NO. |
|---|---|---|---|
| C34A + K93C | 1 | 3.1 | 111 |
| C34A + E294C | 1 | 4.6 | 129 |
| C34A + K93C + E294C | 2 | 2.3 | 141 |
| K93C | 2 | 1.8 | 142 |
| E294C | 2 | 3.9 | 143 |
| K93C + E294C | 3 | 1.6 | 144 |

The variants were purified at scale by a two-step chromatography process. The first purification step was using AlbuPure® chromatography as previously described in Example 3 but washing the column with approximately 4 column volumes of 50 mM sodium acetate, pH 5.3, 10 column volumes of 50 mM sodium phosphate, pH 8.0, and 10 column volumes of 50 mM ammonium acetate pH 8.0 respectively. Bound protein was eluted using between 1 and 3 column volumes of 50 mM ammonium acetate, 10 mM sodium octanoate, pH 7.0. The AlbuPure® eluates were then further purified using ion exchange chromatography via DE-FF as described in Evans et al. (2010), Protein Expression and Purification Volume 73, Issue 2, Pages 113-124. Post purification, the DE-FF eluate samples were concentrated and buffer exchanged by ultrafiltration/diafiltration using 10,000 molecular weight cut-off Vivacell 100 centrifugal concentrators (Sartorius). The samples were centrifuged at 2,000×g for 30 minutes (multiple times) to reduce the volume to below 10 mL before diafiltration against 10 volumes of 25 mM sodium phosphate, 215 mM sodium chloride, pH 6.5. Post diafiltration, sample concentrations were in the range of 124 to 177 mg/mL. The samples were diluted to a final formulation concentration of 50 mg/mL in 25 mM sodium phosphate, 215 mM sodium chloride, pH 6.5.

The thio-albumin variants were conjugated with maleimide-PEG2-biotin as described in Example 4, but with a 3.2-fold molar excess of biotin over the free thiol content (number of free thiols). Due to some variants having multiple free thiol sites available for conjugation, the expected molecular weights for all biotin conjugation permutations are summarised in Table 14. The variants with two or three thiol groups increased by 2×525 Da, and 3×525 Da respectively. The relative peak heights of each peak species were used to calculate the percentage of target conjugate, i.e. the correct percentage of a single, double or triple biotin labelled thio-albumin variant. The K93C+E294C variant had a total of 3 free thiol residues, the MS spectrum for this variant is shown in FIG. 7A. It was evident from the single peak species on the MS spectrum that the variant has successfully conjugated 3 moles of maleimide-PEG2-biotin per mole protein, as indicated by a mass increase of 1575 Da (3×525 Da) to 67968 Da (Table 15). The samples were incubated at 37° C., pH 9, for at least 24 hours for controlled hydrolysis to occur to determine the stability of the thio ether conjugate bond as previously described in Example 4. The results are summarised in Table 15. The yield of the hydrolysed thiol stable K93C+E294C conjugate was in the order of 20% triple conjugate, due to the competing retro-Michael deconjugation of the C34 conjugate during hydrolysis (FIG. 7B). The main species was now a hydrolysed thiol stable double conjugate with a mass of 67476 Da indicating that hydrolysis had occurred to the double conjugate species. It was evident that the variants containing a cysteine at position C34 had significant deconjugation during hydrolysis compared to the variants with a C34A mutation. The double thiol variant C34A+K93C+E294C was 62% double conjugated pre hydrolysis and 56% post hydrolysis. An observed peak species with a mass 66443 Da confirmed that hydrolysis had occurred with minimal conjugate loss (FIG. 7C) compared to the K93C+E294C conjugate which contained a cysteine at C34 (FIG. 7B) highlighting that the K93C and E294C variants had improved conjugate stability when using a maleimide linker.

TABLE 14

Expected molecular weights post conjugation and hydrolysis

| Sample | No. 1 thiols | Free Mr | Single conjugate Mr | | Double conjugate Mr | | Triple conjugate Mr | |
|---|---|---|---|---|---|---|---|---|
| | | | +biotin (525 Da) | Hydrolysed | +2 × biotin | Hydrolysed | +3 × biotin | Hydrolysed |
| C34A + K93C | 1 | 66382 | 66907 | 66925 | n/a | n/a | n/a | n/a |
| C34A + E294C | 1 | 66381 | 66906 | 66924 | n/a | n/a | n/a | n/a |
| C34A + K93C + E294C | 2 | 66356 | 66881 | 66899 | 67406 | 67442 | n/a | n/a |
| K93C | 2 | 66414 | 66939 | 66957 | 67464 | 67500 | n/a | n/a |
| E294C | 2 | 66413 | 66938 | 66956 | 67463 | 67499 | n/a | n/a |
| K93C + E294C | 3 | 66388 | 66913 | 66931 | 67438 | 67474 | 67963 | 68017 | n/a: not applicable

TABLE 15

Conjugation efficiency and controlled hydrolysis results

| | | Post conjugation | | Post hydrolysis | |
|---|---|---|---|---|---|
| Sample Description | Number of thiols | Conjugate intact mass result (Da) | % target conjugate | Conjugate intact mass result (Da) | % target conjugate |
| C34A + K93C | 1 | 66910 | 68 | 66927 | 70 |
| C34A + E294C | 1 | 66908 | 52 | 66927 | 46 |
| C34A + K93C + E294C | 2 | 67410 | 62 | 67443 | 56 |
| K93C | 2 | 67467 | 99 | 67502 | 36 |
| E294C | 2 | 67467 | 87 | 67501 | 40 |
| K93C + E294C | 3 | 67968 | 98 | 68020 | 20 |

The formulated samples were subjected to a six month stability assessment at 2-8° C. by GPHPLC, using the method described in Example 3. The percentage monomer (in brackets) was determined for each sample relative to its wild type control under the same storage conditions. The percentage monomer results are summarized in Table 16, and indicated that aggregation levels were within acceptable limits when the albumin variants were formulated at 50 mg/mL and stored for six months at 2-8° C.

TABLE 16

GPHPLC protein stability assessment at 50 mg/mL, post storage at 2-8° C.

| | | % Monomer at | | | | | Δ % | Protein |
|---|---|---|---|---|---|---|---|---|
| Sample Description | Number of thiols | T = 0 | T = 1 m | T = 2 m | T = 3 m | T = 6 m | Monomer 0-6 month | SEQ ID NO. |
| WT control | 1 | 93.8 (100) | 94.5 (100) | 94.5 (100) | 94.4 (100) | 94.9 (100) | 1.1 | 2 |
| C34A + K93C | 1 | 92.1 (98) | 91.2 (97) | 90.2 (95) | 89.3 (95) | 88.1 (93) | −4.0 | 111 |
| C34A + E294C | 1 | 92.4 (99) | 92.7 (98) | 91.6 (97) | 91.0 (96) | 90.8 (96) | −1.6 | 129 |
| C34A + K93C + E294C | 2 | 84.4 (90) | 81.8 (87) | 79.7 (84) | 78.4 (83) | 75.9 (80) | −8.5 | 141 |
| K93C | 2 | 88.2 (94) | 86.9 (92) | 85.5 (91) | 84.9 (90) | 84.2 (89) | −4.0 | 142 |
| E294C | 2 | 89.3 (95) | 90.2 (95) | 89.7 (95) | 89.0 (94) | 88.9 (94) | −0.4 | 143 |
| K93C + E294C | 3 | 82.1 (88) | 79.8 (84) | 78.4 (83) | 77.3 (82) | 76.8 (81) | −5.3 | 144 | m = month

Example 7. Combination Variants Having Altered FcRn Binding

HSA having the K573P substitution, as described in WO 2011/051489 (incorporated herein by reference), has a higher affinity for FcRn than does wild type HSA. Constructs were produced to combine the mutations in the variants described in Table 12 with the HSA K573P mutation from plasmid pDB4673.
Method 3.

A fragment was removed from plasmids pDB5623, 5624, 5625, 5626, 5627 and 5628 using the PstI and XhoI restriction sites and was purified using a QIAquick Gel Extraction Kit (Qiagen) and ligated into pDB4673 digested with the same enzymes to produce constructs pDB5704, 5707, 5710, 5713, 5716 and 5719 (Table 17). The ligated plasmids were all transformed into *E. coli* NEB 5-alpha (New England Biolabs) and plated onto LB plates supplemented with 50 µg/mL ampicillin. Plasmids were isolated using a Qiagen Plasmid Plus Kit (Qiagen—according to manufacturer's instructions) and sequenced to confirm the presence of the desired mutations within the HSA sequence.

TABLE 17

Summary information for variants having altered FcRn binding

| Variant | Plasmid | Protein SEQ ID NO. |
|---|---|---|
| K573P | pDB4673 | 145 |
| C34A + K93C + K573P | pDB5704 | 146 |
| C34A + E294C + K573P | pDB5707 | 147 |
| C34A + K93C + E294C + K573P | pDB5710 | 148 |
| K93C + K573P | pDB5713 | 149 |
| E294C + K573P | pDB5716 | 150 |
| K93C + E294C + K573P | pDB5719 | 151 |

Production of Expression Plasmid and Yeast Stocks.
Preparation of the expression plasmids and transformation of *S. cerevisiae* was performed as described in WO 2012/150319 by the 48-hour stocking method (incorporated herein by reference). The host strain for the constructs was S. cerevisiae BXP10 Cir⁰ (WO 2015/036579, incorporated herein by reference)). Purification of variants from shake flask was performed as described in WO 2012/150319 (incorporated herein by reference) unless otherwise stated.

Example 8. Aggregation Screening of Combination Variants Having Altered FcRn Binding Shake flask culturing of S. cerevisiae and purification was performed as described in Example 3. A single step Albu-Pure chromatography procedure was used to prepare purified material from 6 variants as described in Example 3. Post purification the 20 mL eluates were concentrated to less than 200 μL using Vivaspin centrifugal concentrators as described in Example 4. Post concentration the samples were buffer exchanged by the addition of 10 ml of 25 mM sodium phosphate, 215 mM sodium chloride, pH 6.5 and the samples centrifuged as before. The final volumes recovered were between 75 μL and 200 μL. The concentration and percentage monomer of the eluate samples was determined by Gel Permeation High Pressure Liquid Chromatography (GP-HPLC) as described in Example 3. The results are summarised in Table 18. Final product concentrations were in the range of 47 to 154 mg/mL. A typical wild type albumin control in Example 4 resulted in a monomer percentage of 87% at 1.1 mg/ml (Table 8A). All variants analysed had monomer percentages equal to or greater than 87% even at significantly higher protein concentrations. This indicated that all variants had minimal propensity to aggregate.

TABLE 18

GPHPLC aggregation screening results

| Sample description | GPHPLC monomer concentration (mg/mL) | % Monomer at T = 0 |
|---|---|---|
| C34A + K93C + K573P | 48.2 | 91.8 |
| C34A + E294C + K573P | 153.5 | 90.8 |
| C34A + K93C + E294C + K573P | 98.8 | 88.4 |
| K93C + K573P | 101.7 | 86.9 |
| E294C + K573P | 115.5 | 87.6 |
| K93C + E294C + K573P | 46.5 | 91.2 |

Example 9. Conjugation Efficiency and Controlled Hydrolysis of Combination Variants Having Altered FcRn Binding The thio-albumin combination variants (Table 17) were conjugated with a 3.2 fold excess of maleimide-PEG2-biotin as described in Example 6. Due to some variants having multiple free thiol sites available for conjugation, the expected molecular weights for all biotin conjugation permutations are summarised in Table 19.

TABLE 19

Expected molecular weights of albumin variants post conjugation and hydrolysis

| Sample | No. thiols | Free Mr | Single conjugate Mr | | Double conjugate Mr | | Triple conjugate Mr | |
|---|---|---|---|---|---|---|---|---|
| | | | +biotin (525 Da) | Hydrolysed | +2 × biotin | Hydrolysed | +3 × biotin | Hydrolysed |
| C34A + K93C + K573P | 1 | 66351 | 66876 | 66894 | n/a | n/a | n/a | n/a |
| C34A + E294C + K573P | 1 | 66350 | 66875 | 66893 | n/a | n/a | n/a | n/a |
| C34A + K93C + E294C + 573P | 2 | 66325 | 66850 | 66868 | 67375 | 67411 | n/a | n/a |
| K93C + K573P | 2 | 66383 | 66908 | 66926 | 67433 | 67469 | n/a | n/a |
| E294C + K573P | 2 | 66382 | 66907 | 66925 | 67432 | 67468 | n/a | n/a |
| K93C + E294C + K573P | 3 | 66357 | 66882 | 66900 | 67407 | 67443 | 67932 | 67986 | n/a: not applicable

The molecular weight of the variants with two or three thiol groups increased by 2×525 Da, and 3×525 Da respectively. The relative peak heights of each peak species were used to calculate the percentage of target conjugate, i.e. the percentage of a single, double or triple biotin labelled thio-albumin variant. The K93C+E294C+K573P variant had a total of 3 free thiol residues (the third thiol being provided by native Cys34); the MS spectrum for this variant is shown in FIG. 8A. It was evident from the single peak species on the MS spectrum that the variant has successfully conjugated with 3 moles of maleimide-PEG2-biotin per mole protein, as indicated by a mass increase of 1575 Da (3×525 Da) to 67940.8 Da. The samples were incubated at 37° C., pH 9, for at least 18 hours for controlled hydrolysis to occur to determine the stability of the thio ether conjugate bond as previously described in Example 4. The results are summarized in Table 20.

The yield of the hydrolysed thiol stable K93C+E294C+K573P conjugate was in the order of 23% triple conjugate, likely due to the competing retro-Michael deconjugation of the C34 conjugate during hydrolysis (FIG. 8B). The main species was now a hydrolysed thiol stable double conjugate with a mass of 67447.3 Da indicating that hydrolysis had occurred to this double conjugate species. It was evident that the variants containing a cysteine at position C34 underwent more pronounced deconjugation during hydrolysis compared to the variants with a C34A mutation.

TABLE 20

Conjugation efficiency and controlled hydrolysis results

| | | Post conjugation | | Post hydrolysis | |
|---|---|---|---|---|---|
| Sample Description | Number of thiols | Conjugate intact mass result (Da) | % target conjugate | Conjugate intact mass result (Da) | % target conjugate |
| C34A + K93C + K573P | 1 | 66878 | 100 | 66896 | 100 |
| C34A + E294C + K573P | 1 | 66880 | 85 | 66897 | 89 |
| C34A + K93C + E294C + K573P | 2 | 67382 | 90 | * | * |
| K93C + K573P | 2 | 67438 | 100 | 67473 | 32 |
| E294C + K573P | 2 | 67441 | 100 | 67474 | 25 |
| K93C + E294C + K573P | 3 | 67941 | 100 | 67989 | 23 |

* low intensity MS spectrum, unable to accurately quantify data phosphate, 215 mM sodium chloride, pH 6.5 using 10,000 molecular weight cut-off Centramate Tangential Flow Filtration Membrane cassettes (PALL) before final formulation at 20 mg/ml in buffer (25 mM sodium phosphate, 215 mM sodium chloride, pH 6.5). Subsequently, a size exclusion chromatography step (Sephacryl® S200, GE Healthcare) was performed. For each sample 25 mL was split equally between two Vivaspin 20 centrifugal concentrators and centrifuged at 4,500×g for two 20 minute time periods to reduce the total volume to 5 mL. The concentrated material was loaded onto a 483 mL S200 column and the monomer peak collected to generate monomeric protein at greater than 98% for FcRn binding analysis by SPR. Post purification, eluates were diluted to 5 mg/ml (±5%). The binding affinity of each variant for the human FcRn receptor was determined both pre and post conjugation with maleimide-PEG2-biotin. Variants were conjugated with a 3.2 fold excess of maleimide-PEG2-biotin as described in Example 6. The percentage conjugation was determined by MS as described in Example 2, but using a 15 minute analytical gradient, and processing data for the protein peak between approximately 7 and 10 minutes. The results are shown in Table 21 and indicated all samples had conjugated to varying extent, depending on the number of thiols.

Example 10. Surface Plasmon Resonance (SPR) Analysis of Combination Variants Having Altered FcRn Binding, Pre and Post Conjugation with Maleimide-PEG2-Biotin Thio-albumin combination variants detailed in Tables 12 and 17 were produced by fed-batch fermentation and purified according to Example 6. Post purification, the samples were concentrated and the buffer was exchanged against a minimum of 7 continuous volumes of 25 mM sodium

TABLE 21

Conjugation efficiency for samples for SPR

| Sample Description | Number of thiols | Unconjugated % | Mono-conjugate % | Di-conjugate % | Tri-conjugate % | Protein SEQ ID NO. |
|---|---|---|---|---|---|---|
| WT control | 1 | 0 | 100 | n/a | n/a | 2 |
| C34A + K93C | 1 | 0 | 100 | n/a | n/a | 111 |
| C34A + E294C | 1 | 74 | 26 | n/a | n/a | 129 |
| C34A + K93C + E294C | 2 | 0 | 74 | 26 | n/a | 141 |
| K93C | 2 | 0 | 26 | 74 | n/a | 142 |
| E294C | 2 | 0 | 81 | 19 | n/a | 143 |
| K93C + E294C | 3 | 0 | 0 | 80 | 20 | 144 |
| K573P | 1 | 8 | 93 | n/a | n/a | 145 |
| C34A + K93C + K573P | 1 | 0 | 100 | n/a | n/a | 146 |
| C34A + E294C + K573P | 1 | 20 | 80 | n/a | n/a | 147 |
| C34A + K93C + E294C + K573P | 2 | 0 | 10 | 90 | n/a | 148 |
| K93C + K573P | 2 | 0 | 0 | 100 | n/a | 149 |

TABLE 21-continued

Conjugation efficiency for samples for SPR

| Sample Description | Number of thiols | Unconjugated % | Mono-conjugate % | Di-conjugate % | Tri-conjugate % | Protein SEQ ID NO. |
|---|---|---|---|---|---|---|
| E294C + K573P | 2 | 0 | 18 | 82 | n/a | 150 |
| K93C + E294C + K573P | 3 | 0 | 0 | 40 | 60 | 151 | n/a: not applicable

SPR analyses were carried out using a Biacore 3000 instrument (GE Healthcare). Flow cells of CM5 sensor chips were coupled with soluble human FcRn (1200-1600 RU) using amine coupling chemistry as described in the protocol provided by the manufacturer (GE Healthcare). The coupling was performed by injecting 5 µg/mL of the protein in 10 mM sodium acetate pH 4.5 (GE healthcare). Phosphate buffer (67 mM phosphate buffer, 0.15 M NaCl, 0.005% Tween 20) at pH 5.5 was used as running buffer and dilution buffer. Regeneration of the surfaces were performed using injections of HBS-EP buffer (0.01 M HEPES, 0.15 M NaCl, 3 mM EDTA, 0.005% surfactant P20) at pH 7.4 (GE Healthcare). Post immobilisation, the chip was left to stabilise with a constant flow (5 µL/min) of running buffer. Chip surface was conditioned by injecting 3× injections of running buffer followed by 3× injections of regeneration buffer. Surfaces were checked for activity with native sequence HSA control. For determination of binding kinetics, serial dilutions of albumin variants (10-0 µM) were injected over immobilized receptor at a constant flow rate (30 µL/min) at 25° C. In all analyses, data were zero adjusted and the reference cell subtracted. Data evaluations were performed using BIAevaluation 4.1 software (BIAcore AB). The results pre and post conjugation are shown in Tables 22 and 23 respectively.

The thio-albumin variants screened over human FcRn bound to the receptor in a reversible, pH-dependent manner.

The thio-albumin variants in a wild type background (i.e. the only amino acid alterations were those that were introduced to affect the number of conjugatable cysteine residues) gave a similar fold increase in binding affinity to FcRn compared to the wild type control (SEQ ID NO: 2) both pre and post conjugation. The thio-albumin variants which also included a K573P mutation (to increase the affinity of the albumin variant to FcRn) maintained their increase in FcRn affinity, compared to the K573P control (SEQ ID NO: 145), pre and post conjugation indicating that neither the change in conjugatable cysteine residues nor the conjugation partner had an observable influence on the binding affinity of the albumin variant to FcRn.

TABLE 22

FcRn affinity for variants pre conjugation

| Sample Description | Number of thiols | Ka ($10^3$/Ms) | Kd ($10^3$/Ms) | KD (µM) | Fold > WT | Protein SEQ ID NO. |
|---|---|---|---|---|---|---|
| WT control | 1 | 7.38 | 54.0 | 7.32 | n/a | 2 |
| C34A + K93C | 1 | 12.4 | 44.9 | 3.62 | 2.02 | 111 |
| C34A + E294C | 1 | 6.13 | 46.7 | 7.61 | 0.96 | 129 |
| C34A + K93C + E294C | 2 | 10.41 | 39.5 | 3.79 | 1.93 | 141 |
| K93C | 2 | 8.19 | 43.45 | 5.30 | 1.38 | 142 |
| E294C | 2 | 5.0 | 46.3 | 9.25 | 0.79 | 143 |
| K93C + E294C | 3 | 7.65 | 37.9 | 4.95 | 1.48 | 144 |
| K573P | 1 | 5.70 | 3.76 | 0.66 | 11.10 | 145 |
| C34A + K93C + K573P | 1 | 8.06 | 3.83 | 0.48 | 15.25 | 146 |
| C34A + E294C + K573P | 1 | 6.07 | 3.96 | 0.65 | 11.26 | 147 |
| C34A + K93C + E294C + K573P | 2 | 8.11 | 3.67 | 0.45 | 16.27 | 148 |
| K93C + K573P | 2 | 8.37 | 4.07 | 0.48 | 15.25 | 149 |
| E294C + K573P | 2 | 5.65 | 4.17 | 0.74 | 9.89 | 150 |
| K93C + E294C + K573P | 3 | 6.8 | 3.82 | 0.56 | 13.07 | 151 | n/a: not applicable
Fold > WT = KD (µM) WT control/KD (µM) variant

TABLE 23

FcRn affinity for samples post conjugation with maleimide-PEG2-biotin

| Sample Description | Number of thiols | Ka ($10^3$/Ms) | Kd ($10^3$/Ms) | KD (µM) | Fold > WT | Protein SEQ ID NO. |
|---|---|---|---|---|---|---|
| WT control | 1 | 9.26 | 25.4 | 2.74 | n/a | 2 |
| C34A + K93C | 1 | 12.95 | 19.85 | 1.53 | 1.79 | 111 |
| C34A + E294C | 1 | 8.07 | 20.15 | 2.50 | 1.09 | 129 |
| C34A + K93C + E294C | 2 | 11.55 | 17.4 | 1.51 | 1.80 | 141 |
| K93C | 2 | 10.2 | 21.0 | 2.06 | 1.33 | 142 |
| E294C | 2 | 9.38 | 19.9 | 2.12 | 1.29 | 143 |
| K93C + E294C | 3 | 11.8 | 19.3 | 1.63 | 1.68 | 144 |
| K573P | 1 | 9.25 | 3.12 | 0.337 | 8.13 | 145 |
| C34A + K93C + K573P | 1 | 14.35 | 2.97 | 0.207 | 13.24 | 146 |

TABLE 23-continued

FcRn affinity for samples post conjugation with maleimide-PEG2-biotin

| Sample Description | Number of thiols | Ka (10³/Ms) | Kd (10³/Ms) | KD (μM) | Fold > WT | Protein SEQ ID NO. |
|---|---|---|---|---|---|---|
| C34A + E294C + K573P | 1 | 10.42 | 2.97 | 0.285 | 9.61 | 147 |
| C34A + K93C + E294C + K573P | 2 | 13.7 | 2.71 | 0.198 | 13.84 | 148 |
| K93C + K573P | 2 | 13.7 | 2.93 | 0.214 | 12.80 | 149 |
| E294C + K573P | 2 | 11.4 | 3.22 | 0.283 | 9.68 | 150 |
| K93C + E294C + K573P | 3 | 13.05 | 3.31 | 0.254 | 10.79 | 151 | n/a: not applicable
Fold > WT = KD (μM) WT control/KD (μM) variant

Example 11. Aggregation Analysis of Combination Variants Having Altered FcRn Binding The thio-albumin combination variants formulated at 5 mg/ml in Example 10 were analysed for their tendency to remain as a monomer in solution. WT HSA, the variant K573P and the variant C34A+L302C were prepared as described in Example 10 and included as controls. The free thiol content for each variant was determined at T=0 and following 3 months storage at 5° ° C. by mass spectrometric analysis of protein sample treated with DTNB reagent, similar to the method of Example 2. For this example, 80 μL of each variant sample was diluted with 920 μL of buffer 1 (100 mM Tris-HCl, 10 mM EDTA, pH 8.0). To each variant sample, 50 μL of buffer 2 (4 mg/mL DTNB, 500 mM sodium phosphate, pH 7.0) was added. The resultant preparation incubated for at least 25 minutes at ambient temperature (20±5° C.) to allow TNB labelling. Post incubation, the samples were subjected to mass spectrometry to determine the intact protein mass post conjugation as per the method described in Example 2, but using a 15 minute analytical gradient, and processing data for the protein peak between approximately 7 and 10 minutes. The results are summarised in Table 24A and Table 24B. An increase in mass of 197 Da upon DTNB incubation is indicative of the presence of one free thiol group on the protein in the sample. An increase of 394 Da and 591 Da is indicative of two or three free thiol groups respectively. All samples had high levels of free thiol at the start of the stability study, and the majority maintained a high free thiol level following 3 months storage at 5° C.

TABLE 24A

Mass Spectrometry DTNB free thiol results

| Sample Description | Number of thiols | Unconjugated % | Mono-conjugate % | Di-conjugate % | Tri-conjugate % | Protein SEQ ID NO. |
|---|---|---|---|---|---|---|
| WT control | 1 | 0 | 91 | 0 | 9 | 2 |
| C34A + L302C | 1 | 0 | 100 | 0 | 0 | 152 |
| C34A + K93C | 1 | 0 | 91 | 0 | 9 | 111 |
| C34A + E294C | 1 | 6 | 94 | 0 | 0 | 129 |
| C34A + K93C + E294C | 2 | 0 | 39 | 61 | 0 | 141 |
| K93C | 2 | 16 | 0 | 84 | 0 | 142 |
| E294C | 2 | 0 | 28 | 84 | 0 | 143 |
| K93C + E294C | 3 | 0 | 0 | 51 | 49 | 144 |
| K573P | 1 | 0 | 91 | 0 | 9 | 145 |
| C34A + K93C + K573P | 1 | 0 | 93 | 0 | 7 | 146 |
| C34A + E294C + K573P | 1 | 7 | 87 | 0 | 6 | 147 |
| C34A + K93C + E294C + K573P | 2 | 0 | 5 | 89 | 0 | 148 |
| K93C + K573P | 2 | 0 | 0 | 92 | 0 | 149 |
| E294C + K573P | 2 | 0 | 7 | 87 | 0 | 150 |
| K93C + E294C + K573P | 3 | 0 | 0 | 22 | 78 | 151 |

TABLE 24B

Mass Spectrometry DTNB free thiol results, post storage at 5° C.

| Sample Description | Number of thiols | Unconjugated % | Mono-conjugate % | Di-conjugate % | Tri-conjugate % | Protein SEQ ID NO. |
|---|---|---|---|---|---|---|
| WT control | 1 | 0 | 94 | 6 | 0 | 2 |
| C34A + L302C | 1 | 0 | 100 | 0 | 0 | 152 |
| C34A + K93C | 1 | 0 | 95 | 0 | 5 | 111 |
| C34A + E294C | 1 | 55 | 45 | 0 | 0 | 129 |
| C34A + K93C + E294C | 2 | 0 | 0 | 54 | 46 | 0 | 141 |
| K93C | 2 | 23 | 0 | 77 | 0 | 142 |

TABLE 24B-continued

Mass Spectrometry DTNB free thiol results, post storage at 5° C.

| Sample Description | Number of thiols | Unconjugated % | Mono-conjugate % | Di-conjugate % | Tri-conjugate % | Protein SEQ ID NO. |
|---|---|---|---|---|---|---|
| E294C | 2 | 0 | 50 | 50 | 0 | 143 |
| K93C + E294C | 3 | 0 | 0 | 73 | 27 | 144 |
| K573P | 1 | 0 | 94 | 0 | 6 | 145 |
| C34A + K93C + K573P | 1 | 0 | 95 | 0 | 5 | 146 |
| C34A + E294C + K573P | 1 | 14 | 86 | 0 | 0 | 147 |
| C34A + K93C + E294C + K573P | 2 | 0 | 10 | 90 | 0 | 148 |
| K93C + K573P | 2 | 0 | 0 | 94 | 0 | 149 |
| E294C + K573P | 2 | 0 | 13 | 87 | 0 | 150 |
| K93C + E294C + K573P | 3 | 0 | 0 | 32 | 68 | 151 |

Samples were stored for 3 months at 5° C. and 40° C. and the aggregation profile determined at various time points by GPHPLC as described in Example 3. The percentage monomer (in brackets) was determined for each sample relative to its wild type control under the same storage conditions. The results for 5° C. and 40° C. are provided in Tables 25 and 26 respectively. All variants had a monomer greater than 98% at T=0. The majority of thio-albumin variants maintained a monomeric protein percentage equal to or greater than 97% during 3 month's storage at 5° C. Relative to the other variants analysed, variant C34A+L302C was more prone to aggregation. It was also evident that the majority of thio-albumin variants maintained a monomeric protein percentage equal to or greater than 80% during 3 months storage at 40° C., even those containing two or three thiol residues. However, it was evident that variant C34A+L302C was more prone to aggregation with a monomer percentage of 73.2% following 3 months storage at 40° C.

TABLE 25

GPHPLC protein stability assessment at 5 mg/mL, post storage at 5° C.

| Sample Description | Number of thiols | T = 0 | T = 1 month | T = 2 month | T = 3 month | Protein SEQ ID NO. |
|---|---|---|---|---|---|---|
| WT control | 1 | 99.8 (100) | 99.3 (100) | 99.7 (100) | 99.7 (100) | 2 |
| C34A + L302C | 1 | 98.3 (99) | 95.5 (96) | 94.9 (95) | 95.0 (95) | 152 |
| C34A + K93C | 1 | 99.5 (100) | 99.2 (100) | 98.9 (99) | 98.7 (99) | 111 |
| C34A + E294C | 1 | 99.5 (100) | 99.4 (100) | 99.2 (100) | 99.2 (100) | 129 |
| C34A + K93C + E294C | 2 | 99.1 (99) | 98.5 (99) | 97.9 (98) | 97.5 (98) | 141 |
| K93C | 2 | 99.5 (100) | 99.3 (100) | 99.0 (99) | 98.8 (99) | 142 |
| E294C | 2 | 99.6 (100) | 99.4 (100) | 99.2 (100) | 99.1 (99) | 143 |
| K93C + E294C | 3 | 99.2 (99) | 98.8 (100) | 98.3 (99) | 97.9 (98) | 144 |
| K573P | 1 | 99.7 (100) | 99.7 (100) | 99.6 (100) | 98.5 (99) | 145 |
| C34A + K93C + K573P | 1 | 99.6 (100) | 99.2 (100) | 99.0 (99) | 98.6 (99) | 146 |
| C34A + E294C + K573P | 1 | 99.4 (100) | 99.1 (100) | 98.8 (99) | 98.5 (99) | 147 |
| C34A + K93C + E294C + K573P | 2 | 99.3 (100) | 98.5 (99) | 97.7 (98) | 96.9 (97) | 148 |
| K93C + K573P | 2 | 99.8 (100) | 99.7 (100) | 99.6 (100) | 98.5 (100) | 149 |
| E294C + K573P | 2 | 99.7 (100) | 98.9 (99) | 99.0 (99) | 98.8 (99) | 150 |
| K93C + E294C + K573P | 3 | 99.5 (100) | 99.1 (100) | 98.8 (99) | 98.5 (99) | 151 |

TABLE 26

GPHPLC protein stability assessment at 5 mg/mL, post storage at 40° C.

| Sample Description | Number of thiols | T = 0 | T = 0.5 month | T = 1 month | T = 2 month | T = 3 month | Protein SEQ ID NO. |
|---|---|---|---|---|---|---|---|
| WT control | 1 | 99.8 (100) | 99.4 (100) | 99.3 (100) | 99.0 (100) | 97.6 (100) | 2 |
| C34A + L302C | 1 | 98.3 (99) | 87.6 (88) | 80.9 (82) | 75.6 (76) | 73.2 (75) | 152 |
| C34A + K93C | 1 | 99.5 (100) | 96.1 (97) | 93.4 (94) | 90.3 (91) | 86.6 (89) | 111 |
| C34A + E294C | 1 | 99.5 (100) | 98.6 (99) | 96.6 (97) | 96.0 (97) | 95.4 (98) | 129 |
| C34A + K93C + E294C | 2 | 99.1 (99) | 93.8 (94) | 89.3 (90) | 85.1 (86) | 80.4 (82) | 141 |
| K93C | 2 | 99.5 (100) | 96.6 (97) | 94.5 (95) | 90.4 (91) | 88.8 (91) | 142 |
| E294C | 2 | 99.6 (100) | 98.1 (99) | 95.7 (96) | 95.1 (96) | 94.2 (97) | 143 |
| K93C + E294C | 3 | 99.2 (99) | 93.9 (95) | 89.3 (90) | 82.9 (84) | 80.0 (82) | 144 |
| K573P | 1 | 99.7 (100) | 99.3 (100) | 99.0 (100) | 98.7 (100) | 97.4 (100) | 145 |
| C34A + K93C + K573P | 1 | 99.6 (100) | 95.5 (96) | 93.0 (94) | 89.5 (90) | 86.5 (89) | 146 |
| C34A + E294C + K573P | 1 | 99.4 | 97.3 | 95.9 | 95.0 | 94.4 | 147 |

TABLE 26-continued

GPHPLC protein stability assessment at 5 mg/mL, post storage at 40° C.

| | | % Monomer at | | | | Protein |
|---|---|---|---|---|---|---|
| Sample Description | Number of thiols | T = 0 | T = 0.5 month | T = 1 month | T = 2 month | T = 3 month | SEQ ID NO. |
| E294C + K573P | | (100) | (98) | (97) | (96) | (97) | |
| C34A + K93C + E294C + K573P | 2 | 99.3 (100) | 91.8 (92) | 88.3 (89) | 82.7 (84) | 80.9 (83) | 148 |
| K93C + K573P | 2 | 99.8 (100) | 98.1 (99) | 96.7 (97) | 94.5 (96) | 92.6 (95) | 149 |
| E294C + K573P | 2 | 99.7 (100) | 97.5 (98) | 95.8 (97) | 94.5 (96) | 94.4 (97) | 150 |
| K93C + E294C + K573P | 3 | 99.5 (100) | 94.9 (96) | 92.0 (93) | 88.7 (90) | 84.1 (86) | 151 |

Example 12. Conjugation of Combination Variants Having Altered FcRn Binding, with Fluorescent Probes Thio-albumin combination variants formulated at 5 mg/mL in Example 10, following 6 weeks storage at 2-8° C., were conjugated using a 3-fold excess of Alexa Fluor® 488-PEG4-Lys(monobromomaleimide)-NH2 dye (FIG. 9A) or 5-carboxyfluorescein-PEG4-Lys(monobromomaleimide)-NH2 dye (FIG. 10A) (Almac Group Ltd., UK, custom synthesis). Variants were diluted with PBS buffer, pH 7.4 to give 1 mL solutions at 1 mg/ml (15.05 nmol). A 1 mg/mL stock solution of Alexa Fluor® 488-PEG4-Lys(monobromomaleimide)-NH2 dye was prepared by reconstituting 1.6 mg material with 1.6 mL PBS buffer pH 7.4. From the Alexa Fluor® 488-PEG4-Lys(monobromomaleimide)-NH2 dye stock solution, 51.5 µL (45.15 nmol) was added to the single thiol variants, 103 µL (90.3 nmol) dye stock solution was added to the double thiol variants, and 154.5 µL (135.3 nmol) dye stock solution was added to the triple thiol variants to give a threefold excess of Alexa Fluor® 488-PEG4-Lys(monobromomaleimide)-NH2 dye over the number of free thiols. A 0.5 mg/mL stock solution of 5-carboxyfluorescein-PEG4-Lys(monobromomaleimide)-NH2 dye was prepared by reconstituting 1.7 mg material with 1.7 mL dimethyl sulfoxide (DMSO) and 1.7 mL PBS pH 7.4 buffer. From the 5-carboxyfluorescein-PEG4-Lys(monobromomaleimide)-NH2 dye stock solution 44.3 µL (45.15 nmol) was added to the single thiol variants, 88.6 µL (90.3 nmol) dye stock solution was added to the double thiol variants, and 132.9 µL (135.3 nmol) dye stock solution was added to the triple thiol variants to give a threefold excess of 5-carboxyfluorescein-PEG4-Lys(monobromomaleimide)-NH2 dye over the number of free thiols. Samples were gently mixed and incubated at ambient temperature overnight in the dark. Post incubation the samples were analysed by mass spectrometry to determine the intact protein mass post conjugation as per the MS method described in Example 2, but using a 15 minute analytical gradient, and processing data for the protein peak between approximately 7 and 10 minutes. The results are summarised in Table 27 and Table 28.

The MS spectrum for the altered FcRn binding variant K573P shown in FIG. 9B, exhibited a single species at 67468.5 Da indicating the correct molecular weight for a K573P variant plus a single addition of Alexa Fluor® 488-PEG4-Lys(monobromomaleimide)-NH2 dye (±1058 Da). This confirmed the variant had a single free thiol located at Cys34 available for conjugation. The thio-albumin variant K93C+E294C+K573P shown in FIG. 9C indicated that conjugation had occurred post an overnight incubation, giving approximately 42% diconjugate and 58% triconjugate species respectively, when comparing the relative peak heights of conjugated species. It was evident that the main peak species had increased by approximately 3174 Da (3×1058 Da) to 69536 Da. This indicated the variant had three free thiols available for conjugation.

The MS spectrum for the altered FcRn binding variant K573P shown in FIG. 10B, exhibited a single species at 67310.6 Da indicating the correct molecular weight for a K573P variant plus a single addition of 5-carboxyfluorescein-PEG4-Lys(monobromomaleimide)-NH2 dye (±901 Da). The thio-albumin variant C34A+K93C+E294C+K573P shown in FIG. 10C indicated that conjugation had occurred post an overnight incubation, giving approximately 9% monoconjugate and 91% diconjugate species respectively, when comparing the relative peak heights of conjugated species. It was evident that the main peak species had increased by approximately 1802 Da (2×901 Da) to 68129.7 Da. This indicated the variant had two free thiols available for conjugation.

TABLE 27

Conjugation efficiency results of thio-albumin variants with Alexa Fluor ® 488-PEG4-Lys(monobromomaleimide)-NH2 dye

| Sample Description | Number of thiols | Unconjugated % | Mono-conjugate % | Di-conjugate % | Tri-conjugate % | Protein SEQ ID NO. |
|---|---|---|---|---|---|---|
| WT control | 1 | 0 | 93 | n/a | n/a | 2 |
| C34A + K93C | 1 | 0 | 100 | n/a | n/a | 111 |
| C34A + E294C | 1 | 100 | 0 | n/a | n/a | 129 |
| C34A + K93C + E294C | 2 | * | * | * | n/a | 141 |
| K93C | 2 | 17 | 0 | 83 | n/a | 142 |
| E294C | 2 | 0 | 89 | 11 | n/a | 143 |
| K93C + E294C | 3 | * | * | * | * | 144 |
| K573P | 1 | 0 | 100 | n/a | n/a | 145 |
| C34A + K93C + K573P | 1 | 0 | 100 | n/a | n/a | 146 |
| C34A + E294C + K573P | 1 | 8 | 92 | n/a | n/a | 147 |

TABLE 27-continued

Conjugation efficiency results of thio-albumin variants with Alexa Fluor ® 488-PEG4-Lys(monobromomaleimide)-NH2 dye

| Sample Description | Number of thiols | Unconjugated % | Mono-conjugate % | Di-conjugate % | Tri-conjugate % | Protein SEQ ID NO. |
|---|---|---|---|---|---|---|
| C34A + K93C + E294C + K573P | 2 | 0 | 7 | 93 | n/a | 148 |
| K93C + K573P | 2 | 0 | 0 | 91 | n/a | 149 |
| E294C + K573P | 2 | 0 | 0 | 100 | n/a | 150 |
| K93C + E294C + K573P | 3 | 0 | 0 | 42 | 58 | 151 | n/a: not applicable
*low intensity MS spectrum, unable to accurately quantify data

TABLE 28

Conjugation efficiency results of thio-albumin variants with 5-carboxyfluorescein-PEG4-Lys(Bromomaleimide)-NH2 dye

| Sample Description | Number of thiols | Unconjugated % | Mono-conjugate % | Di-conjugate % | Tri-conjugate % | Protein SEQ ID NO. |
|---|---|---|---|---|---|---|
| WT control | 1 | 0 | 96 | n/a | n/a | 2 |
| C34A + K93C | 1 | 0 | 100 | n/a | n/a | 111 |
| C34A + E294C | 1 | 100 | 0 | n/a | n/a | 129 |
| C34A + K93C + E294C | 2 | * | * | * | n/a | 141 |
| K93C | 2 | 30 | 0 | 70 | n/a | 142 |
| E294C | 2 | * | * | * | n/a | 143 |
| K93C + E294C | 3 | * | * | * |  | 144 |
| K573P | 1 | 0 | 100 | n/a | n/a | 145 |
| C34A + K93C + K573P | 1 | 0 | 100 | n/a | n/a | 146 |
| C34A + E294C + K573P | 1 | 18 | 82 | n/a | n/a | 147 |
| C34A + K93C + E294C + K573P | 2 | 0 | 9 | 91 | n/a | 148 |
| K93C + K573P | 2 | 1 | 0 | 99 | n/a | 149 |
| E294C + K573P | 2 | * | * | * | n/a | 150 |
| K93C + E294C + K573P | 3 | * | * | * | * | 151 | n/a: not applicable
*low intensity MS spectrum, unable to accurately quantify data Example 13. Conjugation of Combination Variants Having Altered FcRn Binding, with Paclitaxel Thio-albumin combination variants formulated at 5 mg/ml in Example 10, following 3 months storage at 2-8° C., were conjugated using a 1.5 fold excess of paclitaxel which was via an ester group activated with a monobromomaleimide moiety, as shown in FIG. 11A, resulting in the molecule monobromomaleimide-paclitaxel (Almac Group Ltd., UK custom synthesis). Variants were diluted with PBS buffer, pH 7.4 to give 1 mL solutions at 1 mg/ml (15.05 nmol). A 2 mg/mL stock solution of monobromomaleimide-paclitaxel was prepared by reconstituting 6.6 mg material with 3.3 mL DMSO. From the monobromomaleimide-paclitaxel stock solution, 12.24 µL (22.58 nmol) was added to the single thiol variants, 24.47 µL (45.15 nmol) stock solution was added to the double thiol variants, and 36.71 µL (67.73 nmol) stock solution was added to the triple thiol variants to give a threefold excess of monobromomaleimide-paclitaxel over the number of free thiols. Samples were gently mixed and incubated at ambient temperature overnight. Post incubation the samples were subjected to mass spectrometry to determine the intact protein mass post conjugation as per the MS method described in Example 2, but using a 15 minute analytical gradient, and processing data for the protein peak between approximately 7 and 10 minutes. The results are summarised in Table 29.

The MS spectrum for the altered FcRn binding variant K573P shown in FIG. 11B indicated that conjugation had occurred post an overnight incubation, giving approximately 77% monoconjugated and 23% unconjugated species respectively, when comparing the relative peak heights of the protein species. It was evident that the main peak species at 67412.2 Da had increased by approximately 1004 Da due to a single addition of monobromomaleimide-paclitaxel. The MS spectrum for the thio-albumin variant K93C+E294C+K573P shown in FIG. 11C indicated that conjugation had occurred post an overnight incubation, giving approximately 6% monoconjugate, approximately 60% diconjugate and 30% triconjugate species respectively, when comparing the relative peak heights of conjugated species. It was evident that the main peak species had increased by approximately 2008 Da (2×1004 Da) to 68364.2 Da, with a 69383.7 Da species indicative of a 3012 Da triple addition.

TABLE 29

Conjugation efficiency results of thio-albumin variants with monobromomaleimide-paclitaxel

| Sample Description | Number of thiols | Unconjugated % | Mono-conjugate % | Di-conjugate % | Tri-conjugate % | Protein SEQ ID NO. |
|---|---|---|---|---|---|---|
| WT control | 1 | 24 | 76 | n/a | n/a | 2 |
| C34A + K93C | 1 | 50 | 50 | n/a | n/a | 111 |
| C34A + E294C | 1 | 100 | 0 | n/a | n/a | 129 |
| C34A + K93C + E294C | 2 | * | * | * | n/a | 141 |
| K93C | 2 | 30 | 26 | 44 | n/a | 142 |
| E294C | 2 | 0 | 100 | 0 | n/a | 143 |
| K93C + E294C | 3 | * | * | * | 0 | 144 |
| K573P | 1 | 23 | 77 | n/a | n/a | 145 |
| C34A + K93C + K573P | 1 | 59 | 41 | n/a | n/a | 146 |
| C34A + E294C + K573P | 1 | 34 | 66 | n/a | n/a | 147 |
| C34A + K93C + E294C + K573P | 2 | 10 | 50 | 40 | n/a | 148 |
| K93C + K573P | 2 | 8 | 40 | 52 | n/a | 149 |
| E294C + K573P | 2 | 0 | 18 | 68 | n/a | 150 |
| K93C + E294C + K573P | 3 | 0 | 6 | 60 | 30 | 151 | n/a: not applicable
*low intensity MS spectrum, unable to accurately quantify data

Example 14. Conjugation of Combination Variants Having Altered FcRn Binding, with Exenatide Peptide Thio-albumin combination variants formulated at 5 mg/ml in Example 10, following 3 months storage at 2-8° C., were conjugated using a 1.5 fold excess of monobromomaleimide-PEG2-exenatide peptide as shown in FIG. 12A (Almac Group Ltd., UK, custom synthesis). Variants were diluted with PBS buffer, pH 7.4 to give 1 mL solutions at 1 mg/ml (15.05 nmol). A 5 mg/mL stock solution of mono-bromomaleimide-PEG2-exenatide peptide was prepared by reconstituting 5 mg material with 1 mL PBS buffer pH 7.4. From the monobromomaleimide-PEG2-exenatide peptide stock solution, 21.17 μL (22.58 nmol) was added to the single thiol variants, 42.35 μL (45.15 nmol) peptide stock solution was added to the double thiol variants, and 63.52 μL (67.73 nmol) peptide stock solution was added to the triple thiol variants to give a threefold excess of monobromomaleimide-PEG2-exenatide peptide over the number of free thiols. Samples were gently mixed and incubated at ambient temperature overnight. Post incubation the samples were subjected to mass spectrometry to determine the intact protein mass post conjugation as per the MS method described in Example 2, but using a 15 minute analytical gradient, and processing data for the protein peak between approximately 7 and 10 minutes. The results are summarised in Table 30.

The MS spectrum for the altered FcRn binding variant K573P shown in FIG. 12B indicated that conjugation had occurred post an overnight incubation, giving approximately 33% monoconjugate and 67% unconjugated species respectively, when comparing the relative peak heights of protein species. It was evident that the main peak species at 66409.2 Da was unconjugated K573P variant. The second species had increased by approximately 4609 Da due to a single addition of monobromomaleimide-PEG2-exenatide peptide. The thio-albumin variant C34A+K93C+E294C+K573P shown in FIG. 12C indicated that conjugation had occurred post an overnight incubation, giving approximately 33% diconjugate species, approximately 45% monoconjugate species, and approximately 22% unconjugated species respectively, when comparing the relative peak heights of protein species. It was evident that the main peak species had increased by approximately 4609 Da to 70941.7 Da, with a 75557.3 Da species indicative of a 9218 Da addition representing a double conjugation of monobromomaleimide-PEG2-exenatide peptide.

TABLE 30

Conjugation efficiency results of thio-albumin variants with exenatide peptide

| Sample Description | Number of thiols | Unconjugated % | Mono-conjugate % | Di-conjugate % | Tri-conjugate % | Protein SEQ ID NO. |
|---|---|---|---|---|---|---|
| WT control | 1 | 71 | 29 | n/a | n/a | 2 |
| C34A + K93C | 1 | 74 | 26 | n/a | n/a | 111 |
| C34A + E294C | 1 | 100 | 0 | n/a | n/a | 129 |
| C34A + K93C + E294C | 2 | * | * | * | n/a | 141 |
| K93C | 2 | 79 | 0 | 21 | n/a | 142 |
| E294C | 2 | * | * | * | n/a | 143 |
| K93C + E294C | 3 | * | * | * | * | 144 |

TABLE 30-continued

Conjugation efficiency results of thio-albumin variants with exenatide peptide

| Sample Description | Number of thiols | Unconjugated % | Mono-conjugate % | Di-conjugate % | Tri-conjugate % | Protein SEQ ID NO. |
|---|---|---|---|---|---|---|
| K573P | 1 | 67 | 33 | n/a | n/a | 145 |
| C34A + K93C + K573P | 1 | 74 | 26 | n/a | n/a | 146 |
| C34A + E294C + K573P | 1 | 51 | 49 | n/a | n/a | 147 |
| C34A + K93C + E294C + K573P | 2 | 22 | 45 | 33 | n/a | 148 |
| K93C + K573P | 2 | 60 | 0 | 39 | n/a | 149 |
| E294C + K573P | 2 | 21 | 33 | 47 | n/a | 150 |
| K93C + E294C + K573P | 3 | * | * | * | * | 151 | n/a: not applicable
*low intensity MS spectrum, unable to accurately quantify data Example 15. Conjugation of Combination Variants Having Altered FcRn Binding Affinity, with FLAG Peptide Thio-albumin combination variants formulated at 5 mg/mL in Example 10, following 3 months storage at 2-8° C., were conjugated using a 1.5 fold excess of maleimide-propyl-FLAG peptide as shown in FIG. 13A (Peptide Protein Research Ltd., UK, custom synthesis). Variants were diluted with PBS buffer, pH 7.4 to give 1 mL solutions at 1 mg/ml (15.05 nmol). A 1 mg/mL stock solution of maleimide-propyl-FLAG peptide was prepared by reconstituting 5.4 mg material with 5.4 mL PBS buffer pH 7.4. From the maleimide-propyl-FLAG peptide stock solution, 26.28 μL (22.58 nmol) was added to the single thiol variants, 52.56 μL (45.15 nmol) peptide stock solution was added to the double thiol variants, and 78.84 μL (67.73 nmol) peptide stock solution was added to the triple thiol variants to give a threefold excess of maleimide-propyl-FLAG peptide over the number of free thiols. Samples were gently mixed and incubated at ambient temperature overnight. Post incubation the samples were subjected to mass spectrometry to determine the intact protein mass post conjugation as per the MS method described in Example 2 but using a 15 minute analytical gradient, and processing data for the protein peak between approximately 7 and 10 minutes. The results are summarised in Table 31.

The MS spectrum for the altered FcRn binding variant K573P shown in FIG. 13B indicated that conjugation had occurred post an overnight incubation, giving approximately 29% monoconjugate and 71% unconjugated species respectively, when comparing the relative peak heights of protein species. It was evident that the main peak species at 66409.1 Da was unconjugated K573P variant. The second most abundant peak species had increased by approximately 1164 Da due to a single addition of maleimide-propyl-FLAG peptide. The MS spectrum for the thio-albumin variant K93C+E294C+K573P shown in FIG. 13C indicated that conjugation had occurred post an overnight incubation, giving approximately 29% triconjugate species, approximately 50% diconjugate species, approximately 20% monoconjugate species, and approximately 2% unconjugated species respectively, when comparing the relative peak heights of the protein species. It was evident that the main peak species had increased by approximately 2328 Da to 68685.5 Da, with a 69850.5 Da species indicative of a 3492 Da addition representing a triple conjugation of maleimide-propyl-FLAG peptide.

TABLE 31

Conjugation efficiency results of albumin variants with FLAG peptide

| Sample Description | Number of thiols | Unconjugated % | Mono-conjugate % | Di-conjugate % | Tri-conjugate % | Protein SEQ ID NO. |
|---|---|---|---|---|---|---|
| WT control | 1 | 73 | 27 | n/a | n/a | 2 |
| C34A + K93C | 1 | 48 | 52 | n/a | n/a | 111 |
| C34A + E294C | 1 | 80 | 20 | n/a | n/a | 129 |
| C34A + K93C + E294C | 2 | 12 | 77 | 10 | n/a | 141 |
| K93C | 2 | 45 | 30 | 25 | n/a | 142 |
| E294C | 2 | 26 | 63 | 11 | n/a | 143 |
| K93C + E294C | 3 | * | * | * | * | 144 |
| K573P | 1 | 71 | 29 | n/a | n/a | 145 |
| C34A + K93C + K573P | 1 | 47 | 53 | n/a | n/a | 146 |
| C34A + E294C + K573P | 1 | 22 | 78 | n/a | n/a | 147 |
| C34A + K93C + E294C + K573P | 2 | 5 | 34 | 61 | n/a | 148 |

TABLE 31-continued

Conjugation efficiency results of albumin variants with FLAG peptide

| Sample Description | Number of thiols | Unconjugated % | Mono-conjugate % | Di-conjugate % | Tri-conjugate % | Protein SEQ ID NO. |
|---|---|---|---|---|---|---|
| K93C + K573P | 2 | 23 | 50 | 27 | n/a | 149 |
| E294C + K573P | 2 | 10 | 51 | 39 | n/a | 150 |
| K93C + E294C + K573P | 3 | 2 | 20 | 50 | 29 | 151 | n/a: not applicable
*low intensity MS spectrum, unable to accurately quantify data Example 16. Immunogenicity Assessment of Thio-Albumin Variants Using EpiScreen™ Time Course T Cell Assay Thio-albumin variants K93C (SEQ ID NO: 142) and E294C (SEQ ID NO: 143) were prepared as described in Example 10 along with a wild type albumin control (SEQ ID NO: 2). In contrast to Example 10, the size exclusion chromatography eluates were diluted to 4 mg/ml (±5%). Albumin test samples were assessed for their ability to induce CD4+ T cell responses using the EpiScreen™ time course T cell assay (Abzena, Cambridge UK). Briefly, the EpiScreen™ assay was carried out as follows: peripheral blood mononuclear cells from a cohort of 50 healthy donors representing the European and North American population (based on HLA allotypes) were incubated with the test samples. T cell responses were measured using proliferation assays ([3H]-Thymidine uptake) and cytokine secretion assays (IL-2 ELISpot).

The frequency of positive responses in the proliferation assay were low for all samples (ranges from 0% to 8%) and no positive responses were observed in the IL-2 ELISpot assay suggesting a low risk of clinical immunogenicity for all three samples.

The invention claimed is:

1. A conjugation-competent polypeptide comprising an amino acid sequence which is at least 90% identical to a human albumin having a sequence as set forth in SEQ ID NO: 2, or a fragment thereof, and comprising a substitution to cysteine at:

i) a position equivalent to K93 of SEQ ID NO: 2; and
ii) a position equivalent to E294, E227, or A362 of SEQ ID NO: 2.

2. The conjugation-competent polypeptide of claim 1, wherein at a position equivalent to position 34 of SEQ ID NO: 2 there is a conjugation-competent cysteine.

3. The conjugation-competent polypeptide of claim 1, wherein at a position equivalent to position 34 of SEQ ID NO: 2 there is not a conjugation-competent cysteine.

4. The conjugation-competent polypeptide of claim 1, in which the polypeptide has at least 98% sequence identity to SEQ ID NO: 2.

5. A method for increasing the plasma half-life of a molecule selected from the group consisting of a bioactive agent, imaging agent, diagnostic agent, contrast agent, and therapeutic compound, the method comprising conjugating, fusing or associating the molecule with a conjugation-competent polypeptide according to claim 1.

6. A fusion polypeptide comprising a conjugation-competent polypeptide of claim 1 and a fusion partner polypeptide.

7. A conjugate comprising:
(i) a bioactive agent, imaging agent, diagnostic agent, contrast agent or therapeutic compound; and
(ii) the polypeptide according to claim 1,
wherein the bioactive agent, imaging agent, diagnostic agent, contrast agent, or therapeutic compound is linked to the polypeptide through a conjugation-competent cysteine residue of the polypeptide.

8. The conjugate of claim 7, further comprising one or more additional molecules, wherein the additional molecule is a bioactive agent, imaging agent, diagnostic agent, contrast agent or therapeutic compound, each of the one or more additional molecules being linked to the polypeptide through a conjugation-competent cysteine residue of the polypeptide.

9. A composition comprising the conjugate of claim 7, and at least one pharmaceutically acceptable carriers or diluents.

10. The conjugate of claim 7, wherein the bioactive agent, imaging agent, diagnostic agent, contrast agent or therapeutic compound is selected from:
(i) therapeutic compounds comprising 4-1BB ligand, 5-helix, A human C-C chemokine, A human L105 chemokine, A human L105 chemokine designated huL105_3, A monokine induced by gamma-interferon (MIG), A partial CXCR4B protein, A platelet basic protein (PBP), al-antitrypsin, ACRP-30 Homologue, Complement Component C1q C, Adenoid-expressed chemokine (ADEC), aFGF, FGF-1, AGF Protein, albumin, an etoposide, angiostatin, Anthrax vaccine, Antibodies specific for collapsin, antistasin, Anti-TGF beta family antibodies, antithrombin III, APM-1, ACRP-30, Famoxin, apo-lipoprotein species, Arylsulfatase B, b57 Protein, BCMA, Beta-thromboglobulin protein (beta-TG), bFGF, FGF2, Blood coagulation factors, BMP Processing Enzyme Furin, BMP-10, BMP-12, BMP-15, BMP-17, BMP-18, BMP-2B, BMP-4, BMP-5, BMP-6, BMP-9, Bone Morphogenic Protein-2, calcitonin, Calpain-10a, Calpain-10b, Calpain-10c, Cancer Vaccine, Carboxypeptidase, C-C chemokine, MCP2, CCR5 variant, CCR7, CCR7, CD11a Mab, CD137, 4-1BB Receptor Protein, CD20 Mab, CD27, CD27L, CD30, CD30 ligand, CD33 immunotoxin, CD40, CD40L, CD52 Mab, Cerebus Protein, Chemokine Eotaxin, Chemokine hIL-8, Chemokine hMCP1, Chemokine hMCP1a, Chemokine hMCP1b, Chemokine hMCP2, Chemokine hMCP3, Chemokine hSDF1b, Chemokine MCP-4, chemokine TECK and TECK variant, Chemokine-like protein IL-8M1 Full-Length and Mature, Chemokine-like protein IL-8M10 Full-Length and Mature, Chemokine-like protein IL-8M3, Chemokine-like protein IL-8M8 Full-Length and Mature, Chemokine-like protein IL-8M9 Full-Length and Mature, Chemokine-like protein PF4-414 Full-Length and Mature, Chemokine-like protein PF4-426 Full-Length and Mature, Chemokine-like protein PF4-M2 Full-Length and Mature, Cholera vaccine, Chondromodulin-like protein, c-kit ligand, SCF, Mast cell growth factor, MGF, Fibrosarcoma-derived stem cell factor, CNTF, coagulation factors in both pre and active forms, collagens, Complement C5 Mab, Connective tissue activating protein-III, CTAA16.88 Mab, CTAP-III, CTLA4-Ig, CTLA-8, CXC3, CXC chemokine receptor 3, cyanovirin-N, Darbepoetin, designated exodus, designated huL105_7, DIL-40, Dnase, EDAR, EGF Receptor Mab, ENA-78, Endostatin, Eotaxin, Epithelial neutrophil activating protein-78, EPO receptor, EPOR, erythropoietin (EPO) and EPO mimics, Eutropin, Exodus protein, Factor IX, Factor VII, Factor VIII, Factor X and Factor XIII, FAS Ligand Inhibitory Protein, DcR3, FasL, FGF, FGF-12, Fibroblast growth factor homologous factor-1, FGF-15, FGF-16, FGF-18, FGF-3, INT-2, FGF-4, gelonin, HST-1, HBGF-4, FGF-5, FGF-6, Heparin binding secreted transforming factor-2, FGF-8, FGF-9, Glia activating factor, fibrinogen, flt-1, flt-3 ligand, Follicle stimulating hormone Alpha subunit, Follicle stimulating hormone Beta subunit, Follitropin, Fractalkine, myofibrillar protein Troponin I, FSH, Galactosidase, Galectin-4, G-CSF, GDF-1, Gene therapy, Glioma-derived growth factor, glucagon, glucagon-like peptides, Glucocerebrosidase, glucose oxidase, Glucosidase, Glycodelin-A, Progesterone-associated endometrial protein, GM-CSF, gonadotropin, Granulocyte chemotactic protein-2 (GCP-2), Granulocyte-macrophage colony stimulating factor, growth hormone, Growth related oncogene-alpha (GRO-alpha), Growth related oncogene-beta (GRO-beta), Growth related oncogene-gamma (GRO-gamma), hAPO-4, TROY, hCG, Hepatitus B surface Antigen, Hepatitis B Vaccine, HER2 Receptor Mab, hirudin, HIV gp120, HIV gp41, HIV Inhibitor Peptide, HIV Inhibitor Peptide, HIV Inhibitor Peptide, HIV protease inhibiting peptides, HIV-1 protease inhibitors, HPV vaccine, Human 6CKine protein, Human Act-2 protein, Human adipogenesis inhibitory factor, human B cell stimulating factor-2 receptor, Human beta-chemokine H1305 (MCP-2), Human C-C chemokine DGWCC, Human CC chemokine ELC protein, Human CC type chemokine interleukin C, Human CCC3 protein, Human CCF18 chemokine, Human CC-type chemokine protein designated SLC (secondary lymphoid chemokine), Human chemokine beta-8 short forms, Human chemokine C10, Human chemokine CC-2, Human chemokine CC-3, Human chemokine CCR-2, Human chemokine Ckbeta-7, Human chemokine ENA-78, Human chemokine eotaxin, Human chemokine GRO alpha, Human chemokine GROalpha, Human chemokine GRObeta, Human chemokine HCC-1, Human chemokine HCC-1, Human chemokine I-309, Human chemokine IP-10, Human chemokine L105_3, Human chemokine L105_7, Human chemokine MIG, Human chemokine MIG-beta protein, Human chemokine MIP-1alpha, Human chemokine MIP 1beta, Human chemokine MIP-3alpha, Human chemokine MIP-3beta, Human chemokine PF4, Human chemokine protein 331D5, Human chemokine protein 61164, Human chemokine receptor CXCR3, Human chemokine SDF 1alpha, Human chemokine SDF1beta, Human chemokine ZSIG-35, Human Chr19Kine protein, Human CKbeta-9, Human CX3C 111 amino acid chemokine, Human DNAX interleukin-40, Human DVic-1 C-C chemokine, Human EDIRF I protein sequence, Human EDIRF II protein sequence, Human eosinocyte CC type chemokine eotaxin, Human eosinophil-expressed chemokine (EEC), Human fast twitch skeletal muscle troponin C, Human fast twitch skeletal muscle troponin I, Human fast twitch skeletal muscle Troponin subunit C, Human fast twitch skeletal muscle Troponin subunit I Protein, Human fast twitch skeletal muscle Troponin subunit T, Human fast twitch skeletal muscle troponin T, Human foetal spleen expressed chemokine, FSEC, Human GM-CSF receptor, Human gro-alpha chemokine, Human gro-beta chemokine, Human gro-gamma chemokine, Human IL-16 protein, Human IL-1RD10 protein sequence, Human IL-1RD9, Human IL-5 receptor alpha chain, Human IL-6 receptor, Human IL-8 receptor protein hIL8RA, Human IL-8 receptor protein hIL8RB, Human IL-9 receptor protein, Human IL-9 receptor protein variant #3, Human IL-9 receptor protein variant fragment, Human IL-9 receptor protein variant fragment #3, Human interleukin 1 delta, Human interleukin 10, Human interleukin 18, Human interleukin 18 derivatives, Human interleukin-1 beta precursor, Human interleukin-1 beta precursor, Human interleukin-1 receptor accessory protein, Human inter-leukin-1 receptor antagonist beta, Human interleukin-1 type-3 receptor, Human interleukin-10 (precursor), Human interleukin-11 receptor, Human interleukin-12 40 kD subunit, Human interleukin-12 beta-1 receptor, Human interleukin-12 beta-2 receptor, Human inter-leukin-12 p35 protein, Human interleukin-12 p40 protein, Human interleukin-12 receptor, Human inter-leukin-13 alpha receptor, Human interleukin-13 beta receptor, Human interleukin-15, Human interleukin-15 receptor from clone P1, Human interleukin-17 receptor, Human interleukin-18 protein (IL-18), Human inter-leukin-3, human interleukin-3 receptor, Human inter-leukin-3 variant, Human interleukin-4 receptor, Human interleukin-5, Human interleukin-6, Human inter-leukin-7, Human interleukin-7, Human interleukin-8 (IL-8), Human intracellular IL-1 receptor antagonist, Human IP-10 and HIV-1 gp 120 hypervariable region fusion protein, Human IP-10 and human Muc-1 core epitope (VNT) fusion protein, human liver and activation regulated chemokine (LARC), Human Lkn-1 Full-Length and Mature protein, Human mammary associated chemokine (MACK) protein Full-Length and Mature, Human mature chemokine Ckbeta-7, Human mature gro-alpha, Human mature gro-gamma polypeptide used to treat sepsis, Human MCP-3 and human Muc-1 core epitope (VNT) fusion protein, Human Ml10 protein, Human Ml1A protein, Human monocyte chemoattractant factor hMCP-1, Human monocyte chemoattractant factor hMCP-3, Human monocyte chemotactic proprotein (MCPP) sequence, Human neurotactin chemokine like domain, Human non-ELR CXC chemokine H174, Human non-ELR CXC chemokine IP10, Human non-ELR CXC chemokine Mig, Human PAI-1 mutants, Human protein with IL-16 activity, Human protein with IL-16 activity, Human secondary lymphoid chemokine (SLC), Human SISD protein, Human STCP-1, Human stromal cell-derived chemokine, SDF-1, Human T cell mixed lymphocyte reaction expressed chemokine (TMEC), Human thymus and activation regulated cytokine (TARC), Human thymus expressed, Human TNF-alpha, Human TNF-beta (LT-alpha), Human type CC chemokine eotaxin 3 protein sequence, Human type II interleukin-1 receptor, Human wild-type interleukin-4 (hIL-4) protein, Human ZCHEMO-8 protein, Humanized Anti-VEGF Antibodies, and fragments thereof, Humanized Anti-VEGF Antibodies, and fragments thereof, Hyaluronidase, ICE 10 kD subunit, ICE 20 kD subunit, ICE 22 kD subunit, Iduronate-2-sulfatase, Iduronidase, IL-1 alpha, IL-1 beta, IL-1 inhibitor (IL-1i), IL-1 mature, IL-10 receptor, IL-11, IL-11, IL-12 p40 subunit, IL-13, IL-14, IL-15, IL-15 receptor, IL-17, IL-17 receptor, receptor, IL-19, IL-1i fragments, IL1-receptor antagonist, IL-21 (TIF), IL-3 containing fusion protein, IL-3 mutant proteins, IL-3 variants, IL-4, IL-4 muteins, IL-4 mutein Y124G, IL-4 mutein Y124X, IL-5, IL-5 muteins, Il-5 receptor, IL-6, Il-6 receptor, IL-7 receptor clone, IL-8 receptor, IL-9 mature protein variant (Met117 version), immunoglobulins or immunoglobulin-based molecules or fragment of either, including but not limited to plasminogen, Influenza Vaccine, Inhibin alpha, Inhibin beta, insulin, insulin-like growth factor, Integrin Mab, inter-alpha trypsin inhibitor, inter-alpha trypsin inhibitor, Interferon gamma-inducible protein (IP-10), interferons, interleukin 6, interleukin 8 (IL-8) receptor, interleukin 8 receptor B, interleukin-1alpha, interleukin-2 receptor associated protein p43, interleukin-3, interleukin-4 muteins, interleukin-8 (IL-8) protein, interleukin-9, interleukin-9 (IL-9) mature protein (Thr117 version), interleukins, Japanese encephalitis vaccine, Kalikrein Inhibitor, Keratinocyte growth factor, Kunitz domain protein, LACI, lactoferrin, Latent TGF-beta binding protein II, leptin, Liver expressed chemokine-1 (LVEC-1), Liver expressed chemokine-2 (LVEC-2), LT-alpha, LT-beta, Luteinization Hormone, Lyme Vaccine, Lymphotactin, Macrophage derived chemokine analogue MDC (n+1), Macrophage derived chemokine analogue MDC-eyfy, Macrophage derived chemokine analogue MDC-yl, Macrophage-derived chemokine (MDC), Maspin, Protease Inhibitor 5, MCP-1 receptor, MCP-1a, MCP-1b, MCP-3, MCP-4 receptor, M-CSF, Melanoma inhibiting protein, Membrane-bound proteins, Met117 human interleukin 9, MIP-3 alpha, MIP-3 beta, MIP-Gamma, MIRAP, Modified Rantes, monoclonal antibody, MP52, Mutant interleukin 6 S176R, myofibrillar contractile protein Troponin I, Natriuretic Peptide, Nerve Growth Factor-beta, Nerve Growth Factor-beta2, Neuropilin-1, Neuropilin-2, Neurotactin, Neurotrophin-3, Neurotrophin-4, Neurotrophin-4a, Neurotrophin-4b, Neurotrophin-4c, Neurotrophin-4d, Neutrophil activating peptide-2 (NAP-2), NOGO-66 Receptor, NOGO-A, NOGO-B, NOGO-C, Novel beta-chemokine designated PTEC, N-terminal modified chemokine GroHEK/hSDF-1alpha, N-terminal modified chemokine GroHEK/hSDF-1beta, N-terminal modified chemokine met-hSDF-1 alpha, N-terminal modified chemokine met-hSDF-1 beta, OPGL, Osteogenic Protein-1 (OP-1), BMP-7, Osteogenic Protein-2, OX40, ACT-4, OX40L, Oxytocin (Neurophysin I), parathyroid hormone, Patched, Patched-2, PDGF-D, Pertussis toxoid, Pituitary expressed chemokine (PGEC), Placental Growth Factor, Placental Growth Factor-2, Plasminogen Activator Inhibitor-1 (PAI-1), Plasminogen Activator Inhibitor-2 (PAI-2), Platelet derived growth factor, Platelet derived growth factor Bv-sis, Platelet derived growth factor precursor A, Platelet derived growth factor precursor B, Platelet Mab, platelet-derived endothelial cell growth factor (PD-ECGF), Platelet-Derived Growth Factor A chain, Platelet-Derived Growth Factor B chain, polypeptide used to treat sepsis, Preproapolipoprotein "milano" variant, Preproapolipoprotein "paris" variant, pre-thrombin, Primate CC chemokine "ILINCK", Primate CXC chemokine "IBICK", proinsulin, Prolactin, Prolactin2, prosaptide, Protease inhibitor peptides, Protein C, Protein S, pro-thrombin, prourokinase, RANTES, RANTES 8-68, RANTES 9-68, RANTES peptide, RANTES receptor, Recombinant interleukin-16, Resistin, restrictocin, Retroviral protease inhibitors, ricin, Rotavirus Vaccine, RSV Mab, saporin, sarcin, Secreted and Transmembrane polypeptides, serum cholinesterase, serum protein, Soluble BMP Receptor Kinase Protein-3, Soluble VEGF Receptor, Stem Cell Inhibitory Factor, Straphylococcus Vaccine, Stromal Derived Factor-1 alpha, Stromal Derived Factor-1 beta, Substance P (tachykinin), T1249 peptide, T20 peptide, T4 Endonuclease, TACI, Tarc, TGF-beta 1, TGF-beta 2, Thr117 human interleukin 9, thrombin, thrombopoietin, thrombopoietin derivative 1, thrombopoietin derivative 2, thrombopoietin derivative 3, thrombopoietin derivative 4, thrombopoietin derivative 5, thrombopoietin derivative 6, thrombopoietin derivative 7, Thymus expressed chemokine (TECK), Thyroid stimulating Hormone, tick anticoagulant peptide, Tim-1 protein, TNF-alpha precursor, TNF-R, TNF-RII, TNF p75 Receptor, Death Receptor, tissue plasminogen activator (tPA), transferrin, transforming growth factor beta, Troponin peptides, Truncated monocyte chemotactic protein 2 (6-76), Truncated RANTES protein (3-68), tumour necrosis factor, Urate Oxidase, urokinase, Vasopressin (Neurophysin II), VEGF R-3, flt-4, VEGF Receptor, KDR, flk-1, VEGF-110, VEGF-121, VEGF-138, VEGF-145, VEGF-162, VEGF-165, VEGF-182, VEGF-189, VEGF-206, VEGF-D, VEGF-E, VEGF-X, von Willebrand's factor, Wild type monocyte chemotactic protein 2, or ZTGF-beta 9;

(ii) chemotherapy drugs comprising 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Actinomycin-D, Aldesleukin, Alemtuzumab, ALIMTA, Alitretinoin, All-transretinoic Acid, Alpha Interferon, Altretamine, Amethopterin, Amifostine, Aminoglutethimide, Anagrelide, Anastrozole, Arabinosylcytosine, Ara-C, Arsenic Trioxide, Asparaginase, ATRA, Azacitidine, BCG, BCNU, Bevacizumab, Bexarotene, Bicalutamide, BiCNU, Bleomycin, Bortezomib, Busulfan, C225, Calcium Leucovorin, Camptothecin-11, Capecitabine, Carboplatin, Carmustine, Carmustine Wafer, CC-5013, CCNU, CDDP, CeeNU, Cetuximab, Chlorambucil, Cisplatin, Citrovorum Factor, Cladribine, Cortisone, CPT-11, Cyclophosphamide, Cytarabine, Cytarabine LiposomalDacarbazine, Dacogen, Dactinomycin, Darbepoetin Alfa, Dasatinib, Daunomycin, Daunorubicin, Daunorubicin Hydrochloride, Daunorubicin Liposomal, Decadron, Decitabine, Denileukin diftitox, Dexamethasone, Dexamethasone acetate, Dexamethasone Sodium Phosphate, Dexasone, Dexrazoxane, DHAD, DIC, Diodex, Docetaxel, Doxorubicin, Doxorubicin liposomal, DTIC, Epirubicin, Epoetin alfa, Erlotinib, *Erwinia* L-asparaginase, Estramustine, Ethyol, Etoposide, Etoposide Phosphate, Exemestane, Filgrastim, Floxuridine, Fludarabine, Fluorouracil, Fluoxymesterone, Flutamide, Folinic Acid, Fulvestrant, G-CSF, Gefitinib, Gemcitabine, Gemtuzumab ozogamicin, GM-CSF, Goserelin, Granulocyte-Colony Stimulating Factor, Granulocyte Macrophage Colony Stimulating Factor, Hexadrol, Hexamethylmelamine, HMM, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idarubicin, IFN-alpha, Ifosfamide, IL-11, IL-2, Imatinib mesylate, Imidazole Carboxamide, Interferon alfa, Interferon Alfa-2b (PEG Conjugate), interleukin-2, interleukin-11, interferon alfa-2b, Irinotecan, Isotretinoin, Lapatinib, L-asparaginase, LCR, Lenalidomide, Letrozole, Leucovorin, Leukeran, Leuprolide, Leurocristine, Liposomal Ara-C, Lomustine, L-PAM, L-Sarcolysin, Maxidex, Mechlorethamine, Mechlorethamine Hydrochloride, Megestrol, Megestrol Acetate, Melphalan, Mercaptopurine, Mesna, Methotrexate, Methotrexate Sodium, Methylprednisolone, Mitomycin, Mitomycin-C, Mitoxantrone, MTC, MTX, Mustine, Nelarabine, Nilutamide, Nitrogen Mustard, Octreotide, Octreotide acetate, Oprevelkin, Oxaliplatin, Paclitaxel, Paclitaxel Protein-bound, Pamidronate, Panitumumab, PEG Interferon, Pegaspargase, Pegfilgrastim, PEG-L-asparaginase, PEMETREXED, Pentostatin, Phenylalanine Mustard, Prednisolone, Prednisone, Procarbazine, Prolifeprospan 20 with Carmustine Implant, Raloxifene, Rituximab, Interferon Alfa-2a, Rubidomycin hydrochloride, Sargramostim, Sorafenib, STI-571, Streptozocin, SU11248, Sunitinib, Tamoxifen, Temozolomide, Teniposide, TESPA, Thalidomide, Thioguanine, Thiophosphoamide, Thiotepa, Topotecan, Toremifene, Tositumomab, Trastuzumab, Tretinoin, TSPA, VCR, Vinblastine, Vinblastine Sulfate, Vincasar Vincristine, Vinorelbine, Vinorelbine tartrate, VLB, VM-26, Vorinostat, VP-16, Zoledronic acid, Zolinza, or;

(iii) radiopharmaceuticals comprising Carbon-11, Carbon-14, Chromium-51, Cobalt-57, Cobalt-58, Erbium-169, Fluorine-18, Gallium-67, Gold-198, Indium-111, Indium-113m, Iodine-123, Iodine-125, Iodine-131, Iron-59, Krypton-81m, Nitrogen-13, Oxygen-15, Phosphorous-32, Rhenium-186, Rubidium-82, Samarium-153, Selenium-75, Strontium-89, Technetium-99m, Thallium-201, Tritium, Xenon-127, or Xenon-133, Yttrium-90, and (iv) imaging agents comprising Gadolinium, magnetite, manganese, technetium, I125, I131, P32, Tl201, Iopamidol, or PET-FDG.

11. The conjugation-competent polypeptide of claim 1, wherein the conjugation competent polypeptide comprises a substitution to cysteine at i) a position equivalent to K93 of SEQ ID NO: 2 and ii) a position equivalent to E294 of SEQ ID NO: 2.

12. The conjugation-competent polypeptide of claim 1, wherein the conjugation competent polypeptide comprises a substitution to cysteine at i) a position equivalent to K93 of SEQ ID NO: 2 and ii) a position equivalent to E227 of SEQ ID NO: 2.

13. The conjugation-competent polypeptide of claim 1, wherein the conjugation competent polypeptide comprises a substitution to cysteine at i) a position equivalent to K93 of SEQ ID NO: 2 and ii) a position equivalent to A362 of SEQ ID NO: 2.

14. The conjugation-competent polypeptide of claim 1, wherein the conjugation competent polypeptide comprises a substitution to cysteine at i) a position equivalent to K93 of SEQ ID NO: 2, ii) a position equivalent to E294 of SEQ ID NO: 2, and iii) a position equivalent to E227 of SEQ ID NO: 2.

15. The conjugation-competent polypeptide of claim 1, wherein the conjugation competent polypeptide comprises a substitution to cysteine at i) a position equivalent to K93 of SEQ ID NO: 2, ii) a position equivalent to E294 of SEQ ID NO: 2, and iii) a position equivalent to A362 of SEQ ID NO: 2.

16. The conjugation-competent polypeptide of claim 1, wherein the conjugation competent polypeptide comprises a substitution to cysteine at i) a position equivalent to K93 of SEQ ID NO: 2, ii) a position equivalent to E227 of SEQ ID NO: 2, and iii) a position equivalent to A362 of SEQ ID NO: 2.

17. The conjugation-competent polypeptide of claim 1, wherein the conjugation competent polypeptide comprises a substitution to cysteine at i) a position equivalent to K293 of SEQ ID NO: 2, ii) a position equivalent to E294 of SEQ ID NO: 2, iii) a position equivalent to E227 of SEQ ID NO: 2, and iv) a position equivalent to A362 of SEQ ID NO: 2.

* * * * *

UNITED STATES PATENT AND TRADEMARK OFFICE
CERTIFICATE OF CORRECTION

PATENT NO. : 12,116,400 B2
APPLICATION NO. : 17/656728
DATED : October 15, 2024
INVENTOR(S) : Karen Ann Delahay et al.

It is certified that error appears in the above-identified patent and that said Letters Patent is hereby corrected as shown below:

On the Title Page

In Applicant, Column 1, Line 1, delete "SATORIUS ALBUMEDIX" and insert -- SARTORIUS ALBUMEDIX --.

In the Specification

Column 3, Line 44, delete "E230, 1271, E358," and insert -- E230, I271, E358, --.

Column 3, Line 58, delete "E230, 1271, E358," and insert -- E230, I271, E358, --.

Column 22, Line 50, delete "E230, 1271, E358," and insert -- E230, I271, E358, --.

Column 23, Line 6, delete "E230, 1271, and" and insert -- E230, I271, and --.

Column 23, Line 24, delete "E230, 1271, E358," and insert -- E230, I271, E358, --.

Column 23, Line 53, delete "E230, 1271, E358," and insert -- E230, I271, E358, --.

Column 23, Line 62, delete "E230, 1271, E358," and insert -- E230, I271, E358, --.

Column 24, Line 6, delete "E230, 1271, E358," and insert -- E230, I271, E358, --.

Column 24, Line 13, delete "E230, 1271, and" and insert -- E230, I271, and --.

Column 24, Line 18, delete "E230, 1271, E358," and insert -- E230, I271, E358, --.

Column 24, Line 24, delete "E230, 1271, E358," and insert -- E230, I271, E358, --.

Signed and Sealed this
Eleventh Day of March, 2025

Coke Morgan Stewart
*Acting Director of the United States Patent and Trademark Office*

CERTIFICATE OF CORRECTION (continued)
U.S. Pat. No. 12,116,400 B2

Column 26, Line 52, delete "E230, 1271, E358," and insert -- E230, I271, E358, --.

Column 26, Line 64, delete "E230, 1271, E358," and insert -- E230, I271, E358, --.

Column 27, Line 27, delete "E230, 1271 and" and insert -- E230, I271 and --.

Column 27, Line 29, delete "E230, 1271, or" and insert -- E230, I271, or --.

Column 27, Line 30, delete "E230, 1271, or" and insert -- E230, I271, or --.

Column 27, Line 31, delete "E230, 1271, or" and insert -- E230, I271, or --.

Column 27, Line 31, delete "A226, 1271, or" and insert -- A226, I271, or --.

Column 27, Line 33, delete "E230, 1271, or" and insert -- E230, I271, or --.

Column 27, Line 38, delete "Q268, 1271, L275," and insert -- Q268, I271, L275, --.

Column 27, Line 43, delete "Q268, 1271, L275," and insert -- Q268, I271, L275, --.

Column 27, Line 47, delete "Q268, 1271, L275," and insert -- Q268, I271, L275, --.

Column 27, Line 51, delete "Q268, 1271, L275," and insert -- Q268, I271, L275, --.

Column 27, Line 55, delete "Q268, 1271, L275," and insert -- Q268, I271, L275, --.

Column 27, Line 59, delete "Q268, 1271, L275," and insert -- Q268, I271, L275, --.

Column 27, Line 63, delete "Q268, 1271, L275," and insert -- Q268, I271, L275, --.

Column 27, Line 67, delete "Q268, 1271, L275," and insert -- Q268, I271, L275, --.

Column 28, Line 4, delete "Q268, 1271, L275," and insert -- Q268, I271, L275, --.

Column 28, Line 8, delete "Q268, 1271, L275," and insert -- Q268, I271, L275, --.

Column 28, Line 12, delete "Q268, 1271, L275," and insert -- Q268, I271, L275, --.

Column 28, Line 16, delete "Q268, 1271, L275," and insert -- Q268, I271, L275, --.

Column 28, Line 20, delete "Q268, 1271, L275," and insert -- Q268, I271, L275, --.

Column 28, Line 24, delete "Q268, 1271, L275," and insert -- Q268, I271, L275, --.

Column 28, Line 28, delete "Q268, 1271, L275," and insert -- Q268, I271, L275, --.

CERTIFICATE OF CORRECTION (continued)
U.S. Pat. No. 12,116,400 B2

Column 28, Line 32, delete "Q268, 1271, L275," and insert -- Q268, I271, L275, --.

Column 28, Line 36, delete "Q268, 1271, L275," and insert -- Q268, I271, L275, --.

Column 28, Line 40, delete "N267, 1271, L275," and insert -- N267, I271, L275, --.

Column 28, Line 44, delete "Q268, 1271, E277," and insert -- Q268, I271, E277, --.

Column 28, Line 48, delete "Q268, 1271, L275," and insert -- Q268, I271, L275, --.

Column 28, Line 52, delete "Q268, 1271, L275," and insert -- Q268, I271, L275, --.

Column 28, Line 56, delete "Q268, 1271, L275," and insert -- Q268, I271, L275, --.

Column 28, Line 60, delete "Q268, 1271, L275," and insert -- Q268, I271, L275, --.

Column 28, Line 64, delete "Q268, 1271, L275," and insert -- Q268, I271, L275, --.

Column 29, Line 1, delete "Q268, 1271, L275," and insert -- Q268, I271, L275, --.

Column 29, Line 5, delete "Q268, 1271, L275," and insert -- Q268, I271, L275, --.

Column 29, Line 9 (approx.), delete "Q268, 1271, L275," and insert -- Q268, I271, L275, --.

Column 29, Line 14 (approx.), delete "Q268, 1271, L275," and insert -- Q268, I271, L275, --.

Column 29, Line 18 (approx.), delete "Q268, 1271, L275," and insert -- Q268, I271, L275, --.

Column 29, Line 22 (approx.), delete "Q268, 1271, L275," and insert -- Q268, I271, L275, --.

Column 29, Line 26, delete "Q268, 1271, L275," and insert -- Q268, I271, L275, --.

Column 29, Line 30 (approx.), delete "Q268, 1271, L275," and insert -- Q268, I271, L275, --.

Column 29, Line 34 (approx.), delete "Q268, 1271, L275," and insert -- Q268, I271, L275, --.

Column 29, Line 39, delete "Q268, 1271, L275," and insert -- Q268, I271, L275, --.

Column 29, Line 43, delete "Q268, 1271, L275," and insert -- Q268, I271, L275, --.

Column 29, Line 51, delete "Q268, 1271, L275," and insert -- Q268, I271, L275, --.

Column 40, Line 42, delete "E230, 1271, E358," and insert -- E230, I271, E358, --.

Column 43, Line 25, delete "20-0.032UM" and insert -- 20-0.032 µM --.

CERTIFICATE OF CORRECTION (continued) Page 4 of 5
U.S. Pat. No. 12,116,400 B2

Column 44, Line 63, delete "T420A, V4241, E505" and insert -- T420A, V424I, E505 --.

Column 45, Line 17, delete "E383G, E3831, E383L," and insert -- E383G, E383I, E383L, --.

Column 45, Line 18, delete "K402G, K4021, K402L," and insert -- K402G, K402I, K402L, --.

Column 45, Line 27, delete "F509C, F5091, F509L," and insert -- F509C, F509I, F509L, --.

Column 45, Line 35, delete "K525G, K5251, K525L," and insert -- K525G, K525I, K525L, --.

Column 45, Line 37, delete "E531G, E5311, E531L," and insert -- E531G, E531I, E531L, --.

Column 45, Line 39, delete "K538Y, A5391, A539L," and insert -- K538Y, A539I, A539L, --.

Column 45, Line 40, delete "K557G, K5571, K557L," and insert -- K557G, K557I, K557L, --.

Column 45, Line 42, delete "V415T, V4241, V424Q," and insert -- V415T, V424I, V424Q, --.

Column 45, Line 55, delete "459; (I) residues" and insert -- 459; (l) residues --.

Column 46, Line 43, delete "preferably A5391, L" and insert -- preferably A539I, L --.

Column 57, Line 66, delete "technetium, 1125, 1131, P32," and insert -- technetium, I125, I131, P32, --.

Column 58, Line 14 (approx.), delete "E230, 1271, E358," and insert -- E230, I271, E358, --.

Column 63, Line 19, delete "900 g·L 1," and insert -- 900 g·L$^{-1}$, --.

Column 70, Line 53, delete "E230, 1271, E358," and insert -- E230, I271, E358, --.

Column 71, Line 4, delete "E230, 1271, E358" and insert -- E230, I271, E358 --.

Column 71, Line 14 (approx.), delete "E230, 1271, E358" and insert -- E230, I271, E358 --.

Column 71, Line 23 (approx.), delete "E230, 1271, E358" and insert -- E230, I271, E358 --.

Column 72, Line 26, delete "E230, 1271, E358" and insert -- E230, I271, E358 --.

Column 73, Line 20, delete "E230, 1271, E358" and insert -- E230, I271, E358 --.

Column 74, Line 21, delete "D1; (I) E86" and insert -- D1; (l) E86 --.

Column 74, Line 22, delete "(0) S270" and insert -- (o) S270 --.

Column 76, Line 38, delete "preferably A5391, L" and insert -- preferably A539I, L --.

CERTIFICATE OF CORRECTION (continued)
U.S. Pat. No. 12,116,400 B2

Column 78, Line 43, delete "E230, 1271, E358" and insert -- E230, I271, E358 --.

Column 79, Line 53, delete "EDTA PH 7.5" and insert -- EDTA pH 7.5 --.

Column 80, Line 17, delete "EDTA PH 7.5" and insert -- EDTA pH 7.5 --.

Column 80, Line 18, delete "80 UM" and insert -- 80 µM --.

Column 80, Line 19, delete "80 UM final" and insert -- 80 µM final --.

Column 81, Line 31 (approx.), delete "1271C" and insert -- I271C --.

Column 82, Line 10, delete "L398GL398C".

Column 82, Line 44 (approx.), delete "1271C" and insert -- I271C --.

Column 83, Line 40, delete "DTT, PH 7.9" and insert -- DTT, pH 7.9 --.

Column 83, Line 55, delete "9723 bp Acc651-BamHI" and insert -- 9723 bp Acc65I-BamHI --.

Column 83, Line 63, delete "the Acc651 and" and insert -- the Acc65I and --.

Column 83, Line 65, delete "the Acc651 and" and insert -- the Acc65I and --.

Column 84, Line 30, delete "PH 7.5" and insert -- pH 7.5 --.

Column 84, Line 32, delete "80 M s-" and insert -- 80 µM s- --.

Column 84, Line 46, delete "DTT, PH 7.9" and insert -- DTT, pH 7.9 --.

Column 90, Line 6, delete "(±525 Da)." and insert -- (+525 Da). --.

In the Claims

Column 371, Claim 10, Line 41, delete "(PBP), al-antitrypsin," and insert -- (PBP), α1-antitrypsin, --.

Column 376, Claim 10, Line 48, delete "technetium, 1125, I131," and insert -- technetium, I125, I131, --.